United States Patent
Merighi et al.

(10) Patent No.: US 10,415,069 B2
(45) Date of Patent: *Sep. 17, 2019

(54) MICROORGANISMS AND METHODS FOR PRODUCING SIALYLATED AND N-ACETYLGLUCOSAMINE-CONTAINING OLIGOSACCHARIDES

(71) Applicant: Glycosyn LLC, Waltham, MA (US)

(72) Inventors: Massimo Merighi, Somerville, MA (US); Matthew Ian Heidtman, Brighton, MA (US); John M. McCoy, Reading, MA (US)

(73) Assignee: Glycosyn LLC, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/700,978

(22) Filed: Sep. 11, 2017

(65) Prior Publication Data

US 2018/0057849 A1 Mar. 1, 2018

Related U.S. Application Data

(62) Division of application No. 14/776,216, filed as application No. PCT/US2014/029804 on Mar. 14, 2014, now Pat. No. 9,758,803.

(60) Provisional application No. 61/782,999, filed on Mar. 14, 2013.

(51) Int. Cl.
| | | |
|---|---|---|
| *C12P 19/02* | (2006.01) | |
| *C07H 5/06* | (2006.01) | |
| *C07H 13/04* | (2006.01) | |
| *C07H 1/00* | (2006.01) | |
| *C12N 9/10* | (2006.01) | |
| *C12P 19/18* | (2006.01) | |
| *C12P 19/04* | (2006.01) | |
| *C07K 14/245* | (2006.01) | |
| *C12N 15/52* | (2006.01) | |
| *C12P 19/16* | (2006.01) | |
| *C12P 19/26* | (2006.01) | |

(52) U.S. Cl.
CPC ............. *C12P 19/02* (2013.01); *C07H 1/00* (2013.01); *C07H 5/06* (2013.01); *C07H 13/04* (2013.01); *C07K 14/245* (2013.01); *C12N 9/1051* (2013.01); *C12N 9/1081* (2013.01); *C12N 15/52* (2013.01); *C12P 19/04* (2013.01); *C12P 19/18* (2013.01); *C12P 19/26* (2013.01)

(58) Field of Classification Search
CPC .......... C12P 19/26; C12P 19/18; C12P 19/02; C12P 19/04; C07H 1/00; C07H 5/06; C07H 13/04; C07K 14/245; C12N 9/1051; C12N 9/1081; C12N 15/52
See application file for complete search history.

(56) References Cited

U.S. PATENT DOCUMENTS

| | | | |
|---|---|---|---|
| 7,521,212 B1 * | 4/2009 | Samain | C07H 3/06 435/193 |
| 8,507,227 B2 | 8/2013 | Samain | |
| 9,029,136 B2 | 5/2015 | Heidtman et al. | |
| 9,453,230 B2 | 9/2016 | Merighi et al. | |
| 9,758,803 B2 * | 9/2017 | Merighi | C12P 19/02 |
| 2008/0145899 A1 | 6/2008 | Johnson et al. | |
| 2008/0153133 A1 | 6/2008 | Boddy et al. | |
| 2009/0082307 A1 | 3/2009 | Samain et al. | |
| 2011/0014661 A1 | 1/2011 | Samain | |
| 2012/0208181 A1 | 8/2012 | Merighi et al. | |
| 2012/0294840 A1 | 11/2012 | Newburg et al. | |
| 2014/0080201 A1 | 3/2014 | Merighi et al. | |

FOREIGN PATENT DOCUMENTS

| | | |
|---|---|---|
| FR | 2796082 A1 | 1/2001 |
| WO | WO 2007101862 A1 | 9/2007 |
| WO | WO 2008040717 A2 | 4/2008 |
| WO | WO 2015175801 A1 | 11/2015 |

OTHER PUBLICATIONS

Konopka JB., N-acetylglucosamine functions in cell signaling. Scientifica, 2012, vol. 2012: 1-15 (Year: 2012).*
Reichenbach B., Regulation of glucosamine-6-phosphate synthase synthesis by a hierarchical acting cascade composed of two small regulatory RNAs in *Escherichia coli*. Dissertation. Univ., of Gottingen, 2009, pp. 1-190. (Year: 2009).*
Albermann et al. (2001) "Synthesis of the Milk Oligosaccharide 2'-Fucosyllactose Using Recombinant Bacterial Enzymes," Carbohydr. Res. 334(2):97-103.
Altschul et al. (Oct. 5, 1990) "Basic local alignment search tool," J Mol Biol. 215(3):403-410.
Altschul et al. (Sep. 1, 1997) "Gapped BLAST and PSI-BLAST: a new generation of protein database search programs," Nucleic Acids Res. 25(17):3389-3402.
Amonsen et al. (2007) "Human Parainfluenza Viruses hPIV1 and hPIV3 Bind Oligosaccharides with a 2-3-Linked Sialic Acids That are Distinct From Those Bound by H5 Avian Influenza Virus Hemagglutini," J. Virol. 81(15):8341-8345.
Antoine et al. (2003) "Large-scale in vivo synthesis of the carbohydrate moieties of gangliosides GM1 and GM2 by metabolically engineered *E.coli*," Chem Biochem. 4:406-412.
Bao et al. (2008) "Capillary electrophoresis of acidic oligosaccharides from human milk," Electrophoresis. 29:2508-2515.
Belfort et al. (1983) "Characterization of the *Escherichia coli* thyA Gene and its Amplified Thymidylate Synthetase Product," PNAS. 80(7):1858-1861.

(Continued)

*Primary Examiner* — Ganapathirama Raghu
(74) *Attorney, Agent, or Firm* — Mintz Levin Cohn Ferris Glovsky and Popeo, P.C.; Ingrid A. Beattie

(57) ABSTRACT

The invention provides compositions and methods for engineering bacteria to produce sialylated and N-acetylglucosamine-containing oligosaccharides, and the use thereof in the prevention or treatment of infection.

14 Claims, 19 Drawing Sheets

Specification includes a Sequence Listing.

(56) References Cited

OTHER PUBLICATIONS

Bettler et al. (1999) "The Living Factor: In vivo Production of N-Acetyllactosamine Containing Carbohydrates in E. coll," Glycoconj. J. 16(3):205-212.
Bird (Mar. 1981) "Homology between *Escherichia coli* plasmids ColE1 and p15A," J Bacteriol. 145(3):1305-1309.
Blixt et al. (1999) "High-level expression of the Neisseria meningitidis IgtA gene in *Escherichia coli* and characterization of the encoded N-acetylglucosaminyltransferase as a useful catalyst in the synthesis of GlcNAc® 1 3Gal and GalNAc® 1 3Gal linkages," Glycobiology. 9(10):1061-1071.
Broun et al. (1998) "Catalytic plasticity of fatty acid modification enzymes underlying chemical diversity of plant lipids," Science. 282:1315-1317.
Charlwood et al. (1999) "A Detailed Analysis of Neutral and Acidic Carbohydrates in Human Milk," Anal. Biochem. 273(2):261-277.
Chaturvedi et al. (2001) "Fucosylated Human Milk Oligosaccharides Vary Between Individuals and Over the Course of Lactation," Glycobiol. 11(5):365-372.
Chaturvedi et al. (2001) "Survival of Human Milk Oligosaccharides in the Intestine of Infants," Bioactive Components of Human Milk. 34:315-323.
Chica et al. (2005) "Semi-rational approaches to engineering enzyme activity: combining the benefits of directed evolution and rational design," Curr. Opi. Biotechnol. 16:378-384.
Couceiro et al. (1993) "Influenze Virus Strains Selectively Recognize Sialyloligosaccharides on Human Respiratory Epithelium; The Role of the Host Cell in Selection of Hemagglutinin Receptor Specificity," Virus Res. 29(2):155-165.
Court et al. (2002) "Genetic Engineering Using Homologous Recombination," Annu. Rev. Genet. 36:361-388.
Crout et al. (1998) "Glycosidases and Glycosyl Transferases in Glycoside and Oligosaccharide Synthesis," Curr. Opin. Chem. Biol. 2(1):98-111.
Danchin (2009) "Cells Need Safety Valves," Bioessays. 31:769-773.
Devos et al. (2000) "Practical limits of function prediction," Proteins: Structure, Function, and Genetics. 41:98-107.
Drouillard et al. (Jul. 2, 2010) "Efficient synthesis of 6'-sialyllactose, 6,6'-disialyllactose, and 6'-KDO-lactose by metabolically engineered *E. coli* expressing a multifunctional sialyltransferase from the *Photobacterium* sp. JT-ISH-224," Carbohydr Res. 345(10):1394-1399.
Dumon et al. (2006) "Production of Lewis x tetrasaccharides by metabolically engineered *E.coli*," Chem Biochem. 7:359-365.
Endo et al. (1999) "Large-Scale Production of N-Acetyllactosamine Through Bacterial Coupling," Carbohydr. Res. 316(1-4):179-183.
Endo et al. (2000) "Large-Scale Production of Oligosaccharides Using Engineered Bacteria," Curr. Opin. Struct Biol. 10(5):536-541.
Endo et al. (2000) "Large-Scale Production of the CMP-NeuAc and Sialylated Oligosaccharides Through Bacterial Coupling," Appl. Microbiol. Biotechnol. 53(3):257-261.
Endo et al. (2001) "Large-Scale Production of the Carbohydrate Portion of the siayl-Tn Epitope, a-Neup5Ac-(2-*6)-D-GalpNAc, Through Bacterial Coupling," Carbohydr. Res. 330(4):439-443.
Erney et al. (2001) "Human Milk Oligosaccharides," Adv Exp Med Biol. 501:285-297.
Fierfort et al. (2008) "Genetic engineering of *Escherichia coli* for the economical production of sialylated oligosaccharides," J. Biotechnol. 134:261-265.
Flowers (1978) "Chemical Synthesis of Oligosaccharides," Methods Enzymol. 50:93-121.
GenBank Database Accession No. AAF42257.1, Tettelin et al., Jan. 31, 2014, 2 pages Accessible on the Internet at URL: https://www.ncbi.nlm.nih.gov/protein/AAF42257.1.
GenBank Database Accession No. AAF42258.1, Tettelin et al., Jan. 31, 2014, 2 pages Accessible on the Internet at URL: https://www.ncbi.nlm.nih.gov/protein/AAF42258.1.
GenBank Database Accession No. AAG29920, Guerry et al., Jul. 14, 2016, 1 page Accessible on the Internet at URL: https://www.ncbi.nlm.nih.gov/protein/AAG29920.
GenBank Database Accession No. AAG29921, Guerry et al., Jul. 14, 2016, 1 page Accessible on the Internet at URL: https://www.ncbi.nlm.nih.gov/protein/AAG29921.
GenBank Database Accession No. AAK91727.1, Gilbert et al., Jul. 23, 2016, 2 pages Accessible on the Internet at URL: https://www.ncbi.nlm.nih.gov/protein/AAK91727.1.
GenBank Database Accession No. AAK91728.1, Gilbert et al., Jul. 23, 2016, 2 pages Accessible on the Internet at URL: https://www.ncbi.nlm.nih.gov/protein/AAK91728.1.
GenBank Database Accession No. ACF31229.1, Chung et al., Jan. 31, 2014, 1 page Accessible on the Internet at URL: https://www.ncbi.nlm.nih.gov/protein/ACF31229.1.
GenBank Database Accession No. ADN91474, Friis et al. Jan. 30, 2014, 2 pages Accessible on the Internet at URL: https://www.ncbi.nlm.nih.gov/protein/ADN91474.
GenBank Database Accession No. AEZ55696.1, Pohl et al., Mar. 23, 2012, 1 page Accessible on the Internet at URL: https://www.ncbi.nlm.nih.gov/protein/AEZ55696.1.
GenBank Database Accession No. BAA35319.1, Musso et al., Sep. 29, 2018, 12 pages Accessible on the Internet at URL: https://www.ncbi.nlm.nih.gov/protein/BAA35319.
GenBank Database Accession No. BAE77265, Musso et al., Sep. 29, 2018, 12 pages Accessible on the Internet at URL: https://www.ncbi.nlm.nih.gov/protein/BAE77265.
GenBank Database Accession No. BAF92026.1, Tsukamoto et al., Mar. 22, 2008, 1 page Accessible on the Internet at URL: https://www.ncbi.nlm.nih.gov/protein/BAF92026.1.
GenBank Database Accession No. D00067, Ohta et al. Jun. 15, 2010, 2 pages Accessible on the Internet at URL: https://www.ncbi.nlm.nih.gov/nuccore/D00067.
GenBank Database Accession No. M84410, Poch et al., Apr. 27, 1993, 2 pages Accessible on the Internet at URL: https://www.ncbi.nlm.nih.gov/nuccore/M84410.
GenBank Database Accession No. M84410.1, Poch et al., Apr. 27, 1993, 2 pages Accessible on the Internet at URL: https://www.ncbi.nlm.nih.gov/nuccore/M84410.1.
GenBank Database Accession No. NP_207619.1, Raymond et al., Aug. 2, 2016, 2 pages Accessible on the Internet at URL: https://www.ncbi.nlm.nih.gov/protein/NP_207619.1.
GenBank Database Accession No. NP_273962.1, Tettelin et al., Aug. 3, 2016, 2 pages Accessible on the Internet at URL: https://www.ncbi.nlm.nih.gov/protein/NP_273962.1.
GenBank Database Accession No. NP_418185.1, Riley et al., Oct. 11, 2014, 3 pages Accessible on the Internet at URL: https://www.ncbi.nlm.nih.gov/protein/NP_418185.1.
GenBank Database Accession No. V00295.1, Buchel et al., Jul. 26, 2016, 3 pages Accessible on the Internet at URL: https://www.ncbi.nlm.nih.gov/nuccore/V00295.1.
GenBank Database Accession No. V00296.1, Zell et al., Jul. 26, 2016, 3 pages Accessible on the Internet at URL: https://www.ncbi.nlm.nih.gov/nuccore/V00296.1.
GenBank Database Accession No. YP_002392936.1, Touchon et al., Dec. 16, 2014, 2 pages Accessible on the Internet at URL: https://www.ncbi.nlm.nih.gov/protein/YP_002392936.1?report=genpept.
GenBank Database Accession No. YP_003500090.1, Zhou et al., Dec. 17, 2014, 2 pages Accessible on the Internet at URL: https://www.ncbi.nlm.nih.gov/protein/YP_003500090.1?report=genpept.
Hamosh (2001) "Bioactive Factors in Human Milk," Pediatr. Clin. North Am. 48(1):69-86.
Han et al. (Nov.-Dec. 2012) "Biotechnological production of human milk oligosaccharides," Biotechnol Adv. 30(6):1268-1278.
Johnson (1999) "Synthesis of Oligosaccharides by Bacterial Enzymes," Glycoconj. J. 16(2):141-146.
Kisselev (2002) "Polypeptide release factors in prokaryotes and eukaryotes: same function, different structure," Structure. 10:8-9.
Koeller et al. (2000) "Synthesis of Complex Carbohydrates and Glycoconjugates: Enzyme-Based and Programmable One-Pot Strategies," Chem. Rev. 100(12):4465-4493.

(56) References Cited

OTHER PUBLICATIONS

Koizumi et al. (1998) "Large-Scale Production of UDP-Galactose and Globotriose by Coupling Metabolically Engineered Bacteria," Nat. Biotechnol. 16(9):847-850.
Kuhlenschmidt et al. (1999) "Sialic Acid Dependence and Independence of Group A Rotaviruses," Mechanisms in the Pathogenesis of Enteric Disases 2. 33:309-317.
Mahdavi et al. (2002) "Helicobacter pylori SabA Adhesin in Persistent Infection and Chronic Inflammation," Science. 297(5581):573-578.
Martin-Sosa et al. (2003) "Sialyligosaccharides in Human and Bovine Milk and in Infant Formulas: Variations with the Progression of Lactation," J. Dairy Sci. 86(1):52-59.
McCoy et al. (1994) "Expression and Purification of Thioredoxin Fusion Proteins," Current Protocols in Molecular Biology. 16(8):1-14.
Mieschendahl et al. (1986) "A Nogel Prophage Independent TRP Regulated Lambda PL Expression System," Nat. Biotechnol. 4:802-808.
Morrow et al. (2004) "Human Milk Oligosaccharides are Associated with Protection Against Diarrhea in Breast-Fed Infants," J. Pediatr. 145(3):297-303.
Newburg et al. (1998) "Role of Human-Milk Lactadherin in Protection Against Symptomatic Rotavirus Infection," Lancet. 351(9110):1160-1164.
Newburg et al. (1999) "Human Milk Gylcoconjugtes That Inhibit Pathogens," Curr. Med. Chem. 6:117-127.
Newburg et al. (2001) "Bioactive Components of Human Milk," Adv Exp Med Biol. 501:3-10.
Newburg et al. (2004) "Innate Protection Conferred by Fucosylated Oligosaccharides of Human Milk Against Diarrhea in Breastfed Infants," Glycobiol. 14(3):253-263.
Ninoneuvo et al. (2006) "A Strategy for Annotating the Human Milk Glycome," J. Agric. Food Chem. 54(20):7471-7480.
Palcic (1999) "Biocatalytic Synthesis of Oligosaccharides," Curr. Opin. Biotechnol. 10(6):616-624.
Parkkinen et al. (1987) "Isolation of Sialyl Oligosaccharides and Sialyl Oligosaccharide Phosphates From Bovine Colostrum and Human Urine," Methods Enzymol. 138:289-300.
Priem et al. (2002) "A new fermentation process allows large-scale production of human milk oligosaccharides by metabolically engineered bacteria," Glycobiol. 12(4): 235-240.
Qaidi et al. (2008) "Switching control of expression of ptsG from the Mlc regulon to the NagC regulon," J. Bacteriol. 190(13):4677-4686.
Reichenbach et al. (2008) "The small RNA GlmY acts upstream of the sRNA GlmZ in the activation of glmS expression and is subject to regulation by polyadenylation in *Escherichia coli*," Nuc. Acids. Res. 36(8):2570-2580.
Roberfroid et al. (2010) "Prebiotic Concept and Health," NS British Journal of Nutrition. 104(2):1-63.
Ruiz-Palacios et al. (2003) "Campylobacter jejuni Binds Intestinal H(0) Antigen (Fuca1, 2Gal[31, 4GlcNAc), and Fucosyloligosaccharides of Human Milk Inhibit its Binding and Infection," J. Biol. Chem. 278(16):14112-14120.
Rydell et al. (2009) "Human Noroviruses Recognize Sialyl Lewis x Neoglycoprotein," Glycobiol. 19(3):309-320.
Samain et al. (2008) "Genetic engineering of *Escherichia coli* for the economical production of sialylated oligosaccharides," Journal of Biotechnology. 134:261-265.
Sanger et al. (1982) "Nucleotide Sequence of Bacteriophage DNA," J. Mol. Biol. 162:729-773.
Scharfman et al. (2000) "Sialyl-Lex and Sulfo-Sialyl-Lex Determinants are Receptors for P. aeruginosa," Glycoconj. J. 17(10):735-740.
Seeberger (2003) "Automated Carbohydrate Synthesis to Drive Chemical Glycomics," Chem. Commun. 10:1115-1121.
Seffernick et al. (2001) "Melamine deaminase and Atrazine chlorohydrolase: 98 percent identical but functionally different," J. Bacteriol. 183(8):2405-2410.

Sen et al. (2007) "Developments in directed evolution for improving enzyme functions," Appl. Biochem. Biotechnol. 143:212-223.
Shen et al. (2001) "Resolution of Structural Isomers of Sialylated Oligosaccharides by Capillary Electrophoresis," J. Chromatogr. A. 921(2):315-321.
Sleight et al. (May 2010) "In-Fusion BioBrick assembly and re-engineering," Nucleic Acids Res. 38(8):2624-36.
Thomason et al. (Jul. 2007) "*E. coli* Genome Manipulation by P1 Transduction," Current Protocols in Molecular Biology. 1(17):1-8.
Ward et al. (2007) "In vitro fermentability of human milk oligosaccharides by several strains of bifidobacteria," Mol. Nutr. Food Res. 51:1398-1405.
Whisstock et al. (2003) "Prediction of protein function from protein sequence," Q. Rev. Biophysics. 36(3):307-340.
Wishart et al. (1995) "A single mutation converts a novel phosphotyrosine binding domain into a dual-specificity phosphatase," J. Biol. Chem. 270(45):26782-26785.
Witkowski et al. (1999) "Conversion of b-ketoacyl synthase to a Malonyl Decarboxylase by replacement of the active cysteine with glutamine," Biochemistry. 38:11643-11650.
Wolfe et al. (Dec. 15, 1988) "Nucleotide sequence and analysis of the purA gene encoding adenylosuccinate synthetase of *Escherichia coli* K12," J Biol Chem. 263(35):19147-19153.
Wymer et al. (2000) "Enzyme-Catalyzed Synthesis of Carbohydrates," Curr. Opin. Chem. Biol. 4(1):110-119.
GenBank Accession No. AAK91726.1, "putative sialic acid synthase [*Campylobacter jejuni*]," Jul. 23, 2016, 2 pages Accessible on the Internet at URL: https://www.ncbi.nlm.nih.gov/protein/AAK91726.1.
GenBank Accession No. AAL02037.1, "Tn5 neomycin phosphotransferase [Template plasmid pKD13]," Sep. 11, 2001, 1 page Accessible on the Internet at URL: https://www.ncbi.nlm.nih.gov/protein/AAL02037.
GenBank Accession No. AC_000091.1, "*Escherichia coli* str. K-12 substr. W3110, complete sequence," Jun. 21, 2011, 846 pages Accessible on the Internet at URL: https://www.ncbi.nlm.nih.gov/nuccore/AC_000091.1?report=genbank.
GenBank Accession No. AP_003763.1, "hypothetical protein [*Escherichia coli* str. K-12 substr. W3110]," Jun. 21, 2011, 12 pages Accessible on the Internet at URL: https://www.ncbi.nlm.nih.gov/protein/AP_003763.1?report=genpept.
GenBank Accession No. AP_003764.1, "predicted N-acetylmannosamine kinase [*Escherichia coli* str. K-12 substr. W3110]," Jun. 21, 2011, 12 pages Accessible on the Internet at URL: https://www.ncbi.nlm.nih.gov/protein/AP_003764.1?report=genpept.
GenBank Accession No. AP_003765.1, "predicted N-acetylmannosamine-6-P epimerase [*Escherichia coli* str. K-12 substr. W3110]," Jun. 21, 2011, 12 pages Accessible on the Internet at URL: https://www.ncbi.nlm.nih.gov/protein/AP_003765.1?report=genpept.
GenBank Accession No. AP_003766.1, "sialic acid transporter [*Escherichia coli* str. K-12 substr. W3110]," Jun. 21, 2011, 12 pages Accessible on the Internet at URL: https://www.ncbi.nlm.nih.gov/protein/AP_003766.1?report=genpept.
GenBank Accession No. AP_003767.1, "N-acetylneuraminate lyase [*Escherichia coli* str. K-12 substr. W3110]," Jun. 21, 2011, 12 pages Accessible on the Internet at URL: https://www.ncbi.nlm.nih.gov/protein/AP_003767.1?report=genpept.
GenBank Accession No. AP_003768.1, "DNA-binding transcriptional dual regulator [*Escherichia coli* str. K-12 substr. W3110]," Jun. 21, 2011, 12 pages Accessible on the Internet at URL: https://www.ncbi.nlm.nih.gov/protein/AP_003768.1?report=genpept.
GenBank Accession No. AP_003769.1, "predicted transporter [*Escherichia coli* str. K-12 substr. W3110]," Jun. 21, 2011, 12 pages Accessible on the Internet at URL: https://www.ncbi.nlm.nih.gov/protein/AP_003769.1?report=genpept.
GenBank Accession No. BAE76126.1, "beta-D-galactosidase [*Escherichia coli* str. K-12 substr. W3110]," Sep. 29, 2018, 12 pages Accessible on the Internet at URL: https://www.ncbi.nlm.nih.gov/protein/BAE76126.
GenBank Accession No. BAE76896.1, "thymidylate synthetase [*Escherichia coli* str. K-12 substr. W3110]," Sep. 29, 2018, 12 pages Accessible on the Internet at URL: https://www.ncbi.nlm.nih.gov/protein/BAE76896.1.

(56) References Cited

OTHER PUBLICATIONS

GenBank Accession No. BAE76897.1, "phosphatidylglycerol-prolipoprotein diacylglyceryl transferase [*Escherichia coli* str. K-12 substr. W3110]," Sep. 29, 2018, 12 pages Accessible on the Internet at URL: https://www.ncbi.nlm.nih.gov/protein/BAE76897.
GenBank Accession No. NC_000913, "*Escherichia coli* str. K-12 substr. MG1655, complete genome," Oct. 11, 2018, 3 pages Accessible on the Internet at URL: https://www.ncbi.nlm.nih.gov/nuccore/NC_000913.
GenBank Accession No. NP_417303.1, "conserved protein PpdA [*Escherichia coli* str. K-12 substr. MG1655]," Oct. 11, 2018, 3 pages Accessible on the Internet at URL: https://www.ncbi.nlm.nih.gov/protein/NP_417303.1.
GenBank Accession No. T43329.1, "6592 Lambda-PRL2 Arabidopsis thaliana cDNA clone 117I3T7, mRNA sequence," Jan. 28, 2011, 1 page Accessible on the Internet at URL: https://www.ncbi.nlm.nih.gov/nuccore/T43329.
GenBank Accession No. WP_006881452.1, "acylneuraminate cytidylyltransferase family protein [*Vibrio brasiliensis*]," Jul. 24, 2017, 1 page Accessible on the Internet at URL: https://www.ncbi.nlm.nih.gov/protein/WP_006881452.1.
GenBank Accession No. WP_023580510.1, "N-acetylneuraminate synthase [*Flavobacterium limnosediminis*]," Feb. 8, 2016, 1 page Accessible on the Internet at URL: https://www.ncbi.nlm.nih.gov/protein/WP_023580510.1.
Antoine et al. (Feb. 18, 2005) "Highly efficient biosynthesis of the oligosaccharide moiety of the GD3 ganglioside by using metabolically engineered *Escherichia coli*," Angewandte Chemie. 44(9):1350-1352.

\* cited by examiner

_US 10,415,069 B2_

MICROORGANISMS AND METHODS FOR PRODUCING SIALYLATED AND N-ACETYLGLUCOSAMINE-CONTAINING OLIGOSACCHARIDES

RELATED APPLICATIONS

This application is a divisional of U.S. patent application Ser. No. 14/776,216, now U.S. Pat. No. 9,758,803, filed on Sep. 14, 2015, which is a national stage application, filed under 35 U.S.C. § 371, of International Application No. PCT/US2014/029804, filed on Mar. 14, 2014, which claims the benefit of, and priority to, U.S. Provisional Application No. 61/782,999, filed on Mar. 14, 2013; the contents of each of which are hereby incorporated by reference in their entireties.

INCORPORATION-BY-REFERENCE OF SEQUENCE LISTING

The contents of the text file named "37847_512001WO_ST25.txt", which was created on Sep. 11, 2017, and is 144 kilobytes in size, are hereby incorporated by reference in their entireties.

FIELD OF THE INVENTION

The invention provides compositions and methods for producing purified oligosaccharides, in particular certain N-acetylglucosamine-containing and/or sialylated oligosaccharides that are typically found in human milk.

BACKGROUND OF THE INVENTION

Human milk contains a diverse and abundant set of neutral and acidic oligosaccharides (human milk oligosaccharides, hMOS). Many of these molecules are not utilized directly by infants for nutrition, but they nevertheless serve critical roles in the establishment of a healthy gut microbiome, in the prevention of disease, and in immune function. Prior to the invention described herein, the ability to produce hMOS inexpensively at large scale was problematic. For example, hMOS production through chemical synthesis was limited by stereo-specificity issues, precursor availability, product impurities, and high overall cost. As such, there is a pressing need for new strategies to inexpensively manufacture large quantities of hMOS for a variety of commercial applications.

SUMMARY OF THE INVENTION

The invention described herein features efficient and economical methods for producing N-acetylglucosamine-containing and/or sialylated oligosaccharides.

The invention provides a method for producing an N-acetylglucosamine-containing oligosaccharide in a bacterium comprising the following steps: providing a bacterium that comprises an exogenous UDP-GlcNAc:Galα/β-R β 3-N-acetylglucosaminyltransferase and a functional lactose permease; and culturing the bacterium in the presence of lactose. The N-acetylglucosamine-containing oligosaccharide is then retrieved from the bacterium or from a culture supernatant of the bacterium.

The invention further provides a method for producing a sialylated oligosaccharide in a bacterium comprising the following steps: providing a bacterium that comprises an exogenous sialyl-transferase gene, a deficient sialic acid catabolic pathway, a sialic acid synthetic capability, and a functional lactose permease gene; and culturing the bacterium in the presence of lactose. The sialylated oligosaccharide is then retrieved from the bacterium or from a culture supernatant of the bacterium. Specifically, a sialic acid synthetic capability comprises expressing exogenous CMP-Neu5Ac synthetase, an exogenous sialic acid synthase, and an exogenous UDP-GlcNAc-2-epimerase, or a functional variant or fragment thereof.

In both methods for producing N-acetylglucosamine-containing and/or sialylated oligosaccharides, it is preferable that the bacterium further comprises the capability for increased UDP-GlcNAc production. By "increased production capability" is meant that the host bacterium produces greater than 10%, 20%, 50%, 100%, 2-fold, 5-fold, 10-fold, or more of a product than the native, endogenous bacterium. Preferably, the bacterium over-expresses a positive endogenous regulator of UDP-GlcNAc synthesis. For example, the bacterium overexpresses the nagC gene of _Escherichia coli_. Alternatively, the bacterium over-expresses the _Escherichia coli_ glmS (L-glutamine:D-fructose-6-phosphate aminotransferase) gene, or alternatively, over-expresses the _Escherichia coli_ glmY gene (a positive translational regulator of glmS), or, alternatively over-expresses the _Escherichia coli_ glmZ gene (another positive translational regulator of glmS: glmY and glmZ are described in Reichenbach et al _Nucleic Acids Res_ 36, 2570-80 (2008)). Alternatively, the bacterium over-expresses any combination of such approaches. For example, the bacterium over-expresses nagC and glmS. Alternatively, the bacterium over-expresses nagC and glmY. Alternatively, the bacterium over-expresses nagC and glmZ. The methods also further encompass over-expressing any functional variant or fragment of nagC, glmS, glmY and glmZ and any combination thereof. By "overexpression" is meant that the gene transcript or encoded gene product is 10%, 20%, 50%, 2-fold, 5-fold, 10-fold, or more than the level expressed or produced by the corresponding native, naturally-occurring, or endogenous gene.

The invention described herein details the manipulation of genes and pathways within bacteria such as the enterobacterium _Escherichia coli_ K12 (_E. coli_) leading to high level synthesis of hMOS. Other strains of _E. coli_ for suitable for use in the present invention include _E. coli_ MG1655, _E. coli_ W3110, _E. coli_ DH5aE, _E. coli_ B, _E. coli_ C, and _E. coli_ W. A variety of bacterial species are suitable for use in the oligosaccharide biosynthesis methods, for example _Erwinia herbicola_ (_Pantoea agglomerans_), _Citrobacter freundii_, _Pantoea citrea_, _Pectobacterium carotovorum_, or _Xanthomonas campestris_. Bacteria of the genus _Bacillus_ are suitable for use, including _Bacillus subtilis, Bacillus licheniformis, Bacillus coagulans, Bacillus thermophilus, Bacillus laterosporus, Bacillus megaterium, Bacillus mycoides, Bacillus pumilus, Bacillus lentus, Bacillus cereus_, and _Bacillus circulans_. Similarly, bacteria of the genera _Lactobacillus_ and _Lactococcus_ are modified using the methods of this invention, including but not limited to _Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii_, and _Lactococcus lactis. Streptococcus thermophiles_ and _Proprionibacterium freudenreichii_ are also suitable bacterial species for the invention described herein. Also included as part of this invention are strains, modified as described here, from the genera _Enterococcus_ (e.g., _Enterococcus faecium_ and Enterococcus thermophiles), Bacteroides (e.g., Bacteroides caccae, Bacteroides cellulosilyticus, Bacteroides dorei, Bacteroides eggerthii, Bacteroides fine goldii, Bacteroides fragilis, Bacteroides nordii, Bacteroides ovatus, Bacteroides salyersiae, Bacteroides thetaiotaomicron, Bacteroides uniformis, Bacteroides vulgatus and Bacteroides xylanisolvens), Bifidobacterium (e.g., Bifidobacterium longum, Bifidobacterium infantis, and Bifidobacterium bifidum), Parabacteroides (e.g. Parabacteroides distasonis, Parabacteroides goldsteinii, Parabacteroides johnsonii and Parabacteroides merdae), Prevotella (e.g., Prevotella copri), Sporolactobacillus spp., Micromomospora spp., Micrococcus spp., Rhodococcus spp., and Pseudomonas (e.g., Pseudomonas fluorescens and Pseudomonas aeruginosa). Bacteria comprising the characteristics described herein are cultured in the presence of lactose, and an N-acetylglucosamine-containing or sialylated oligosaccharide is retrieved, either from the bacterium itself or from a culture supernatant of the bacterium. The N-acetylglucosamine-containing or sialylated oligosaccharide is purified for use in therapeutic or nutritional products, or the bacteria are used directly in such products.

The bacterium comprises a deleted or inactivated (i.e., non-functional) endogenous β-galactosidase gene. For example, the β-galactosidase gene comprises an E. coli lacZ gene (e.g., GenBank Accession Number V00296.1 (GI: 41901), incorporated herein by reference). The endogenous lacZ gene of the E. coli is deleted or functionally inactivated, but in such a way that expression of the downstream lactose permease (lacY) gene remains intact, i.e. a functional lactose permease gene is also present in the bacterium. By deleted is meant that a portion or the whole coding sequence is absent, such that no gene product is produced. An "inactivated" gene does not produce a gene product that functions as the native, naturally-occurring, or endogenous gene. For example, the functional activity of an inactivated β-galactosidase gene product is reduced to 10%, 20%, 50%, or 100%, 1-fold, 2-fold, 5-fold, or 10-fold less than the functional activity of the native, naturally-occuring, endogenous gene product.

The lactose permease gene is an endogenous lactose permease gene or an exogenous lactose permease gene. For example, the lactose permease gene comprises an E. coli lacY gene (e.g., GenBank Accession Number V00295.1 (GI: 41897), incorporated herein by reference). Many bacteria possess the inherent ability to transport lactose from the growth medium into the cell, by utilizing a transport protein that is either a homolog of the E. coli lactose permease (e.g., as found in Bacillus licheniformis), or a transporter that is a member of the ubiquitous PTS sugar transport family (e.g., as found in Lactobacillus casei and Lactobacillus rhamnosus). For bacteria lacking an inherent ability to transport extracellular lactose into the cell cytoplasm, this ability is conferred by an exogenous lactose transporter gene (e.g., E. coli lacY) provided on recombinant DNA constructs, and supplied either on a plasmid expression vector or as exogenous genes integrated into the host chromosome.

For the production of N-acetylglucosamine-containing oligosaccharides, the bacterium comprises an exogenous UDP-GlcNAc:Galα/β-R β 3-N-acetylglucosaminyltransferase gene or a functional variant or fragment thereof. This exogenous UDP-GlcNAc:Galα/β-R β 3-N-acetylglucosaminyltransferase gene is obtained from any one of a number of sources, e.g., the LgtA gene described from N. meningitides (SEQ ID NO:16 Genbank protein Accession AAF42258.1, incorporated herein by reference) or N. gonorrhoeae (Genbank protein Accession ACF31229.1). Optionally, an additional exogenous glycosyltransferase gene is co-expressed in the bacterium comprising an exogenous UDP-GlcNAc:Galα/β-R β 3-N-acetylglucosaminyltransferase. For example, a β-1,4-galactosyltransferase gene is co-expressed with the UDP-GlcNAc:Galα/β-R β 3-N-acetylglucosaminyltransferase gene. This exogenous β-1,4-galactosyltransferase gene is obtained from any one of a number of sources, e.g., that described from N. meningitidis, the LgtB gene (Genbank protein Accession AAF42257.1), or from H. pylori, the Lex2B gene (SEQ ID NO:17 Genbank protein Accession NP_207619.1, incorporated herein by reference). Optionally, the additional exogenous glycosyltransferase gene co-expressed in the bacterium comprising an exogenous UDP-GlcNAc:Galα/β-R β 3-N-acetylglucosaminyltransferase gene is a β-1,3-galactosyltransferase gene, e.g., that described from E. coli O55:H7, the WbgO gene (SEQ ID NO:18 Genbank protein Accession YP_003500090.1, incorporated herein by reference), or from H. pylori, the jhp0563 gene (Genbank protein Accession AEZ55696.1). Functional variants and fragments of any of the enzymes described above are also encompassed by the present invention.

In one embodiment, the N-acetylglucosamine-containing oligosaccharides produced by the methods described herein include Lacto-N-triose 2 (LNT2), Lacto-N-tetraose (LNT), Lacto-N-neotetraose (LNnT), Lacto-N-fucopentaose I (LNF I), Lacto-N-fucopentaose II (LNF II), Lacto-N-fucopentaose III (LNF III), Lacto-N-fucopentaose V (LNF V), Lacto-N-difucohexaose I (LDFH I), Lacto-N-difucohexaose II (LDFH II), and Lacto-N-neodifucohexaose II (LFNnDFH II).

For the production of sialyl-oligosaccharides, the bacterium comprises an exogenous sialyl-transferase gene. For example, the exogenous sialyl-transferase gene encodes α(2,3) sialyl-transferase or the exogenous sialyl-transferase gene encodes α(2,6) sialyl-transferase or the exogenous sialyl-transferase gene encodes α(2,8) sialyltransferase. The exogenous sialyl-transferase genes is obtained from any one of a number of sources, e.g., those described from N. meningitidis, N. gonorrhoeae, and from a number of organisms of the genus Photobacterium. Examples of α(2,8) sialyltransferases, useful for the production of polysialic acid for example, are found in Campylobacter jejuni (CstII: ADN52706) and Neisseria meningitides (or siaD: AAA20478).

The bacteria used herein to produce hMOS are genetically engineered to comprise an increased intracellular lactose pool (as compared to wild type) and to comprise UDP-GlcNAc:Galα/β-R β 3-N-acetylglucosaminyltransferase and/or sialyl-transferase activity. Optionally, they also comprise β-1,4-galactosyltransferase or β-1,3-galactosyltransferase activity, and/or α-1,2-, α-1,3- and/or α-1,4-fucosyltransferase activity. In some cases, the bacterium further comprises a functional, wild-type E. coli lacZ$^+$ gene inserted into an endogenous gene, for example, the ion gene in E. coli or the thyA gene in E. coli. In this manner, the bacterium further comprises a mutation in a ion gene or a mutation in the thyA gene. In these cases, the endogenous lacZ gene of the E. coli is deleted or functionally inactivated, but in such a way that expression of the downstream lactose permease (lacY) gene remains intact. The organism so manipulated maintains the ability to transport lactose from the growth medium, and to develop an intracellular lactose pool for use as an acceptor sugar in oligosaccharide synthesis, while also maintaining a low level of intracellular beta-galactosidase activity useful for a variety of additional purposes. For example, the invention also includes: a) methods for phenotypic marking of a gene locus in a β-galactosidase negative host cell by utilizing a β-galactosidase (e.g., lacZ) gene insert engineered to produce a low but readily detectable level of β-galactosidase activity, b) methods for readily detecting lytic bacteriophage contamination in fermentation runs through release and detection of cytoplasmic β-galactosidase in the cell culture medium, and c) methods for depleting a bacterial culture of residual lactose at the end of production runs. a), b) and c) are each achieved by utilizing a functional β-galactosidase (e.g., lacZ) gene insert carefully engineered to direct the expression of a low, but detectable level of (β-galactosidase activity in an otherwise β-galactosidase negative host cell. The bacterium optionally further comprises a mutation in a lacA gene. Preferably, the bacterium accumulates an increased intracellular lactose pool, and produces a low level of beta-galactosidase. An increased intracellular pool is wherein the concentration of lactose in the host bacterium at least 10%, 20%, 50%, 2-fold, 5-fold, or 10-fold higher than that of the native, naturally-occurring bacterium.

In one aspect, the human milk oligosaccharide produced by engineered bacteria comprising an exogenous nucleic acid molecule encoding an UDP-GlcNAc:Galα/β-R β 3-N-acetylglucosaminyltransferase and an exogenous nucleic acid encoding β-1,4-galactosyltransferase is lacto-N-neotetraose (LNnT). In another aspect, the human milk oligosaccharide produced by engineered bacteria comprising an exogenous nucleic acid molecule encoding a UDP-GlcNAc:Galα/β-R β 3-N-acetylglucosaminyltransferase and an exogenous nucleic acid encoding β-1,3-galactosyltransferase is lacto-N-tetraose (LNT).

Described herein are compositions comprising a bacterial cell that produces the human milk oligosaccharide LNnT (lacto-N-neotetraose), wherein the bacterial cell comprises an exogenous UDP-GlcNAc:Galα/β-R β 3-N-acetylglucosaminyltransferase and an exogenous nucleic acid encoding a β-1,4-galactosyltransferase. Preferably, the bacterial cell is *E. coli*. The exogenous UDP-GlcNAc:Galα/β-R β 3-N-acetylglucosaminyltransferase gene is obtained from any one of a number of sources, e.g., the LgtA gene described from *N. meningitides*. The exogenous β-1,4-galactosyltransferase gene is obtained from any one of a number of sources, e.g., that described from *N. meningitidis*, the LgtB gene, or from *H. pylori*, the jhp0765 gene.

Additionally, the bacterium preferably comprises increased production of UDP-GlcNAc. An exemplary means to achieve this is by over-expression of a positive endogenous regulator of UDP-GlcNAc synthesis, for example, overexpression of the nagC gene of *Escherichia coli*. In one aspect, this nagC over-expression is achieved by providing additional copies of the nagC gene on a plasmid vector or by integrating additional nagC gene copies into the host cell chromosome. Alternatively, over-expression is achieved by modulating the strength of the ribosome binding sequence directing nagC translation or by modulating the strength of the promoter directing nagC transcription. As further alternatives the intracellular UDP-GlcNAc pool may be enhanced by other means, for example by over-expressing the *Escherichia coli* glmS (L-glutamine:D-fructose-6-phosphate aminotransferase) gene, or alternatively by over-expressing the *Escherichia coli* glmY gene (a positive translational regulator of glmS), or alternatively by over-expressing the *Escherichia coli* glmZ gene (another positive translational regulator of glmS), or alternatively by simultaneously using a combination of approaches. In one preferred embodiment, for example, the nagC (SEQ ID NO:19 Genbank protein Accession BAA35319.1, incorporated herein by reference) and glmS (SEQ ID NO:20 Genbank protein Accession NP_418185.1, incorporated herein by reference) genes which encode the sequences provided herein are overexpressed simultaneously in the same host cell in order to increase the intracellular pool of UDP-GlcNAc. Other components of UDP-GlcNAc metabolism include: (GlcNAc-1-P) N-acetylglucosamine-1-phosphate; (GlcN-1-P) glucosamine-1-phosphate; (GlcN-6-P) glucosamine-6-phosphate; (GlcNAc-6-P) N-acetylglucosamine-6-phosphate; and (Fruc-6-P) Fructose-6-phosphate. Bacteria comprising the characteristics described herein are cultured in the presence of lactose, and lacto-N-neotetraose is retrieved, either from the bacterium itself (i.e., by lysis) or from a culture supernatant of the bacterium.

Also within the invention is an isolated *E. coli* bacterium as described above and characterized as comprising a deleted or inactivated endogenous β-galactosidase gene, an inactivated or deleted lacA gene, and a functional lactose permease (lacY) gene.

Also described herein are compositions comprising a bacterial cell that produces the human milk oligosaccharide 6'-SL (6'-sialyllactose), wherein the bacterial cell comprises an exogenous sialyl-transferase gene encoding α(2,6)sialyltransferase. Preferably, the bacterial cell is *E. coli*. The exogenous sialyl-transferase gene utilized for 6'-SL production is obtained from any one of a number of sources, e.g., those described from a number of organisms of the genus *Photobacterium*. In yet another aspect, the human milk oligosaccharide produced by engineered bacteria comprising an exogenous nucleic acid molecule encoding an α(2,3) sialyltransferase is 3'-SL (3'-sialyllactose). The exogenous sialyltransferase gene utilized for 3'-SL production is obtained from any one of a number of sources, e.g., those described from *N. meningitidis* and *N. gonorrhoeae*.

Additionally, the bacterium contains a deficient sialic acid catabolic pathway. By "sialic acid catabolic pathway" is meant a sequence of reactions, usually controlled and catalyzed by enzymes, which results in the degradation of sialic acid. An exemplary sialic acid catabolic pathway in *Escherichia coli* is described herein. In the sialic acid catabolic pathway described herein, sialic acid (Neu5Ac; N-acetylneuraminic acid) is degraded by the enzymes NanA (N-acetylneuraminic acid lyase) and NanK (N-acetylmannosamine kinase) and NanE (N-acetylmannosamine-6-phosphate epimerase), all encoded in the nanATEK-yhcH operon, and repressed by NanR (ecocyc.org/ECOLI). A deficient sialic acid catabolic pathway is engineered in *Escherichia coli* by way of a mutation in endogenous nanA (N-acetylneuraminate lyase) (e.g., GenBank Accession Number D00067.1 (GI: 216588), incorporated herein by reference) and/or nanK (N-acetylmannosamine kinase) genes (e.g., GenBank Accession Number (amino acid) BAE77265.1 (GI: 85676015), incorporated herein by reference), and/or nanE (N-acetylmannosamine-6-phosphate epimerase, GI: 947745, incorporated herein by reference). Optionally, the nanT (N-acetylneuraminate transporter) gene is also inactivated or mutated. Other intermediates of sialic acid metabolism include: (ManNAc-6-P) N-acetylmannosamine-6-phosphate; (GlcNAc-6-P) N-acetylglucosamine-6-phosphate; (GlcN-6-P) Glucosamine-6-phosphate; and (Fruc-6-P) Fructose-6-phosphate. In some preferred embodiments, nanA is mutated. In other preferred embodiments, nanA and nanK are mutated, while nanE remains functional. In another preferred embodiment, nanA and nanE are mutated, while nanK has not been mutated, inactivated or deleted. A mutation is one or more changes in the nucleic acid sequence coding the gene product of nanA, nanK, nanE, and/or nanT. For example, the mutation may be 1, 2, 5, 10, 25, 50 or 100 changes in the nucleic acid sequence. For example, the nanA, nanK, nanE, and/or nanT is mutated by a null mutation. Null mutations as described herein encompass amino acid substitutions, additions, deletions, or insertions that either cause a loss of function of the enzyme (i.e., reduced or no activity) or loss of the enzyme (i.e., no gene product). By deleted is meant that the coding region is removed in whole or in part such that no gene product is produced. By inactivated is meant that the coding sequence has been altered such that the resulting gene product is functionally inactive or encodes a gene product with less than 100%, 80%, 50%, or 20% of the activity of the native, naturally-occuring, endogenous gene product. A "not mutated" gene or protein does not differ from a native, naturally-occurring, or endogenous coding sequence by 1, 2, 5, 10, 20, 50, 100, 200 or 500 more codons, or to the corresponding encoded amino acid sequence.

Moreover, the bacterium (e.g., *E. coli*) also comprises a sialic acid synthetic capability. For example, the bacterium comprises a sialic acid synthetic capability through provision of an exogenous UDP-GlcNAc 2-epimerase (e.g., neuC of *Campylobacter jejuni* (SEQ ID NO: 13, GenBank AAK91727.1; GI: 15193223, incorporated herein by reference) or equivalent (e.g. *E. coli* S88 neuC GenBank YP_002392936.1; GI: 218560023), a Neu5Ac synthase (e.g., neuB of *C. jejuni* (SEQ ID NO:14 AAK91726.1GenBank GI: 15193222, incorporated herein by reference) or equivalent, (e.g. *Flavobacterium limnosediminis* sialic acid synthase, GenBank GI: 559220424), and/or a CMP-Neu5Ac synthetase (e.g., neuA of *C. jejuni* (SEQ ID NO: 15 GenBank AAK91728.1; GI: 15193224, incorporated herein by reference) or equivalent, (e.g. *Vibrio brasiliensis* CMP-sialic acid synthase, GenBank GI: 493937153). Functional variants and fragments are also disclosed herein.

Additionally, the bacterium comprising a sialic acid synthetic capability preferably increased production of UDP-GlcNAc. An exemplary means to achieve this is by over-expression of a positive endogenous regulator of UDP-GlcNAc synthesis, for example, simultaneous overexpression of the nagC and glmS genes of *Escherichia coli*. This nagC and glmS over-expression is achieved by providing additional copies of the nagC and glmS genes on a plasmid vector, or by integrating additional nagC and glmS gene copies into the host cell chromosome. Alternatively, over-expression is achieved by modulating the strength of the ribosome binding sequence directing nagC (described by Sleight et al, Nucleic Acids Res. May 2010; 38(8): 2624-2636) and/or glmS translation, or by modulating the strength of the promoter/s directing nagC and glmS transcription (Sleight et al, *Nucleic Acids Res. May* 2010; 38(8): 2624-2636)

Bacteria comprising the characteristics described herein are cultured in the presence of lactose, and, in the instance where cells comprise an α(2,6) sialyltransferase (e.g. *Photobacterium* spp JT-ISH-224 (SEQ ID NO:21 Genbank protein Accession BAF92026.1, incorporated herein by reference), 6'-sialyllactose is retrieved, either from the bacterium itself or from a culture supernatant of the bacterium. In the instance where cells comprise an α(2,3) sialyltransferase, (e.g. *Neisseria meningitidis* 1st (Genbank protein Accession NP273962.1) 3'-sialyllactose is recovered either from the bacterium itself (e.g., by lysis of the bacterium) or from a culture supernatant of the bacterium.

Also within the invention is an isolated *E. coli* bacterium as described above and characterized as comprising a deleted or inactivated endogenous β-galactosidase gene, an exogenous sialyl-transferase gene, a deficient sialic acid catabolic pathway, a sialic acid synthetic capability, a deleted lacA gene, and a functional lactose permease (lacY) gene. A purified N-acetylglucosamine-containing or sialylated oligosaccharide produced by the methods described above is also within the invention. A purified oligosaccharide, e.g., 6'-SL, is one that is at least 90%, 95%, 98%, 99%, or 100% (w/w) of the desired oligosaccharide by weight. Purity is assessed by any known method, e.g., thin layer chromatography or other electrophoretic or chromatographic techniques known in the art. The invention includes a method of purifying an N-acetylglucosamine-containing or sialylated oligosaccharide produced by the genetically engineered bacteria described above, which method comprises separating the desired N-acetylglucosamine-containing or sialylated oligosaccharide (e.g., 6'-SL) from contaminants in a bacterial cell extract or lysate, or bacterial cell culture supernatant. Contaminants include bacterial DNA, protein and cell wall components, and yellow/brown sugar caramels sometimes formed in spontaneous chemical reactions in the culture medium.

The oligosaccharides are purified and used in a number of products for consumption by humans as well as animals, such as companion animals (dogs, cats) as well as livestock (bovine, equine, ovine, caprine, or porcine animals, as well as poultry). For example, a pharmaceutical composition comprising purified 6'-sialyllactose (6'-SL) and an excipient is suitable for oral administration. Large quantities of 6'-SL are produced in bacterial hosts, e.g., an *E. coli* bacterium comprising a heterologous sialyltransferase, e.g., a heterologous α(2,6)sialyltransferase. An *E. coli* bacterium comprising an enhanced cytoplasmic pool of each of the following: lactose and CMP-Neu5Ac, is useful in such production systems. In the case of lactose, endogenous *E. coli* metabolic pathways and genes are manipulated in ways that result in the generation of increased cytoplasmic concentrations of lactose, as compared to levels found in wild type *E. coli*. For example, the bacteria contain at least 10%, 20%, 50%, 2×, 5×, 10× or more of the levels in a corresponding wild type bacteria that lacks the genetic modifications described above. In the case of CMP-Neu5Ac, endogenous Neu5Ac catabolism genes are inactivated and exogenous CMP-NeuSAc biosynthesis genes introduced into *E. coli* resulting in the generation of a cytoplasmic pool of CMP-Neu5Ac not found in the wild type bacterium.

A method of producing a pharmaceutical composition comprising a purified hMOS is carried out by culturing the bacterium described above, purifying the hMOS produced by the bacterium, and combining the hMOS with an excipient or carrier to yield a dietary supplement for oral administration. These compositions are useful in methods of preventing or treating enteric and/or respiratory diseases in infants and adults. Accordingly, the compositions are administered to a subject suffering from or at risk of developing such a disease using known methods of clinical therapy.

The invention also provides for increasing, in *E. coli*, the intracellular concentration of the nucleotide sugar uridine diphosphate N-acetylglucosamine (UDP-GlcNAc). This is achieved by over-expressing the bi-functional endogenous positive regulator of UDP-GlcNac synthesis and repressor of glucosamine and N-acetylglucosamine catabolism, nagC, simultaneously with the gene encoding L-glutamine:D-fructose-6-phosphate aminotransferase, glmS.

The invention also provides for increasing the intracellular concentration of lactose in *E. coli*, for cells grown in the presence of lactose, by using manipulations of endogenous *E. coli* genes involved in lactose import, export, and catabolism. In particular, described herein are methods of increasing intracellular lactose levels in *E. coli* genetically engineered to produce a human milk oligosaccharide by incorporating a lacA mutation into the genetically modified *E. coli*. The lacA mutation prevents the formation of intracellular acetyl-lactose, which not only removes this molecule as a contaminant from subsequent purifications, but also eliminates *E. coli*'s ability to export excess lactose from its cytoplasm, thus greatly facilitating purposeful manipulations of the *E. coli* intracellular lactose pool.

Also described herein are bacterial host cells with the ability to accumulate a intracellular lactose pool while simultaneously possessing low, functional levels of cytoplasmic β-galactosidase activity, for example as provided by the introduction of a functional recombinant *E. coli* lacZ gene, or by a β-galactosidase gene from any of a number of other organisms (e.g., the lac4 gene of *Kluyveromyces lactis* (e.g., GenBank Accession Number M84410.1 (GI: 173304), incorporated herein by reference). Low, functional levels of cytoplasmic β-galactosidase include β-galactosidase activity levels of between 0.05 and 200 units, e.g., between 0.05 and 5 units, between 0.05 and 4 units, between 0.05 and 3 units, or between 0.05 and 2 units (for standard definition see: Miller J H, Laboratory CSH. Experiments in molecular genetics. Cold Spring Harbor Laboratory Cold Spring Harbor, N.Y.; 1972; incorporated herein by reference). This low level of cytoplasmic β-galactosidase activity, while not high enough to significantly diminish the intracellular lactose pool, is nevertheless very useful for tasks such as phenotypic marking of desirable genetic loci during construction of host cell backgrounds, for detection of cell lysis due to undesired bacteriophage contaminations in fermentation processes, for the facile removal of undesired residual lactose at the end of fermentations, or for in-process fermentation QC purposes (i.e. as a non-standard phenotype the provision of a weak lacZ phenotype aids in culture purity assessments).

Methods of purifying a N-acetylglucosamine-containing or sialylated oligosaccharide produced by the methods described herein are carried out by binding the oligosaccharide from a bacterial cell lysate or bacterial cell culture supernatant of the bacterium to a carbon column, and subsequently eluting it from the column. Purified N-acetylglucosamine-containing or sialylated oligosaccharides are produced by the methods described herein.

Optionally, the invention features a vector, e.g., a vector containing a nucleic acid. The vector can further include one or more regulatory elements, e.g., a heterologous promoter. The regulatory elements can be operably linked to a protein gene, fusion protein gene, or a series of genes linked in an operon in order to express the fusion protein. To maintain the plasmid vector stably within the cell a selectable marker is included within its sequence, such as an antibiotic resistance gene or a gene that complements a nutritional auxotrophy of the host bacterium. For example, in *E. coli*, a thymidine deficiency caused by a chromosomal defect in the thymidylate synthase gene (thyA) can be complemented by a plasmid borne wild type copy of the thyA (M. Belfort, G. F. Maley, F. Maley, *Proceedings of the National Academy of Sciences* 80, 1858 (1983)) gene. Alternatively an adenine deficiency caused by a chromosomal deficiency in the adenylosuccinate synthetase (purA) gene (S. A. Wolfe, J. M. Smith, *J Biol Chem* 263, 19147-53 (1988)) can be complemented by a plasmid borne wild type copy of purA. Two plasmid vectors may be utilized simultaneously within the same bacterial cell by employing separate selectable markers, for example one plasmid utilizing thyA selection and one utilizing purA selection, and by utilizing two compatible plasmid replicons, for example in *E. coli* two such compatible replicons comprise the ColE1 (pUC) replicon and the p15A (pACYC) replicon (R. E. Bird, *J Bacteriol* 145, 1305-9 (1981)). In yet another aspect, the invention comprises an isolated recombinant cell, e.g., a bacterial cell containing aforementioned nucleic acid molecule/s or vector/s. The nucleic acid sequences can be optionally integrated into the genome.

The invention provides a method of treating, preventing, or reducing the risk of infection in a subject comprising administering to said subject a composition comprising a human milk oligosaccharide, purified from a culture of a recombinant strain of the current invention, wherein the hMOS binds to a pathogen and wherein the subject is infected with or at risk of infection with the pathogen. In one aspect, the infection is caused by a Norwalk-like virus or *Campylobacter jejuni*. The subject is preferably a mammal in need of such treatment. The mammal is, e.g., any mammal, e.g., a human, a primate, a mouse, a rat, a dog, a cat, a cow, a horse, or a pig. In a preferred embodiment, the mammal is a human. For example, the compositions are formulated into animal feed (e.g., pellets, kibble, mash) or animal food supplements for companion animals, e.g., dogs or cats, as well as livestock or animals grown for food consumption, e.g., cattle, sheep, pigs, chickens, and goats. Preferably, the purified hMOS is formulated into a powder (e.g., infant formula powder or adult nutritional supplement powder, each of which is mixed with a liquid such as water or juice prior to consumption) or in the form of tablets, capsules or pastes or is incorporated as a component in dairy products such as milk, cream, cheese, yogurt or kefir, or as a component in any beverage, or combined in a preparation containing live microbial cultures intended to serve as probiotics, or in prebiotic preparations intended to enhance the growth of beneficial microorganisms either in vitro or in vivo. For example, the purified sugar (e.g., LNnT or 6'-SL) can be mixed with a *Bifidobacterium* or *Lactobacillus* in a probiotic nutritional composition. (i.e. Bifidobacteria are beneficial components of a normal human gut flora and are also known to utilize hMOS for growth.

All genes described herein also include a description of the corresponding encoded gene products. As such, the uses of exogenous genes as described herein encompass nucleic acids that encode the gene product sequences disclosed herein. The person skilled in the art could readily generate nucleic acid sequences that encode the protein sequences described herein and introduce such sequences into expression vectors to carry out the present invention.

The term "substantially pure" in reference to a given polypeptide, polynucleotide or oligosaccharide means that the polypeptide, polynucleotide or oligosaccharide is substantially free from other biological macromolecules. The substantially pure polypeptide, polynucleotide or oligosaccharide is at least 75% (e.g., at least 80, 85, 95, or 99%) pure by dry weight. Purity can be measured by any appropriate calibrated standard method, for example, by column chromatography, polyacrylamide gel electrophoresis, thin layer chromatography (TLC) or HPLC analysis.

Polynucleotides, polypeptides, and oligosaccharides of the invention are purified and/or isolated. Purified defines a degree of sterility that is safe for administration to a human subject, e.g., lacking infectious or toxic agents. Specifically, as used herein, an "isolated" or "purified" nucleic acid molecule, polynucleotide, polypeptide, protein or oligosaccharide, is substantially free of other cellular material, or culture medium when produced by recombinant techniques, or chemical precursors or other chemicals when chemically synthesized. For example, purified hMOS compositions are at least 60% by weight (dry weight) the compound of interest. Preferably, the preparation is at least 75%, more preferably at least 90%, and most preferably at least 99%, by weight the compound of interest. Purity is measured by any appropriate calibrated standard method, for example, by column chromatography, polyacrylamide gel electrophoresis, thin layer chromatography (TLC) or HPLC analysis. For example, a "purified protein" refers to a protein that has been separated from other proteins, lipids, and nucleic acids with which it is naturally associated. Preferably, the protein constitutes at least 10, 20, 50 70, 80, 90, 95, 99-100% by dry weight of the purified preparation.

By "isolated nucleic acid" is meant a nucleic acid that is free of the genes that flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide.

A "heterologous promoter", when operably linked to a nucleic acid sequence, refers to a promoter which is not naturally associated with the nucleic acid sequence.

The term "over-express" as used herein refers to gene transcript or encoded gene product is 10%, 20%, 50%, 2-fold, 5-fold, 10-fold, or more than the level expressed or produced by a native, naturally-occurring, or endogenous gene in a bacterium in which it naturally occurs. For example, the host bacterium described herein are engineered to over-express an exogenous gene transcript or encoded gene product of UDP-GlcNAc:Galα/β-R β 3-N-acetylglucosaminyltransferase, nagC, glmS, glmY, glmZ, a sialyltransferase, a β-galactosyltransferase, an α-fucosyltransferase, CMP-Neu5Ac synthetase, a sialic acid synthase, or a UDP-GlcNAc 2-epimerase, i.e., a gene or gene product with a sequence corresponding to that of a bacterium other than the host bacterium.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause.

By the terms "effective amount" and "therapeutically effective amount" of a formulation or formulation component is meant a nontoxic but sufficient amount of the formulation or component to provide the desired effect.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

N-acetylmannosamine; (ΔnanK) mutated N-acetylmannosamine kinase; (nanE) wild-type N-acetylmannosamine-6-phosphate epimerase; (ManNAc-6-P) N-acetylmannosamine-6-phosphate; (GlcNAc-6-P) N-acetylglucosamine-6-phosphate; (GlcN-6-P) Glucosamine-6-phosphate; (Fruc-6-P) Fructose-6-phosphate; (neuA), CMP-N-acetylneuraminic acid synthetase; (CMP-Neu5Ac) CMP-N-acetylneuraminic acid; (neuB), N-acetylneuraminic acid synthase; (neuC) UDP-GlcNAc-2-epimerase; and (UDP-GlcNAc) uridine diphosphate N-acetylglucosamine.

Figure 4:
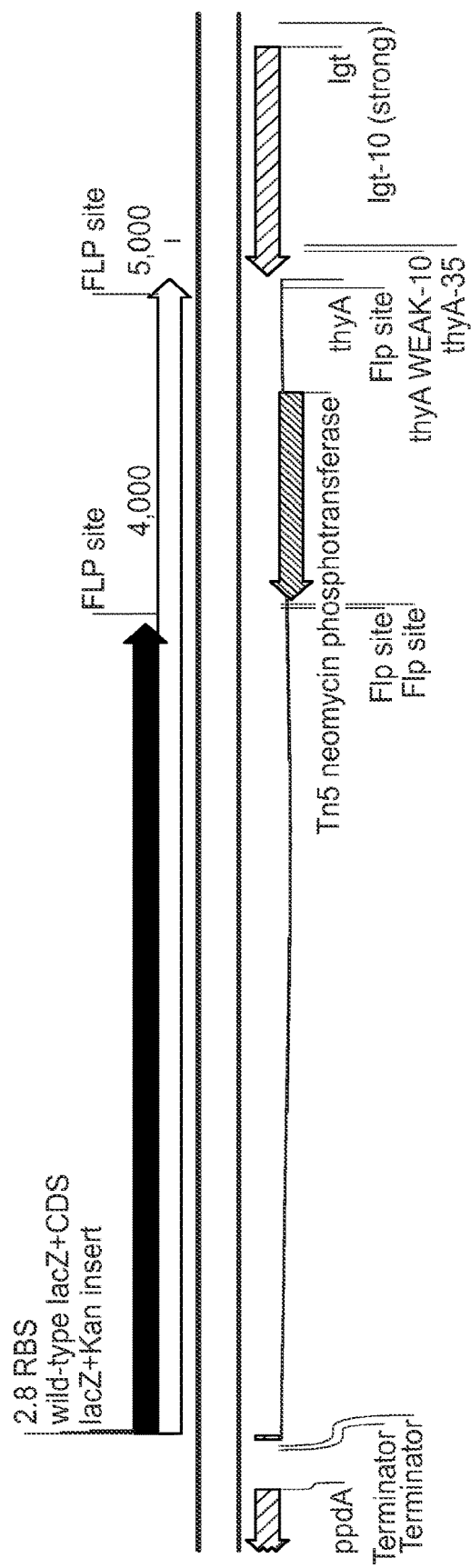

FIG. 4 is a schematic that illustrates the new configuration of genes engineered at the *Escherichia coli* thyA locus in strains used to produce N-acetylglucosamine-containing oligosaccharides.

Figure 5:
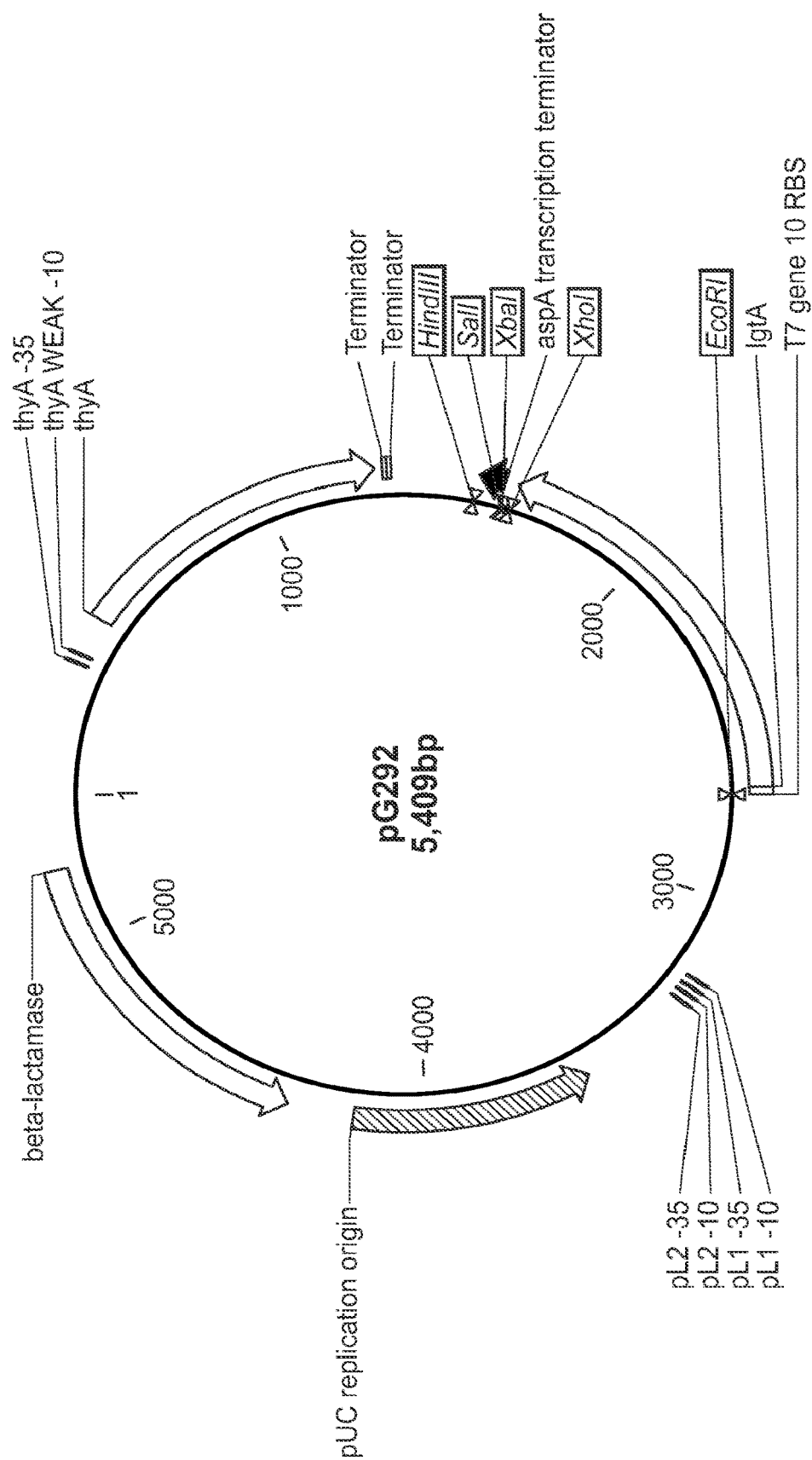

FIG. 5 is a plasmid map of pG292, which expresses the *N. meningitidis* β(1,3)-N-acetylglucosaminyltransferase gene lgtA.

Figure 6:
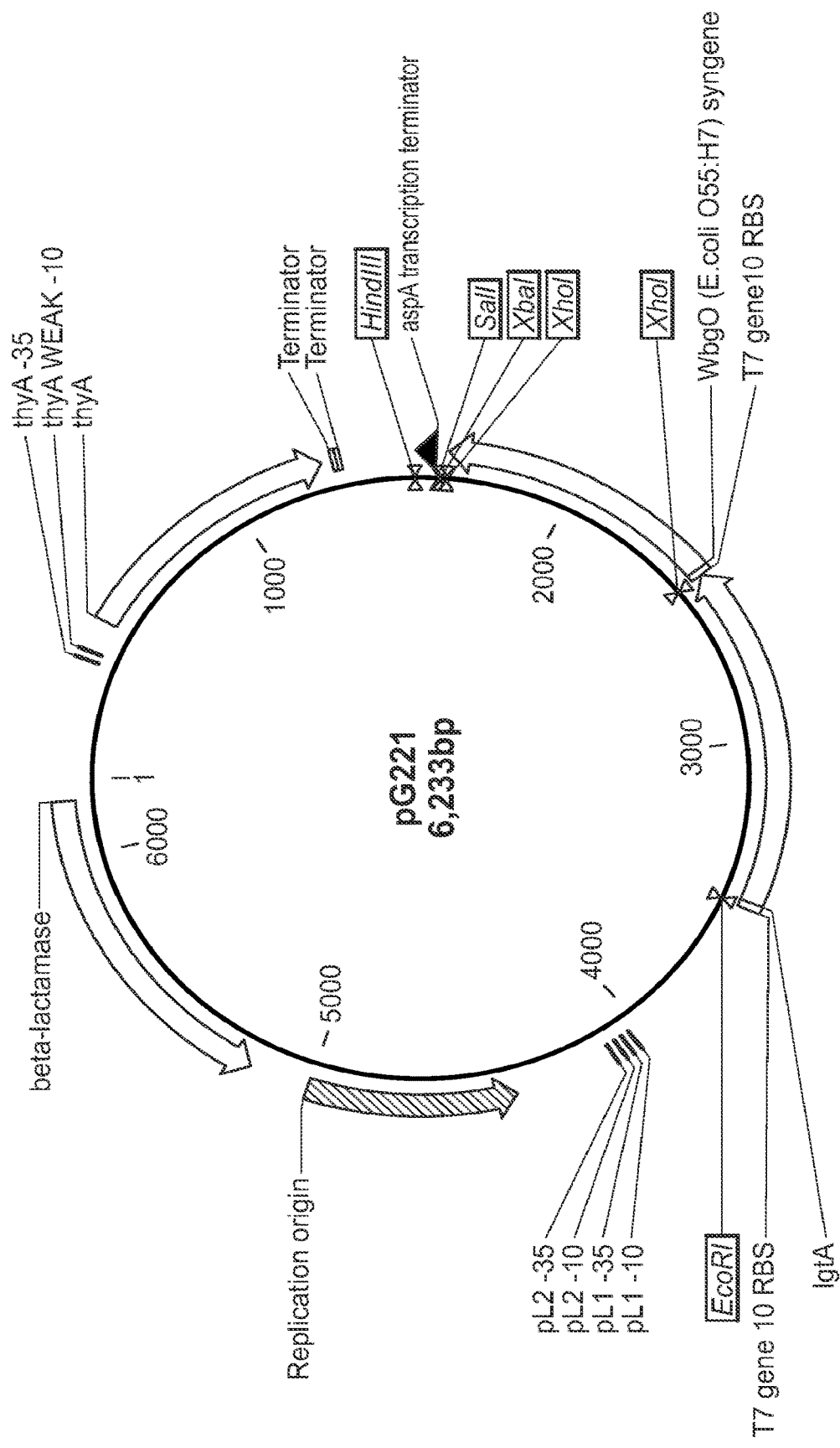

FIG. 6 is a plasmid map of pG221, which expresses, as an operon, the *N. meningitidis* β(1,3)-N-acetylglucosaminyltransferase gene lgtA and the *E. coli* O55:H7 wbgO β(1,3)-galactosyltransferase gene.

Figure 7:
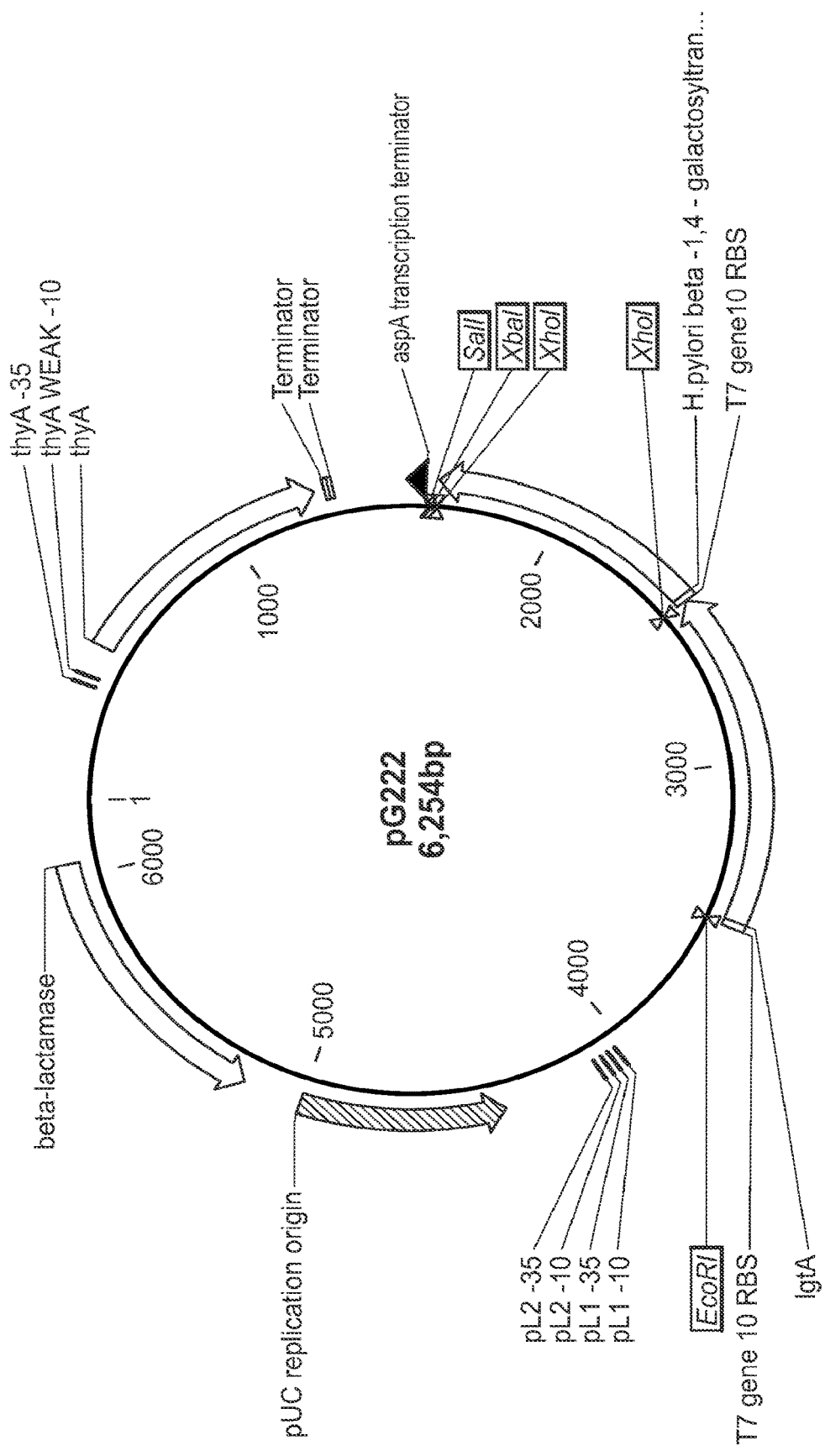

FIG. 7 is a plasmid map of pG222, which expresses, as an operon, the *N. meningitidis* β(1,3)-N-acetylglucosaminyltransferase gene lgtA and the *H. pylori* 4GalT (jhp0765) β(1,4)-galactosyltransferase gene.

Figure 8:
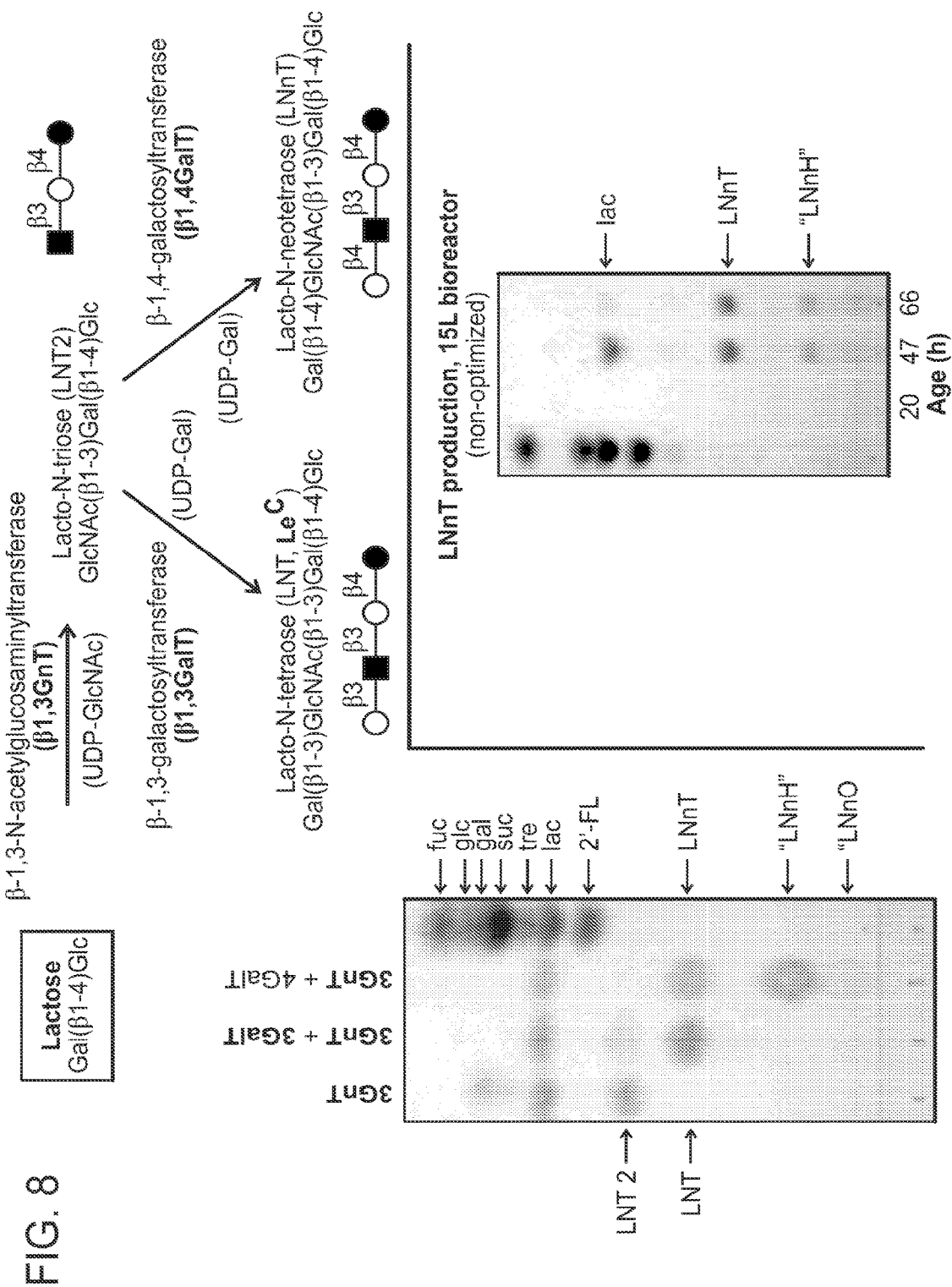

FIG. 8 illustrates schematically the enzymatic reactions necessary to produce from lactose, via the intermediate trisaccharide lacto-N-triose 2 (LNT2), the two human milk oligosaccharides: Lacto-N-tetraose (LNT) and Lacto-N-neotetraose (LNnT). A thin layer chromatogram (on left) is presented of culture medium samples taken from small scale *E. coli* cultures and demonstrating synthesis of LNT2, LNT and LNnT. A second thin layer chromatogram (on right) is presented of culture medium samples taken from a 15 L *E. coli* bioreactor culture—demonstrating synthesis of LNnT.

Figure 9:
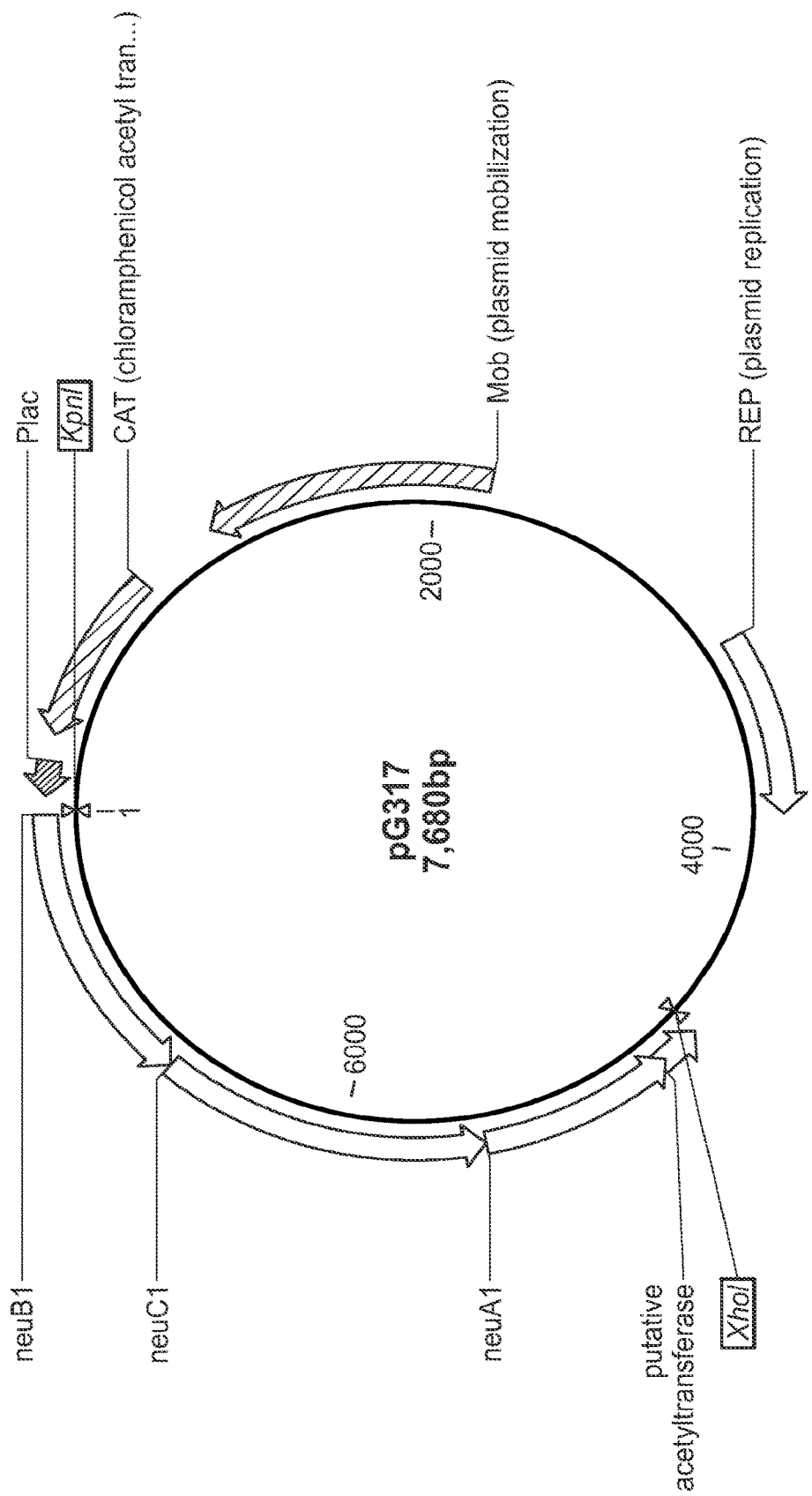

FIG. 9 is a plasmid map of pG317, a low-copy vector which expresses as an operon, under the control of the *E. coli* lac promoter, the *Campylobacter jejuni* ATCC43438 neuB, neuC and neuA genes, encoding N-acetylneuraminate synthase, UDP-N-acetylglucosamine 2-epimerase, and N-acetylneuraminate cytidylyltransferase, respectively.

Figure 10:
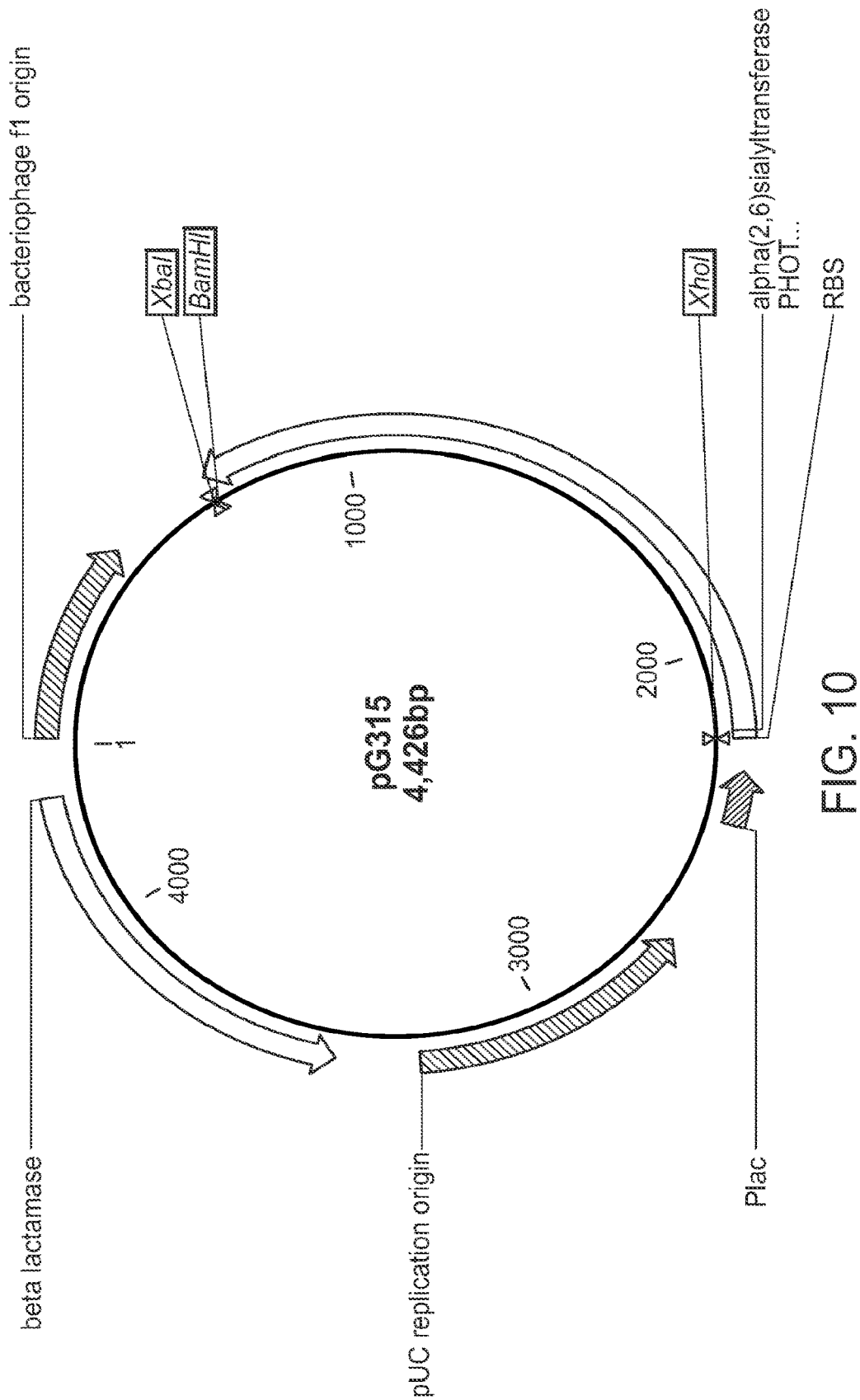

FIG. 10 is a plasmid map of pG315, a multi-copy vector which expresses a gene encoding an α(2,6) sialyltransferase from *Photobacterium* spp JT-ISH-224, under the control of the *E. coli* lac promoter.

Figure 11:
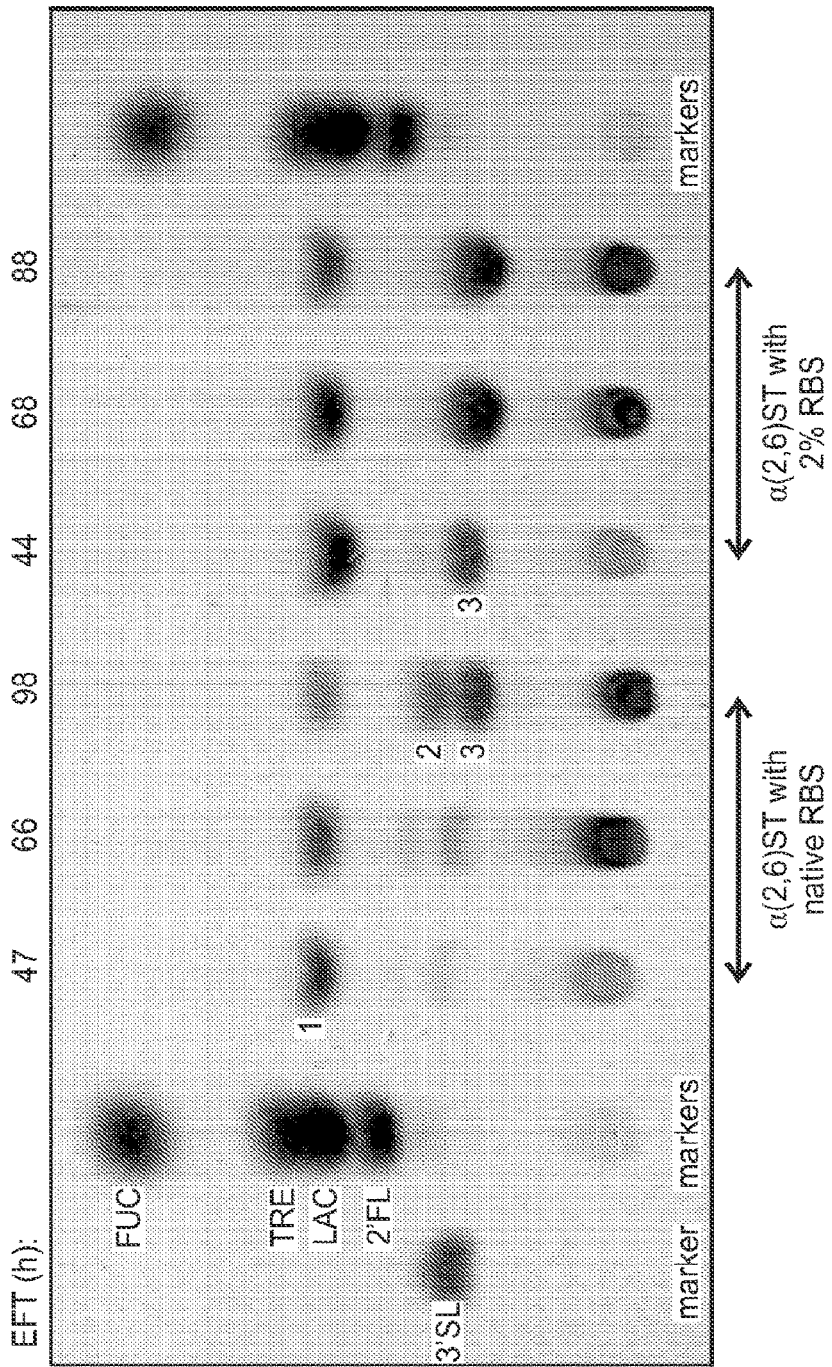

FIG. 11 is a photograph of a thin layer chromatogram showing 6'-SL in culture medium produced by *E. coli* strain E547 (ΔnanRATEK), containing plasmids expressing a bacterial α(2,3)sialyltransferase and neuA, neuB and neuC. FIG. 11 also shows a TLC analysis of culture supernatants from two fermentations producing 6'-sialyllactose (6'-SL). Samples to the left of the figure are taken from a fermentation of an *E. coli* strain containing pG315 (carrying a strong RBS in front of the α(2,6)sialyltransferase gene in the vector). Samples on the right of the figure are taken from a fermentation of an *E. coli* strain containing a close variant of pG315 that carries a weaker RBS in front of the α(2,6) sialyltransferase gene.

Figure 12:
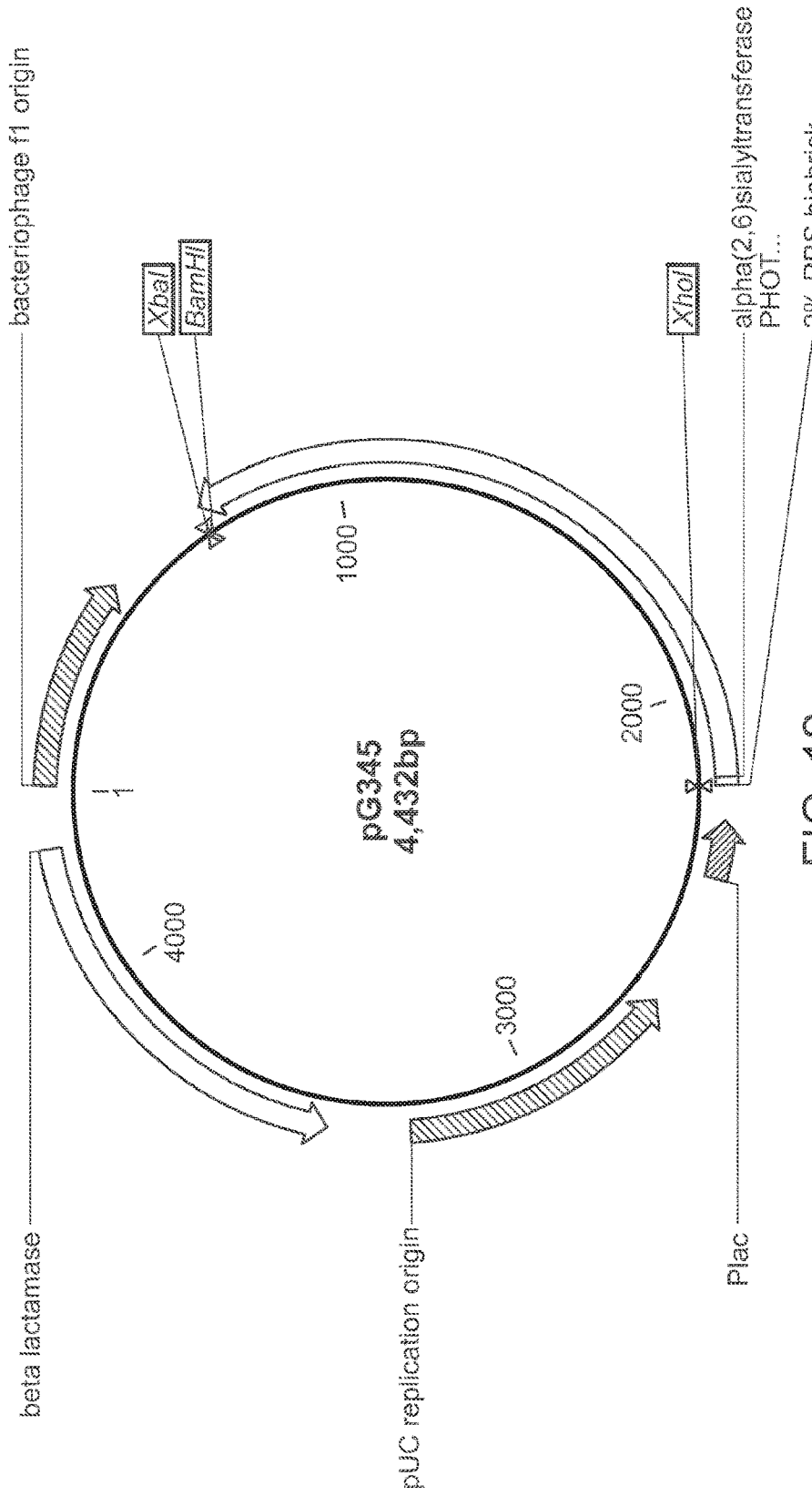

FIG. 12 is a plasmid map of pG345, a multi-copy vector which expresses a gene encoding an α(2,6) sialyltransferase from *Photobacterium* spp JT-ISH-224, under the control of a weaker ribosomal binding site (SEQ ID NO:8) and the *E. coli* lac promoter.

Figure 13:
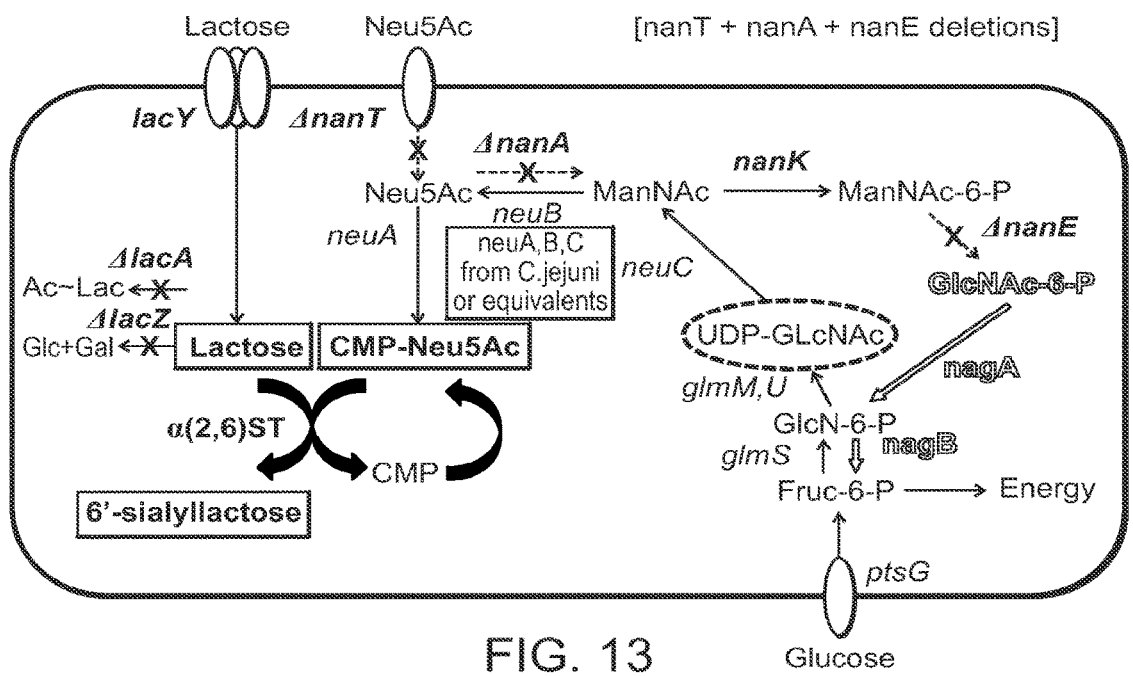

FIG. 13 is a schematic demonstrating metabolic pathways and a second example (utilizing nanT, nanA and nanE deletions) of the changes introduced into them to engineer 6'-sialyllactose (6'-SL) synthesis in *E. coli*. Abbreviations include: (Neu5Ac) N-acetylneuraminic acid, sialic acid; (ΔnanT) mutated N-acetylneuraminic acid transporter; (ΔnanA) mutated N-acetylneuraminic acid lyase; (ManNAc) N-acetylmannosamine; (nanK) wild-type N-acetylmannosamine kinase; (ΔnanE) mutated N-acetylmannosamine-6-phosphate epimerase; (ManNAc-6-P) N-acetylmannosamine-6-phosphate; (GlcNAc-6-P) N-acetylglucosamine-6-phosphate; (GlcN-6-P) Glucosamine-6-phosphate; (Fruc-6-P) Fructose-6-phosphate; (neuA), CMP-N-acetylneuraminic acid synthetase; (CMP-Neu5Ac) CMP-N-acetylneuraminic acid; (neuB), N-acetylneuraminic acid synthase; (neuC) UDP-GlcNAc-2-epimerase; and (UDP-GlcNAc) uridine diphosphate N-acetylglucosamine.

Figure 14:
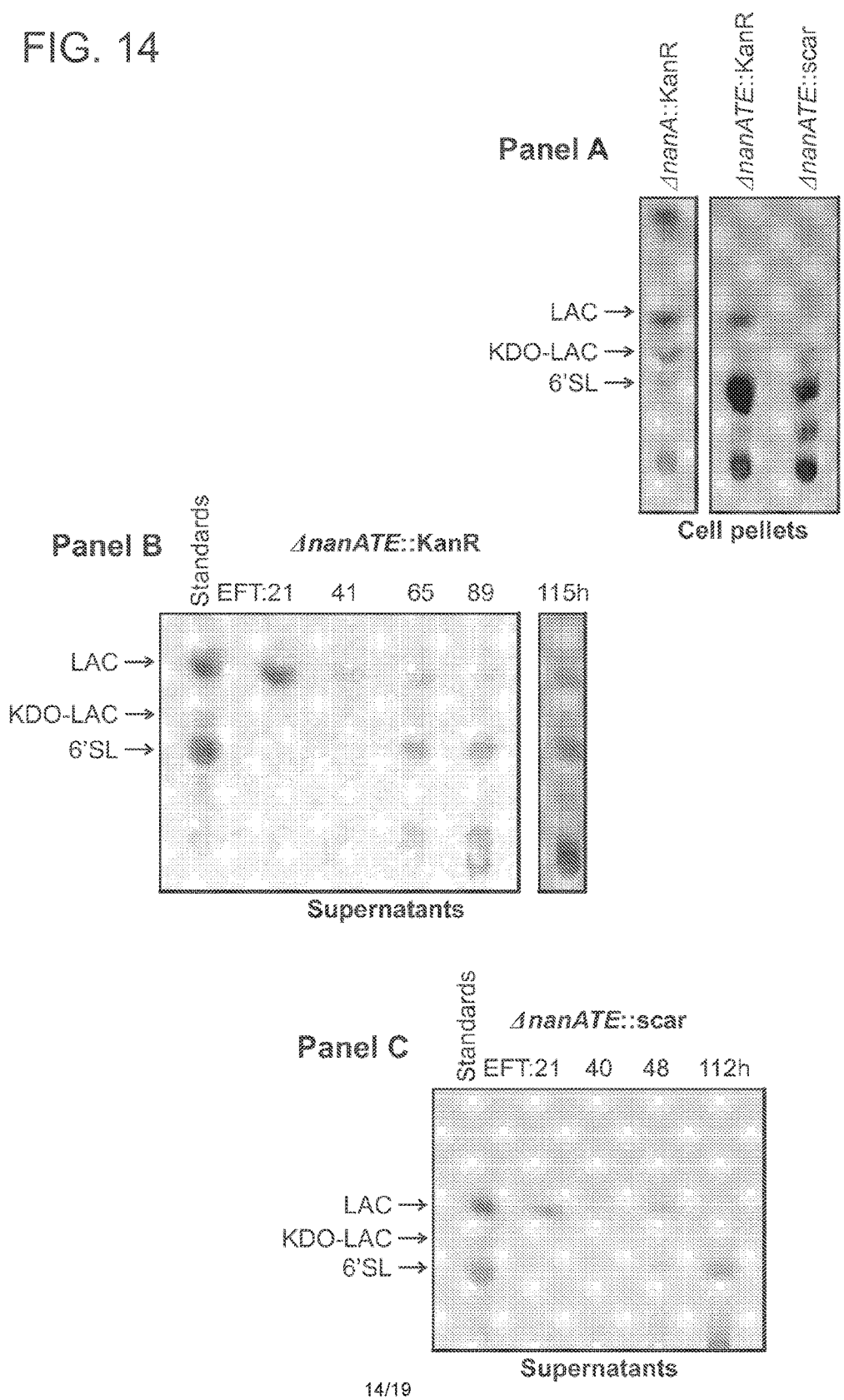
Figure 15:
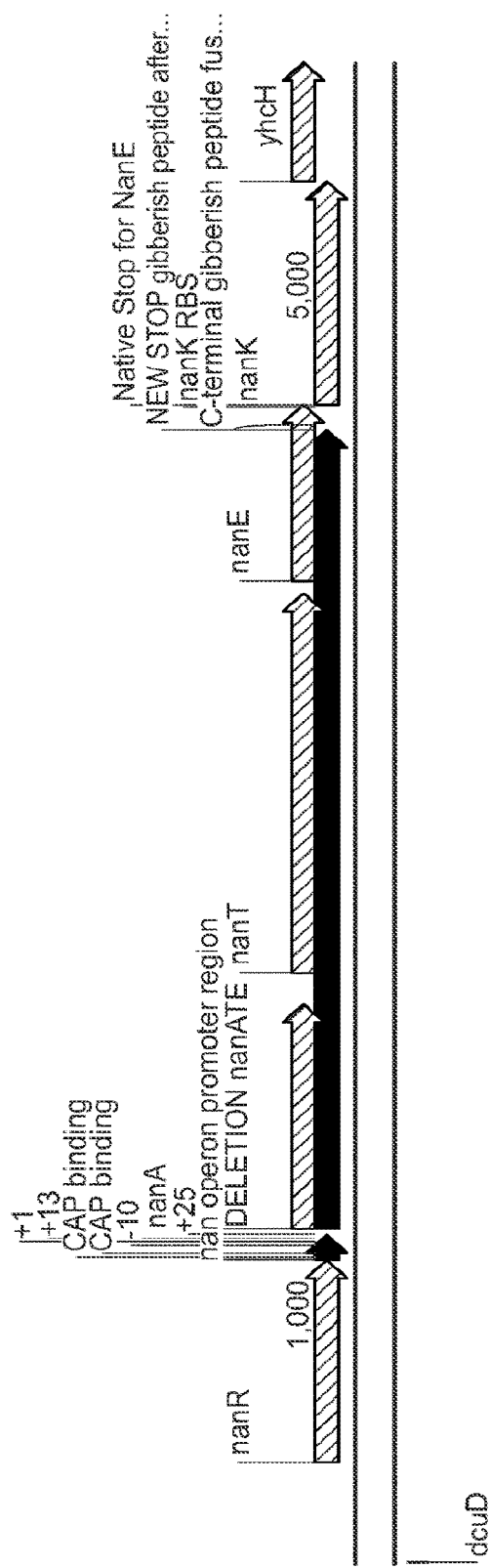

FIG. 14 illustrates the TLC analysis of cell pellets and or supernatants from a three pilot scale fermentation experiments using three *E. coli* strains carrying various combinations of nan mutations FIG. 15 is a schematic illustrating the location of the gene deletion made within the *E. coli* nan operon to generate the [nanR+, nanA, nanT, nanE, nanK+] mutant locus of strains E1017 and E1018.

Figure 16:
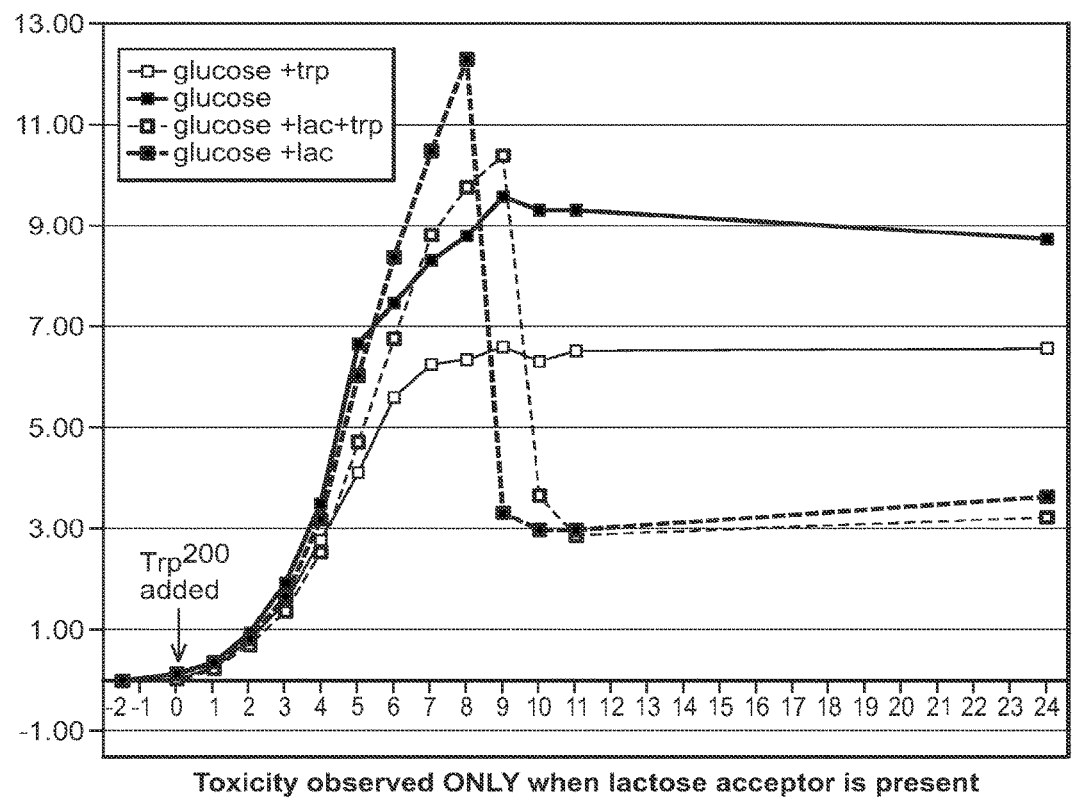

FIG. 16 is a cell density growth curve plot of four cultures of E680 transformed with pG292, induced or un-induced by tryptophan addition, and in the presence or absence of lactose in the growth medium. Abundant cell lysis is seen in the lactose-containing cultures.

Figure 17:
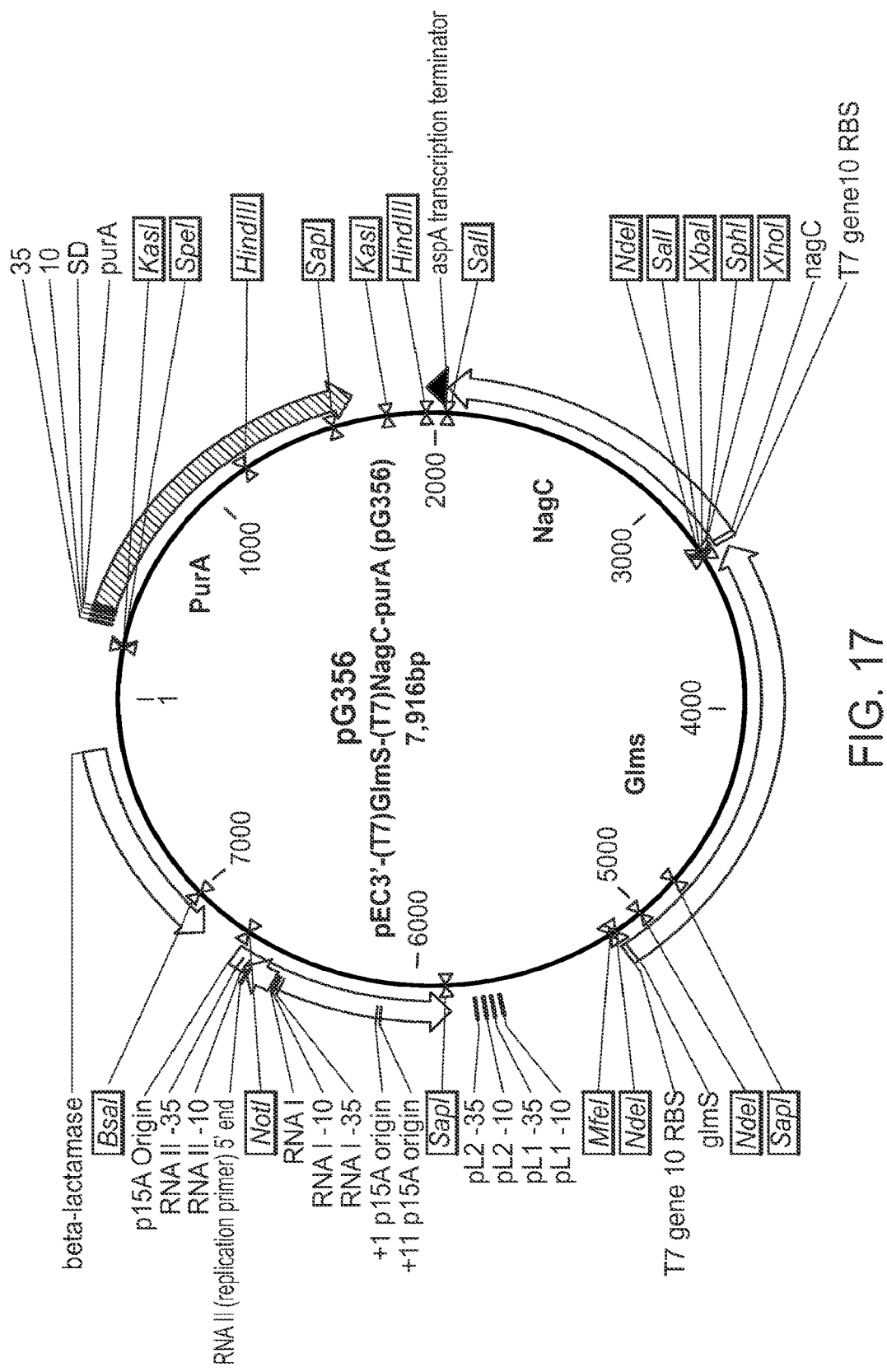

FIG. 17 is a plasmid map of pG356, which expresses, as an operon, the *E. coli* glmS and nagC genes. pG356 carries a p15A replication origin and both ampC and purA selectable markers.

Figure 18:
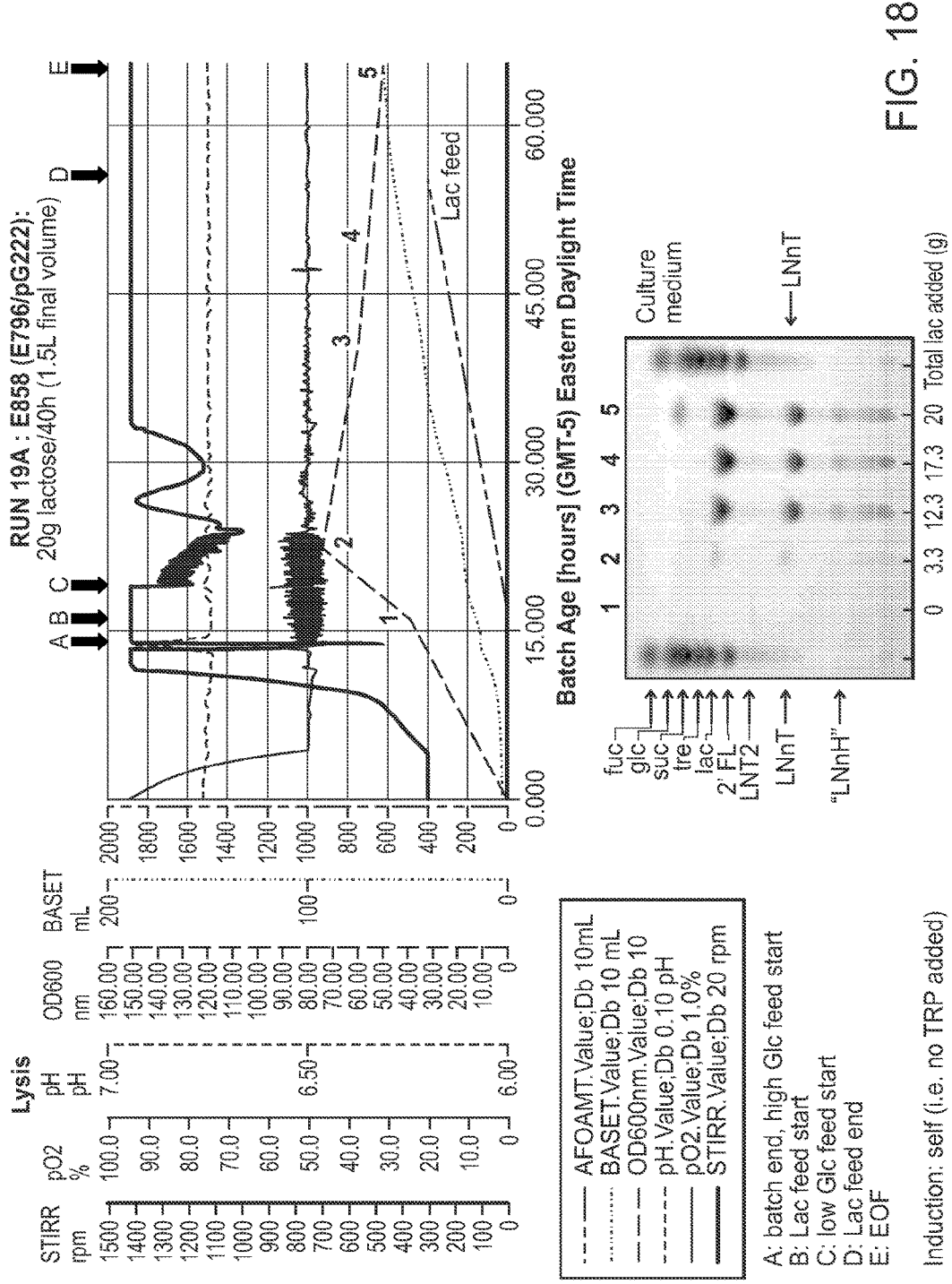

FIG. 18 is a fementation parameter trace and TLC culture supernatant analysis (for LNnT production) of a 1.5 L bioreactor culture of E796 transformed with pG222.

Figure 19:
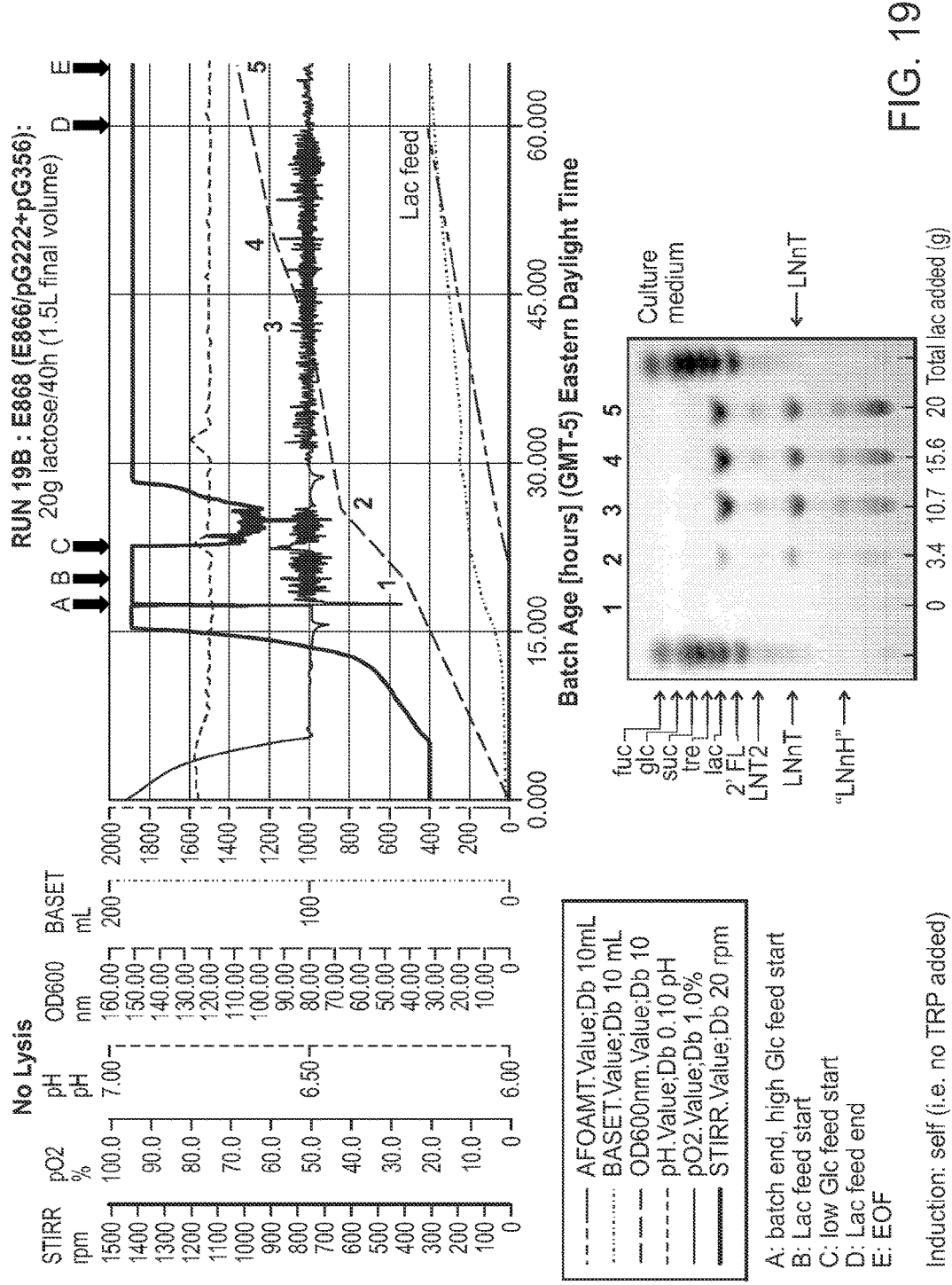

FIG. 19 is a fementation parameter trace and TLC culture supernatant analysis (for LNnT production) of a 1.5 L bioreactor culture of E866 transformed with both pG222 and pG356.

DETAILED DESCRIPTION OF THE INVENTION

Described herein are genetic constructs and methods for production of N-acetylglucosamine-containing human milk oligosaccharides (hMOS) and sialyloligosaccharides. In order to make both N-acetylglucosamine-containing and sialyl-containing hMOS, one needs to tap into the cellular UDP-GlcNAc pool. Doing so can be challenging, since UDP-GlcNAc is an essential metabolite for bacteria (used to make the cell wall). The constructs, compositions, and methods of the invention overcome difficulties of the past by enhancing the UDP-GlcNAc pool, a strategy that represents an advantage in the production of both classes of hMOS. Other distinctions over earlier approaches represent improvements and/or confer advantages over those earlier strategies.

hMOS

Human milk glycans, which comprise both oligosaccharides (hMOS) and their glycoconjugates, play significant roles in the protection and development of human infants, and in particular the infant gastrointestinal (GI) tract. Milk oligosaccharides found in various mammals differ greatly, and their composition in humans is unique (Hamosh M., 2001 Pediatr Clin North Am, 48:69-86; Newburg D. S., 2001 Adv Exp Med Biol, 501:3-10). Moreover, glycan levels in human milk change throughout lactation and also vary widely among individuals (Morrow A. L. et al., 2004 J Pediatr, 145:297-303; Chaturvedi P et al., 2001 Glycobiology, 11:365-372). Previously, a full exploration of the roles of hMOS was limited by the inability to adequately characterize and measure these compounds. In recent years sensitive and reproducible quantitative methods for the analysis of both neutral and acidic hMOS have been developed (Erney, R., Hilty, M., Pickering, L., Ruiz-Palacios, G., and Prieto, P. (2001) *Adv Exp Med Biol* 501, 285-297. Bao, Y., and Newburg, D. S. (2008) *Electrophoresis* 29, 2508-2515). Approximately 200 distinct oligosaccharides have been identified in human milk, and combinations of a small number of simple epitopes are responsible for this diversity (Newburg D. S., 1999 Curr Med Chem, 6:117-127; Ninonuevo M. et al., 2006 J Agric Food Chem, 54:7471-74801). hMOS are composed of 5 monosaccharides: D-glucose (Glc), D-galactose (Gal), N-acetylglucosamine (GlcNAc), L-fucose (Fuc), and sialic acid (N-acetyl neuraminic acid, Neu5Ac, NANA). hMOS are usually divided into two groups according to their chemical structures: neutral compounds containing Glc, Gal, GlcNAc, and Fuc, linked to a lactose (Galβ1-4Glc) core, and acidic compounds including the same sugars, and often the same core structures, plus NANA (Charlwood J. et al., 1999 Anal_Biochem, 273:261-277; Martin-Sosa et al., 2003 J Dairy Sci, 86:52-59; Parkkinen J. and Finne J., 1987 Methods Enzymol, 138:289-300; Shen Z. et al., 2001 J Chromatogr A, 921:315-321). Approximately 70-80% of oligosaccharides in human milk are fucosylated. A smaller proportion of the oligosaccharides in human milk are sialylated, or are both fucosylated and sialylated.

Interestingly, hMOS as a class, survive transit through the intestine of infants very efficiently, a function of their being poorly transported across the gut wall and of their resistance to digestion by human gut enzymes (Chaturvedi, P., Warren, C. D., Buescher, C. R., Pickering, L. K. & Newburg, D. S. Adv Exp Med Biol 501, 315-323 (2001)). One consequence of this survival in the gut is that hMOS are able to function as prebiotics, i.e. they are available to serve as an abundant carbon source for the growth of resident gut commensal microorganisms (Ward, R. E., Niñonuevo, M., Mills, D. A., Lebrilla, C. B., and German, J. B. (2007) *Mol Nutr Food Res* 51, 1398-1405). Recently, there is burgeoning interest in the role of diet and dietary prebiotic agents in determining the composition of the gut microflora, and in understanding the linkage between the gut microflora and human health (Roberfroid, M., Gibson, G. R., Hoyles, L., McCartney, A. L., Rastall, R., Rowland, I., Wolvers, D., Watzl, B., Szajewska, H., Stahl, B., Guarner, F., Respondek, F., Whelan, K., Coxam, V., Davicco, M. J., Léotoing, L., Wittrant, Y., Delzenne, N. M., Cani, P. D., Neyrinck, A. M., and Meheust, A. (2010) *Br J Nutr* 104 Suppl 2, S1-63).

A number of human milk glycans possess structural homology to cell receptors for enteropathogens, and serve roles in pathogen defense by acting as molecular receptor "decoys". For example, pathogenic strains of *Campylobacter* bind specifically to glycans in human milk containing the H-2 epitope, i.e., 2'-fucosyl-N-acetyllactosamine or 2'-fucosyllactose (2'-FL); *Campylobacter* binding and infectivity are inhibited by 2'-FL and other glycans containing this H-2 epitope (Ruiz-Palacios, G. M., Cervantes, L. E., Ramos, P., Chavez-Munguia, B., and Newburg, D. S. (2003) *J Biol Chem* 278, 14112-14120). Similarly, some diarrheagenic *E. coli* pathogens are strongly inhibited in vivo by hMOS containing 2'-linked fucose moieties. Several major strains of human caliciviruses, especially the noroviruses, also bind to 2'-linked fucosylated glycans, and this binding is inhibited by human milk 2'-linked fucosylated glycans. Consumption of human milk that has high levels of these 2'-linked fucosyloligosaccharides has been associated with lower risk of norovirus, *Campylobacter*, ST of *E. coli*-associated diarrhea, and moderate-to-severe diarrhea of all causes in a Mexican cohort of breastfeeding children (Newburg D. S. et al., 2004 Glycobiology, 14:253-263; Newburg D. S. et al., 1998 Lancet, 351:1160-1164). Several pathogens are also known to utilize sialylated glycans as their host receptors, such as influenza (Couceiro, J. N., Paulson, J. C. & Baum, L. G. Virus Res 29, 155-165 (1993)), parainfluenza (Amonsen, M., Smith, D. F., Cummings, R. D. & Air, G. M. J Virol 81, 8341-8345 (2007), and rotoviruses (Kuhlenschmidt, T. B., Hanafin, W. P., Gelberg, H. B. & Kuhlenschmidt, M. S. Adv Exp Med Biol 473, 309-317 (1999)). The sialyl-Lewis X epitope is used by *Helicobacter pylori* (Mandavi, J., Sondén, B., Hurtig, M., Olfat, F. O., et al. Science 297, 573-578 (2002)), *Pseudomonas aeruginosa* (Scharfman, A., Delmotte, P., Beau, J., Lamblin, G., et al. Glycoconj J 17, 735-740 (2000)), and some strains of noroviruses (Rydell, G. E., Nilsson, J., Rodriguez-Diaz, J., Ruvoën-Clouet, N., et al. Glycobiology 19, 309-320 (2009)).

The nucleotide sugar uridine diphosphate N-acetylglucosamine (UDP-GlcNAc) is a key metabolic intermediate in bacteria, where it is involved in the synthesis and maintenance of the cell envelope. In all known bacterial classes, UDP-GlcNAc is used to make peptidoglycan (murein); a polymer comprising the bacterial cell wall whose structural integrity is absolutely essential for growth and survival. In addition, gram-negative bacteria use UDP-GlcNAc for the synthesis of lipid A, an important component of the outer cell membrane. Thus, for bacteria, the ability to maintain an adequate intracellular pool of UDP-GlcNAc is critical.

Figure 1:
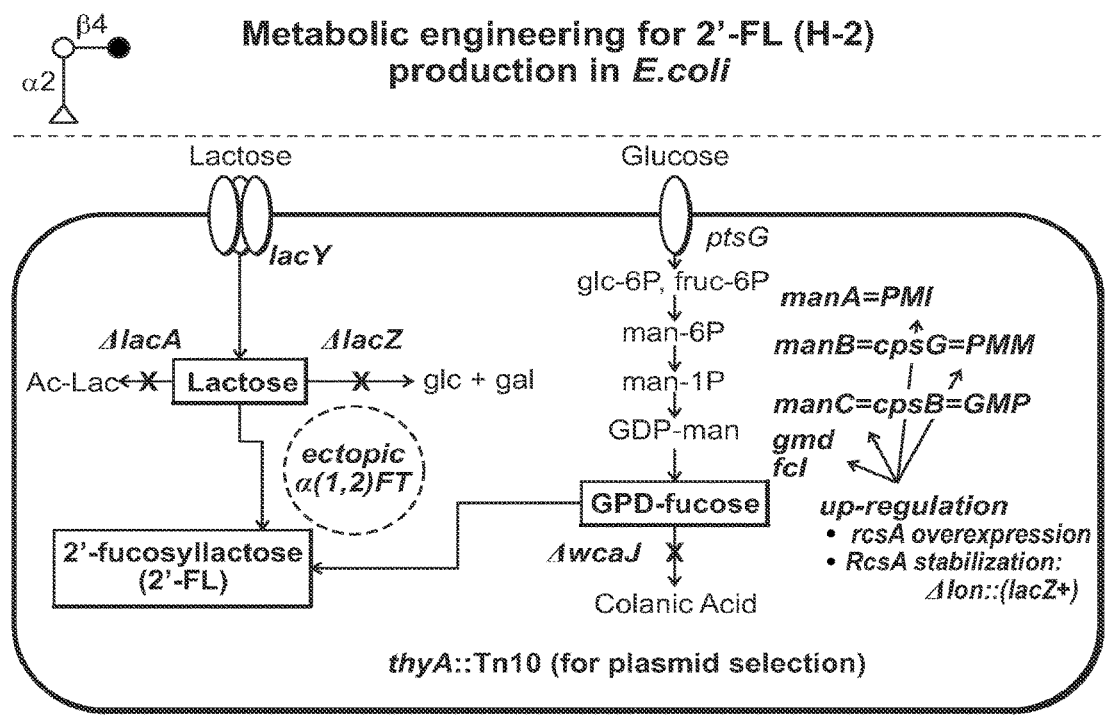
FIG. 1 is a schematic demonstrating metabolic pathways and the changes introduced into them to engineer 2'-fucosyllactose (2'-FL) synthesis in *Escherichia coli* (*E. coli*). Specifically, the lactose synthesis pathway and the GDP-fucose synthesis pathway are illustrated. In the GDP-fucose synthesis pathway: manA=phosphomannose isomerase (PMI), manB=phosphomannomutase (PMM), manC=mannose-1-phosphate guanylyltransferase (GMP), gmd=GDP-mannose-4,6-dehydratase, fcl=GDP-fucose synthase (GFS), and ΔwcaJ=mutated UDP-glucose lipid carrier transferase.

Biosynthesis of certain human milk oligosaccharides (hMOS) has been achieved in engineered strains of the bacterium, *Escherichia coli* K12. As described herein, simple fucosylated hMOS, e.g. 2'-fucosyllactose (2'-FL), 3-fucosyllactose (3-FL), and lactodifucotetraose (LDFT), are produced efficiently by live *E. coli* through artificially enhancing existing intracellular pools of GDP-fucose (the nucleotide sugar donor) and lactose (the accepting sugar), and by then using these enhanced pools as substrates for heterologous recombinant fucosyltransferases (FIG. 1). Since neither the lactose nor GDP-fucose pools are essential for *E. coli* survival, biosynthesis of simple fucosylated hMOS is achieved at good yields without negative consequences on the host bacterium's growth or viability. However, to synthesize more complex hMOS in *E. coli*, use of the critical bacterial UDP-GlcNAc pool is required, with consequent potential impacts on cell viability.

Figure 2:
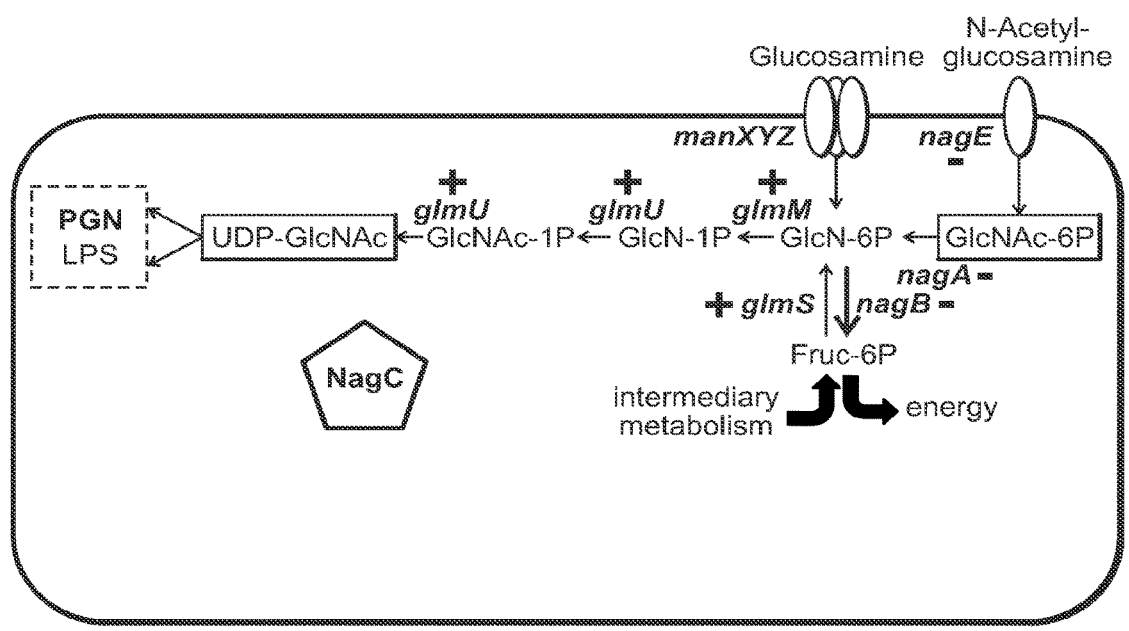
FIG. 2 is a schematic demonstrating metabolic pathways involved in the synthesis of UDP-GlcNAc (uridine diphosphate N-acetylglucosamine) and catabolism of glucosamine and N-acetylglucosamine in *E. coli*. In the schematic: (GlcNAc-1-P) N-acetylglucosamine-1-phosphate; (GlcN-1-P) glucosamine-1-phosphate; (GlcN-6-P) glucosamine-6-phosphate; (GlcNAc-6-P) N-acetylglucosamine-6-phosphate; and (Fruc-6-P) Fructose-6-phosphate; glmS (L-glutamine:D-fructose-6-phosphate aminotransferase), glmM (phosphoglucosamine mutase), glmU (fused N-acetyl glucosamine-1-phosphate uridyltransferase and glucosamine-1-phosphate acetyl transferase), nagC (bifunctional transcriptional activator/repressor protein), nagA (N-acetylglucosamine-6-phosphate deacetylase) and nagB (glucosamine-6-phosphate deaminase), nagE (N-acetylglucosamine transporter] and manXYZ [glucosamine transporter).

The UDP-GlcNAc pool in *E. coli* is produced through the combined action of three glm genes, glmS (L-glutamine:D-fructose-6-phosphate aminotransferase), glmM (phosphoglucosamine mutase), and the bifunctional glmU (fused N-acetyl glucosamine-1-phosphate uridyltransferase and glucosamine-1-phosphate acetyl transferase) (FIG. 2). These three genes direct a steady flow of carbon to UDP-GlcNAc, a flow that originates with fructose-6-phosphate (an abundant molecule of central energy metabolism). Expression of the glm genes is under positive control by the transcriptional activator protein, NagC.

When *E. coli* encounters glucosamine or N-acetyl-glucosamine in its environment, these molecules are each transported into the cell via specific membrane transport proteins and are used either to supplement the flow of carbon to the UDP-GlcNAc pool, or alternatively they are consumed to generate energy, under the action of nag operon gene products (i.e. nagA [N-acetylglucosamine-6-phosphate deacetylase] and nagB [glucosamine-6-phosphate deaminase]). In contrast to the glm genes, expression of nagA and nagB are under negative transcriptional control, but by the same regulatory protein as the glm genes, i.e. NagC. NagC is thus bi-functional, able to activate UDP-GlcNAc synthesis, while at the same time repressing the degradation of glucosamine-6-phosphate and N-acetylglucosamine-6-phosphate.

The binding of NagC to specific regulatory DNA sequences (operators), whether such binding results in gene activation or repression, is sensitive to fluctuations in the cytoplasmic level of the small-molecule inducer and metabolite, GlcNAc-6-phosphate. Intracellular concentrations of GlcNAc-6-phosphate increase when N-acetylglucosamine is available as a carbon source in the environment, and thus under these conditions the expression of the glm genes (essential to maintain the vital UDP-GlcNAc pool) would decrease, unless a compensatory mechanism is brought into play. E. coli maintains a baseline level of UDP-GlcNAc synthesis through continuous expression of nagC directed by two constitutive promoters, located within the upstream nagA gene. This constitutive level of nagC expression is supplemented approximately threefold under conditions where the degradative nag operon is induced, and by this means E. coli ensures an adequate level of glm gene expression under all conditions, even when N-acetylglucosamine is being utilized as a carbon source.

Figure 3:
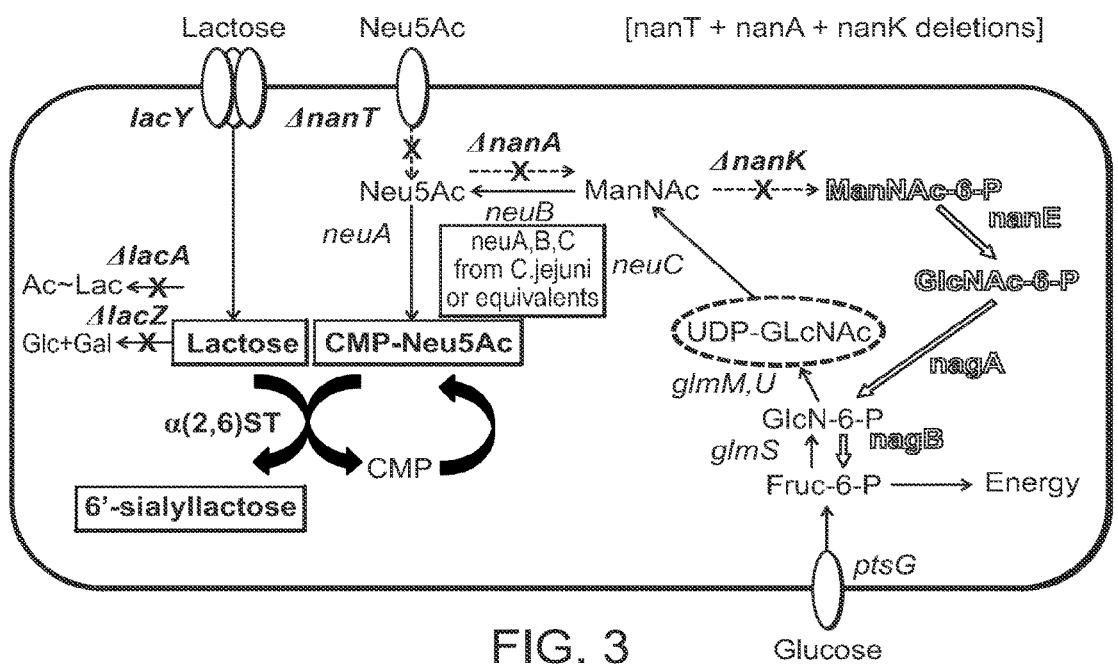
FIG. 3 is a schematic demonstrating metabolic pathways and one example (utilizing nanT, nanA and nanK deletions) of the changes introduced into them to engineer 6'-sialyllactose (6'-SL) synthesis in *E. coli*. Abbreviations include: (Neu5Ac) N-acetylneuraminic acid, sialic acid; (ΔnanT) mutated N-acetylneuraminic acid transporter; (ΔnanA) mutated N-acetylneuraminic acid lyase; (ManNAc)

Many hMOS incorporate GlcNAc into their structures directly, and many also incorporate sialic acid, a sugar whose synthesis involves consumption of UDP-GlcNAc (FIG. 3, FIG. 13). Thus, synthesis of many types of hMOS in engineered E. coli carries the significant risk of reduced product yield and compromised cell viability resulting from depletion of the bacterium's UDP-GlcNAc pool. One way to address this problem during engineered synthesis of GlcNAc- or sialic acid-containing hMOS is to boost the UDP-GlcNAc pool through simultaneous over-expression of nagC, or preferably by simultaneous over-expression of both nagC and glmS.

While studies suggest that human milk glycans could be used as prebiotics and as antimicrobial anti-adhesion agents, the difficulty and expense of producing adequate quantities of these agents of a quality suitable for human consumption has limited their full-scale testing and perceived utility. What has been needed is a suitable method for producing the appropriate glycans in sufficient quantities at reasonable cost. Prior to the invention described herein, there were attempts to use several distinct synthetic approaches for glycan synthesis. Novel chemical approaches can synthesize oligosaccharides (Flowers, H. M. Methods Enzymol 50, 93-121 (1978); Seeberger, P. H. Chem Commun (Camb) 1115-1121 (2003)), but reactants for these methods are expensive and potentially toxic (Koeller, K. M. & Wong, C. H. Chem Rev 100, 4465-4494 (2000)). Enzymes expressed from engineered organisms (Albermann, C., Piepersberg, W. & Wehmeier, U. F. Carbohydr Res 334, 97-103 (2001); Bettler, E., Samain, E., Chazalet, V., Bosso, C., et al. Glycoconj J 16, 205-212 (1999); Johnson, K. F. Glycoconj J 16, 141-146 (1999); Palcic, M. M. Curr Opin Biotechnol 10, 616-624 (1999); Wymer, N. & Toone, E. J. Curr Opin Chem Biol 4, 110-119 (2000)) provide a precise and efficient synthesis (Palcic, M. M. Curr Opin Biotechnol 10, 616-624 (1999)); Crout, D. H. & Vic, G. Curr Opin Chem Biol 2, 98-111 (1998)), but the high cost of the reactants, especially the sugar nucleotides, limits their utility for low-cost, large-scale production. Microbes have been genetically engineered to express the glycosyltransferases needed to synthesize oligosaccharides from the bacteria's innate pool of nucleotide sugars (Endo, T., Koizumi, S., Tabata, K., Kakita, S. & Ozaki, A. Carbohydr Res 330, 439-443 (2001); Endo, T., Koizumi, S., Tabata, K. & Ozaki, A. Appl Microbiol Biotechnol 53, 257-261 (2000); Endo, T. & Koizumi, S. Curr Opin Struct Biol 10, 536-541 (2000); Endo, T., Koizumi, S., Tabata, K., Kakita, S. & Ozaki, A. Carbohydr Res 316, 179-183 (1999); Koizumi, S., Endo, T., Tabata, K. & Ozaki, A. Nat Biotechnol 16, 847-850 (1998)). However, low overall product yields and high process complexity have limited the commercial utility of these approaches.

Prior to the invention described herein, which enables the inexpensive production of large quantities of neutral and acidic hMOS, it had not been possible to fully investigate the ability of this class of molecule to inhibit pathogen binding, or indeed to explore their full range of potential additional functions.

Prior to the invention described herein, chemical syntheses of hMOS were possible, but were limited by stereospecificity issues, precursor availability, product impurities, and high overall cost (Flowers, H. M. Methods Enzymol 50, 93-121 (1978); Seeberger, P. H. Chem Commun (Camb) 1115-1121 (2003); Koeller, K. M. & Wong, C. H. Chem Rev 100, 4465-4494 (2000)). Also, prior to the invention described herein, in vitro enzymatic syntheses were also possible, but were limited by a requirement for expensive nucleotide-sugar precursors. The invention overcomes the shortcomings of these previous attempts by providing new strategies to inexpensively manufacture large quantities of human milk oligosaccharides for use as dietary supplements. The invention described herein makes use of an engineered bacterium E. coli (or other bacteria) engineered to produce sialylated oligosaccharides in commercially viable levels, for example the methods described herein enable the production of 3'-SL at >50 g/L in bioreactors.

Variants and Functional Fragments

The present invention features introducing exogenous genes into bacterium to manipulate the pathways to increase UDP-GlcNAc pools, to produce sialylated oligosaccharides and to produce N-acetylglucosamine-containing oligosaccharides. In any of the methods described herein, the genes or gene products may be variants or functional fragments thereof.

A variant of any of genes or gene products disclosed herein may have 50%, 55%, 60%, 65%, 70%, 75%, 80%, 85%, 90%, 95%, 96%, 97%, 98%, or 99% sequence identity to the nucleic acid or amino acid sequences described herein. The term "% identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. For example, % identity is relative to the entire length of the coding regions of the sequences being compared, or the length of a particular fragment or functional domain thereof.

Variants as disclosed herein also include homolog, orthologs, or paralogs of the genes or gene products described herein that retain the same biological function as the genes or gene products specified herein. These variants can be used interchangeably with the genes recited in these methods. Such variants may demonstrate a percentage of homology or identity, for example, 50%, 55%, 60%, 65%, 70%, 75%, 80%, 85%, 90%, 95%, 96%, 97%, 98%, or 99% identity conserved domains important for biological function, preferably in a functional domain, e.g. catalytic domain.

For sequence comparison, one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Percent identity is determined using BLAST and PSI-BLAST (Altschul et al., 1990, J Mol Biol 215:3, 403-410; Altschul et al., 1997, Nucleic Acids Res 25:17, 3389-402). For the PSI-BLAST search, the following exemplary parameters are employed: (1) Expect threshold was 10; (2) Gap cost was Existence:11 and Extension:1; (3) The Matrix employed was BLOSUM62; (4) The filter for low complexity regions was "on".

Changes can be introduced by mutation into the nucleic acid sequence or amino acid sequence of any of the genes or gene products described herein, leading to changes in the amino acid sequence of the encoded protein or enzyme, without altering the functional ability of the protein or enzyme. For example, nucleotide substitutions leading to amino acid substitutions at "non-essential" amino acid residues can be made in the sequence of any of sequences expressly disclosed herein. A "non-essential" amino acid residue is a residue at a position in the sequence that can be altered from the wild-type sequence of the polypeptide without altering the biological activity, whereas an "essential" amino acid residue is a residue at a position that is required for biological activity. For example, amino acid residues that are conserved among members of a family of proteins are not likely to be amenable to mutation. Other amino acid residues, however, (e.g., those that are poorly conserved among members of the protein family) may not be as essential for activity and thus are more likely to be amenable to alteration. Thus, another aspect of the invention pertains to nucleic acid molecules encoding the proteins or enzymes disclosed herein that contain changes in amino acid residues relative to the amino acid sequences disclosed herein that are not essential for activity.

An isolated nucleic acid molecule encoding a protein homologous to any of the genes described herein can be created by introducing one or more nucleotide substitutions, additions or deletions into the corresponding nucleotide sequence, such that one or more amino acid substitutions, additions or deletions are introduced into the encoded protein.

Mutations can be introduced into a nucleic acid sequence such that the encoded amino acid sequence is altered by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. Certain amino acids have side chains with more than one classifiable characteristic. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, tryptophan, cysteine), nonpolar side chains (e.g., alanine, valine, leucine, isoleucine, proline, phenylalanine, methionine, tyrosine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a given polypeptide is replaced with another amino acid residue from the same side chain family. Alternatively, in another embodiment, mutations can be introduced randomly along all or part of a given coding sequence, such as by saturation mutagenesis, and the resultant mutants can be screened for given polypeptide biological activity to identify mutants that retain activity. Conversely, the invention also provides for variants with mutations that enhance or increase the endogenous biological activity. Following mutagenesis of the nucleic acid sequence, the encoded protein can be expressed by any recombinant technology known in the art and the activity of the protein can be determined. An increase, decrease, or elimination of a given biological activity of the variants disclosed herein can be readily measured by the ordinary person skilled in the art, i.e., by measuring the capability for mediating oligossacharide modification, synthesis, or degradation (via detection of the products).

The present invention also provides for functional fragments of the genes or gene products described herein. A fragment, in the case of these sequences and all others provided herein, is defined as a part of the whole that is less than the whole. Moreover, a fragment ranges in size from a single nucleotide or amino acid within a polynucleotide or polypeptide sequence to one fewer nucleotide or amino acid than the entire polynucleotide or polypeptide sequence. Finally, a fragment is defined as any portion of a complete polynucleotide or polypeptide sequence that is intermediate between the extremes defined above.

For example, fragments of any of the proteins or enzymes disclosed herein or encoded by any of the genes disclosed herein can be 10 to 20 amino acids, 10 to 30 amino acids, 10 to 40 amino acids, 10 to 50 amino acids, 10 to 60 amino acids, 10 to 70 amino acids, 10 to 80 amino acids, 10 to 90 amino acids, 10 to 100 amino acids, 50 to 100 amino acids, 75 to 125 amino acids, 100 to 150 amino acids, 150 to 200 amino acids, 200 to 250 amino acids, 250 to 300 amino acids, 300 to 350 amino acids, 350 to 400 amino acids, 400 to 450 amino acids, or 450 to 500 amino acids. The fragments encompassed in the present invention comprise fragments that retain functional fragments. As such, the fragments preferably retain the catalytic domains that are required or are important for functional activity. Fragments can be determined or generated by using the sequence information herein, and the fragments can be tested for functional activity using standard methods known in the art. For example, the encoded protein can be expressed by any recombinant technology known in the art and the activity of the protein can be determined. The biological function of said fragment can be measured by measuring ability to synthesize or modify a substrate oligosaccharide, or conversely, to catabolize an oligosaccharide substrate.

Example 1: Engineering of *E. Coli* to Generate Host Strains for the Production of N-Acetylglucosamine-Containing Human Milk Oligosaccharides The *E. coli* K12 prototroph, W3110, was chosen as the parent background for hMOS biosynthesis. This strain had previously been modified at the ampC locus by the introduction of a tryptophan-inducible $P_{trpB}$-cI+ repressor construct (McCoy, J. & Lavallie, E. Current protocols in molecular biology/edited by Frederick M. Ausubel et al., (2001)), enabling economical production of recombinant proteins from the phage λ P$_L$ promoter (Sanger, F., Coulson, A. R., Hong, G. F., Hill, D. F. & Petersen, G. B. J Mol Biol 162, 729-773 (1982)) through induction with millimolar concentrations of tryptophan (Mieschendahl, M., Petri, T. & Hänggi, U. Nature Biotechnology 4, 802-808 (1986)). The strain GI724, an *E. coli* W3110 derivative containing the tryptophan-inducible P$_{trpB}$-cI+ repressor construct in ampC, was used at the basis for further *E. coli* strain manipulations Biosynthesis of hMOS requires the generation of an enhanced cellular pool of lactose. This enhancement was achieved in strain GI724 through several manipulations of the chromosome using λ Red recombineering (Court, D. L., Sawitzke, J. A. & Thomason, L. C. Annu Rev Genet 36, 361-388 (2002)) and generalized P1 phage transduction (Thomason, L. C., Costantino, N. & Court, D. L. Mol Biol Chapter 1, Unit 1.17 (2007)). The ability of the *E. coli* host strain to accumulate intracellular lactose was first engineered by simultaneous deletion of the endogenous β-galactosidase gene (lacZ) and the lactose operon repressor gene (lacI). During construction of this deletion, the lacIq promoter was placed immediately upstream of the lactose permease gene, lacY. The modified strain thus maintains its ability to transport lactose from the culture medium (via LacY), but is deleted for the wild-type copy of the lacZ (β-galactosidase) gene responsible for lactose catabolism. An intracellular lactose pool is therefore created when the modified strain is cultured in the presence of exogenous lactose.

An additional modification useful for increasing the cytoplasmic pool of free lactose (and hence the final yield of hMOS) is the incorporation of a lacA mutation. LacA is a lactose acetyltransferase that is only active when high levels of lactose accumulate in the *E. coli* cytoplasm. High intracellular osmolarity (e.g., caused by a high intracellular lactose pool) can inhibit bacterial growth, and *E. coli* has evolved a mechanism for protecting itself from high intra cellular osmolarity caused by lactose by "tagging" excess intracellular lactose with an acetyl group using LacA, and then actively expelling the acetyl-lactose from the cell (Danchin, A. Bioessays 31, 769-773 (2009)). Production of acetyl-lactose in *E. coli* engineered to produce human milk oligosaccharides is therefore undesirable: it reduces overall yield. Moreover, acetyl-lactose is a side product that complicates oligosaccharide purification schemes. The incorporation of a lacA mutation resolves these problems, as carrying a deletion of the lacA gene renders the bacterium incapable of synthesizing acetyl-lactose.

A thyA (thymidylate synthase) mutation was introduced by almost entirely deleting the thyA gene and replacing it by an inserted functional, wild-type, but promoter-less *E. coli* lacZ$^+$ gene carrying the 2.8 ribosome binding site (SEQ ID NO: 10) (ΔthyA::(2.8RBS lacZ$^+$, kan$^r$). λ Red recombineering was used to perform the construction. FIG. 4 illustrates the new configuration of genes thus engineered at the thyA locus. The complete DNA sequence of the region, with annotations in GenBank format is disclosed herein. Genomic DNA sequence surrounding the lacZ+ insertion into the thyA region is set forth in SEQ ID NO: 1.

The thyA defect can be complemented in trans by supplying a wild-type thyA gene on a multicopy plasmid (Belfort, M., Maley, G. F. & Maley, F. Proceedings of the National Academy of Sciences 80, 1858 (1983)). This complementation is used herein as a means of plasmid maintenance (eliminating the need for a more conventional antibiotic selection scheme to maintain plasmid copy number).

The genotype of strain E680 is given below. E680 incorporates all the changes discussed above and is a host strain suitable for the production of N-acetylglucosamine-containing oligosaccharides.

F'402 proA+B+, PlacIq-lacY, Δ(lacI-lacZ) 158, ΔlacA398/araC, Δgpt-mhpC, ΔthyA::(2.8RBS lacZ+, KAN), rpoS+, rph+, ampC::(Ptrp T7g10 RBS-λcI+, CAT)

E796 is a strain similar to E680 and carries a thyA (thymidylate synthase) mutation, introduced by almost entirely deleting the thyA gene and replacing it by an inserted functional, wild-type, but promoter-less *E. coli* lacZ$^+$ gene but carrying the 0.8 ribosome binding site (SEQ ID NO: 11) [ΔthyA::(0.8RBS lacZ+, KAN)]. The genotype of strain E796 is given below. E796 incorporates all the changes discussed above and is a host strain suitable for the production of N-acetylglucosamine-containing oligosaccharides.

F'402 proA+B+, PlacIq-lacY, Δ(lacI-lacZ) 158, ΔlacA398/araC, Δgpt-mhpC, ΔthyA::(2.8RBS lacZ+, KAN), rpoS+, rph+, ampC::(Ptrp T7g10 RBS-λcI+, CAT)

E866 is a strain similar to E796 and is useful for dual plasmid selection. E866 also carries a thyA (thymidylate synthase) mutation, introduced by almost entirely deleting the thyA gene and replacing it by an inserted functional, wild-type, but promoter-less *E. coli* lacZ$^+$ gene and carrying the 0.8 ribosome binding site (SEQ ID NO: 11) [ΔthyA::(0.8RBS lacZ+)]. In addition to the thyA deletion E866 also carries a deletion of the purA gene. The genotype of strain E866 is given below. E866 incorporates all the changes discussed above and is a host strain suitable for the production of N-acetylglucosamine-containing oligosaccharides.

F'402 proA+B+, PlacIq-lacY, Δ(lacI-lacZ) 158, ΔlacA398/araC, Δgpt-mhpC, ΔthyA::(0.8RBS lacZ+), rpoS+, rph+, ampC::(Ptrp T7g10 RBS-λcI+, CAT), ΔpurA727::KAN Example 2. Production of N-Acetylglucosamine-Containing Human Milk Oligosaccharides in *E. Coli*: Lacto-N-Tetraose (LNT) and Lacto-N-Neotetraose (LNnT)

The first step in the synthesis (from a lactose precursor) of both Lacto-N-tetraose (LNT) and Lacto-N-neotetraose (LNnT) is the addition of a β(1,3)N-acetylglucosamine residue to lactose, utilizing a heterologous β(1,3)-N-acetylglucosaminyltransferase to form Lacto-N-triose 2 (LNT2). The plasmid pG292 (ColE1, thyA+, bla+, P$_L$-lgtA) (SEQ ID NO: 2, FIG. 5) carries the lgtA β(1,3)-N-acetylglucosaminyltransferase gene of *N. meningitidis* and can direct the production of LNT2 in *E. coli* strain E680 under appropriate culture conditions. pG221 (ColE1, thyA+, bla+, P$_L$-lgtA-wbgO) (SEQ ID NO: 3, FIG. 6) is a derivative of pG292 that carries (arranged as an operon) both the lgtA β(1,3)-N-acetylglucosaminyltransferase gene of *N. meningitidis* and the wbgO β(1,3)-galactosyltransferase gene of *E. coli* O55:H7. pG221 directs the production of LNT in *E. coli* strain E680 under appropriate culture conditions. pG222 (ColE1, thyA+, bla+, P$_L$-lgtA-4GalT) (SEQ ID NO: 4, FIG. 7) is a derivative of pG292 that carries (arranged as an operon) both the lgtA β(1,3)-N-acetylglucosaminyltransferase gene of *N. meningitidis* and the 4GalT (jhp0765) β(1,4)-galactosyltransferase gene of *H. pylori*. pG222 directs the production of LNnT in *E. coli* strain E680 under appropriate culture conditions.

The addition of tryptophan to the lactose-containing growth medium of cultures of any one of the E680-derivative strains transformed with plasmids pG292, pG221 or pG222 leads, for each particular E680/plasmid combination, to activation of the host *E. coli* tryptophan utilization repressor TrpR, subsequent repression of $P_{trpB}$, and a consequent decrease in cytoplasmic cI levels, which results in a derepression of $P_L$, expression of lgtA, lgtA+wbgO, or lgtA+4GalT respectively, and production of LNT2, LNT, or LNnT respectively.

For LNT2, LNT, or LNnT production in small scale laboratory cultures (<100 ml), strains were grown at 30° C. in a selective medium lacking both thymidine and tryptophan to early exponential phase (e.g., M9 salts, 0.5% glucose, 0.4% casaminoacids). Lactose was then added to a final concentration of 0.5 or 1%, along with tryptophan (200 µM final) to induce expression of the respective glycosyltransferases, driven from the $P_L$ promoter. At the end of the induction period (~24 h), TLC analysis was performed on aliquots of cell-free culture medium. FIG. 8 illustrates schematically the enzymatic reactions necessary to produce from lactose, via the intermediate trisaccharide lacto-N-triose 2 (LNT2), the two human milk oligosaccharides; Lacto-N-tetraose (LNT) and Lacto-N-neotetraose (LNnT). A thin layer chromatogram (on left) is presented of culture medium samples taken from small scale *E. coli* cultures and demonstrating synthesis of LNT2, LNT, and LNnT (utilizing induced, lactose-containing cultures of E680 transformed with pG292, pG221 or pG222 respectively). A second thin layer chromatogram (on right) is presented of culture medium samples taken from an *E. coli* E680/pG222 15 L bioreactor culture and demonstrating synthesis of LNnT (as well as the higher molecular weight hMOS, Lacto-N-neohexaose, LNnH).

Although the above results clearly demonstrate how it is possible to synthesize GlcNAc-containing oligosaccharides (i.e. LNT2, LNT and LNnT) in engineered *E. coli*, FIG. 14 illustrates a serious problem faced when attempting to use the *E. coli* UDP-GlcNAc pool during such syntheses. In FIG. 14 four separate cultures of E680, transformed with pG292, were grown in the presence and absence of lactose, and with LgtA expression both induced and uninduced by tryptophan addition. It can clearly be seen that massive cell lysis occurs in the cultures where lactose is present—i.e. in those cultures where LgtA draws down the cellular UDP-GlcNAc pool by adding GlcNAc to lactose (and making LNT2). In so doing, UDP-GlcNAc is diverted from cell wall biosynthesis towards hMOS biosynthesis, and cell lysis results. This lysis can be monitored readily not only by the precipitous drop in culture density as seen in the figure, but also by the appearance of DNA in the culture medium.

Example 3. Boosting the Cellular UDP-GlcNAc Pool Prevents Cell Lysis During the Biosynthesis of LNnT in Engineered *E. Coli*

To examine the impact of enhancing the *E. coli* cellular UDP-GlcNAc pool during synthesis of N-acetylglucosamine-containing hMOS the p15A replicon plasmid pG356 was constructed (FIG. 19 and SEQ ID NO:12). pG356 carries a p15A replicon (compatible with ColE1 replicons), purA and ampC selectable markers, and a synthetic operon (under control of the pL promoter) carrying the *E. coli* glmS (encoding L-glutamine:D-fructose-6-phosphate aminotransferase) and nagC (encoding the bi-functional transcriptional activator/repressor of glm and nag operons) genes. When pL is active in strains carrying the plasmid pG356, the UDP-GlcNAc pool increases. Strain E796 (see example 1) was transformed with pG222 (FIG. 7), and strain E866 (see example 1) was transformed with both pG222 (FIG. 7) and pG356 (FIG. 19). (Strains E796 and E866 are isogenic save for the purA mutation found in E866 that is used for pG356 plasmid retention). Identical 1.5 L fermentation runs were performed on each of the transformed strains. Optical density of the cultures and LNnT biosynthesis was followed, along with standard fermentation parameters. As can be seen in FIG. 18, the E796/pG222 culture produced LNnT, but lysed when the cell density reached 75 OD600, and achieved a final cell density at end-of-fermentation of only 50 OD600. In contrast (FIG. 19) with the E866/pG222+pG356 culture (where expression of the glmS and bagC genes enhance the intracellular UDP-GlcNAc pool) LNnT was also produced, but with no cell lysis observed. In this culture end-of-fermentation cell density reached 108 OD600—more than twice the density achieved for E796/pG222.

Example 4. Production of 6'-Sialyllactose (6'-SL) by Engineered *E. Coli* (ΔnanRATEK)

For the production of 6' sialyllactose, *Escherichia coli* GI724 (ATCC55151) was engineered with a set of mutations that cause cytoplasmic accumulation of non-acetylated lactose precursor and prevent the degradation of N-acetyl-5-neuraminic acid (FIG. 3). In particular, the lacZ (β-galactosidase) and lacA (lactose acetyl transferase) genes from the lac operon were deleted, leaving the LacIq repressor and the LacY permease fully functional. The LacY permease can be driven by weak (e.g. lac8) or strong (e.g. Ptac) promoters. The entire nan operon (nanRATEK; structural and regulatory genes involved in neuraminic acid degradation) was deleted in this example. *E. coli* genome manipulations were achieved using a combination of standard molecular genetics techniques, specifically lambda-Red recombineering, allele exchanges with positive selection suicide vectors, and P1 transductions (FIG. 3). The host genotype of strain E781, suitable for production of sialylated hMOS, is presented below:

ampC::(Ptrp-λcI+), lacIq lacPL8, ΔnanRATEK471, ΔlacZ690, ΔlacA 745

To produce 6'-sialyllactose, the cellular UDP-GlcNAc pool must be converted into the sugar-nucleotide activated precursor, CMP-NeuAc, which in turn can function as a donor molecule for a sugar acceptor (i.e. lactose) in a sialyltransferase-catalyzed reaction (FIG. 3). To this purpose, three genes from *Campylobacter jejuni* ATCC43438, encoding i) UDP-N-acetylglucosamine 2-epimerase (NeuC), ii) N-acetylneuraminate synthase (NeuB), and iii) N-Acetylneuraminate cytidylyltransferase (NeuA), were constitutively co-expressed in the engineered *E. coli* strain described above, along with a gene encoding an α(2,6) sialyltransferase from *Photobacterium* spp JT-ISH-224 (SEQ ID NO:21 Genbank protein Accession BAF92026, incorporated herein by reference). The neu genes were expressed from a low copy number plasmid vector (pG317, FIG. 9, SEQ ID NO: 5) carrying a constitutive lac promoter (pBBR1 ori, cat+, Plac), while the α(2,6)sialyltransferase gene was expressed from a high copy number plasmid vector (pG315, FIG. 10, SEQ ID NO: 6) carrying a constitutive lac promoter (ColE1 ori, bla+, Plac). To prevent the synthesis of side-products, the relative expression for the α(2,6)sialyltransferase gene compared to the neu genes is modulated by engineering differing ribosomal binding sites (RBS) providing various degrees of translational efficiency upstream of the α(2,6)sialyltransferase gene. Engineered strains were grown to high density in pilot scale fermentors using a batch to fed-batch strategy. FIG. 11 is a TLC analysis of culture supernatants from two such fermentations, with samples to the left of the figure being taken from a fermentation of a strain containing pG315 (and thus carrying the RBS presented in SEQ ID NO: 7 in front of the α(2,6) sialyltransferase gene in the vector). Samples on the right of the figure are taken from a fermentation of a strain containing a close variant of pG315 (pG345, FIG. 12, SEQ ID NO:9, carrying the weaker RBS presented in SEQ ID NO: 8 in front of the α(2,6)sialyltransferase gene and replacing the RBS presented in SEQ ID NO: 7). In both cases, the lactose precursor was added at a cell density of 50 $OD_{600}$ and efficient conversion to final products was achieved within 48 hours from the lactose addition. The final yield of 6' SL was increased when utilizing the plasmid with the weaker RBS upstream of the α(2,6)sialyltransferase gene, and moreover the level of KDO-lactose side product is very significantly decreased using this weaker RBS. The identity of the 6'-SL purified using activated carbon column chromatography was confirmed by ESI mass spectrometry and NMR.

Example 5. Production of 6'-Sialyllactose (6'-SL) by Engineered E. Coli. (ΔnanA, ΔnanATE)

For the production of 6' sialyllactose, Escherichia coli GI724 (ATCC55151) was engineered with a set of mutations that cause cytoplasmic accumulation of non-acetylated lactose precursor and prevent the degradation of N-acetyl-5-neuraminic acid (FIG. 13). In particular, the lacZ (β-galactosidase) and lacA (lactose acetyl transferase) genes from the lac operon were deleted, leaving the LacIq repressor and the LacY permease fully functional. The LacY permease can be driven by weak (e.g. lac8) or strong (e.g. Ptac) promoters. While the entire nan operon (nanRATEK; structural and regulatory genes involved in neuraminic acid degradation) can be deleted to abolish neuraminic acid catabolism as in Example 4, lesser deletions encompassing just the nanA, or nanA, nanT and nanE, or nanA and nanE genes, are also suitable. In all the instances where the nanE gene was mutated, the last 104 bp of the nanE gene were left intact to allow for undisturbed transcription/translation of downstream nanK, although other lengths of residual nanE sequence are possible. E. coli genome manipulations were achieved using a combination of standard molecular genetics techniques, specifically lambda-Red recombineering, allele exchanges with positive selection suicide vectors, and P1 transductions (FIG. 13). The host genotypes of strains E971, E1017 and E1018, suitable for production of sialylated hMOS with various yield and purity, are presented below:

ampC::(Ptrp-λcI+), lacIq lacPL8, ΔnanA:: kanR, ΔlacZ690, ΔlacA::scar, ampC::(Ptrp-λcI+), lacIq lacPL8, ΔnanATE::kanR::nanK+, ΔlacZ690, ΔlacA::scar and ampC::(Ptrp-λcI+), lacIq lacPL8, ΔnanATE::scar::nanK+, ΔlacZ690, ΔlacA::scar respectively To produce 6'-sialyllactose, the cellular UDP-GlcNAc pool must be converted into the sugar-nucleotide activated precursor, CMP-NeuAc, which in turn can function as a donor molecule for a sugar acceptor (i.e. lactose) in a sialyltransferase-catalyzed reaction (FIG. 13). To this purpose, three genes from Campylobacter jejuni ATCC43438, encoding i) UDP-N-acetylglucosamine 2-epimerase (NeuC), ii) N-acetylneuraminate synthase (NeuB), and iii) N-Acetylneuraminate cytidylyltransferase (NeuA), were constitutively co-expressed in the engineered E. coli strain described above, along with a gene encoding an α(2,6) sialyltransferase from Photobacterium spp JT-ISH-224. The neu genes were expressed from a low copy number plasmid vector (pG317, FIG. 9, SEQ ID NO: 5) carrying a constitutive lac promoter (pBBR1 ori, cat+, Plac), while the α(2,6)sialyltransferase gene was expressed from the weak RBS of SEQ ID NO: 8 in a high copy number plasmid vector (pG345, FIG. 12, SEQ ID NO: 9) carrying a constitutive lac promoter (ColE1 ori, bla+, Plac). Engineered strains were grown to high density in pilot scale fermentors using a batch to fed-batch strategy. FIG. 14 is a TLC analysis of culture pellets or supernatants from three such fermentations. Panel A shows production and accumulation of 6'SL in the cells of three genetic backgrounds (only the relevant nan mutations are shown for strains E971, E1017 and E1018), Panel B and C show production and accumulation of 6'SL in the extracellular milieu (supernatants) in strains E971, E1017 and E1018 (only the relevant nan mutations are shown) with estimated maximum volumetric yields of 15 g per liter of supernatant. In all cases, the lactose precursor was added at a cell density of 40 $OD_{600}$ and steady state conversion to final products was achieved within approximately 90 hours from the lactose addition (EFT is elapsed fermentation time).

The various sequences presented herein are recited below.

SEQ ID NO: 1

```
>E680_thyA::2.8RBS_lacZ Escherichia coli str.
GCAGCGGAACTCACAAGGCACCATAACGTCCCCTCCCTGATAACGCTGATACTGTGGTCG

CGGTTATGCCAGTTGGCATCTTCACGTAAATAGAGCAAATAGTCCCGCGCCTGGCTGGCG

GTTTGCCATAGCCGTTGCGACTGCTGCCAGTATTGCCAGCCATAGAGTCCACTTGCGCTT

AGCATGACCAAAATCAGCATCGCGACCAGCGTTTCAATCAGCGTATAACCACGTTGTGTT

TTCATGCCGGCAGTATGGAGCGAGGAGAAAAAAAGACGAGGGCCAGTTTCTATTTCTTCG

GCGCATCTTCCGGACTATTTACGCCGTTGCAGGACGTTGCAAAATTTCGGGAAGGCGTCT

CGAAGAATTTAACGGAGGGTAAAAAAACCGACGCACACTGGCGTCGGCTCTGGCAGGATG

TTTCGTAATTAGATAGCCACCGGCGCTTTattaaacctactATGACCATGATTACGGATT

CACTGGCCGTCGTTTTACAACGTCGTGACTGGGAAAACCCTGGCGTTACCCAACTTAATC

GCCTTGCAGCACATCCCCCTTTCGCCAGCTGGCGTAATAGCGAAGAGGCCCGCACCGATC

GCCCTTCCCAACAGTTGCGCAGCCTGAATGGCGAATGGCGCTTTGCCTGGTTTCCGGCAC
```

```
CAGAAGCGGTGCCGGAAAGCTGGCTGGAGTGCGATCTTCCTGAGGCCGATACTGTCGTCG

TCCCCTCAAACTGGCAGATGCACGGTTACGATGCGCCCATCTACACCAACGTGACCTATC

CCATTACGGTCAATCCGCCGTTTGTTCCCACGGAGAATCCGACGGGTTGTTACTCGCTCA

CATTTAATGTTGATGAAAGCTGGCTACAGGAAGGCCAGACGCGAATTATTTTTGATGGCG

TTAACTCGGCGTTTCATCTGTGGTGCAACGGGCGCTGGGTCGGTTACGGCCAGGACAGTC

GTTTGCCGTCTGAATTTGACCTGAGCGCATTTTTACGCGCCGGAGAAAACCGCCTCGCGG

TGATGGTGCTGCGCTGGAGTGACGGCAGTTATCTGGAAGATCAGGATATGTGGCGGATGA

GCGGCATTTTCCGTGACGTCTCGTTGCTGCATAAACCGACTACACAAATCAGCGATTTCC

ATGTTGCCACTCGCTTTAATGATGATTTCAGCCGCGCTGTACTGGAGGCTGAAGTTCAGA

TGTGCGGCGAGTTGCGTGACTACCTACGGGTAACAGTTTCTTTATGGCAGGGTGAAACGC

AGGTCGCCAGCGGCACCGCGCCTTTCGGCGGTGAAATTATCGATGAGCGTGGTGGTTATG

CCGATCGCGTCACACTACGTCTGAACGTCGAAAACCCGAAACTGTGGAGCGCCGAAATCC

CGAATCTCTATCGTGCGGTGGTTGAACTGCACACCGCCGACGGCACGCTGATTGAAGCAG

AAGCCTGCGATGTCGGTTTCCGCGAGGTGCGGATTGAAAATGGTCTGCTGCTGCTGAACG

GCAAGCCGTTGCTGATTCGAGGCGTTAACCGTCACGAGCATCATCCTCTGCATGGTCAGG

TCATGGATGAGCAGACGATGGTGCAGGATATCCTGCTGATGAAGCAGAACAACTTTAACG

CCGTGCGCTGTTCGCATTATCCGAACCATCCGCTGTGGTACACGCTGTGCGACCGCTACG

GCCTGTATGTGGTGGATGAAGCCAATATTGAAACCCACGGCATGGTGCCAATGAATCGTC

TGACCGATGATCCGCGCTGGCTACCGGCGATGAGCGAACGCGTAACGCGAATGGTGCAGC

GCGATCGTAATCACCCGAGTGTGATCATCTGGTCGCTGGGGAATGAATCAGGCCACGGCG

CTAATCACGACGCGCTGTATCGCTGGATCAAATCTGTCGATCCTTCCCGCCCGGTGCAGT

ATGAAGGCGGCGGAGCCGACACCACGGCCACCGATATTATTTGCCCGATGTACGCGCGCG

TGGATGAAGACCAGCCCTTCCCGGCTGTGCCGAAATGGTCCATCAAAAAATGGCTTTCGC

TACCTGGAGAGACGCGCCCGCTGATCCTTTGCGAATACGCCCACGCGATGGGTAACAGTC

TTGGCGGTTTCGCTAAATACTGGCAGGCGTTTCGTCAGTATCCCCGTTTACAGGGCGGCT

TCGTCTGGGACTGGGTGGATCAGTCGCTGATTAAATATGATGAAAACGGCAACCCGTGGT

CGGCTTACGGCGGTGATTTTGGCGATACGCCGAACGATCGCCAGTTCTGTATGAACGGTC

TGGTCTTTGCCGACCGCACGCCGCATCCAGCGCTGACGGAAGCAAAACACCAGCAGCAGT

TTTTCCAGTTCCGTTTATCCGGGCAAACCATCGAAGTGACCAGCGAATACCTGTTCCGTC

ATAGCGATAACGAGCTCCTGCACTGGATGGTGGCGCTGGATGGTAAGCCGCTGGCAAGCG

GTGAAGTGCCTCTGGATGTCGCTCCACAAGGTAAACAGTTGATTGAACTGCCTGAACTAC

CGCAGCCGGAGAGCGCCGGGCAACTCTGGCTCACAGTACGCGTAGTGCAACCGAACGCGA

CCGCATGGTCAGAAGCCGGGCACATCAGCGCCTGGCAGCAGTGGCGTCTGGCGGAAAACC

TCAGTGTGACGCTCCCCGCCGCGTCCCACGCCATCCCGCATCTGACCACCAGCGAAATGG

ATTTTTGCATCGAGCTGGGTAATAAGCGTTGGCAATTTAACCGCCAGTCAGGCTTTCTTT

CACAGATGTGGATTGGCGATAAAAAACAACTGtTGACGCCGCTGCGCGATCAGTTCACCC

GTGCACCGCTGGATAACGACATTGGCGTAAGTGAAGCGACCCGCATTGACCCTAACGCCT

GGGTCGAACGCTGGAAGGCGGCGGGCCATTACCAGGCCGAAGCAGCGTTGTTGCAGTGCA

CGGCAGATACACTTGCTGATGCGGTGCTGATTACGACCGCTCACGCGTGGCAGCATCAGG

GGAAAACCTTATTTATCAGCCGGAAAACCTACCGGATTGATGGTAGTGGTCAAATGGCGA
```

-continued

```
TTACCGTTGATGTTGAAGTGGCGAGCGATACACCGCATCCGGCGCGGATTGGCCTGAACT
GCCAGCTGGCGCAGGTAGCAGAGCGGGTAAACTGGCTCGGATTAGGGCCGCAAGAAAACT
ATCCCGACCGCCTTACTGCCGCCTGTTTTGACCGCTGGGATCTGCCATTGTCAGACATGT
ATACCCCGTACGTCTTCCCGAGCGAAAACGGTCTGCGCTGCGGGACGCGCGAATTGAATT
ATGGCCCACACCAGTGGCGCGGCGACTTCCAGTTCAACATCAGCCGCTACAGTCAACAGC
AACTGATGGAAACCAGCCATCGCCATCTGCTGCACGCGGAAGAAGGCACATGGCTGAATA
TCGACGGTTTCCATATGGGGATTGGTGGCGACGACTCCTGGAGCCCGTCAGTATCGGCGG
AATTCCAGCTGAGCGCCGGTCGCTACCATTACCAGTTGGTCTGGTGTCAAAAATAAGCGG
CCGCtTTATGTAGGCTGGAGCTGCTTCGAAGTTCCTATACTTTCTAGAGAATAGGAACTT
CGGAATAGGAACTTCAAGATCCCCTTATTAGAAGAACTCGTCAAGAAGGCGATAGAAGGC
GATGCGCTGCGAATCGGGAGCGGCGATACCGTAAAGCACGAGGAAGCGGTCAGCCCATTC
GCCGCCAAGCTCTTCAGCAATATCACGGGTAGCCAACGCTATGTCCTGATAGCGGTCCGC
CACACCCAGCCGGCCACAGTCGATGAATCCtGAAAAGCGGCCATTTTCCACCATGATATT
CGGCAAGCAGGCATCGCCATGGGTCACGACGAGATCCTCGCCGTCGGGCATGCGCGCCTT
GAGCCTGGCGAACAGTTCGGCTGGCGCGAGCCCCTGATGCTCTTCGTCCAGATCATCCTG
ATCGACAAGACCGGCTTCCATCCGAGTACGTGCTCGCTCGATGCGATGTTTCGCTTGGTG
GTCGAATGGGCAGGTAGCCGGATCAAGCGTATGCAGCCGCCGCATTGCATCAGCCATGAT
GGATACTTTCTCGGCAGGAGCAAGGTGAGATGACAGGAGATCCTGCCCCGGCACTTCGCC
CAATAGCAGCCAGTCCCTTCCCGCTTCAGTGACAACGTCGAGCACAGCTGCGCAAGGAAC
GCCCGTCGTGGCCAGCCACGATAGCCGCGCTGCCTCGTCCTGCAGTTCATTCAGGGCACC
GGACAGGTCGGTCTTGACAAAAAGAACCGGGCGCCCCTGCGCTGACAGCCGGAACACGGC
GGCATCAGAGCAGCCGATTGTCTGTTGTGCCCAGTCATAGCCGAATAGCCTCTCCACCCA
AGCGGCCGGAGAACCTGCGTGCAATCCATCTTGTTCAATCATGCGAAACGATCCTCATCC
TGTCTCTTGATCAGATCTTGATCCCCTGCGCCATCAGATCCTTGGCGGCAAGAAAGCCAT
CCAGTTTACTTTGCAGGGCTTCCCAACCTTACCAGAGGGCGCCCCAGCTGGCAATTCCGG
TTCGCTTGCTGTCCATAAAACCGCCCAGTCTAGCTATCGCCATGTAAGCCCACTGCAAGC
TACCTGCTTTCTCTTTGCGCTTGCGTTTTCCCTTGTCCAGATAGCCCAGTAGCTGACATT
CATCCGGGGTCAGCACCGTTTCTGCGGACTGGCTTTCTACGTGTTCCGCTTCCTTTAGCA
GCCCTTGCGCCCTGAGTGCTTGCGGCAGCGTGAGCTTCAAAAGCGCTCTGAAGTTCCTAT
ACTTTCTAGAGAATAGGAACTTCGAACTGCAGGTCGACGGATCCCCGGAATCATGGTTCC
TCAGGAAACGTGTTGCTGTGGGCTGCGACGATATGCCCAGACCATCATGATCACACCCGC
GACAATCATCGGGATGGAAAGAATTTGCCCCATGCTGATGTACTGCACCCAGGCACCGGT
AAACTGCGCGTCGGGCTGGCGGAAAAACTCAACAATGATGCGAAACGCGCCGTAACCAAT
CAGGAACAAACCTGAGACAGCTCCCATTGGGCGTGGTTTACGAATATACAGGTTGAGGAT
AATAAACAGCACCACACCTTCCAGCAGCAGCTCGTAAAGCTGTGATGGGTGGCGCGGCAG
CACACCGTAAGTGTCGAAAATGGATTGCCACTGCGGGTTGGTTTGCAGCAGCAAAATATC
TTCTGTACGGGAGCCAGGGAACAGCATGGCAAACGGGAAGTTCGGGTCAACGCGGCCCCA
CAATTCACCGTTAATAAAGTTGCCCAGACGCCCGGCACCAAGACCAAACGGAATGAGTGG
TGCGATAAAATCAGAGACCTGGAAGAAGGAACGTTTAGTACGGCGGGCGAAGATAATCAT
CACCACGATAACGCCAATCAGGCCGCCGTGGAAAGACATGCCGCCGTCCCAGACACGGAA
CAGATACAGCGGATCGGCCATAAACTGCGGGAAATTGTAGAACAGAACATAACCAATACG
```

```
TCCCCCGAGGAAGACGCCGAGGAAGCCCGCATAGAGTAAGTTTTCAACTTCATTTTTGGT

CCAGCCGCTGCCCGGACGATTCGCCCGTCGTGTTGCCAGCCACATTGCAAAAATGAAACC

CACCAGATACATCAGGCCGTACCAGTGAAGCGCCACGGGTCCTATTGAGAAAATGACCGG

ATCAAACTCCGGAAAATGCAGATAGCTACTGGTCATCTGTCACCACAAGTTCTTGTTATT

TCGCTGAAAGAGAACAGCGATTGAAATGCGCGCCGCAGGTTTCAGGCGCTCCAAAGGTGC

GAATAATAGCACAAGGGGACCTGGCTGGTTGCCGGATACCGTTAAAAGATATGTATA
```

SEQ ID NO: 2

```
>pG292, complete sequence.
TCGCGCGTTTCGGTGATGACGGTGAAAACCTCTGACACATGCAGCTCCCGGAGACGGTCA

CAGCTTGTCTGTAAGCGGATGCCGGGAGCAGACAAGCCCGTCAGGGCGCGTCAGCGGGTG

TTGGCGGGTGTCGGGGCTGGCTTAACTATGCGGCATCAGAGCAGATTGTACTGAGAGTGC

ACCATATATGCGGTGTGAAATACCGCACAGATGCGTAAGGAGAAAATACCGCATCAggcg ccTCCTCAACCTGTATATTCGTAAACCACGCCCAATGGGAGCTGTCTCAGGTTTGTTCCT

GATTGGTTACGGCGCGTTTCGCATCATTGTTGAGTTTTTCCGCCAGCCCGACGCGCAGTT

TACCGGTGCCTGGGTGCAGTACATCAGCATGGGGCAAATTCTTTCCATCCCGATGATTGT

CGCGGGTGTGATCATGATGGTCTGGGCATATCGTCGCAGCCCACAGCAACACGTTTCCTG

AGGAACCATGAAACAGTATTTAGAACTGATGCAAAAAGTGCTCGACGAAGGCACACAGAA

AAACGACCGTACCGGAACCGGAACGCTTTCCATTTTTGGTCATCAGATGCGTTTTAACCT

GCAAGATGGATTCCCGCTGGTGACAACTAAACGTTGCCACCTGCGTTCCATCATCCATGA

ACTGCTGTGGTTTCTGCAGGGCGACACTAACATTGCTTATCTACACGAAAACAATGTCAC

CATCTGGGACGAATGGGCCGATGAAAACGGCGACCTCGGGCCAGTGTATGGTAAACAGTG

GCGCGCCTGGCCAACGCCAGATGGTCGTCATATTGACCAGATCACTACGGTACTGAACCA

GCTGAAAAACGACCCGGATTCGCGCCGCATTATTGTTTCAGCGTGGAACGTAGGCGAACT

GGATAAAATGGCGCTGGCACCGTGCCATGCATTCTTCCAGTTCTATGTGGCAGACGGCAA

ACTCTCTTGCCAGCTTTATCAGCGCTCCTGTGACGTCTTCCTCGGCCTGCCGTTCAACAT

TGCCAGCTACGCGTTATTGGTGCATATGATGGCGCAGCAGTGCGATCTGGAAGTGGGTGA

TTTTGTCTGGACCGGTGGCGACACGCATCTGTACAGCAACCATATGGATCAAACTCATCT

GCAATTAAGCCGCGAACCGCGTCCGCTGCCGAAGTTGATTATCAAACGTAAACCCGAATC

CATCTTCGACTACCGTTTCGAAGACTTTGAGATTGAAGGCTACGATCCGCATCCGGGCAT

TAAAGCGCCGGTGGCTATCTAATTACGAAACATCCTGCCAGAGCCGACGCCAGTGTGCGT

CGGTTTTTTTACCCTCCGTTAAATTCTTCGAGACGCCTTCCCGAAggcgccATTCGCCAT

TCAGGCTGCGCAACTGTTGGGAAGGGCGATCGGTGCGGGCCTCTTCGCTATTACGCCAGC

TGGCGAAAGGGGGATGTGCTGCAAGGCGATTAAGTTGGGTAACGCCAGGGTTTTCCCAGT

CACGACGTTGTAAAACGACGGCCAGTGCCAAGCTTACTGCTCACAAGAAAAAAGGCACGT

CATCTGACGTGCCTTTTTTATTTGTACTACCCTGTACGATTACTGCAGGTCGACTCTAGA

TGCATGCTCGAGTCAACGGTTTTTCAGCAATCGGTGCAAAATGCCGAAGTATTGCCTCAA

GGTAAACAGCCGCCGCATCCTGCCGTCTGCCGCAAAATCCAGCCACGCGCCGGCGGGCAG

CGTGTCCGTCCGTTTGAAGCATTGGTACAAAAACCGGCGGGCGCGTTCAAAATCTTCTTC

CGGCAAATGTTTCTCCAGCAATTCATACGCTACTGCTTTTATTTGGCGGTATTCAAGGCT

GTCGAACCGGGTTTAAAACCCATAGACTGCAAAAAATCGTTTCTGGCGGTTTTTTGGAT

GCCTTGCGCGATTTCGTGTTGGCGGATGCTGTATTTGGATGAAACCTGATTGGCGTGAAG
```

-continued

```
GCGGTATTTGACCAAGGCTTCGGGATAATAAGCCAGCCTGCCCAATTTGCTGACATCGTA
CCAAAATTGGTAATCTTCCGCCCAATCCCGCTCGGTGTTGTAACGCAAACCGCCGTCAAT
GACGCTGCGCCTCATAATCATCGTGTTGTTGTGTATGGGGTTGCCGAAAGGGAAAAAGTC
GGCAATGTCTTCGTGTCGGGTCGGTTTTTTCCAAATTTTGCCGTGTTCGTGGTGCCGCGC
CAGCCGGTTGCCGTCCTTTTCTTCCGACAAAACTTCCAGCCACGCACCCATCGCGATGAT
GCTGCGGTCTTTTTCCATCTCACCCACGATTTTCTCAATCCAGTCGGGGCGGCAATATC
GTCTGCATCGGTGCGCGCAATATATTCCCCCCCCCCCCCCGACTTTGCCAATTCATCCAG
CCCGATGTTTAAAGAGGGAATCAGACCGGAATTGCGCGGCTGCGCGAGGATGCGGATGCG
GCCGTCCTGTTCTTGGAAACGCTGGGCAATGGCAAGCGTACCGTCCGTCGAGCCGTCATC
GACAATCAAAATATCCAAGTTGCGCCAAGTTTGATTCACGACGGCGGCTAATGATTGGGC
GAAATATTTTTCTACGTTGTAGGCGCAAATCAATACGCTGACTAAAGGCTGCAATTTATT
CTCCCGATAGGCACGATGCCGTCTGAAGGCTTCAGACGGCATATGtatatctccttcttg
aaTTCTAACAATTGATTGAATGTATGCAAATAAATGCATACACCATAGGTGTGGTTTAAT
TTGATGCCCTTTTTCAGGGCTGGAATGTGTAAGAGCGGGGTTATTTATGCTGTTGTTTTT
TTGTTACTCGGGAAGGGCTTTACCTCTTCCGCATAAACGCTTCCATCAGCGTTTATAGTT
AAAAAAATCTTTCGGAACTGGTTTTGCGCTTACCCCAACCAACAGGGGATTTGCTGCTTT
CCATTGAGCCTGTTTCTCTGCGCGACGTTCGCGGCGGCGTGTTTGTGCATCCATCTGGAT
TCTCCTGTCAGTTAGCTTTGGTGGTGTGTGGCAGTTGTAGTCCTGAACGAAAACCCCCCG
CGATTGGCACATTGGCAGCTAATCCGGAATCGCACTTACGGCCAATGCTTCGTTTCGTAT
CACACACCCCAAAGCCTTCTGCTTTGAATGCTGCCCTTCTTCAGGGCTTAATTTTTAAGA
GCGTCACCTTCATGGTGGTCAGTGCGTCCTGCTGATGTGCTCAGTATCACCGCCAGTGGT
ATTTATGTCAACACCGCCAGAGATAATTTATCACCGCAGATGGTTATCTGTATGTTTTTT
ATATGAATTTATTTTTTGCAGGGGGGCATTGTTTGGTAGGTGAGAGATCAATTCTGCATT
AATGAATCGGCCAACGCGCGGGGAGAGGCGGTTTGCGTATTGGGCGCTCTTCCGCTTCCT
CGCTCACTGACTCGCTGCGCTCGGTCGTTCGGCTGCGGCGAGCGGTATCAGCTCACTCAA
AGGCGGTAATACGGTTATCCACAGAATCAGGGGATAACGCAGGAAAGAACATGTGAGCAA
AAGGCCAGCAAAAGGCCAGGAACCGTAAAAAGGCCGCGTTGCTGGCGTTTTTCCATAGGC
TCCGCCCCCTGACGAGCATCACAAAAATCGACGCTCAAGTCAGAGGTGGCGAAACCCGA
CAGGACTATAAAGATACCAGGCGTTTCCCCCTGGAAGCTCCCTCGTGCGCTCTCCTGTTC
CGACCCTGCCGCTTACCGGATACCTGTCCGCCTTTCTCCCTTCGGGAAGCGTGGCGCTTT
CTCATAGCTCACGCTGTAGGTATCTCAGTTCGGTGTAGGTCGTTCGCTCCAAGCTGGGCT
GTGTGCACGAACCCCCCGTTCAGCCCGACCGCTGCGCCTTATCCGGTAACTATCGTCTTG
AGTCCAACCCGGTAAGACACGACTTATCGCCACTGGCAGCAGCCACTGGTAACAGGATTA
GCAGAGCGAGGTATGTAGGCGGTGCTACAGAGTTCTTGAAGTGGTGGCCTAACTACGGCT
ACACTAGAAGGACAGTATTTGGTATCTGCGCTCTGCTGAAGCCAGTTACCTTCGGAAAAA
GAGTTGGTAGCTCTTGATCCGGCAAACAAACCACCGCTGGTAGCGGTGGTTTTTTTGTTT
GCAAGCAGCAGATTACGCGCAGAAAAAAAGGATCTCAAGAAGATCCTTTGATCTTTTCTA
CGGGGTCTGACGCTCAGTGGAACGAAAACTCACGTTAAGGGATTTTGGTCATGAGATTAT
CAAAAAGGATCTTCACCTAGATCCTTTTAAATTAAAAATGAAGTTTTAAATCAATCTAAA
GTATATATGAGTAAACTTGGTCTGACAGTTACCAATGCTTAATCAGTGAGGCACCTATCT
CAGCGATCTGTCTATTTCGTTCATCCATAGTTGCCTGACTCCCCGTCGTGTAGATAACTA
```

```
CGATACGGGAGGGCTTACCATCTGGCCCCAGTGCTGCAATGATACCGCGAGACCCACGCT

CACCGGCTCCAGATTTATCAGCAATAAACCAGCCAGCCGGAAGGGCCGAGCGCAGAAGTG

GTCCTGCAACTTTATCCGCCTCCATCCAGTCTATTAATTGTTGCCGGGAAGCTAGAGTAA

GTAGTTCGCCAGTTAATAGTTTGCGCAACGTTGTTGCCATTGCTACAGGCATCGTGGTGT

CACGCTCGTCGTTTGGTATGGCTTCATTCAGCTCCGGTTCCCAACGATCAAGGCGAGTTA

CATGATCCCCATGTTGTGCAAAAAAGCGGTTAGCTCCTTCGGTCCTCCGATCGTTGTCA

GAAGTAAGTTGGCCGCAGTGTTATCACTCATGGTTATGGCAGCACTGCATAATTCTCTTA

CTGTCATGCCATCCGTAAGATGCTTTTCTGTGACTGGTGAGTACTCAACCAAGTCATTCT

GAGAATAGTGTATGCGGCGACCGAGTTGCTCTTGCCCGGCGTCAATACGGGATAATACCG

CGCCACATAGCAGAACTTTAAAAGTGCTCATCATTGGAAAACGTTCTTCGGGGCGAAAAC

TCTCAAGGATCTTACCGCTGTTGAGATCCAGTTCGATGTAACCCACTCGTGCACCCAACT

GATCTTCAGCATCTTTTACTTTCACCAGCGTTTCTGGGTGAGCAAAAACAGGAAGGCAAA

ATGCCGCAAAAAAGGGAATAAGGGCGACACGGAAATGTTGAATACTCATACTCTTCCTTT

TTCAATATTATTGAAGCATTTATCAGGGTTATTGTCTCATGAGCGGATACATATTTGAAT

GTATTTAGAAAAATAAACAAATAGGGGTTCCGCGCACATTTCCCCGAAAAGTGCCACCTG

ACGTCTAAGAAACCATTATTATCATGACATTAACCTATAAAAATAGGCGTATCACGAGGC

CCTTTCGTC
```

SEQ ID NO: 3
>pG221, complete sequence.
```
TCGCGCGTTTCGGTGATGACGGTGAAAACCTCTGACACATGCAGCTCCCGGAGACGGTCA

CAGCTTGTCTGTAAGCGGATGCCGGGAGCAGACAAGCCCGTCAGGGCGCGTCAGCGGGTG

TTGGCGGGTGTCGGGGCTGGCTTAACTATGCGGCATCAGAGCAGATTGTACTGAGAGTGC

ACCATATATGCGGTGTGAAATACCGCACAGATGCGTAAGGAGAAAATACCGCATCAggcg ccTCCTCAACCTGTATATTCGTAAACCACGCCCAATGGGAGCTGTCTCAGGTTTGTTCCT

GATTGGTTACGGCGCGTTTCGCATCATTGTTGAGTTTTTCCGCCAGCCCGACGCGCAGTT

TACCGGTGCCTGGGTGCAGTACATCAGCATGGGGCAAATTCTTTCCATCCCGATGATTGT

CGCGGGTGTGATCATGATGGTCTGGGCATATCGTCGCAGCCCACAGCAACACGTTTCCTG

AGGAACCATGAAACAGTATTTAGAACTGATGCAAAAAGTGCTCGACGAAGGCACACAGAA

AAACGACCGTACCGGAACCGGAACGCTTTCCATTTTTGGTCATCAGATGCGTTTTAACCT

GCAAGATGGATTCCCGCTGGTGACAACTAAACGTTGCCACCTGCGTTCCATCATCCATGA

ACTGCTGTGGTTTCTGCAGGGCGACACTAACATTGCTTATCTACACGAAAACAATGTCAC

CATCTGGGACGAATGGGCCGATGAAAACGGCGACCTCGGGCCAGTGTATGGTAAACAGTG

GCGCGCCTGGCCAACGCCAGATGGTCGTCATATTGACCAGATCACTACGGTACTGAACCA

GCTGAAAAACGACCCGGATTCGCGCCGCATTATTGTTTCAGCGTGGAACGTAGGCGAACT

GGATAAAATGGCGCTGGCACCGTGCCATGCATTCTTCCAGTTCTATGTGGCAGACGGCAA

ACTCTCTTGCCAGCTTTATCAGCGCTCCTGTGACGTCTTCCTCGGCCTGCCGTTCAACAT

TGCCAGCTACGCGTTATTGGTGCATATGATGGCGCAGCAGTGCGATCTGGAAGTGGGTGA

TTTTGTCTGGACCGGTGGCGACACGCATCTGTACAGCAACCATATGGATCAAACTCATCT

GCAATTAAGCCGCGAACCGCGTCCGCTGCCGAAGTTGATTATCAAACGTAAACCCGAATC

CATCTTCGACTACCGTTTCGAAGACTTTGAGATTGAAGGCTACGATCCGCATCCGGGCAT

TAAAGCGCCGGTGGCTATCTAATTACGAAACATCCTGCCAGAGCCGACGCCAGTGTGCGT
```

-continued

```
CGGTTTTTTTACCCTCCGTTAAATTCTTCGAGACGCCTTCCCGAAggcgccATTCGCCAT
TCAGGCTGCGCAACTGTTGGGAAGGGCGATCGGTGCGGGCCTCTTCGCTATTACGCCAGC
TGGCGAAAGGGGGATGTGCTGCAAGGCGATTAAGTTGGGTAACGCCAGGGTTTTCCCAGT
CACGACGTTGTAAAACGACGGCCAGTGCCAAGCTTACTGCTCACAAGAAAAAAGGCACGT
CATCTGACGTGCCTTTTTTATTTGTACTACCCTGTACGATTACTGCAGGTCGACTCTAGA
TGCATGCTCGAGTTATTATTTAATATATTTACAATAGATGAAGGACGCAATCGTACGGAT
ACCGCCGAACAGGTAGTTAATGTTACCGGTCAGGAAGAAGCACTTCATTTTGATAACCAG
GTCGTTAACCATCACCATGTACAGGTTTTTTTTTGCGGTAGACTGACCTTCGTGCAGGCG
GTAGTAGAACAGGTATTCCGGCAGGTTTTGGAACTTGATTTTTGCCAGGCTCAGACGGTT
CCACAGCTCGTAATCTTCGGAGTAGTTAGAAAACATATAACCACCGATGCTCGCGATGAC
TTTTTTACGAAACATTACGCTCGGGTGAACAATACAACACTTATACGGCAGGTTTTTAAC
GATGTCCAGGTTCTCTTCCGGCAGTTTGGTCTTGTTGATTTCACGACCTTTGTCGTCAAT
AAAGATTGCGTTGGTACCCACAACATCTACGTACGGATTGTTCTTCAGGAAGTCAACCTG
TTTAGTAAAACGGTCCGGGTGAGAGATGTCGTCAGAGTCCATACGGGCAATAAATTCGCC
GTTGCTCAGGTCGATCGCTTTGTTCAGGGAGTACGGCAGGTAAGCGATGTTAGTGCGGAT
CAGTTTGATTTTGTCGTTAACTTTGTGTTTCAGTTCGTTATAGAAGTCGTCAGTGCAGCA
GTTCGCAACGATGATTTCGAAGCTGCTGAAGGTCTGAGACAGGATGCTGTTGATCGC
TTCGTCCAGAAAAGGGTTTTTCTTGTTAACAGGCAGGATAACGCTCACAACCGGGTGGGT
AGATTCCGCGGATTCCGCTTCATCGATGATCATATGTATATCTCCTTCTTCTCGAGTCAA
CGGTTTTTCAGCAATCGGTGCAAAATGCCGAAGTATTGCCTCAAGGTAAACAGCCGCCGC
ATCCTGCCGTCTGCCGCAAAATCCAGCCACGCGCCGGCGGGCAGCGTGTCCGTCCGTTTG
AAGCATTGGTACAAAAACCGGCGGGCGCGTTCAAAATCTTCTTCCGGCAAATGTTTCTCC
AGCAATTCATACGCTACTGCTTTTATTTGGCGGTATTCAAGGCTGTCGAACCGGGTTTTA
AAACCCATAGACTGCAAAAAATCGTTTCTGGCGGTTTTTTGGATGCCTTGCGCGATTTCG
TGTTGGCGGATGCTGTATTTGGATGAAACCTGATTGGCGTGAAGGCGGTATTTGACCAAG
GCTTCGGGATAATAAGCCAGCCTGCCCAATTTGCTGACATCGTACCAAAATTGGTAATCT
TCCGCCCAATCCCGCTCGGTGTTGTAACGCAAACCGCCGTCAATGACGCTGCGCCTCATA
ATCATCGTGTTGTTGTGTATGGGGTTGCCGAAAGGGAAAAAGTCGGCAATGTCTTCGTGT
CGGGTCGGTTTTTTCCAAATTTTGCCGTGTTCGTGGTGCCGCGCCAGCCGGTTGCCGTCC
TTTTCTTCCGACAAAACTTCCAGCCACGCACCCATCGCGATGATGCTGCGGTCTTTTTCC
ATCTCACCCACGATTTTCTCAATCCAGTCGGGGCGGCAATATCGTCTGCATCGGTGCGC
GCAATATATTCCCCCCCCCCCCCCGACTTTGCCAATTCATCCAGCCCGATGTTTAAAGAG
GGAATCAGACCGGAATTGCGCGGCTGCGCGAGGATGCGGATGCGGCCGTCCTGTTCTTGG
AAACGCTGGGCAATGGCAAGCGTACCGTCCGTCGAGCCGTCATCGACAATCAAAATATCC
AAGTTGCGCCAAGTTTGATTCACGACGGCGGCTAATGATTGGGCGAAATATTTTTCTACG
TTGTAGGCGCAAATCAATACGCTGACTAAAGGCTGCAATTTATTCTCCCGATAGGCACGA
TGCCGTCTGAAGGCTTCAGACGGCATATGtatatctccttcttgaaTTCTAACAATTGAT
TGAATGTATGCAAATAAATGCATACACCATAGGTGTGGTTTAATTTGATGCCCTTTTTCA
GGGCTGGAATGTGTAAGAGCGGGGTTATTTATGCTGTTGTTTTTTTGTTACTCGGGAAGG
GCTTTACCTCTTCCGCATAAACGCTTCCATCAGCGTTTATAGTTAAAAAAATCTTTCGGA
ACTGGTTTTGCGCTTACCCCAACCAACAGGGGATTTGCTGCTTTCCATTGAGCCTGTTTC
```

-continued

```
TCTGCGCGACGTTCGCGGCGGCGTGTTTGTGCATCCATCTGGATTCTCCTGTCAGTTAGC

TTTGGTGGTGTGTGGCAGTTGTAGTCCTGAACGAAAACCCCCGCGATTGGCACATTGGC

AGCTAATCCGGAATCGCACTTACGGCCAATGCTTCGTTTCGTATCACACACCCCAAAGCC

TTCTGCTTTGAATGCTGCCCTTCTTCAGGGCTTAATTTTTAAGAGCGTCACCTTCATGGT

GGTCAGTGCGTCCTGCTGATGTGCTCAGTATCACCGCCAGTGGTATTTATGTCAACACCG

CCAGAGATAATTTATCACCGCAGATGGTTATCTGTATGTTTTTATATGAATTTATTTTT

TGCAGGGGGCATTGTTTGGTAGGTGAGAGATCAATTCTGCATTAATGAATCGGCCAACG

CGCGGGGAGAGGCGGTTTGCGTATTGGGCGCTCTTCCGCTTCCTCGCTCACTGACTCGCT

GCGCTCGGTCGTTCGGCTGCGGCGAGCGGTATCAGCTCACTCAAAGGCGGTAATACGGTT

ATCCACAGAATCAGGGGATAACGCAGGAAAGAACATGTGAGCAAAAGGCCAGCAAAAGGC

CAGGAACCGTAAAAAGGCCGCGTTGCTGGCGTTTTTCCATAGGCTCCGCCCCCCTGACGA

GCATCACAAAAATCGACGCTCAAGTCAGAGGTGGCGAAACCCGACAGGACTATAAAGATA

CCAGGCGTTTCCCCCTGGAAGCTCCCTCGTGCGCTCTCCTGTTCCGACCCTGCCGCTTAC

CGGATACCTGTCCGCCTTTCTCCCTTCGGGAAGCGTGGCGCTTTCTCATAGCTCACGCTG

TAGGTATCTCAGTTCGGTGTAGGTCGTTCGCTCCAAGCTGGGCTGTGTGCACGAACCCCC

CGTTCAGCCCGACCGCTGCGCCTTATCCGGTAACTATCGTCTTGAGTCCAACCCGGTAAG

ACACGACTTATCGCCACTGGCAGCAGCCACTGGTAACAGGATTAGCAGAGCGAGGTATGT

AGGCGGTGCTACAGAGTTCTTGAAGTGGTGGCCTAACTACGGCTACACTAGAAGGACAGT

ATTTGGTATCTGCGCTCTGCTGAAGCCAGTTACCTTCGGAAAAAGAGTTGGTAGCTCTTG

ATCCGGCAAACAAACCACCGCTGGTAGCGGTGGTTTTTTTGTTTGCAAGCAGCAGATTAC

GCGCAGAAAAAAAGGATCTCAAGAAGATCCTTTGATCTTTTCTACGGGGTCTGACGCTCA

GTGGAACGAAAACTCACGTTAAGGGATTTTGGTCATGAGATTATCAAAAAGGATCTTCAC

CTAGATCCTTTTAAATTAAAAATGAAGTTTTAAATCAATCTAAAGTATATATGAGTAAAC

TTGGTCTGACAGTTACCAATGCTTAATCAGTGAGGCACCTATCTCAGCGATCTGTCTATT

TCGTTCATCCATAGTTGCCTGACTCCCCGTCGTGTAGATAACTACGATACGGGAGGGCTT

ACCATCTGGCCCCAGTGCTGCAATGATACCGCGAGACCCACGCTCACCGGCTCCAGATTT

ATCAGCAATAAACCAGCCAGCCGGAAGGGCCGAGCGCAGAAGTGGTCCTGCAACTTTATC

CGCCTCCATCCAGTCTATTAATTGTTGCCGGGAAGCTAGAGTAAGTAGTTCGCCAGTTAA

TAGTTTGCGCAACGTTGTTGCCATTGCTACAGGCATCGTGGTGTCACGCTCGTCGTTTGG

TATGGCTTCATTCAGCTCCGGTTCCCAACGATCAAGGCGAGTTACATGATCCCCCATGTT

GTGCAAAAAAGCGGTTAGCTCCTTCGGTCCTCCGATCGTTGTCAGAAGTAAGTTGGCCGC

AGTGTTATCACTCATGGTTATGGCAGCACTGCATAATTCTCTTACTGTCATGCCATCCGT

AAGATGCTTTTCTGTGACTGGTGAGTACTCAACCAAGTCATTCTGAGAATAGTGTATGCG

GCGACCGAGTTGCTCTTGCCCGGCGTCAATACGGGATAATACCGCGCCACATAGCAGAAC

TTTAAAAGTGCTCATCATTGGAAAACGTTCTTCGGGGCGAAAACTCTCAAGGATCTTACC

GCTGTTGAGATCCAGTTCGATGTAACCCACTCGTGCACCCAACTGATCTTCAGCATCTTT

TACTTTCACCAGCGTTTCTGGGTGAGCAAAAACAGGAAGGCAAAATGCCGCAAAAAAGGG

AATAAGGGCGACACGGAAATGTTGAATACTCATACTCTTCCTTTTTCAATATTATTGAAG

CATTTATCAGGGTTATTGTCTCATGAGCGGATACATATTTGAATGTATTTAGAAAAATAA

ACAAATAGGGGTTCCGCGCACATTTCCCCGAAAAGTGCCACCTGACGTCTAAGAAACCAT
```

-continued
TATTATCATGACATTAACCTATAAAAATAGGCGTATCACGAGGCCCTTTCGTC

SEQ ID NO: 4

>pG222, complete sequence.
TCGCGCGTTTCGGTGATGACGGTGAAAACCTCTGACACATGCAGCTCCCGGAGACGGTCA

CAGCTTGTCTGTAAGCGGATGCCGGGAGCAGACAAGCCCGTCAGGGCGCGTCAGCGGGTG

TTGGCGGGTGTCGGGGCTGGCTTAACTATGCGGCATCAGAGCAGATTGTACTGAGAGTGC

ACCATATATGCGGTGTGAAATACCGCACAGATGCGTAAGGAGAAAATACCGCATCAggcg ccTCCTCAACCTGTATATTCGTAAACCACGCCCAATGGGAGCTGTCTCAGGTTTGTTCCT

GATTGGTTACGGCGCGTTTCGCATCATTGTTGAGTTTTTCCGCCAGCCCGACGCGCAGTT

TACCGGTGCCTGGGTGCAGTACATCAGCATGGGGCAAATTCTTTCCATCCCGATGATTGT

CGCGGGTGTGATCATGATGGTCTGGGCATATCGTCGCAGCCCACAGCAACACGTTTCCTG

AGGAACCATGAAACAGTATTTAGAACTGATGCAAAAAGTGCTCGACGAAGGCACACAGAA

AAACGACCGTACCGGAACCGGAACGCTTTCCATTTTTGGTCATCAGATGCGTTTTAACCT

GCAAGATGGATTCCCGCTGGTGACAACTAAACGTTGCCACCTGCGTTCCATCATCCATGA

ACTGCTGTGGTTTCTGCAGGGCGACACTAACATTGCTTATCTACACGAAAACAATGTCAC

CATCTGGGACGAATGGGCCGATGAAAACGGCGACCTCGGGCCAGTGTATGGTAAACAGTG

GCGCGCCTGGCCAACGCCAGATGGTCGTCATATTGACCAGATCACTACGGTACTGAACCA

GCTGAAAAACGACCCGGATTCGCGCCGCATTATTGTTTCAGCGTGGAACGTAGGCGAACT

GGATAAAATGGCGCTGGCACCGTGCCATGCATTCTTCCAGTTCTATGTGGCAGACGGCAA

ACTCTCTTGCCAGCTTTATCAGCGCTCCTGTGACGTCTTCCTCGGCCTGCCGTTCAACAT

TGCCAGCTACGCGTTATTGGTGCATATGATGGCGCAGCAGTGCGATCTGGAAGTGGGTGA

TTTTGTCTGGACCGGTGGCGACACGCATCTGTACAGCAACCATATGGATCAAACTCATCT

GCAATTAAGCCGCGAACCGCGTCCGCTGCCGAAGTTGATTATCAAACGTAAACCCGAATC

CATCTTCGACTACCGTTTCGAAGACTTTGAGATTGAAGGCTACGATCCGCATCCGGGCAT

TAAAGCGCCGGTGGCTATCTAATTACGAAACATCCTGCCAGAGCCGACGCCAGTGTGCGT

CGGTTTTTTTACCCTCCGTTAAATTCTTCGAGACGCCTTCCCGAAggcgccATTCGCCAT

TCAGGCTGCGCAACTGTTGGGAAGGGCGATCGGTGCGGGCCTCTTCGCTATTACGCCAGC

TGGCGAAAGGGGATGTGCTGCAAGGCGATTAAGTTGGGTAACGCCAGGGTTTTCCCAGT

CACGACGTTGTAAAACGACGGCCAGTGCCAAGCTTACTGCTCACAAGAAAAAGGCACGT

CATCTGACGTGCCTTTTTTATTTGTACTACCCTGTACGATTACTGCAGGTCGACTCTAGA

TGCATGctcgagTTATACAAACTGCCAATATTTCAAATATTTAAAATGGAGTTCTCTCAT

TAAGGCGATTTTAGGGCTATAAGGTTCTTCTTTTCGTGCTATCGTAGAGATTTGCTCATC

ATCAGCGATCACAAAAGGTTGTAACACCAGATTTTTCACGCCATGGATAAAAGTAGCGTC

CATTATCGTATCCACAGGAACAACCCATTTTCGGCTGCATTTCAAAAAAACTTTGGCAAT

CTTAGGCGTGATCACATAGCCTTGAGTCCCCACCCCTTCGCTATAAGCTTTAATGATCCC

CACACGCTCTTGTATCTCGTGGTTTTTATGGCTCAATGGCTCACTTTTTACACTGGCATC

ATACAATAAATGCATCAAGCGGATATAGCCTAACTCTTGGATGTGTTTTTCTAAAAAATC

CAAGCCCTCTTTAAAATCCTCTTTCAAGGTTATATCGTCTTCTAAAATACAGATCGCTTC

ATTGAGTTCTATGCATTTTTCCCACAAGGAATAATGACTCGCATAGCACCCAAGCTCCCC

CAAGCTCATAAACTTCGCATGGTATTTTAAAGCGTAATAAAACTTAGAAACCTCACTGAT

GAGATTGGTTGTAATCCCCATGTCTTTGATGTTTTGCGTGATGAAATAAGGGTGTAAATG

CTTTTTTCACTAAGGGGTGCAACCCGCCTTCAAAAGTTTTAGAATAAATCGCATCAAAAT

-continued

```
TTGCGCTTGGTGGTGGGTGGCATTGATGCTATTGAGTAAAGTTGTGGTGTCTCTAAAAAC

TAAACCAAATGTATCGCACACTTTTTGATTTAAAGAAATGGCAAAAACACGCAtATGtat atctccttcttCTCGAGTCAACGGTTTTTCAGCAATCGGTGCAAAATGCCGAAGTATTGC

CTCAAGGTAAACAGCCGCCGCATCCTGCCGTCTGCCGCAAAATCCAGCCACGCGCCGGCG

GGCAGCGTGTCCGTCCGTTTGAAGCATTGGTACAAAAACCGGCGGGCGCGTTCAAAATCT

TCTTCCGGCAAATGTTTCTCCAGCAATTCATACGCTACTGCTTTTATTTGGCGGTATTCA

AGGCTGTCGAACCGGGTTTTAAAACCCATAGACTGCAAAAAATCGTTTCTGGCGGTTTTT

TGGATGCCTTGCGCGATTTCGTGTTGGCGGATGCTGTATTTGGATGAAACCTGATTGGCG

TGAAGGCGGTATTTGACCAAGGCTTCGGGATAATAAGCCAGCCTGCCCAATTTGCTGACA

TCGTACCAAAATTGGTAATCTTCCGCCCAATCCCGCTCGGTGTTGTAACGCAAACCGCCG

TCAATGACGCTGCGCCTCATAATCATCGTGTTGTTGTGTATGGGGTTGCCGAAAGGGAAA

AAGTCGGCAATGTCTTCGTGTCGGGTCGGTTTTTTCCAAATTTTGCCGTGTTCGTGGTGC

CGCGCCAGCCGGTTGCCGTCCTTTTCTTCCGACAAAACTTCCAGCCACGCACCCATCGCG

ATGATGCTGCGGTCTTTTTCCATCTCACCCACGATTTTCTCAATCCAGTCGGGGCGGCA

ATATCGTCTGCATCGGTGCGCGCAATATATTCCCCCCCCCCCCCCGACTTTGCCAATTCA

TCCAGCCCGATGTTTAAAGAGGGAATCAGACCGGAATTGCGCGGCTGCGCGAGGATGCGG

ATGCGGCCGTCCTGTTCTTGGAAACGCTGGGCAATGGCAAGCGTACCGTCCGTCGAGCCG

TCATCGACAATCAAAATATCCAAGTTGCGCCAAGTTTGATTCACGACGGCGGCTAATGAT

TGGGCGAAATATTTTTCTACGTTGTAGGCGCAAATCAATACGCTGACTAAAGGCTGCAAT

TTATTCTCCCGATAGGCACGATGCCGTCTGAAGGCTTCAGACGGCATATGtatatctcct tcttgaaTTCTAACAATTGATTGAATGTATGCAAATAAATGCATACACCATAGGTGTGGT

TTAATTTGATGCCCTTTTTCAGGGCTGGAATGTGTAAGAGCGGGGTTATTTATGCTGTTG

TTTTTTTGTTACTCGGGAAGGGCTTTACCTCTTCCGCATAAACGCTTCCATCAGCGTTTA

TAGTTAAAAAAATCTTTCGGAACTGGTTTTGCGCTTACCCCAACCAACAGGGGATTTGCT

GCTTTCCATTGAGCCTGTTTCTCTGCGCGACGTTCGCGGCGGCGTGTTTGTGCATCCATC

TGGATTCTCCTGTCAGTTAGCTTTGGTGGTGTGTGGCAGTTGTAGTCCTGAACGAAAACC

CCCCGCGATTGGCACATTGGCAGCTAATCCGGAATCGCACTTACGGCCAATGCTTCGTTT

CGTATCACACACCCCAAAGCCTTCTGCTTTGAATGCTGCCCTTCTTCAGGGCTTAATTTT

TAAGAGCGTCACCTTCATGGTGGTCAGTGCGTCCTGCTGATGTGCTCAGTATCACCGCCA

GTGGTATTTATGTCAACACCGCCAGAGATAATTTATCACCGCAGATGGTTATCTGTATGT

TTTTTATATGAATTTATTTTTTGCAGGGGGGCATTGTTTGGTAGGTGAGAGATCAATTCT

GCATTAATGAATCGGCCAACGCGCGGGGAGAGGCGGTTTGCGTATTGGGCGCTCTTCCGC

TTCCTCGCTCACTGACTCGCTGCGCTCGGTCGTTCGGCTGCGGCGAGCGGTATCAGCTCA

CTCAAAGGCGGTAATACGGTTATCCACAGAATCAGGGGATAACGCAGGAAAGAACATGTG

AGCAAAAGGCCAGCAAAAGGCCAGGAACCGTAAAAAGGCCGCGTTGCTGGCGTTTTTCCA

TAGGCTCCGCCCCCCTGACGAGCATCACAAAAATCGACGCTCAAGTCAGAGGTGGCGAAA

CCCGACAGGACTATAAAGATACCAGGCGTTTCCCCCTGGAAGCTCCCTCGTGCGCTCTCC

TGTTCCGACCCTGCCGCTTACCGGATACCTGTCCGCCTTTCTCCCTTCGGGAAGCGTGGC

GCTTTCTCATAGCTCACGCTGTAGGTATCTCAGTTCGGTGTAGGTCGTTCGCTCCAAGCT

GGGCTGTGTGCACGAACCCCCCGTTCAGCCCGACCGCTGCGCCTTATCCGGTAACTATCG
```

-continued
```
TCTTGAGTCCAACCCGGTAAGACACGACTTATCGCCACTGGCAGCAGCCACTGGTAACAG
GATTAGCAGAGCGAGGTATGTAGGCGGTGCTACAGAGTTCTTGAAGTGGTGGCCTAACTA
CGGCTACACTAGAAGGACAGTATTTGGTATCTGCGCTCTGCTGAAGCCAGTTACCTTCGG
AAAAAGAGTTGGTAGCTCTTGATCCGGCAAACAAACCACCGCTGGTAGCGGTGGTTTTTT
TGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGAG
ATTATCAAAAGGATCTTCACCTAGATCCTTTTAAATTAAAAATGAAGTTTTAAATCAAT
CTAAAGTATATATGAGTAAACTTGGTCTGACAGTTACCAATGCTTAATCAGTGAGGCACC
TATCTCAGCGATCTGTCTATTTCGTTCATCCATAGTTGCCTGACTCCCCGTCGTGTAGAT
AACTACGATACGGGAGGGCTTACCATCTGGCCCCAGTGCTGCAATGATACCGCGAGACCC
ACGCTCACCGGCTCCAGATTTATCAGCAATAAACCAGCCAGCCGGAAGGGCCGAGCGCAG
AAGTGGTCCTGCAACTTTATCCGCCTCCATCCAGTCTATTAATTGTTGCCGGGAAGCTAG
AGTAAGTAGTTCGCCAGTTAATAGTTTGCGCAACGTTGTTGCCATTGCTACAGGCATCGT
GGTGTCACGCTCGTCGTTTGGTATGGCTTCATTCAGCTCCGGTTCCCAACGATCAAGGCG
AGTTACATGATCCCCCATGTTGTGCAAAAAAGCGGTTAGCTCCTTCGGTCCTCCGATCGT
TGTCAGAAGTAAGTTGGCCGCAGTGTTATCACTCATGGTTATGGCAGCACTGCATAATTC
TCTTACTGTCATGCCATCCGTAAGATGCTTTTCTGTGACTGGTGAGTACTCAACCAAGTC
ATTCTGAGAATAGTGTATGCGGCGACCGAGTTGCTCTTGCCCGGCGTCAATACGGGATAA
TACCGCGCCACATAGCAGAACTTTAAAAGTGCTCATCATTGGAAAACGTTCTTCGGGGCG
AAAACTCTCAAGGATCTTACCGCTGTTGAGATCCAGTTCGATGTAACCCACTCGTGCACC
CAACTGATCTTCAGCATCTTTTACTTTCACCAGCGTTTCTGGGTGAGCAAAAACAGGAAG
GCAAAATGCCGCAAAAAAGGGAATAAGGGCGACACGGAAATGTTGAATACTCATACTCTT
CCTTTTTCAATATTATTGAAGCATTTATCAGGGTTATTGTCTCATGAGCGGATACATATT
TGAATGTATTTAGAAAAATAAACAAATAGGGGTTCCGCGCACATTTCCCCGAAAAGTGCC
ACCTGACGTCTAAGAAACCATTATTATCATGACATTAACCTATAAAAATAGGCGTATCAC
GAGGCCCTTTCGTC
```
                                                        SEQ ID NO: 5
>pG317, complete sequence.
```
GTACCCAGCTTTTGTTCCCTTTAGTGAGGGTTAATTGCGCGCTTGGCGTAATCATGGTCA
TAGCTGTTTCCTGTGTGAAATTGTTATCCGCTCACAATTCCACACAACATACGAGCCGGA
AGCATAAAGTGTAAAGCCTGGGGTGCCTAATGAGTGAGCTAACTCACATTAATTGCGTTG
CGCTCACTGCCCGCTTTCCAGTCGGGAAACCTGTCGTGCCAGCTGCATTAATGAATCGGC
CAACGCGCGGGGAGAGGCGGTTTGCGTATTGGGCGCATGCATAAAAACTGTTGTAATTCA
TTAAGCATTCTGCCGACATGGAAGCCATCACAAACGGCATGATGAACCTGAATCGCCAGC
GGCATCAGCACCTTGTCGCCTTGCGTATAATATTTGCCCATGGTGAAAACGGGGGCGAAG
AAGTTGTCCATATTGGCCACGTTTAAATCAAAACTGGTGAAACTCACCCAGGGATTGGCT
GAGACGAAAAACATATTCTCAATAAACCCTTTAGGGAAATAGGCCAGGTTTTCACCGTAA
CACGCCACATCTTGCGAATATATGTGTAGAAACTGCCGGAAATCGTCGTGGTATTCACTC
CAGAGCGATGAAAACGTTTCAGTTTGCTCATGGAAAACGGTGTAACAAGGGTGAACACTA
TCCCATATCACCAGCTCACCGTCTTTCATTGCCATACGGAATTCCGGATGAGCATTCATC
AGGCGGGCAAGAATGTGAATAAAGGCCGGATAAAACTTGTGCTTATTTTCTTTACGGTC
TTTAAAAGGCCGTAATATCCAGCTGAACGGTCTGGTTATAGGTACATTGAGCAACTGAC
```

-continued

```
TGAAATGCCTCAAAATGTTCTTTACGATGCCATTGGGATATATCAACGGTGGTATATCCA
GTGATTTTTTTCTCCATTTTAGCTTCCTTAGCTCCTGAAAATCTCGATAACTCAAAAAAT
ACGCCCGGTAGTGATCTTATTTCATTATGGTGAAAGTTGGAACCTCTTACGTGCCGATCA
ACGTCTCATTTTCGCCAAAAGTTGGCCCAGGGCTTCCCGGTATCAACAGGGACACCAGGA
TTTATTTATTCTGCGAAGTGATCTTCCGTCACAGGTATTTATTCGAAGACGAAAGGGCCT
CGTGATACGCCTATTTTTATAGGTTAATGTCATGATAATAATGGTTTCTTAGACGTCAGG
TGGCACTTTTCGGGGAAATGTGCGCGCCCGCGTTCCTGCTGGCGCTGGGCCTGTTTCTGG
CGCTGGACTTCCCGCTGTTCCGTCAGCAGCTTTTCGCCCACGGCCTTGATGATCGCGGCG
GCCTTGGCCTGCATATCCCGATTCAACGGCCCCAGGGCGTCCAGAACGGGCTTCAGGCGC
TCCCGAAGGTCTCGGGCCGTCTCTTGGGCTTGATCGGCCTTCTTGCGCATCTCACGCGCT
CCTGCGGCGGCCTGTAGGGCAGGCTCATACCCCTGCCGAACCGCTTTTGTCAGCCGGTCG
GCCACGGCTTCCGGCGTCTCAACGCGCTTTGAGATTCCCAGCTTTTCGGCCAATCCCTGC
GGTGCATAGGCGCGTGGCTCGACCGCTTGCGGGCTGATGGTGACGTGGCCCACTGGTGGC
CGCTCCAGGGCCTCGTAGAACGCCTGAATGCGCGTGTGACGTGCCTTGCTGCCCTCGATG
CCCCGTTGCAGCCCTAGATCGGCCACAGCGGCCGCAAACGTGGTCTGGTCGCGGGTCATC
TGCGCTTTGTTGCCGATGAACTCCTTGGCCGACAGCCTGCCGTCCTGCGTCAGCGGCACC
ACGAACGCGGTCATGTGCGGGCTGGTTTCGTCACGGTGGATGCTGGCCGTCACGATGCGA
TCCGCCCCGTACTTGTCCGCCAGCCACTTGTGCGCCTTCTCGAAGAACGCCGCCTGCTGT
TCTTGGCTGGCCGACTTCCACCATTCCGGGCTGGCCGTCATGACGTACTCGACCGCCAAC
ACAGCGTCCTTGCGCCGCTTCTCTGGCAGCAACTCGCGCAGTCGGCCCATCGCTTCATCG
GTGCTGCTGGCCGCCCAGTGCTCGTTCTCTGGCGTCCTGCTGGCGTCAGCGTTGGGCGTC
TCGCGCTCGCGGTAGGCGTGCTTGAGACTGGCCGCCACGTTGCCCATTTTCGCCAGCTTC
TTGCATCGCATGATCGCGTATGCCGCCATGCCTGCCCCTCCCTTTTGGTGTCCAACCGGC
TCGACGGGGGCAGCGCAAGGCGGTGCCTCCGGCGGGCCACTCAATGCTTGAGTATACTCA
CTAGACTTTGCTTCGCAAAGTCGTGACCGCCTACGGCGGCTGCGGCGCCCTACGGGCTTG
CTCTCCGGGCTTCGCCCTGCGCGGTCGCTGCGCTCCCTTGCCAGCCCGTGGATATGTGGA
CGATGGCCGCGAGCGGCCACCGGCTGGCTCGCTTCGCTCGGCCCGTGGACAACCCTGCTG
GACAAGCTGATGGACAGGCTGCGCCTGCCCACGAGCTTGACCACAGGGATTGCCCACCGG
CTACCCAGCCTTCGACCACATACCCACCGGCTCCAACTGCGCGGCCTGCGGCCTTGCCCC
ATCAATTTTTTAATTTTCTCTGGGGAAAAGCCTCCGGCCTGCGGCCTGCGCGCTTCGCT
TGCCGGTTGGACACCAAGTGGAAGGCGGGTCAAGGCTCGCGCAGCGACCGCGCAGCGGCT
TGGCCTTGACGCGCCTGGAACGACCCAAGCCTATGCGAGTGGGGGCAGTCGAAGGCGAAG
CCCGCCCGCCTGCCCCCCGAGCCTCACGGCGGCGAGTGCGGGGGTTCCAAGGGGGCAGCG
CCACCTTGGGCAAGGCCGAAGGCCGCGCAGTCGATCAACAAGCCCCGGAGGGGCCACTTT
TTGCCGGAGGGGAGCGCGCCGAAGGCGTGGGGGAACCCCGCAGGGGTGCCCTTCTTTG
GGCACCAAAGAACTAGATATAGGGCGAAATGCGAAAGACTTAAAAATCAACAACTTAAAA
AAGGGGGGTACGCAACAGCTCATTGCGGCACCCCCCGCAATAGCTCATTGCGTAGGTTAA
AGAAAATCTGTAATTGACTGCCACTTTTACGCAACGCATAATTGTTGTCGCGCTGCCGAA
AAGTTGCAGCTGATTGCGCATGGTGCCGCAACCGTGCGGCACCCTACCGCATGGAGATAA
GCATGGCCACGCAGTCCAGAGAAATCGGCATTCAAGCCAAGAACAAGCCCGGTCACTGGG
```

-continued

```
TGCAAACGGAACGCAAAGCGCATGAGGCGTGGGCCGGGCTTATTGCGAGGAAACCCACGG

CGGCAATGCTGCTGCATCACCTCGTGGCGCAGATGGGCCACCAGAACGCCGTGGTGGTCA

GCCAGAAGACACTTTCCAAGCTCATCGGACGTTCTTTGCGGACGGTCCAATACGCAGTCA

AGGACTTGGTGGCCGAGCGCTGGATCTCCGTCGTGAAGCTCAACGGCCCCGGCACCGTGT

CGGCCTACGTGGTCAATGACCGCGTGGCGTGGGGCCAGCCCCGCGACCAGTTGCGCCTGT

CGGTGTTCAGTGCCGCCGTGGTGGTTGATCACGACGACCAGGACGAATCGCTGTTGGGGC

ATGGCGACCTGCGCCGCATCCCGACCCTGTATCCGGGCGAGCAGCAACTACCGACCGGCC

CCGGCGAGGAGCCGCCCAGCCAGCCCGGCATTCCGGGCATGGAACCAGACCTGCCAGCCT

TGACCGAAACGGAGGAATGGGAACGGCGCGGGCAGCAGCGCCTGCCGATGCCCGATGAGC

CGTGTTTTCTGGACGATGGCGAGCCGTTGGAGCCGCCGACACGGGTCACGCTGCCGCGCC

GGTAGCACTTGGGTTGCGCAGCAACCCGTAAGTGCGCTGTTCCAGACTATCGGCTGTAGC

CGCCTCGCCGCCCTATACCTTGTCTGCCTCCCCGCGTTGCGTCGCGGTGCATGGAGCCGG

GCCACCTCGACCTGAATGGAAGCCGGCGGCACCTCGCTAACGGATTCACCGTTTTTATCA

GGCTCTGGGAGGCAGAATAAATGATCATATCGTCAATTATTACCTCCACGGGGAGAGCCT

GAGCAAACTGGCCTCAGGCATTTGAGAAGCACACGGTCACACTGCTTCCGGTAGTCAATA

AACCGGTAAACCAGCAATAGACATAAGCGGCTATTTAACGACCCTGCCCTGAACCGACGA

CCCGGTCGAATTTGCTTTCGAATTTCTGCCATTCATCCGCTTATTATCACTTATTCAGGC

GTAGCACCAGGCGTTTAAGGGCACCAATAACTGCCTTAAAAAAATTACGCCCCGCCCTGC

CACTCATCGCAGTCGGCCTATTGGTTAAAAAATGAGCTGATTTAACAAAAATTTAACGCG

AATTTTAACAAAATATTAACGCTTACAATTTCCATTCGCCATTCAGGCTGCGCAACTGTT

GGGAAGGGCGATCGGTGCGGGCCTCTTCGCTATTACGCCAGCTGGCGAAAGGGGGATGTG

CTGCAAGGCGATTAAGTTGGGTAACGCCAGGGTTTTCCCAGTCACGACGTTGTAAAACGA

CGGCCAGTGAGCGCGCGTAATACGACTCACTATAGGGCGAATTGGAGCTCCACCGCGGTG

GCGGCCGCTCTAGAACTAGTGGATCCCCCGGGCTGCAGGAATTCGATATCAAGCTTATCG

ATACCGTCGACCTCGAGTTAAGTCTCTAATCGATTGTTTTCCAATGGAATGGTTATAAAA

TCTTTGGTTTTTAGTCTTGAAAATCTTCTAGGATTTTCTATGTAAGTTTTTGTATAAATA

TTATATTGCTTTAATAAATTTAATATATTTTTATTGCATTTTAAGGTTATTTTTTCCATA

TCTGTTCAACCTTTTTTAAATCCTCCAAACAGTCAATATCTAAACTTGAGCTTTCGTCCA

TTAAAAAATGCTTGGTTTTGCTTTGTAAAAAGCTAGGATTGTTTAAAAATTCTTTTATCT

TTAAAATATAAATTGCACCATTGCTCATATAAGTTTAGGCAATTTTTGCCTTGGCATAA

AAGGATATTCATCATTACAAATCCCTGCTAAATCGCCACAATCATTACAAACAAAGGCTT

TTAGAATTTTATTATCACATTCGCTTACGCTAATTAGGGCATTTGCATTGCTATTTTTAT

AAAGATTAAAAGCTTCATTAATATGAATATTTGTTCTTAGCGGTGAAGTGGGTTGTAAAA

AAACTACATCTTCATAATCTTTATAAAATTTTAGAGCATGTAACAGCACTTTATCGCTTG

TGGTATCATCTTGTGCAAGGCTAATTGGGCGTTTTAAAATATCAACATTTTGACTTTTTG

CATAATTTAAAATTTCATCACTATCACTGCTTACAACAACTTTACTAATGCTTTTAGCAT

TTAGTGCAGCTTTGATCGTGTAGTAAATTAAAGGTTTATTGTTTAATAAAACCAAATTTT

TATTTTTAATACCCTTTGAGCCACCACGAGCAGGGATTATTGCTAAGCTCATTTTATATC

CTTAAAAACTTTTTGTGTGCTGAGTTTAAAAAAAATCTCCGCTTTGTAAATATTCAAAAAA

TAATTTTGAGCTATCTAAAATCTCTAACTTAGCGCTAAATAAATCTTGTTTTTTATGAAT

AGTGTTAATAGCTTTTAGTATTTCATCACTATTTGCATTAACTTTTAGTGTATTTTCATT
```

```
GCCAAGTCTTCCATTTTGTCTTGAGCCAACTAAAATCCCTGCTGTTTTTAAGTATAAGGC

CTCTTTTAAAATACAACTTGAATTACCTATTATAAAATCAGCATTTTTTAACAAAGTTAT

AAAATACTCAAATCTAAGCGATGGAAAAAGCTTAAATCTAGGGTTATTTTTAAACTCTTC

ATAGCTTTGCAAGATTAATTCAAAACCTAAATCATTATTTGGATAAATAACAATATAATT

TTTATTACTTTGTATCAGTGCTTTTACTAAATTGTCTGCTTGATTTTTAATGCTAGTAAT

TTCAGTTGTAACAGGATGAAACATAAGCAAAGCGTAGTTTTCATAATTTATATCATAATA

TTTTTTTGCTTCGCTAAGTGAAATTTTATTATCGTTTAAAAGTTCTAAATCAGGCGAACC

TATGATAAAAATAGATTTTTCATCTTCTCCAAGCTGCATTAAACGCCTTTTTGCAAACTC

ATCATTTACTAAATGAATATGAGCTAGTTTTGATATAGCGTGGCGTAAGCTATCGTCAAT

AGTTCCTGAAATCTCTCCGCCTTCAATATGCGCTACTAAGATATTATTTAATGCTCCAAC

AATAGCTGCTGCTAAAGGCTCAATTCTATCTCCATGTACTACGATTAAATCAGGTTTTAG

CTCATTTGCATACCTTGAAAATCCATCAATTGTAGTAGCTAAAGCCTTATCAGTTTGATA

ATATTTATCATAATTTATAAATTCATAAATATTTTAAAGCCATTTTTATAAAGTTCTTT

AACTGTATAGCCAAAATTTTTACTTAAGTGCATTCCTGTTGCAAAGATGTAAAGTTCAAA

TTCGCTTGAGTTTTGCACCCTGTACATTAAAGATTTAATCTTAGAATAATCAGCCCTAGA

GCCTGTTATAAAAGGATTTTTTTCACGCAAAATCCTCATAGCTTAACTGAGCATCATTT

TCTATATCTCTTAATGCTTTTTGCCTAAAATATTTTCAAATTCAGCCGCACTAATTCCA

CCAAGTCCAGGTCTTTTAACCCAAATATTATCCATAGATAAAACTTCGCCTTTTTTAATA

TCTTTAATGCTAACTACACTTGCAAAGGCAAAATCAATTGTAACTTGTTCTTGTTTAGCC

GCTTTTTTACTTTCATTATTTCCTCTTATTATAGCCATTTGCTCACTTTGTATAATTAGC

TCTTTTAAAGCCTTTGTATCCATAGAACAAACTATATCAGGGCCACTTCTATGCATACTA

TCAGTAAAATGTCTTTCAAGCACACAAGCTCCAAGTACAACTGCACCTAAACACGCAAGA

TTATCTGTTGTGTGGTCGCTTAAGCCTACCATACAAGAAAATTCTTTTTTTAACTCAAGC

ATAGCGTTTAATCTTACAAGATTATGCGGGGTTGGGTAAAGATTGGTCGTGTGCATTAAA

ACAAAAGGAATTTCATTGTCTAATAAGATTTTTACAGTTGGTTTTATACTTTCAATACTA

TTCATTCCTGTGCTAACTATCATAGGCTTTTTAAAGGCTGCTATGTGTTTAATAAGCGGA

TAATTATTACACTCACCTGAACCAATCTTAAAAGCACTAACTCCCATATCTTCTAAGCGG

TTCGCACCTGCACGAGAAAAAGGTGTGCTAAGATAAACAAGACCTAATTTTTCTGTGTAT

TCTTTAAGTGCTAGCTCATCTTTATAATCCAAAGCACATTTTTGCATAATCTCATAAATG

CTTATTTTTGCATTACCAGGAATTACTTTTTTAGCGGCCTTACTCATCTCATCTTCAACA

ATATGAGTTTGATGCTTTATAATCTTAGCACCTGCGCTAAAGGCTGCATCTACCATAATT

TTAGCTAGTTCTAAACTGCCATTATGATTAATGCCTATTTCAGGTACGACTAAGGGTGCT

TTTTCTTCACTTATGATTATATTTTGTATTTTTATTTCTTTCATTTATTTTCCTCCTTAG
```

SEQ ID NO: 6
>pG315, complete sequence
```
CTAAATTGTAAGCGTTAATATTTTGTTAAAATTCGCGTTAAATTTTTGTTAAATCAGCTC

ATTTTTTAACCAATAGGCCGAAATCGGCAAAATCCCTTATAAATCAAAAGAATAGACCGA

GATAGGGTTGAGTGTTGTTCCAGTTTGGAACAAGAGTCCACTATTAAAGAACGTGGACTC

CAACGTCAAAGGGCGAAAAACCGTCTATCAGGGCGATGGCCCACTACGTGAACCATCACC

CTAATCAAGTTTTTTGGGGTCGAGGTGCCGTAAAGCACTAAATCGGAACCCTAAAGGGAG

CCCCCGATTTAGAGCTTGACGGGGAAAGCCGGCGAACGTGGCGAGAAAGGAAGGGAAGAA
```

-continued

```
AGCGAAAGGAGCGGGCGCTAGGGCGCTGGCAAGTGTAGCGGTCACGCTGCGCGTAACCAC

CACACCCGCCGCGCTTAATGCGCCGCTACAGGGCGCGTCCCATTCGCCATTCAGGCTGCG

CAACTGTTGGGAAGGGCGATCGGTGCGGGCCTCTTCGCTATTACGCCAGCTGGCGAAAGG

GGGATGTGCTGCAAGGCGATTAAGTTGGGTAACGCCAGGGTTTTCCCAGTCACGACGTTG

TAAAACGACGGCCAGTGAGCGCGCGTAATACGACTCACTATAGGGCGAATTGGAGCTCCA

CCGCGGTGGCGGCCGCTCTAGAACTAGTGGATCCCTAGACTGCAATACAAACACCTGTTT

CACAATTTGGCAGATCAGCCCAAAAAAGTACATTCTCTTCTTTTACAATACCTAGTTTTA

TCATTACTTGAACTAAAGGACTTCTCAAAGCAGTTTCACGATCAGTTATAGTTTCTGTCG

ATGTAAAAACTATAAATTTAATTTTTTCAGCTGGTATCGTGAAATATAAAGAGCTCGCTA

TACCAGCAACTGCATCAGGAAGCATATCTGTCATCATCAAAACTTCAAATGATATTTTTG

ATGGAATATCAACCATTGAAGGATAGTTTTGCATTATTAATGTATTAATGATACCGCCAC

CAGGGTGACCTTTGAAGAACAAATCATAACTATTGCCTAAATAATGTGGGCTCGATTCAT

TAATTGCATTATTAATGACATTAATTTGTTGTTTCGCATAATACTCTCTTTCATGGTTAC

CAGCCCATACAGTCGTACCTGTAAACACAAAGTTTGGTAAATTAGATGAATTATATTCAT

TTTGTAATTTTTGTTTGTCAAAATTAACAATCGATAAGAATAATTCTTGTTGTTTGCTAT

TGAATTTTTTGAAACCATCCCATTGCATTTGCTTTAAACTATCACCAATATAGTCTCGTA

ACTCATGTAATGATGGTTCTAAAGTTAAATAATCTTTTCTTAAAAAATGGTAGTTAGCTG

GATATAGTTTTTGCCAGTTATAAACAGATGATGTTCCTGTATTTGAAGTGTCTTCATTGA

TACCATTAATGACATCCTCAAGATAATCTTTACCAATTTTTAAATTATCTGTTTTATTTA

ATGTATCTCTCCAGTTATATAAATTTACATATTCTGCTGAACCATCATCATATAAATCTA

TATTTGTTACCGTAACGTTATTAAACGAATTTAATTCTTTTAGTATTGGCACTAAATTAT

CAAATGAATGAGCAGTGTTAGAGCTAAGTTTAACATTCAATCTATGCTTTGTTTGTGCTT

GCTTAACAATTTCTTGTACTAAGTCAGCTGGTGTATGGTTATTTATCAATGCAAACGATG

TAATATTTAACTCTTTCATTTGCTCATCAGTCGGAACTATTCTCCCCCAAGCTATATATC

TTTGTGCTGTAGGATTTTCTTCTTCCGATTTAATAATATCCATTAGCTGCTGAAGAGTTG

GAAGAGATGCATGATCAACATAAACCTCTAAAGATGGAGCCACTACGTTAATGTTACTT

TTGTTATATATTTTTCACCTTTATTACTAACACCATTAAAATCAAAGCAGTACTTTTCAT

CGTCATCTAATCGTGGCGCCACTACAGATAATGATATTGACTCTTTATTTTGTTCTGTTA

ATAGTTGTTGCGTACCACAAGTTTGTACCCAAGAGTGTTTTGTAAAAGAGATGTTTGATT

GATTAATTGGCTCTAAATTAACATACTCCTCATCAATAATAGTTTTATTAATATCATTTT

TAATAATAGATTGTGTATTTTCTTCTGACATggtctgtttcctcCTCGAGGGGGGCCCG

GTACCCAGCTTTTGTTCCCTTTAGTGAGGGTTAATTGCGCGCTTGGCGTAATCATGGTCA

TAGCTGTTTCCTGTGTGAAATTGTTATCCGCTCACAATTCCACACAACATACGAGCCGGA

AGCATAAAGTGTAAAGCCTGGGGTGCCTAATGAGTGAGCTAACTCACATTAATTGCGTTG

CGCTCACTGCCCGCTTTCCAGTCGGGAAACCTGTCGTGCCAGCTGCATTAATGAATCGGC

CAACGCGCGGGAGAGGCGGTTTGCGTATTGGGCGCTCTTCCGCTTCCTCGCTCACTGAC

TCGCTGCGCTCGGTCGTTCGGCTGCGGCGAGCGGTATCAGCTCACTCAAAGGCGGTAATA

CGGTTATCCACAGAATCAGGGGATAACGCAGGAAAGAACATGTGAGCAAAAGGCCAGCAA

AAGGCCAGGAACCGTAAAAAGGCCGCGTTGCTGGCGTTTTTCCATAGGCTCCGCCCCCCT

GACGAGCATCACAAAAATCGACGCTCAAGTCAGAGGTGGCGAAACCCGACAGGACTATAA

AGATACCAGGCGTTTCCCCCTGGAAGCTCCCTCGTGCGCTCTCCTGTTCCGACCCTGCCG
```

-continued

```
CTTACCGGATACCTGTCCGCCTTTCTCCCTTCGGGAAGCGTGGCGCTTTCTCATAGCTCA

CGCTGTAGGTATCTCAGTTCGGTGTAGGTCGTTCGCTCCAAGCTGGGCTGTGTGCACGAA

CCCCCCGTTCAGCCCGACCGCTGCGCCTTATCCGGTAACTATCGTCTTGAGTCCAACCCG

GTAAGACACGACTTATCGCCACTGGCAGCAGCCACTGGTAACAGGATTAGCAGAGCGAGG

TATGTAGGCGGTGCTACAGAGTTCTTGAAGTGGTGGCCTAACTACGGCTACACTAGAAGG

ACAGTATTTGGTATCTGCGCTCTGCTGAAGCCAGTTACCTTCGGAAAAAGAGTTGGTAGC

TCTTGATCCGGCAAACAAACCACCGCTGGTAGCGGTGGTTTTTTTGTTTGCAAGCAGCAG

ATTACGCGCAGAAAAAAAGGATCTCAAGAAGATCCTTTGATCTTTTCTACGGGGTCTGAC

GCTCAGTGGAACGAAAACTCACGTTAAGGGATTTTGGTCATGAGATTATCAAAAAGGATC

TTCACCTAGATCCTTTTAAATTAAAAATGAAGTTTTAAATCAATCTAAAGTATATATGAG

TAAACTTGGTCTGACAGTTACCAATGCTTAATCAGTGAGGCACCTATCTCAGCGATCTGT

CTATTTCGTTCATCCATAGTTGCCTGACTCCCCGTCGTGTAGATAACTACGATACGGGAG

GGCTTACCATCTGGCCCCAGTGCTGCAATGATACCGCGAGACCCACGCTCACCGGCTCCA

GATTTATCAGCAATAAACCAGCCAGCCGGAAGGGCCGAGCGCAGAAGTGGTCCTGCAACT

TTATCCGCCTCCATCCAGTCTATTAATTGTTGCCGGGAAGCTAGAGTAAGTAGTTCGCCA

GTTAATAGTTTGCGCAACGTTGTTGCCATTGCTACAGGCATCGTGGTGTCACGCTCGTCG

TTTGGTATGGCTTCATTCAGCTCCGGTTCCCAACGATCAAGGCGAGTTACATGATCCCCC

ATGTTGTGCAAAAAAGCGGTTAGCTCCTTCGGTCCTCCGATCGTTGTCAGAAGTAAGTTG

GCCGCAGTGTTATCACTCATGGTTATGGCAGCACTGCATAATTCTCTTACTGTCATGCCA

TCCGTAAGATGCTTTTCTGTGACTGGTGAGTACTCAACCAAGTCATTCTGAGAATAGTGT

ATGCGGCGACCGAGTTGCTCTTGCCCGGCGTCAATACGGGATAATACCGCGCCACATAGC

AGAACTTTAAAAGTGCTCATCATTGGAAAACGTTCTTCGGGGCGAAAACTCTCAAGGATC

TTACCGCTGTTGAGATCCAGTTCGATGTAACCCACTCGTGCACCCAACTGATCTTCAGCA

TCTTTTACTTTCACCAGCGTTTCTGGGTGAGCAAAAACAGGAAGGCAAAATGCCGCAAAA

AAGGGAATAAGGGCGACACGGAAATGTTGAATACTCATACTCTTCCTTTTTCAATATTAT

TGAAGCATTTATCAGGGTTATTGTCTCATGAGCGGATACATATTTGAATGTATTTAGAAA

AATAAACAAATAGGGGTTCCGCGCACATTTCCCCGAAAAGTGCCAC
```

SEQ ID NO: 7
```
CTCGAGgaggaaacagaccATG
```

SEQ ID NO: 8
```
CTCGAGgaaagaggggacaaactagATG
```

SEQ ID NO: 9
>pG345, complete sequence
```
CTAAATTGTAAGCGTTAATATTTTGTTAAAATTCGCGTTAAATTTTTGTTAAATCAGCTC

ATTTTTTAACCAATAGGCCGAAATCGGCAAAATCCCTTATAAATCAAAAGAATAGACCGA

GATAGGGTTGAGTGTTGTTCCAGTTTGGAACAAGAGTCCACTATTAAAGAACGTGGACTC

CAACGTCAAAGGGCGAAAAACCGTCTATCAGGGCGATGGCCCACTACGTGAACCATCACC

CTAATCAAGTTTTTTGGGGTCGAGGTGCCGTAAAGCACTAAATCGGAACCCTAAAGGGAG

CCCCCGATTTAGAGCTTGACGGGGAAAGCCGGCGAACGTGGCGAGAAAGGAAGGGAAGAA

AGCGAAAGGAGCGGGCGCTAGGGCGCTGGCAAGTGTAGCGGTCACGCTGCGCGTAACCAC

CACACCCGCCGCGCTTAATGCGCCGCTACAGGGCGCGTCCCATTCGCCATTCAGGCTGCG

CAACTGTTGGGAAGGGCGATCGGTGCGGGCCTCTTCGCTATTACGCCAGCTGGCGAAAGG
```

-continued

```
GGGATGTGCTGCAAGGCGATTAAGTTGGGTAACGCCAGGGTTTTCCCAGTCACGACGTTG

TAAAACGACGGCCAGTGAGCGCGCGTAATACGACTCACTATAGGGCGAATTGGAGCTCCA

CCGCGGTGGCGGCCGCTCTAGAACTAGTGGATCCCTAGACTGCAATACAAACACCTGTTT

CACAATTTGGCAGATCAGCCCAAAAAAGTACATTCTCTTCTTTTACAATACCTAGTTTTA

TCATTACTTGAACTAAAGGACTTCTCAAAGCAGTTTCACGATCAGTTATAGTTTCTGTCG

ATGTAAAAACTATAAATTTAATTTTTTCAGCTGGTATCGTGAAATATAAAGAGCTCGCTA

TACCAGCAACTGCATCAGGAAGCATATCTGTCATCATCAAAACTTCAAATGATATTTTTG

ATGGAATATCAACCATTGAAGGATAGTTTTGCATTATTAATGTATTAATGATACCGCCAC

CAGGGTGACCTTTGAAGAACAAATCATAACTATTGCCTAAATAATGTGGGCTCGATTCAT

TAATTGCATTATTAATGACATTAATTTGTTGTTTCGCATAATACTCTCTTTCATGGTTAC

CAGCCCATACAGTCGTACCTGTAAACACAAAGTTTGGTAAATTAGATGAATTATATTCAT

TTTGTAATTTTTGTTTGTCAAAATTAACAATCGATAAGAATAATTCTTGTTGTTTGCTAT

TGAATTTTTTGAAACCATCCCATTGCATTTGCTTTAAACTATCACCAATATAGTCTCGTA

ACTCATGTAATGATGGTTCTAAAGTTAAATAATCTTTTCTTAAAAAATGGTAGTTAGCTG

GATATAGTTTTTGCCAGTTATAAACAGATGATGTTCCTGTATTTGAAGTGTCTTCATTGA

TACCATTAATGACATCCTCAAGATAATCTTTACCAATTTTTAAATTATCTGTTTTATTTA

ATGTATCTCTCCAGTTATATAAATTTACATATTCTGCTGAACCATCATCATATAAATCTA

TATTTGTTACCGTAACGTTATTAAACGAATTTAATTCTTTTAGTATTGGCACTAAATTAT

CAAATGAATGAGCAGTGTTAGAGCTAAGTTTAACATTCAATCTATGCTTTGTTTGTGCTT

GCTTAACAATTTCTTGTACTAAGTCAGCTGGTGTATGGTTATTTATCAATGCAAACGATG

TAATATTTAACTCTTTCATTTGCTCATCAGTCGGAACTATTCTCCCCCAAGCTATATATC

TTTGTGCTGTAGGATTTTCTTCTTCCGATTTAATAATATCCATTAGCTGCTGAAGAGTTG

GAAGAGATGCATGATCAACATAAACCTCTAAAGATGGAGCCACTACGTTTAATGTTACTT

TTGTTATATATTTTTCACCTTTATTACTAACACCATTAAAATCAAAGCAGTACTTTTCAT

CGTCATCTAATCGTGGCGCCACTACAGATAATGATATTGACTCTTTATTTTGTTCTGTTA

ATAGTTGTTGCGTACCACAAGTTTGTACCCAAGAGTGTTTTGTAAAAGAGATGTTTGATT

GATTAATTGGCTCTAAATTAACATACTCCTCATCAATAATAGTTTTATTAATATCATTTT

TAATAATAGATTGTGTATTTTCTTCTGACATctagtttgtccctctttcCTCGAGGGGG

GGCCCGGTACCCAGCTTTTGTTCCCTTTAGTGAGGGTTAATTGCGCGCTTGGCGTAATCA

TGGTCATAGCTGTTTCCTGTGTGAAATTGTTATCCGCTCACAATTCCACACAACATACGA

GCCGGAAGCATAAAGTGTAAAGCCTGGGGTGCCTAATGAGTGAGCTAACTCACATTAATT

GCGTTGCGCTCACTGCCCGCTTTCCAGTCGGGAAACCTGTCGTGCCAGCTGCATTAATGA

ATCGGCCAACGCGCGGGGAGAGGCGGTTTGCGTATTGGGCGCTCTTCCGCTTCCTCGCTC

ACTGACTCGCTGCGCTCGGTCGTTCGGCTGCGGCGAGCGGTATCAGCTCACTCAAAGGCG

GTAATACGGTTATCCACAGAATCAGGGGATAACGCAGGAAAGAACATGTGAGCAAAAGGC

CAGCAAAAGGCCAGGAACCGTAAAAAGGCCGCGTTGCTGGCGTTTTTCCATAGGCTCCGC

CCCCCTGACGAGCATCACAAAAATCGACGCTCAAGTCAGAGGTGGCGAAACCCGACAGGA

CTATAAAGATACCAGGCGTTTCCCCCTGGAAGCTCCCTCGTGCGCTCTCCTGTTCCGACC

CTGCCGCTTACCGGATACCTGTCCGCCTTTCTCCCTTCGGGAAGCGTGGCGCTTTCTCAT

AGCTCACGCTGTAGGTATCTCAGTTCGGTGTAGGTCGTTCGCTCCAAGCTGGGCTGTGTG

CACGAACCCCCCGTTCAGCCCGACCGCTGCGCCTTATCCGGTAACTATCGTCTTGAGTCC
```

-continued

```
AACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACT
AGAAGGACAGTATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTTGTTTGCAAG
CAGCAGATTACGCGCAGAAAAAAAGGATCTCAAGAAGATCCTTTGATCTTTTCTACGGGG
TCTGACGCTCAGTGGAACGAAAACTCACGTTAAGGGATTTTGGTCATGAGATTATCAAAA
AGGATCTTCACCTAGATCCTTTTAAATTAAAAATGAAGTTTTAAATCAATCTAAAGTATA
TATGAGTAAACTTGGTCTGACAGTTACCAATGCTTAATCAGTGAGGCACCTATCTCAGCG
ATCTGTCTATTTCGTTCATCCATAGTTGCCTGACTCCCCGTCGTGTAGATAACTACGATA
CGGGAGGGCTTACCATCTGGCCCCAGTGCTGCAATGATACCGCGAGACCCACGCTCACCG
GCTCCAGATTTATCAGCAATAAACCAGCCAGCCGGAAGGGCCGAGCGCAGAAGTGGTCCT
GCAACTTTATCCGCCTCCATCCAGTCTATTAATTGTTGCCGGGAAGCTAGAGTAAGTAGT
TCGCCAGTTAATAGTTTGCGCAACGTTGTTGCCATTGCTACAGGCATCGTGGTGTCACGC
TCGTCGTTTGGTATGGCTTCATTCAGCTCCGGTTCCCAACGATCAAGGCGAGTTACATGA
TCCCCCATGTTGTGCAAAAAAGCGGTTAGCTCCTTCGGTCCTCCGATCGTTGTCAGAAGT
AAGTTGGCCGCAGTGTTATCACTCATGGTTATGGCAGCACTGCATAATTCTCTTACTGTC
ATGCCATCCGTAAGATGCTTTTCTGTGACTGGTGAGTACTCAACCAAGTCATTCTGAGAA
TAGTGTATGCGGCGACCGAGTTGCTCTTGCCCGGCGTCAATACGGGATAATACCGCGCCA
CATAGCAGAACTTTAAAAGTGCTCATCATTGGAAAACGTTCTTCGGGGCGAAAACTCTCA
AGGATCTTACCGCTGTTGAGATCCAGTTCGATGTAACCCACTCGTGCACCCAACTGATCT
TCAGCATCTTTTACTTTCACCAGCGTTTCTGGGTGAGCAAAAACAGGAAGGCAAAATGCC
GCAAAAAAGGGAATAAGGGCGACACGGAAATGTTGAATACTCATACTCTTCCTTTTTCAA
TATTATTGAAGCATTTATCAGGGTTATTGTCTCATGAGCGGATACATATTTGAATGTATT
TAGAAAAATAAACAAATAGGGGTTCCGCGCACATTTCCCCGAAAAGTGCCAC
```

```
                                                                SEQ ID NO: 10
CTTTattaaacctactATG
```

```
                                                                SEQ ID NO: 11
CTTTcttcaacctactATG
```

```
                                                                SEQ ID NO: 12
>pEC3'-(T7)GlmS-(T7)NagC-purA_(pG356)
TCGCGCGTTTCGGTGATGACGGTGAAAACCTCTGACACATGCAGCTCCCGGAGACGGTCA
CAGCTTGTCTGTAAGCGGATGCCGGGAGCAGACAAGCCCGTCAGGGCGCGTCAGCGGGTG
TTGGCGGGTGTCGGGGCTGGCTTAACTATGCGGCATCAGAGCAGATTGTACTGAGAGTGC
ACCATATATGCGGTGTGAAATACCGCACAGATGCGTAAGGAGAAAATACCGCATCAGGCG
CCactagtGTTGAGGAAAACGATTGGCTGAACAAAAAACAGACTGATCGAGGTCATTTTT
GAGTGCAAAAAGTGCTGTAACTCTGAAAAAGCGATGGTAGAATCCATTTTTAAGCAAACG
GTGATTTTGAAAAATGGGTAACAACGTCGTCGTACTGGGCACCCAATGGGGTGACGAAGG
TAAAGGTAAGATCGTCGATCTTCTGACTGAACGGGCTAAATATGTTGTACGCTACCAGGG
CGGTCACAACGCAGGCCATACTCTCGTAATCAACGGTGAAAAAACCGTTCTCCATCTTAT
TCCATCAGGTATTCTCCGCGAGAATGTAACCAGCATCATCGGTAACGGTGTTGTGCTGTC
TCCGGCCGCGCTGATGAAAGAGATGAAAGAACTGGAAGACCGTGGCATCCCCGTTCGTGA
GCGTCTGCTGCTGTCTGAAGCATGTCCGCTGATCCTTGATTATCACGTTGCGCTGGATAA
```

```
CGCGCGTGAGAAAGCGCGTGGCGCGAAAGCGATCGGCACCACCGGTCGTGGTATCGGGCC

TGCTTATGAAGATAAAGTAGCACGTCGCGGTCTGCGTGTTGGCGACCTTTTCGACAAAGA

AACCTTCGCTGAAAAACTGAAAGAAGTGATGGAATATCACAACTTCCAGTTGGTTAACTA

CTACAAAGCTGAAGCGGTTGATTACCAGAAAGTTCTGGATGATACGATGGCTGTTGCCGA

CATCCTGACTTCTATGGTGGTTGACGTTTCTGACCTGCTCGACCAGGCGCGTCAGCGTGG

CGATTTCGTCATGTTTGAAGGTGCGCAGGGTACGCTGCTGGATATCGACCACGGTACTTA

TCCGTACGTAACTTCTTCCAACACCACTGCTGGTGGCGTGGCGACCGGTTCCGGCCTGGG

CCCGCGTTATGTTGATTACGTTCTGGGTATCCTCAAAGCTTACTCCACTCGTGTAGGTGC

AGGTCCGTTCCCGACCGAACTGTTTGATGAAACTGGCGAGTTCCTCTGCAAGCAGGGTAA

CGAATTCGGCGCAACTACGGGCGTCGTCGTCGTACCGGCTGGCTGGACACCGTTGCCGT

TCGTCGTGCGGTACAGCTGAACTCCCTGTCTGGCTTCTGCCTGACTAAACTGGACGTTCT

GGATGGCCTGAAAGAGGTTAAACTCTGCGTGGCTTACCGTATGCCGGATGGTCGCGAAGT

GACTACCACTCCGCTGGCAGCTGACGACTGGAAAGGTGTAGAGCCGATTTACGAAACCAT

GCCGGGCTGGTCTGAATCCACCTTCGGCGTGAAAGATCGTAGCGGCCTGCCGCAGGCGGC

GCTGAACTATATCAAGCGTATTGAAGAGCTGACTGGTGTGCCGATCGATATCATCTCTAC

CGGTCCGGATCGTACTGAAACCATGATTCTGCGCGACCCGTTCGACGCGTAATTCTGGTA

CGCCTGGCAGATATTTTGCCTGCCGGGCGAACAGTGTGATACATTGCTGTGTCGGGTAAG

CCATTACGCTATCCGACACAGTGTTAAATCCTCGCTTTTTTCCTTCCCCagatctGGCGC

CATTCGCCATTCAGGCTGCGCAACTGTTGGGAAGGGCGATCGGTGCGGGCCTCTTCGCTA

TTACGCCAGCTGGCGAAAGGGGGATGTGCTGCAAGGCGATTAAGTTGGGTAACGCCAGGG

TTTTCCCAGTCACGACGTTGTAAAACGACGGCCAGTGCCAAGCTTACTGCTCACAAGAAA

AAAGGCACGTCATCTGACGTGCCTTTTTTATTTGTACTACCCTGTACGATTACTGCAGGT

CGACTTAATTTTCCAGCAAATGCTGGAGCAAAATACCGTTGAGCATGGCGCGTTTTACCA

GCGCAAAAGCGCCGATTGCCGAGCGGTGATCCAGCTCAGAACGTACCACCGGCAGATTAG

TGCGAAACGCCTTCAGCGCCTGGGTATTAATGCAGCTTTCAATAGCAGGGAGCAGCACTT

TATCGGCTTCGGTGATTTCACCGGCAATAACAATTTTTTGCGGATTAAATAAGTTGATAG

CAATGGCGATGGTTTTACCCAGATGACGACCGACATACTCAATTACTTCCGACGCCAGAC

TATCGCCTTTGTTCGCGGCTTTGCAGATAGTTTTGATGGTGCAGTCGTCCAGCGGCACGC

GGCTCTGGTAGCCCTGCTTTAACAGATTCAACACCCGTTGTTCAATGGCAGCGTTGGCAG

CGATAGTTTCCAGGCAGCCAAAGTTGCCGCAGTGGCAGCGTTCACCCAGCGGTTCGACCT

GAATATGGCCAATTTCACCGACGTTGCCGTTGCGGCCAATAAAAATGCGCCCGTTAGAGA

TAATCCCGGCCCCGGTTCCGCGATGGACACGCACCAGAATGGAGTCTTCGCAATCCTGAC

TTGCACCGAAGTAGTGCTCCGCCAGCGCCAGACTACGGATATCGTGACCAACGAAACAGG

TCACTTTAAAACGTTCTTCCAGAGCTTCTACCAGCCCCCAGTTTTCTACCTGAATATGCG

GCATGTAATGAATTTTGCCGCTGTCCGGGTCAACAAGCCCTGGCAGGATCACCGAAATCG

CGATCAGCTCGCGCAGTTTGCGCTGGTAGCTATCAATAAACTGAGCAATGGCATTCAACA

GGGCATGTTCCAGCGTTTGCTGGGTACGTTCCGGCAGCGGGTAATGTTCTTCTGCCAGCA

CTTTGCTGCTGAGATCAAACAGAGTGATGGTGGCGTCATGACGACCAAGCCGTACGCCGA

TTGCGTGGAAATTGCGGGTTTCGGTGACGATGGAGATAGCGCGGCGGCCCCCGGTGGAGG

CCTGCTGATCAACTTCTTTGATCAGCCCGCGTTCGATAAGCTGACGCGTAATTTTGGTTA

CGCTGGCGGGGGCAAGCTGGCTTTGCTCGGCAATCTGAATCCGCGAGATTGGCCCGTACT
```

-continued

```
GGTCAATCAGGCGATAAACCGCCGCGCTGTTAAGCTGTTTTACGAGATCAACATTACCTA
TCTGAGCTTGTCCGCCTGGTGTCATATGTATATCTCCTTCTTgtcgacTCTAGATGCATG
CTCGAGATTACTCAACCGTAACCGATTTTGCCAGGTTACGCGGCTGGTCAACGTCGGTGC
CTTTGATCAGCGCGACATGGTAAGCCAGCAGCTGCAGCGGAACGGTGTAGAAGATCGGTG
CAATCACCTCTTCCACATGCGGCATCTCGATGATGTGCATGTTATCGCTACTTACAAAAC
CCGCATCCTGATCGGCGAAGACATACAACTGACCGCCACGCGCGCGAACTTCTTCAATGT
TGGATTTCAGTTTTTCCAGCAATTCGTTGTTCGGTGCAACAACAATAACCGGCATATCGG
CATCAATTAGCGCCAGCGGACCGTGTTTCAGTTCGCCAGCAGCGTAGGCTTCAGCGTGAA
TGTAAGAGATCTCTTTCAACTTCAATGCGCCTTCCAGCGCGATTGGGTACTGATCGCCAC
GGCCCAGGAACAGCGCGTGATGTTTGTCAGAGAAATCTTCTGCCAGCGCTTCAATGCGTT
TGTCCTGAGACAGCATCTGCTCAATACGGCTCGGCAGCGCCTGCAGACCATGCACGATGT
CATGTTCAATGGAGGCATCCAGACCTTTCAGGCGAGACAGCTTCGCCACCAGCATCAACA
GCACAGTTAACTGAGTGGTGAATGCTTTAGTGGATGCCACGCCGATTTCTGTACCCGCGT
TGGTCATTAGCGCCAGATCGGATTCGCGCACCAGAGAAGAACCCGGAACGTTACAGATTG
CCAGTGAACCAAGGTAACCCAGCTCTTTCGACAGACGCAGGCCAGCCAGGGTATCCGCGG
TTTCGCCAGACTGTGACAAGGTGATCATCAGGCTGTTACGACGCACGGCAGATTTGCGAT
AGCGGAATTCAGAGGCGATTTCGACGTCGCACGGAATACCTGCTAGCGATTCAAACCAGT
AGCGGGAAACCATACCGGAGTTATAAGAAGTACCACAGGCGAGGATCTGAATATGCTCAA
CCTTCGACAGCAGTTCGTCGGCGTTCGGTCCCAGCTCGCTTAAATCAACCTGACCGTGGC
TGATGCGTCCGGTAAGGGTGTTTTTGATCGCGTTCGGCTGTTCGTAGATCTCTTTCTGCA
TGTAGTGACGGTAAATGCCTTTATCGCCCGCGTCATATTGCAGATTGGATTCGATATCCT
GACGTTTTACTTCCGCGCCAGTTTTATCGAAGATGTTTACCGAACGGCGAGTGATTTCCG
CAATATCGCCCTCTTCAAGGAAGATAAAGCGACGGGTCACCGGCAACAGCGCCAGCTGGT
CAGAAGCGATAAAGTTTTCGCCCATCCCCAGGCCAATCACCAGCGGACTACCAGAACGTG
CCGCCAGCAGGGTATCCGGGTGACGGGAGTCCATGATCACTGTACCGTACGCACCACGCA
GCTGCGGGATAGCACGCAGAACGGCCTCACGCAGAGTCCCGCCTTGTTTCAGCTCCCAGT
TCACCAGATGGGCAATCACTTCGGTGTCGGTTTCAGAAACGAAGGTATAGCCACGCGCTT
TTAGCTCTTCACGCAGCGGTTCATGGTTTTCGATGATGCCGTTATGCACCACCACAATGT
GTTCAGAAACATGCGGATGCGCATTCACTTCTGAAGGTTCACCGTGGGTCGCCCAGCGAG
TGTGAGCAATACCAGTGCCGCCATGCAGAGGATGTTCTTCCGCTGCCTGTGCCAGCATCT
GGACTTTACCGAGGCGACGCAGGCGGGTCATATGACCTTCTGCATCAACAACGGCCAGAC
CGGCAGAGTCATATCCGCGGTATTCCAGACGACGTAAACCTTCAAGAAGGATTTCTGCTA
CATCACGTTGCGCGATCGCGCCAACAATTCCACACATATGtatatctccttcttgaaTTC
TAACAATTGATTGAATGTATGCAAATAAATGCATACACCATAGGTGTGGTTTAATTTGAT
GCCCTTTTTCAGGGCTGGAATGTGTAAGAGCGGGGTTATTTATGCTGTTGTTTTTTTGTT
ACTCGGGAAGGGCTTTACCTCTTCCGCATAAACGCTTCCATCAGCGTTTATAGTTAAAAA
AATCTTTCGGAACTGGTTTTGCGCTTACCCCAACCAACAGGGGATTTGCTGCTTTCCATT
GAGCCTGTTTCTCTGCGCGACGTTCGCGGCGGCGTGTTTGTGCATCCATCTGGATTCTCC
TGTCAGTTAGCTTTGGTGGTGTGTGGCAGTTGTAGTCCTGAACGAAAACCCCCCGCGATT
GGCACATTGGCAGCTAATCCGGAATCGCACTTACGGCCAATGCTTCGTTTCGTATCACAC
```

-continued

```
ACCCCAAAGCCTTCTGCTTTGAATGCTGCCCTTCTTCAGGGCTTAATTTTTAAGAGCGTC
ACCTTCATGGTGGTCAGTGCGTCCTGCTGATGTGCTCAGTATCACCGCCAGTGGTATTTA
TGTCAACACCGCCAGAGATAATTTATCACCGCAGATGGTTATCTGTATGTTTTTATATG
AATTTATTTTTTGCAGGGGGGCATTGTTTGGTAGGTGAGAGATCAATTCTGCATTAATGA
ATCGGCCAACGCGCGGGGAGAGGCGGTTTGCGTATTGGGCGCTCTTCCGCTGCTAGCGGA
GTGTATACTGGCTTACTATGTTGGCACTGATGAGGGTGTCAGTGAAGTGCTTCATGTGGC
AGGAGAAAAAAGGCTGCACCGGTGCGTCAGCAGAATATGTGATACAGGATATATTCCGCT
TCCTCGCTCACTGACTCGCTACGCTCGGTCGTTCGACTGCGGCGAGCGGAAATGGCTTAC
GAACGGGGCGGAGATTTCCTGGAAGATGCCAGGAAGATACTTAACAGGGAAGTGAGAGGG
CCGCGGCAAAGCCGTTTTTCCATAGGCTCCGCCCCCCTGACAAGCATCACGAAATCTGAC
GCTCAAATCAGTGGTGGCGAAACCCGACAGGACTATAAAGATACCAGGCGTTTCCCCCTG
GCGGCTCCCTCGTGCGCTCTCCTGTTCCTGCCTTTCGGTTTACCGGTGTCATTCCGCTGT
TATGGCCGCGTTTGTCTCATTCCACGCCTGACACTCAGTTCCGGGTAGGCAGTTCGCTCC
AAGCTGGACTGTATGCACGAACCCCCCGTTCAGTCCGACCGCTGCGCCTTATCCGGTAAC
TATCGTCTTGAGTCCAACCCGGAAAGACATGCAAAAGCACCACTGGCAGCAGCCACTGGT
AATTGATTTAGAGGAGTTAGTCTTGAAGTCATGCGCCGGTTAAGGCTAAACTGAAAGGAC
AAGTTTTGGTGACTGCGCTCCTCCAAGCCAGTTACCTCGGTTCAAAGAGTTGGTAGCTCA
GAGAACCTTCGAAAAACCGCCCTGCAAGGCGGTTTTTTCGTTTTCAGAGCAAGAGATTAC
GCGCAGACCAAAACGATCTCAAGAAGATCATCTTATTAATCAGATAAAATATTTCTAGGC
ggccgcGAACGAAAACTCACGTTAAGGGATTTTGGTCATGAGATTATCAAAAAGGATCTT
CACCTAGATCCTTTTAAATTAAAAATGAAGTTTTAAATCAATCTAAAGTATATATGAGTA
AACTTGGTCTGACAGTTACCAATGCTTAATCAGTGAGGCACCTATCTCAGCGATCTGTCT
ATTTCGTTCATCCATAGTTGCCTGACTCCCCGTCGTGTAGATAACTACGATACGGGAGGG
CTTACCATCTGGCCCCAGTGCTGCAATGATACCGCGAGACCCACGCTCACCGGCTCCAGA
TTTATCAGCAATAAACCAGCCAGCCGGAAGGGCCGAGCGCAGAAGTGGTCCTGCAACTTT
ATCCGCCTCCATCCAGTCTATTAATTGTTGCCGGGAAGCTAGAGTAAGTAGTTCGCCAGT
TAATAGTTTGCGCAACGTTGTTGCCATTGCTACAGGCATCGTGGTGTCACGCTCGTCGTT
TGGTATGGCTTCATTCAGCTCCGGTTCCCAACGATCAAGGCGAGTTACATGATCCCCCAT
GTTGTGCAAAAAAGCGGTTAGCTCCTTCGGTCCTCCGATCGTTGTCAGAAGTAAGTTGGC
CGCAGTGTTATCACTCATGGTTATGGCAGCACTGCATAATTCTCTTACTGTCATGCCATC
CGTAAGATGCTTTTCTGTGACTGGTGAGTACTCAACCAAGTCATTCTGAGAATAGTGTAT
GCGGCGACCGAGTTGCTCTTGCCCGGCGTCAATACGGGATAATACCGCGCCACATAGCAG
AACTTTAAAAGTGCTCATCATTGGAAAACGTTCTTCGGGGCGAAAACTCTCAAGGATCTT
ACCGCTGTTGAGATCCAGTTCGATGTAACCCACTCGTGCACCCAACTGATCTTCAGCATC
TTTTACTTTCACCAGCGTTTCTGGGTGAGCAAAAACAGGAAGGCAAAATGCCGCAAAAAA
GGGAATAAGGGCGACACGGAAATGTTGAATACTCATACTCTTCCTTTTTCAATATTATTG
AAGCATTTATCAGGGTTATTGTCTCATGAGCGGATACATATTTGAATGTATTTAGAAAAA
TAAACAAATAGGGGTTCCGCGCACATTTCCCCGAAAAGTGCCACCTGACGTCTAAGAAAC
CATTATTATCATGACATTAACCTATAAAAATAGGCGTATCACGAGGCCCTTTCGTC
```

```
                                                          SEQ ID NO: 13
>neuC_N-acetylglucosamine-6-phosphate-2-epimerase_GI_15193223_in_pG317
MKKILFITGSRADYSKIKSLMYRVQNSSEFELYIFATGMHLSKNFGYTVKELYKNGFKNI

YEFINYDKYYQTDKALATTIDGFSRYANELKPDLIVVHGDRIEPLAAAIVGALNNILVAH

IEGGEISGTIDDSLRHAISKLAHIHLVNDEFAKRRLMQLGEDEKSIFIIGSPDLELLNDN

KISLSEAKKYYDINYENYALLMFHPVTTEITSIKNQADNLVKALIQSNKNYIVIYPNNDL

GFELILQSYEEFKNNPRFKLFPSLRFEYFITLLKNADFIIGNSSCILKEALYLKTAGILV

GSRQNGRLGNENTLKVNANSDEILKAINTIHKKQDLFSAKLEILDSSKLFFEYLQSGDFF

KLSTQKVFKDIK

SEQ ID NO: 14
>neuB_sialic_acid_synthase_GI_15193222_in_pG317
MKEIKIQNIIISEEKAPLVVPEIGINHNGSLELAKIMVDAAFSAGAKIIKHQTHIVEDEM

SKAAKKVIPGNAKISIYEIMQKCALDYKDELALKEYTEKLGLVYLSTPFSRAGANRLEDM

GVSAFKIGSGECNNYPLIKHIAAFKKPMIVSTGMNSIESIKPTVKILLDNEIPFVLMHTT

NLYPTPHNLVRLNAMLELKKEFSCMVGLSDHTTDNLACLGAVVLGACVLERHFTDSMHRS

GPDIVCSMDTKALKELIIQSEQMAIIRGNNESKKAAKQEQVTIDFAFASVVSIKDIKKGE

VLSMDNIWVKRPGLGGISAAEFENILGKKALRDIENDAQLSYEDFA

SEQ ID NO: 15
>neuA_CMP-Neu5Ac_synthase_GI_15193224_in_pG317
MSLAIIPARGGSKGIKNKNLVLLNNKPLIYYTIKAALNAKSISKVVVSSDSDEILNYAKS

QNVDILKRPISLAQDDTTSDKVLLHALKFYKDYEDVVFLQPTSPLRTNIHINEAFNLYKN

SNANALISVSECDNKILKAFVCNDCGDLAGICNDEYPFMPRQKLPKTYMSNGAIYILKIK

EFLNNPSFLQSKTKHFLMDESSSLDIDCLEDLKKVEQIWKK

SEQ ID NO: 16
>AAF42258 lacto-N-neotetraose biosynthesis glycosyl transferase LgtA
[Neisseria meningitidis MC58].
MPSEAFRRHRAYRENKLQPLVSVLICAYNVEKYFAQSLAAVVNQTWRNLDILIVDDGSTD

GTLAIAQRFQEQDGRIRILAQPRNSGLIPSLNIGLDELAKSGGGGEYIARTDADDIAAPD

WIEKIVGEMEKDRSIIAMGAWLEVLSEEKDGNRLARHHEHGKIWKKPTRHEDIADFFPFG

NPIHNNTMIMRRSVIDGGLRYNTERDWAEDYQFWYDVSKLGRLAYYPEALVKYRLHANQV

SSKYSIRQHEIAQGIQKTARNDFLQSMGFKTRFDSLEYRQIKAVAYELLEKHLPEEDFER

ARRFLYQCFKRTDTLPAGAWLDFAADGRMRRLFTLRQYFGILHRLLKNR

SEQ ID NO: 17
>NP_207619 lipooligosaccharide 5G8 epitope biosynthesis-associated
protein Lex2B [Helicobacter pylori_26695].
MRVFAISLNQKVCDTFGLVFRDTTTLLNSINATHHQAQIFDAIYSKTFEGGLHPLVKKHL

HPYFITQNIKDMGITTNLISEVSKFYYALKYHAKFMSLGELGCYASHYSLWEKCIELNEA

ICILEDDITLKEDFKEGLDFLEKHIQELGYIRLMHLLYDASVKSEPLSHKNHEIQERVGI

IKAYSEGVGTQGYVITPKIAKVFLKCSRKWVPVDTIMDATFIHGVKNLVLQPFVIADDE

QISTIARKEEPYSPKIALMRELHFKYLKYWQFV

SEQ ID NO: 18
>E.coli_WbgO_YP_003500090 putative glycosyltransferase WbgO [Escherichia
coli O55: H7 str. CB9615].
MIIDEAESAESTHPVVSVILPVNKKNPFLDEAINSILSQTFSSFEIIIVANCCTDDFYNE

LKHKVNDKIKLIRTNIAYLPYSLNKAIDLSNGEFIARMDSDDISHPDRFTKQVDFLKNNP

YVDVVGTNAIFIDDKGREINKTKLPEENLDIVKNLPYKCCIVHPSVMFRKKVIASIGGYM

FSNYSEDYELWNRLSLAKIKFQNLPEYLFYYRLHEGQSTAKKNLYMVMVNDLVIKMKCFF

LTGNINYLFGGIRTIASFIYCKYIK
```

SEQ ID NO: 19
>BAA35319 DNA-binding transcriptional dual regulator nagC [*Escherichia coli* str. K-12 substr. W3110].
MTPGGQAQIGNVDLVKQLNSAAVYRLIDQYGPISRIQIAEQSQLAPASVTKITRQLIERG

LIKEVDQQASTGGRRAISIVTETRNFHAIGVRLGRHDATITLFDLSSKVLAEEHYPLPER

TQQTLEHALLNAIAQFIDSYQRKLRELIAISVILPGLVDPDSGKIHYMPHIQVENWGLVE

ALEERFKVTCFVGHDIRSLALAEHYFGASQDCEDSILVRVHRGTGAGIISNGRIFIGRNG

NVGEIGHIQVEPLGERCHCGNFGCLETIAANAAIEQRVLNLLKQGYQSRVPLDDCTIKTI

CKAANKGDSLASEVIEYVGRHLGKTIAIAINLFNPQKIVIAGEITEADKVLLPAIESCIN

TQALKAFRTNLPVVRSELDHRSAIGAFALVKRAMLNGILLQHLLEN

SEQ ID NO: 20
>NP_418185 L-glutamtne: D-fructose-6-phosphate aminotransferase glmS [*Escherichia coli* str. K-12 substr. MG1655].
MCGIVGAIAQRDVAEILLEGLRRLEYRGYDSAGLAVVDAEGHMTRLRRLGKVQMLAQAAE

EHPLHGGTGIAHTRWATHGEPSEVNAHPHVSEHIVVVHNGIIENHEPLREELKARGYTFV

SETDTEVIAHLVNWELKQGGTLREAVLRAIPQLRGAYGTVIMDSRHPDTLLAARSGSPLV

IGLGMGENFIASDQLALLPVTRRFIFLEEGDIAEITRRSVNIFDKTGAEVKRQDIESNLQ

YDAGDKGIYRHYMQKEIYEQPNAIKNTLTGRISHGQVDLSELGPNADELLSKVEHIQILA

CGTSYNSGMVSRYWFESLAGIPCDVEIASEFRYRKSAVRRNSLMITLSQSGETADTLAGL

RLSKELGYLGSLAICNVPGSSLVRESDLALMTNAGTEIGVASTKAFTTQLTVLLMLVAKL

SRLKGLDASIEHDIVHGLQALPSRIEQMLSQDKRIEALAEDFSDKHHALFLGRGDQYPIA

LEGALKLKEISYIHAEAYAAGELKHGPLALIDADMPVIVVAPNNELLEKLKSNIEEVRAR

GGQLYVFADQDAGFVSSDNMHIIEMPHVEEVIAPIFYTVPLQLLAYHVALIKGTDVDQPR

NLAKSVTVE

SEQ ID NO: 21
>BAF92026 beta-galactoside alpha-2,6-stalyltransferase [*Photobacterium* sp. JT-ISH-224].
MKNFLLLTLILLTACNNSEENTQSIIKNDINKTIIDEEYVNLEPINQSNISFTKHSWVQT

CGTQQLLTEQNKESISLSVVAPRLDDDEKYCFDFNGVSNKGEKYITKVTLNVVAPSLEVY

VDHASLPTLQQLMDIIKSEEENPTAQRYIAWGRIVPTDEQMKELNITSFALINNHTPADL

VQEIVKQAQTKHRLNVKLSSNTAHSFDNLVPILKELNSFNNVTVTNIDLYDDGSAEYVNL

YNWRDTLNKTDNLKIGKDYLEDVINGINEDTSNTGTSSVYNWQKLYPANYHFLRKDYLTL

EPSLHELRDYIGDSLKQMQWDGFKKFNSKQQELFLSIVNFDKQKLQNEYNSSNLPNFVFT

GTTVWAGNHEREYYAKQQINVINNAINESSPHYLGNSYDLFFKGHPGGGIINTLIMQNYP

SMVDIPSKISFEVLMMTDMLPDAVAGIASSLYFTIPAEKIKFIVFTSTETITDRETALRS

PLVQVMIKLGIVKEENVLFWADLPNCETGVCIAV

Provided below is the DNA sequence in Genbank format of the new configuration of genes engineered at the *Escherichia coli* thyA locus in strains used to produce N-acetylglucosamine-containing oligosaccharides.

```
LOCUS       E680_thyA::2.8RBS_lacZ 5877 bp DNA linear BCT
            04-MAR-2013
DEFINITION  Escherichia coli str. K-12 substr. MG1655, complete genome.
ACCESSION   NC_000913
VERSION     NC_000913.2 GI: 49175990
KEYWORDS    .
SOURCE      Escherichia coli str. K-12 substr. MG1655 (unknown)
ORGANISM    Escherichia coli str. K-12 substr. MG1655
            Bacteria; Proteobacteria; Gammaproteobacteria;
            Enterobacteriales; Enterobacteriaceae; Escherichia.
```

```
REFERENCE    1 (bases 1 to 4639675)
AUTHORS      Riley, M., Abe, T., Arnaud, M. B., Berlyn, M. K., Blattner, F. R.,
             Chaudhuri, R. R., Glasner, J. D., Horiuchi, T., Keseler, I .M.,
             Kosuge, T.,
             Mori, H., Perna, N. T., Plunkett, G. III, Rudd, K. E., Serres, M. H.,
             Thomas, G. H., Thomson, N. R., Wishart, D. and Wanner, B. L.
TITLE        Escherichia coli K-12: a cooperatively developed annotation
             snapshot--2005
JOURNAL      Nucleic Acids Res. 34 (1), 1-9 (2006)
PUBMED       16397293
REMARK       Publication Status: Online-Only REFERENCE    2 (bases 1 to 4639675)
AUTHORS      Blattner, F. R., Plunkett, G. III, Bloch, C. A., Perna, N. T.,
             Burland, V.,
             Riley, M., Collado-Vides, J., Glasner, J. D., Rode, C. K.,
             Mayhew, G. F.,
             Gregor, J., Davis, N. W., Kirkpatrick, H. A., Goeden, M. A.,
             Rose, D. J.,
             Mau, B. and Shao, Y.
TITLE        The complete genome sequence of +i Escherichia coli+l +0K-12
JOURNAL      Science 277 (5331), 1453-1474 (1997)
PUBMED       9278503

REFERENCE    3 (bases 1 to 4639675)
AUTHORS      Arnaud, M., Berlyn, M. K. B., Blattner, F. R., Galperin, M. Y.,
             Glasner, J. D., Horiuchi, T., Kosuge, T., Mori, H., Perna, N. T.,
             Plunkett, G. III, Riley, M., Rudd, K. E., Serres, M. H., Thomas, G. H.
             and Wanner, B. L.
TITLE        Workshop on Annotation of +i Escherichia coli+l +0K-12
JOURNAL      Unpublished
REMARK       Woods Hole, Mass., on 14-18 Nov. 2003 (sequence
             corrections)

REFERENCE    4 (bases 1 to 4639675)
AUTHORS      Glasner, J. D., Perna, N. T., Plunkett, G. III, Anderson, B. D.,
             Bockhorst, J., Hu, J. C., Riley, M., Rudd, K. E. and Serres, M. H.
TITLE        ASAP: +i Escherichia coli+l +0K-12 strain MG1655 version m56
JOURNAL      Unpublished
REMARK       ASAP download 10 Jun. 2004 (annotation updates)

REFERENCE    5 (bases 1 to 4639675)
AUTHORS      Hayashi, K., Morooka, N., Mori, H. and Holiuchi, T.
TITLE        A more accurate sequence comparison between genomes of
             Escherichia coli K12 W3110 and MG1655 strains
JOURNAL      Unpublished
REMARK       GenBank accessions AG613214 to AG613378 (sequence corrections)

REFERENCE    6 (bases 1 to 4639675)
AUTHORS      Perna, N. T.
TITLE        Escherichia coli K-12 MG1655 yqiK-rfaE intergenic region,
             genomic sequence correction
JOURNAL      Unpublished
REMARK       GenBank accession AY605712 (sequence corrections)

REFERENCE    7 (bases 1 to 4639675)
AUTHORS      Rudd, K. E.
TITLE        A manual approach to accurate translation start site
             annotation: an E. coli K-12 case study
JOURNAL      Unpublished REFERENCE    8 (bases 1 to 4639675)
CONSRTM      NCBI Genome Project
TITLE        Direct Submission
JOURNAL      Submitted (04-MAR.-2013) National Center for Biotechnology
             Information, NIH, Bethesda, MD 20894, USA REFERENCE    9 (bases 1 to 4639675)
AUTHORS      Rudd, K. E.
TITLE        Direct Submission
JOURNAL      Submitted (06-FEB.-2013) Department of Biochemistry and
             Molecular Biology, University of Miami Miller School of Medicine, 118
             Gautier Bldg., Miami, FL 33136, USA
REMARK       Sequence update by submitter REFERENCE    10 (bases 1 to 4639675)
AUTHORS      Rudd, K. E.
TITLE        Direct Submission
JOURNAL      Submitted (24-APR.-2007) Department of Biochemistry and
             Molecular Biology, University of Miami Miller School of Medicine,
             118 Gautier Bldg., Miami, FL 33136, USA
```

```
-continued
REMARK      Annotation update from ecogene.org as a multi-database
            collaboration REFERENCE   11 (bases 1 to 4639675)
AUTHORS     Plunkett, G. III.
TITLE       Direct Submission
JOURNAL     Submitted (07-FEB.-2006) Laboratory of Genetics, University of
            Wisconsin, 425G Henry Mall, Madison, WI 53706-1580, USA
REMARK      Protein updates by submitter REFERENCE   12 (bases 1 to 4639675)
AUTHORS     Plunkett, G. III.
TITLE       Direct Submission
JOURNAL     Submitted (10-JUN.-2004) Laboratory of Genetics, University of
            Wisconsin, 425G Henry Mall, Madison, WI 53706-1580, USA
REMARK      Sequence update by submitter REFERENCE   13 (bases 1 to 4639675)
AUTHORS     Plunkett, G. III.
TITLE       Direct Submission
JOURNAL     Submitted (13-OCT.-1998) Laboratory of Genetics, University of
            Wisconsin, 425G Henry Mall, Madison, WI 53706-1580, USA REFERENCE   14 (bases 1 to 4639675)
AUTHORS     Blattner, F. R. and Plunkett, G. III.
TITLE       Direct Submission
JOURNAL     Submitted (02-SEP.-1997) Laboratory of Genetics, University of
            Wisconsin, 425G Henry Mall, Madison, WI 53706-1580, USA REFERENCE   15 (bases 1 to 4639675)
AUTHORS     Blattner, F. R. and Plunkett, G. III.
TITLE       Direct Submission
JOURNAL     Submitted (16-JAN.-1997) Laboratory of Genetics, University of
            Wisconsin, 425G Henry Mall, Madison, WI 53706-1580, USA
COMMENT     PROVISIONAL REFSEQ: This record has not yet been subject to final
            NCBI review. The reference sequence is identical to U00096.
            On Jun. 24, 2004 this sequence version replaced gi: 16127994.
            Current U00096 annotation updates are derived from EcoGene
            ecogene.org. Suggestions for updates can be sent to Dr.
            Kenneth Rudd (krudd@miami.edu). These updates are being
            generated from a collaboration that also includes ASAP/ERIC,
            the Coli Genetic Stock Center, EcoliHub, EcoCyc, RegulonDB and
            UniProtKB/Swiss-Prot.

COMPLETENESS:  full length.
FEATURES       Location/Qualifiers
gene           complement(<1 . . . 245)
               /gene = "ppdA"
               /locus_tag = "b2826"
               /gene_synonym = "ECK2822; JW2794"
               /db_xref = "EcoGene: EG12081"
               /db_xref = "GeneID: 945393"

CDS            complement(<1 . . . 245)
               /gene = "ppdA"
               /locus_tag = "b2826"
               /gene_synonym = "ECK2822; JW2794"
               /function = "putative enzyme; Not classified"
               /GO_component = "GO: 0009289 - pilus"
               /GO_process = "GO: 0009101 - glycoprotein biosynthetic
               process"
               /note = "prepilin peptidase dependent protein A"
               /codon_start = 1
               /transl_table = 11
               /product = "hypothetical protein"
               /protein_id = "NP_417303.1"
               /db_xref = "GI: 16130730"
               /db_xref = "ASAP: ABE-0009266"
               /db_xref = "UniProtKB/Swiss-Prot: P33554"
               /db_xref = "EcoGene: EG12081"
               /db_xref = "GeneID: 945393"

/translation = "MKTQRGYTLIETLVAMLILVMLSASGLYGWQYWQQSQRLWQTAS
QARDYLLYLREDANWHNRDHSISVIREGTLWCLVSSAAGANTCHGSSPLVFVPRWPEV
EMSDLTPSLAFFGLRNTAWAGHIRFKNSTGEWWLVVSPWGRLRLCQQGETEGCL" (SEQ ID NO: 22)

source         join(<1 . . . 449, 4852 . . . >5877)
               /organism = "Escherichia coli str. K-12 substr. MG1655"
               /mol_type = "genomic DNA"
               /strain = "K-12"
```

```
                        /sub_straIn = "MG1655"
                        /db_xref = "taxon: 511145"

primer          346 . . . 366
     /note = cagtcagtcaggcgccTTCGGGAAGGCGTCTCGAAGA (SEQ ID
     NO: 23)
                        /label = 0268-THYA-R misc_feature    complement(388 . . . 394)
                        /feature_type = "Hairpin loop"
                        /label = Terminator primer          400 . . . 449
     /note = GGCGTCGGCTCTGGCAGGATGTTTCGTAATTAGATAGCCACCGGCGCTTTag
     GaaacctactATGACCATGATTACGGATTCAC (SEQ ID NO: 24)
                        /label = "50 bp thyA 3 prime homology"

primer          400 . . . 483
     /note = GGCGTCGGCTCTGGCAGGATGTTTCGTAATTAGATAGCCACCGGCGCTTTat
     taaacctactATGACCATGATTACGGATTCAC (SEQ ID NO: 25)
                        /label = 1389-thyAKANlacZ-R-2-8 primer          400 . . . 483
     /note = GGCGTCGGCTCTGGCAGGATGTTTCGTAATTAGATAGCCACCGGCGCTTTCt
     tCaacctactATGACCATGATTACGGATTCAC (SEQ ID NO: 26)
                        /label = 1516-thyAKANlacZ-R-0-8 primer          400 . . . 483
     /note = GGCGTCGGCTCTGGCAGGATGTTTCGTAATTAGATAGCCACCGGCGCTTTag
     GaaacctactATGACCATGATTACGGATTCAC (SEQ ID NO: 27)
                        /label = "1041-thyAKANlacZ-R (4-8)"

misc_feature    complement(401 . . . 407)
                        /feature_type = "Hairpin loop"
                        /label = Terminator primer          405 . . . 472
     /note = CGGCTCTGGCAGGATGTTTCGTAATTAGATAGCCACCGGCGCTTTaTTaaac (SEQ ID NO: 28)
     ctactATGACCATGAT
                        /label = 1394-2/8-F gene            complement(join(429 . . . 449, 4852 . . . 4854))
                        /gene = "thyA"

CDS             complement(join(429 . . . 449, 4852 . . . 4854))
                        /gene = "thyA"
                        /note = "ECK2823: JW2795: b2827"
                        /codon_start = 1
                        /transl_table = 11
                        /product = "thymidylate synthetase"
                        /protein_id = "BAE76896.1"
                        /db_xref = "GI: 85675643"

/translation = "MKQYLELMQKVLDEGTQKNDRTGTGTLSIFGHQMRFNLQDGFPL
     VTTKRCHLRSIIHELLWFLQGDTNIAYLHENNVTIWDEWADENGDLGPVYGKQWRAWP
     TPDGRHIDQITTVLNQLKNDPDSRRIIVSAWNVGELDKMALAPCHAFFQFYVADGKLS
     CQLYQRSCDVFLGLPFNIASYALLVHMMAQQCDLEVGDFVWTGGDTHLYSNHMDQTHL
     QLSREPRPLPKLIIKRKPESIFDYRFEDFEIEGYDPHPGIKAPVAI" (SEQ
     ID NO: 43)

RBS             450 . . . 461
                        /label = "2.8 RBS"

source          450 . . . 3536
                        /organism = "Escherichia coli W3110"
                        /mol_type = "genomic DNA"
                        /strain = "K-12"
                        /sub_strain = "W3110"
                        /db_xref = "taxon: 316407"
                        /note = "synonym: +i Escherichia coli+l +0str. K12 substr.
                        W3110"

misc_feature    450 . . . 4851
                        /feature_type = Insertion
                        /note = "originates from KanR-lacZRBS (E403)"
                        /label = Insert misc_feature    449^450
                        /feature_type = "RBS variation site"
                        /label = "C in 0/8"
```

```
-continued misc_feature    450 . . . 453
                /feature_type = "RBS variation site"
                /label = "CTTC In 0/8"

misc_feature    451 . . . 452
                /feature_type = "RBS variation site"
                /label = "GG In 4/8"

misc_feature    451 . . . 452
                /feature_type = "RBS variation site"
                /label = "TT in 2/8"

CDS             462 . . . 3536
                /gene = "lacZ"
                /note = "ECK0341: JW0335: b0344"
                /codon_start = 1
                /transl_table = 11
                /product = "beta-D-galactosidase"
                /protein_id = "BAE76126.1"
                /db_xref = "GI: 85674486"

/translation = "MTMITDSLAVVLQRRDWENPGVTQLNRLAAHPPFASWRNSEEAR
TDRPSQQLRSLNGEWRFAWFPAPEAVPESWLECDLPEADTVVVPSNWQMHGYDAPIYT
NVTYPITVNPPFVPTENPTGCYSLTFNVDESWLQEGQTRIIFDGVNSAFHLWCNGRWV
GYGQDSRLPSEFDLSAFLRAGENRLAVMVLRWSDGSYLEDQDMWRMSGIFRDVSLLHK
PTTQISDFHVATRFNDDFSRAVLEAEVQMCGELRDYLRVTVSLWQGETQVASGTAPFG
GEIIDERGGYADRVTLRLNVENPKLWSAEIPNLYRAVVELHTADGTLIEAEACDVGFR
EVRIENGLLLLNGKPLLIRGVNRHEHHPLHGQVMDEQTMVQDILLMKQNNFNAVRCSH
YPNHPLWYTLCDRYGLYVVDEANIETHGMVPMNRLTDDPRWLPAMSERVTRMVQRDRN
HPSVIIWSLGNESGHGANHDALYRWIKSVDPSRPVQYEGGGADTTATDIICPMYARVD
EDQPFPAVPKWSIKKWLSLPGETRPLILCEYAHAMGNSLGGFAKYWQAFRQYPRLQGG
FVWDWVDQSLIKYDENGNPWSAYGGDFGDTPNDRQFCMNGLVFADRTPHPALTEAKHQ
QQFFQFRLSGQTIEVTSEYLFRHSDNELLHWMVALDGKPLASGEVPLDVAPQGKQLIE
LPELPQPESAGQLWLTVRVVQPNATAWSEAGHISAWQQWRLAENLSVTLPAASHAIPH
LTTSEMDFCIELGNKRWQFNRQSGFLSQMWIGDKKQLLTPLRDQFTRAPLDNDIGVSE
ATRIDPNAWVERWKAAGHYQAEAALLQCTADTLADAVLITTAHAWQHQGKTLFISRKT
YRIDGSGQMAITVDVEVASDTPHPARIGLNCQLAQVAERVNWLGLGPQENYPDRLTAA
CFDRWDLPLSDMYTPYVFPSENGLRCGTRELNYGPHQWRGDFQFNISRYSQQQLMETS
HRHLLHAEEGTWLNIDGFHMGIGGDDSWSPSVSAEFQLSAGRYHYQLVWCQK"
(SEQ ID NO: 29)
                /label = "wild-type lacZ + CDS"

primer          complement(1325 . . . 1345)
                /note = TTCAGACGTAGTGTGACGCGA
                /label = 1042-thyAlacZcheck primer          2754 . . . 2776
                /note = TTTCTTTCACAGATGTGGATTGG
                /label = "1395-mid lacZ-F"

primer          complement(2779 . . . 2801)
                /note = CGGCGTCAGCAGTTGTTTTTAT
                /label = "1396-mid lacZ-R"

mutation        2793
                /label = "C in MG1655 lacZ (silent change)"

Scar            complement(3549 . . . 3567)
                /label = "KD13 downstream scar sequence"

source          3549 . . . 4851
                /organism = "Template plasmid pKD13"
                /mol_type = "genomic DNA"
                /db_xref = "taxon: 170493"

primer          3549 . . . 3568
                /label = "0339 P1w-P2b"

repeat_unit     3568 . . . 3579
                /label = "FLP site"

misc_feature    complement(3568 . . . 3601)
                /feature_type = "FRT site"
                /label = "34 bp FRT site"

note            complement(3568 . . . 4789)
                /label = "excised region upon pCP20 introduction"

repeat_unit     complement(3590 . . . 3601)
                /label = "Flp site"
```

```
misc_feature    complement(3602 . . . 3615)
                /feature_type = "FRT site"
                /note = "natural FRT site"
                /label = "upstream FRT site"

repeat_unit     complement(3604 . . . 3615)
                /label = "Flp site"

misc_feature    complement(3628 . . . 4422)
                /feature_type = "CDS (KAN resistance)"
                /note = "kanamycin resistance"
                /codon_start = 1
                /transl_table = 11
                /product = "Tn5 neomycin phosphotransferase"
                /protein_id = "AAL02037.1"
                /db_xref = "GI: 15554336"

/translation = "MIEQDGLHAGSPAAWVERLFGYDWAQQTIGCSDAAVFRLSAQGR
PVLFVKTDLSGALNELQDEAARLSWLATTGVPCAAVLDVVTEAGRDWLLLGEVPGQDL
LSSHLAPAEKVSIMADAMRRLHTLDPATCPFDHQAKHRIERARTRMEAGLVDQDDLDE
EHQGLAPAELFARLKARMPDGEDLVVTHGDACLPNIMVENGRFSGFIDCGRLGVADRY
QDIALATRDIAEELGGEWADRFLVLYGIAAPDSQRIAFYRLLDEFF" (SEQ
ID NO: 30)

primer          complement(3677 . . . 3696)
                /label = "0389 KD13_K4"

primer_bind     3791 . . . 3810
                /label = "common priming site kt"

primer          3791 . . . 3810
                /label = "0344 Wanner Kt primer"

mutation        3811
                /label = "A in wt (silent change)"

primer          complement(4242 . . . 4261)
                /label = "0343 Wanner K2 primer"

primer_bind     4261 . . . 4280
                /label = "common priming site k2"

primer_bind     4352 . . . 4371
                /label = "common priming site k1"

primer          4352 . . . 4371
                /label = "0342 Wanner K1 primer"

repeat_unit     4790 . . . 4801
                /label = "FLP site"

Scar            complement(4790 . . . 4851)
                /label = "KD13 upstream scar"

misc_feature    complement(4790 . . . 4823)
                /feature_type = "FRT site"
                /label = "34 bp FRT site"

repeat_unit     complement(4812 . . . 4823)
                /label = "Flp site"

primer          complement(4832 . . . 4851)
                /label = "0338 P4w-P1b"

primer          complement(4832 . . . 4901)
/note = TCTGGGCATATCGTCGCAGCCCACAGCAACACGTTTCCTGAGGAACCATGAT
TCCGGGGATCCGTCGACC (SEQ ID NO: 31)
                /label = 1040-thyAKANlacZ-F Site            complement(4858 . . . 4863)
                /site_type = "binding site"
                /label = "thyA RBS"

gene            complement(4861 . . . 5736)
                /gene = "lgt"

CDS             complement(4861 . . . 5736)
                /gene = "lgt"
                /note = "ECK2824: JW2796: b2828"
                /codon_start = 1
                /transl_table = 11
```

-continued

```
                /product = "phosphatidylglycerol-prolipoprotein
                diacylglyceryl transferase"
                /protein_id = "BAE76897.1"
                /db_xref = "GI: 85675644"

/translation = "MTSSYLHFPEFDPVIFSIGPVALHWYGLMYLVGFIFAMWLATRR
ANRPGSGWTKNEVENLLYAGFLGVFLGGRIGYVLFYNFPQFMADPLYLFRVWDGGMSF
HGGLIGVIVVMIIFARRTKRSFFQVSDFIAPLIPFGLGAGRLGNFINGELWGRVDPNF
PFAMLFPGSRTEDILLLQTNPQWQSIFDTYGVLPRHPSQLYELLLEGVVLFIILNLYI
RKPRPMGAVSGLFLIGYGAFRIIVEFFRQPDAQFTGAWVQYISMGQILSIPMIVAGVI
MMVWAYRRSPQQHVS" (SEQ ID NO: 32)

promoter        complement(4957 . . . 4962)
                /label = "thyA WEAK -10"

promoter        complement(4978 . . . 4983)
                /label = "thyA -35"

primer          complement(5076 . . . 5099)
                /note = cagtcagtcaggcgccTCCTCAACCTGTATATTCGTAAAC (SEQ
                ID NO: 33)
                /label = 0267-THYA-F Site            complement(5739 . . . 5744)
                /site_type = "binding site"
                /label = "lgt RBS"

promoter        complement(5823 . . . 5828)
                /label = "lgt -10 (strong)"

ORIGIN
        1   GCAGCGGAAC TCACAAGGCA CCATAACGTC CCCTCCCTGA TAACGCTGAT ACTGTGGTCG
       61   CGGTTATGCC AGTTGGCATC TTCACGTAAA TAGAGCAAAT AGTCCCGCGC CTGGCTGGCG
      121   GTTTGCCATA GCCGTTGCGA CTGCTGCCAG TATTGCCAGC CATAGAGTCC ACTTGCGCTT
      181   AGCATGACCA AAATCAGCAT CGCCGACCAGC GTTTCAATCA GCGTATAACC ACGTTGTGTT
      241   TTCATGCCGG CAGTATGGAG CGAGGAGAAA AAAGACGAG GGCCAGTTTC TATTTCTTCG
      301   GCGCATCTTC CGGACTATTT ACGCCGTTGC AGGACGTTGC AAAATTTCGG GAAGGCGTCT
      361   CGAAGAATTT AACGGAGGGT AAAAAAACCG ACGCACACTG GCGTCGGCTC TGGCAGGATG
      421   TTTCGTAATT AGATAGCCAC CGGCGCTTTa ttaaacctac tATGACCATG ATTACGGATT
      481   CACTGGCCGT CGTTTTACAA CGTCGTGACT GGGAAAACCC TGGCGTTACC CAACTTAATG
      541   GCCTTGCAGC ACATCCCCCT TTCGCCAGCT GGCGTAATAG CGAAGAGGCC CGCACCGATC
      601   GCCCTTCCCA ACAGTTGCGC AGCCTGAATG GCGAATGGCG CTTTGCCTGG TTTCCGGCAC
      661   CAGAAGCGGT GCCGGAAAGC TGGCTGGAGT GCGATCTTCC TGAGGCCGAT ACTGTCGTCG
      721   TCCCCTCAAA CTGGCAGATG CACGGTTACG ATGCGCCCAT CTACACCAAC GTGACCTATC
      781   CCATTACGGT CAATCCGCCG TTTGTTCCCA CGGAGAATCC GACGGGTTGT TACTCGCTCA
      841   CATTTAATGT TGATGAAAGC TGGCTACAGG AAGGCCAGAC GCGAATTATT TTTGATGGCG
      901   TTAACTCGGC GTTTCATCTG TGGTGCAACG GGCGCTGGGT CGGTTACGGC CAGGACAGTC
      961   GTTTGCCGTC TGAATTTGAC CTGAGCGCAT TTTTACGCGC CGGAGAAAAC GCCCTCGCGG
     1021   TGATGGTGCT GCGCTGGAGT GACGGCAGTT ATCTGGAAGA TCAGGATATG TGGCGGATGA
     1081   GCGGCATTTT CCGTGACGTC TCGTTGCTGC ATAAACCGAC TACACAAATC AGCGATTTCC
     1141   ATGTTGCCAC TCGCTTTAAT GATGATTTCA GCCGCGCTGT ACTGGAGGCT GAAGTTCAGA
     1201   TGTGCGGCGA GTTGCGTGAC TACCTACGGG TAACAGTTTC TTTATGGCAG GGTGAAACGC
     1261   AGGTCGCCAG CGGCACCGCG CCTTTCGGCG GTGAAATTAT CGATGAGCGT GGTGGTTATG
     1321   CCGATCGCGT CACACTACGT CTGAACGTCG AAAACCCGAA ACTGTGGAGC GCCGAAATCC
     1381   CGAATCTCTA TCGTGCGGTG GTTGAACTGC ACACCGCCGA CGGCACGCTG ATTGAAGCAG
     1441   AAGCCTGCGA TGTCGGTTTC CGCGAGGTGC GGATTGAAAA TGGTCTGCTG CTGCTGAACG
     1501   GCAAGCCGTT GCTGATTCGA GGCGTTAACC GTCACGAGCA TCATCCTCTG CATGGTCAGG
     1561   TCATGGATGA GCAGACGATG GTGCAGGATA TCCTGCTGAT GAAGCAGAAC AACTTTAACG
     1621   CCGTGCGCTG TTCGCATTAT CCGAACCATC CGCTGTGGTA CACGCTGTGC GACCGCTACG
     1681   GCCTGTATGT GGTGGATGAA GCCAATATTG AAACCCACGG CATGGTGCCA ATGAATCGTC
     1741   TGACCGATGA TCCGCGCTGG CTACCGGCGA TGAGCGAACG CGTAACGCGA ATGGTGCAGC
     1801   GCGATCGTAA TCACCCGAGT GTGATCATCT GGTCGCTGGG GAATGAATCA GGCCACGGCG
     1861   CTAATCACGA CGCGCTGTAT CGCTGGATCA AATCTGTCGA TCCTTCCCGC CCGGTGCAGT
     1921   ATGAAGGCGG CGGAGCCGAC ACCACGGCCA CCGATATTAT TTGCCCGATG TACGCGCTGT
     1981   GGATGAAGA CCAGCCCTTC CCGGCTGTGC CGAAATGGTC CATCAAAAAA TGGCTTTCGC
     2041   TACCTGGAGA GACGCGCCCG CTGATCCTTT GCGAATACGC CCACGCGATG GGTAACAGTC
     2101   TTGGCGGTTT CGCTAAATAC TGGCAGGCGT TCGTCAGTA TCCCCGTTTA CAGGGCGGCT
     2161   TCGTCTGGGA CTGGGTGGAT CAGTCGCTGA TTAAATATGA TGAAAACGGC AACCCGTGGT
     2221   CGGCTTACGG CGGTGATTTT GGCGATACGC CGAACGATCG CCAGTTCGT ATGAACGGTC
     2281   TGGTCTTTGC CGACCGCACG CCGCATCCAG CGCTGACGGA AGCAAAACAC CAGCAGCAGT
     2341   TTTTCCAGTT CCGTTTATCC GGGCAAACCA TCGAAGTGAC CAGCGAATAC CTGTTCCGTC
     2401   ATAGCGATAA CGAGCTCCTG CACTGGATGG TGGCGCTGGA TGGTAAGCCG CTGGCAAGCG
     2461   GTGAAGTGCC TCTGGATGTC GCTCCACAAG GTAAACAGTT GATTGAACTG CCTGAACTAC
     2521   CGCAGCCGGA GAGCGCCGGG CAACTCTGGC TCACAGTACG CGTAGTGCAA CCGAACGCGA
     2581   CCGCATGGTC AGAAGCCGGG CACATCAGCG CCTGGCAGCA GTGGCGTCTG GCGGAAAACC
     2641   TCAGTGTGAC GCTCCCCGCC GCGTCCCACG CCATCCCGCA TCTGACCACC AGCGAAATGG
     2701   ATTTTTGCAT CGAGCTGGGT AATAAGCGTT GGCAATTTAA CCGCCAGTCA GGCTTTCTTT
     2761   CACAGATGTG GATTGCGAT AAAAACAAC TGtTGACGCC GCTGCGCGAT CAGTTCACCC
     2821   GTGCACCGCT GGATAACGAC ATTGGCGTAA GTGAAGCGAC CCGCATTGAC CCTAACGCCT
     2881   GGGTCGAACG CTGAAGGCG GCGGGCCATT ACCAGGCCGA AGCAGCGTTG TTGCAGTGCA
     2941   CGGCAGATAC ACTTGCTGAT GCGGTGCTGA TTACGACCGC TCACGCGTGG CAGCATCAGG
```

```
                -continued
3001    GGAAAACCTT ATTTATCAGC CGGAAAACCT ACCGGATTGA TGGTAGTGGT CAAATGGCGA
3061    TTACCGTTGA TGTTGAAGTG GCGAGCGATA CACCGCATCC GGCGCGGATT GGCCTGAACT
3121    GCCAGCTGGC GCAGGTAGCA GAGCGGGTAA ACTGGCTCGG ATTAGGGCCG CAAGAAAACT
3181    ATCCCGACCG CCTTACTGCC GCCTGTTTTG ACCGCTGGGA TCTGCCATTG TCAGACATGT
3241    ATACCCGTA CGTCTTCCCG AGCGAAAACG GTCTGCGCTG CGGGACGCGC GAATTGAATT
3301    ATGGCCCACA CCAGTGGCGC GGCGACTTCC AGTTCAACAT CAGCCGCTAC AGTCAACAGC
3361    AACTGATGGA AACCAGCCAT CGCCATCTGC TGCACGCGGA AGAAGGCACA TGGCTGAATA
3421    TCGACGGTTT CCATATGGGG ATTGGTGGCG ACGACTCCTG GAGCCCGTCA GTATCGGCGG
3481    AATTCCAGCT GAGCGCCGGT CGCTACCATT ACCAGTTGGT CTGGTGTCAA AAATAAGCGG
3541    CCGCtTTATG TAGGCTGGAG CTGCTTCGAA GTTCCTATAC TTTCTAGAGA ATAGGAACTT
3601    CGGAATAGGA ACTTCAAGAT CCCCTTATTA GAAGAACTCG TCAAGAAGGC GATAGAAGGC
3661    GATGCGCTGC GAATCGGGAG CGGCGATACC GTAAAGCACG AGGAAGCGGT CAGCCCATTC
3721    GCCGCCAAGC TCTTCAGCAA TATCACGGGT AGCCAACGCT ATGTCCTGAT AGCGGTCCGC
3781    CACACCCAGC CGGCCACAGT CGATGAATCC tGAAAAGCGG CCATTTTCCA CCATGATATT
3841    CGGCAAGCAG GCATCGCCAT GGGTCACGAC GAGATCCTCG CCGTCGGGCA TGCGCGCCTT
3901    GAGCCTGGCG AACAGTTCGG CTGGCGCGAG CCCCTGATGC TCTTCGTCCA GATCATCCTG
3961    ATCGACAAGA CCGGCTTCCA TCCGAGTACG TGCTCGCTCG ATGCGATGTT TCGCTTGGTG
4021    GTCGAATGGG CAGGTAGCCG GATCAAGCGT ATGCAGCCGC CGCATTGCAT CAGCCATGAT
4081    GGATACTTTC TCGGCAGGAG CAAGGTGAGA TGACAGGAGA TCCTGCCCCG GCACTTCGCC
4141    CAATAGCAGC CAGTCCCTTC CCGCTTCAGT GACAACGTCG AGCACAGCTG CGCAAGGAAC
4201    GCCCGTCGTG GCCAGCCACG ATAGCCGCGC TGCCTCGTCC TGCAGTTCAT TCAGGGCACC
4261    GGACAGGTCG GTCTTGACAA AAAGAACCGG GCGCCCCTGC GCTGACAGCC GGAACACGGC
4321    GGCATCAGAG CAGCCGATTG TCTGTTGTGC CCAGTCATAG CCGAATAGCC TCTCCACCCA
4381    AGCGGCCGGA GAACCTGCGT GCAATCCATC TTGTTCAATC ATGCGAAACG ATCCTCATCC
4441    TGTCTCTTGA TCAGATCTTG ATCCCCTGCG CCATCAGATC CTTGGCGGCA AGAAAGCCAT
4501    CCAGTTTACT TTGCAGGGCT TCCCAACCTT ACCAGAGCGC GCCCCAGCTG GCAATTCCGG
4561    TTCGCTTGCT GTCCATAAAA CCGCCCAGTC TAGCTATCGC CATGTAAGCC CACTGCAAGC
4621    TACCTGCTTT CTCTTTGCGC TTGCGTTTTC CCTTGTCCAG ATAGCCCAGT AGCTGACATT
4681    CATCCGGGGT CAGCACCGTT TCTGCGGACT GGCTTTCTAC GTGTTCCGCT TCCTTTAGCA
4741    GCCCTTGCGC CCTGAGTGCT TGCGGCAGCG TGAGCTTCAA AAGCGCTCTG AAGTTCCTAT
4801    ACTTTCTAGA GAATAGGAAC TTCGAACTGC AGGTCGACGG ATCCCCGGAA TCATGGTTCC
4861    TCAGGAAACG TGTTGCTGTG GGCTGCGACG ATATGCCCAG ACCATCATGA TCACACCCGC
4921    GACAATCATC GGGATGGAAA GAATTTGCCC CATGCTGATG TACTGCACCC AGGCACCGGT
4981    AAACTGCGCG TCGGGCTGGC GGAAAAACTC AACAATGATG CGAAACGCGC CGTAACCAAT
5041    CAGGAACAAA CCTGAGACAG CTCCCATTGG GCGTGGTTTA CGAATATACA GGTTGAGGAT
5101    AATAAACAGC ACCACACCTT CCAGCAGCAG CTCGTAAAGC TGTGATGGGT GGCGCGGCAG
5161    CACACCGTAA GTGTCGAAAA TGGATTGCCA CTGCGGGTTG GTTTCAGCA GCAAAATATC
5221    TTCTGTACGG GAGCCAGGGA ACAGCATGGC AAACGGGAAG TTCGGGTCAA CGCGGCCCCA
5281    CAATTCACCG TTAATAAAGT TGCCCAGACG CCCGGCACCA AGACCAAACG GAATGAGTGG
5341    TGCGATAAAA TCAGAGACCT GGAAGAAGGA ACGTTTAGTA CGGCGGGCGA AGATAATCAT
5401    CACCACGATA ACGCCAATCA GGCCGCCGTG GAAAGACATG CCGCCGTCCC AGACACGGAA
5461    CAGATACAGC GGATCGGCCA TAAACTGCGG GAAATTGTAA ACAGAACAT AACCAATACG
5521    TCCCCCGAGG AAGACGCCGA GGAAGCCCGC ATAGAGTAAG TTTTCAACTT CATTTTTGGT
5581    CCAGCCGCTG CCCGGACGAT TCGCCCGTCG TGTTGCCAGC CACATTGCAA AAATGAAACC
5641    CACCAGATAC ATCAGGCCGT ACCAGTGAAG CGCCACGGGT CCTATTGAGA AAATGACCGG
5701    ATCAAACTCG GAAAATGCA GATAGCTACT GGTCATCTGT CACCACAAGT TCTTGTTATT
5761    TCGCTGAAAG AGAACAGCGA TTGAAATGCG CGCCGCAGGT TTCAGGCGCT CCAAAGGTGC
5821    GAATAATAGC ACAAGGGGAC CTGGCTGGTT GCCGGATACC GTTAAAAGAT ATGTATA
(SEQ ID NO: 34)
//
```

Provided below is the DNA sequence in Genbank format of the configuration of genes at the *Escherichia coli* nan locus, and the details of the deletion endpoints found in engineered strains E1017 and E1018.

```
LOCUS       W3110_nanRATEKyhcH_region 5861 bp DNA linear BCT
            19-FEB.-2009
DEFINITION  Escherichia coli str. K-12 substr. W3110 strain K-12.
ACCESSION   AC_000091
VERSION     AC_000091.1 GI: 89106884
KEYWORDS    .
SOURCE      Escherichia coli str. K-12 substr. W3110 (unknown)
ORGANISM    Escherichia coli str. K-12 substr. W3110
            Bacteria; Proteobacteria; Gammaproteobacteria;
            Enterobacteriales;
            Enterobacteriaceae; Escherichia.

REFERENCE   1
AUTHORS     Riley, M., Abe, T., Arnaud, M. B., Berlyn, M. K., Blattner, F. R.,
            Chaudhuri, R.R., Glasner, J. D., Horiuchi, T., Keseler, I.M., Kosuge, T.,
            Mori, H., Perna, N. T., Plunkett, G. III, Rudd, K. E., Serres, M. H.,
            Thomas, G. H., Thomson, N. R., Wishart, D. and Wanner, B. L.
TITLE       Escherichia coli K-12: a cooperatively developed annotation
            snapshot--2005
JOURNAL     Nucleic Acids Res. 34 (1), 1-9 (2006)
PUBMED      16397293
REMARK      Publication Status: Online-Only
```

```
REFERENCE   2  (bases 1 to 4646332)
AUTHORS     Hayashi, K., Morooka, N., Yamamoto, Y., Fujita, K., Isono, K.,
            Choi, S., Ohtsubo, E., Baba, T., Wanner, B. L., Mori, H. and Horiuchi, T.
TITLE       Highly accurate genome sequences of Escherichia coli K-12
            strains  MG1655 and W3110
JOURNAL     Mol. Syst. Bio. 2, 2006 (2006)
PUBMED      16738553

REFERENCE   3
AUTHORS     Yamamoto, Y., Aiba, H., Baba, T., Hayashi, K., Inada, T., Isono, K.,
            Itoh, T., Kimura, S., Kitagawa, M., Makino, K., Miki, T., Mitsuhashi, N.,
            Mizobuchi, K., Mori, H., Nakade, S., Nakamura, Y., Nashimoto, H.,
            Oshima, T., Oyama, S., Saito, N., Sampei, G., Satoh, Y.,
            Siyasundaram, S., Tagami, H., Takahashi, H., Takeda, J., Takemoto, K.,
            Uehara, K., Wada, C., Yamagata, S. and Horiuchi, T.
TITLE       Construction of a contiguous 874-kb sequence of the Escherichia
            coli -K12 genome corresponding to 50.0-68.8 min on the linkage  map
            and analysis of its sequence features
JOURNAL     DNA Res. 4 (2), 91-113 (1997)
PUBMED      9205837

REFERENCE   4
AUTHORS     Itoh, T., Aiba, H., Baba, T., Hayashi, K., Inada, T., Isono, K.,
            Kasai, H., Kimura, S., Kitakawa, M., Kitagawa, M., Makino, K.,
            Miki, T.,  Mizobuchi, K., Mori, H., Mori, T., Motomura, K., Nakade, S.,
            Nakamura, Y., Nashimoto, H., Nishio, Y., Oshima, T., Saito, N.,
            Sampei, G., Seki, Y., Siyasundaram, S., Tagami, H., Takeda, J.,
            Takemoto, K., Wada, C., Yamamoto, Y. and Horiuchi, T.
TITLE       A 460-kb DNA sequence of the Escherichia coli K-12 genome
            corresponding to the 40.1-50.0 min region on the linkage map
JOURNAL     DNA Res. 3 (6), 379-392 (1996)
PUBMED      9097040

REFERENCE   5
AUTHORS     Aiba, H., Baba, T., Hayashi, K., Inada, T., Isono, K., Itoh, T.,
            Kasai, H., Kashimoto, K., Kimura, S., Kitakawa, M., Kitagawa, M.,
            Makino, K., Miki, T., Mizobuchi, K., Mori, H., Mori, T.,
            Motomura, K.,  Nakade, S., Naka-
            mura, Y., Nashimoto, H., Nishio, Y., Oshima, T.,
            Saito, N., Sampei, G., Seki, Y., Siyasundaram, S., Tagami, H.,
            Takeda, J., Takemoto, K., Takeuchi, Y., Wada, C., Yamamoto, Y. and
            Horiuchi, T.
TITLE       A 570-kb DNA sequence of the Escherichia coli K-12 genome
            corresponding to the 28.0-40.1 min region on the linkage map
JOURNAL     DNA Res. 3 (6), 363-377 (1996)
PUBMED      9097039

REFERENCE   6
AUTHORS     Arn, E. A. and Abelson, J. N.
TITLE       The 2'-5'RNA ligase of Escherichia coli. Purification,
            cloning, and genomic disruption
JOURNAL     J. Biol. Chem. 271 (49), 31145-31153 (1996)
PUBMED      8940112

REFERENCE   7
AUTHORS     Oshima, T., Aiba, H., Baba, T., Fujita, K., Hayashi, K., Honjo, A.,
            Ikemoto, K., Inada, T., Itoh, T., Kajihara, M., Kanai, K.,
            Kashimoto, K., Kimura, S., Kitagawa, M., Makino, K., Masuda, S., Miki, T.,
            Mizobuchi, K., Mori, H., Motomura, K., Nakamura, Y., Nashimoto, H.,
            Nishio, Y., Saito, N., Sampei, G., Seki, Y., Tagami, H.,
            Takemoto, K., Wada, C., Yamamoto, Y., Yano, M. and Horlichi, T.
TITLE       A 718-kb DNA sequence of the Escherichia coli K-12 genome
            corresponding to the 12.7-28.0 min region on the linkage map
JOURNAL     DNA Res. 3 (3), 137-155 (1996)
PUBMED      8905232

REFERENCE   8
AUTHORS     Fujita, N., Mori, H., Yura, T. and Ishliama, A.
TITLE       Systematic sequencing of the Escherichia coli genome: analysis
            of the 2.4-4.1 min (110, 917-193, 643 bp) region
JOURNAL     Nucleic Acids Res. 22 (9), 1637-1639 (1994)
PUBMED      8202364

REFERENCE   9
AUTHORS     Janosi, L., Shimizu, I. and Kaji, A.
TITLE       Ribosome recycling factor (ribosome releasing factor) is
            essential for bacterial growth
JOURNAL     Proc. Natl. Acad. Sci. U.S.A. 91 (10), 4249-4253 (1994)
PUBMED      8183897
```

-continued

```
REFERENCE   10
AUTHORS     Allikmets, R., Gerrard, B., Court, D. and Dean, M.
TITLE       Cloning and organization of the abc and mdl genes of
            Escherichia coli: relationship to eukaryotic multidrug resistance
JOURNAL     Gene 136 (1-2), 231-236 (1993)
PUBMED      7904973

REFERENCE   11
AUTHORS     van Heeswijk, W. C., Rabenberg, M., Westerhoff, H. V. and Kahn, D.
TITLE       The genes of the glutamine synthetase adenylylation cascade
            are not regulated by nitrogen in Escherichia coli
JOURNAL     Mol. Microbiol. 9 (3), 443-457 (1993)
PUBMED      8412694

REFERENCE   12
AUTHORS     Zhao, S., Sandt, C. H., Feulner, G., Vlazny, D. A., Gray, J. A. and
            Hill, C.W.
TITLE       Rhs elements of Escherichia coli K-12: complex composites of
            shared and unique components that have different evolutionary
            histories
JOURNAL     J. Bacteriol. 175 (10), 2799-2808 (1993)
PUBMED      8387990

REFERENCE   13
AUTHORS     Yamada, M., Asaoka, S., Saier, M. H. Jr. and Yamada, Y.
TITLE       Characterization of the gcd gene from Escherichia coli K-12
            W3110 and regulation of its expression
JOURNAL     J. Bacteriol. 175 (2), 568-571 (1993)
PUBMED      8419307

REFERENCE   14
AUTHORS     Cormack, R. S. and Mackli, G. A.
TITLE       Structural requirements for the processing of Escherichia coli
            5 S ribosomal RNA by RNase E in vitro
JOURNAL     J. Mol. Biol. 228 (4), 1078-1090 (1992)
PUBMED      1474579

REFERENCE   15
AUTHORS     Gervali, F. G. and Drapeau, G. R.
TITLE       Identification, cloning, and characterization of rcsF, a new
            regulator gene for exopolysaccharide synthesis that suppresses
            the division mutation ftsZ84 in Escherichia coli K-12
JOURNAL     J. Bacteriol. 174 (24), 8016-8022 (1992)
PUBMED      1459951

REFERENCE   16
AUTHORS     Yamanaka, K., Ogura, T., Niki, H. and Hiraga, S.
TITLE       Identification and characterization of the smbA gene, a
            suppressor of the mukB null mutant of Escherichia coli
JOURNAL     J. Bacteriol. 174 (23), 7517-7526 (1992)
PUBMED      1447125

REFERENCE   17
AUTHORS     Condon, C., Philips, J., Fu, Z. Y., Squires, C. and Squires, C. L.
TITLE       Comparison of the expression of the seven ribosomal RNA
            operons in Escherichia coli
JOURNAL     EMBO J. 11 (11), 4175-4185 (1992)
PUBMED      1396599

REFERENCE   18
AUTHORS     Arnqvist, A., Olsen, A., Pfeifer, J., Russell, D. G. and Normark, S.
TITLE       The Crl protein activates cryptic genes for curl formation
            and fibronectin binding in Escherichia coli HB101
JOURNAL     Mol. Microbiol. 6 (17), 2443-2452 (1992)
PUBMED      1357528

REFERENCE   19
AUTHORS     Talarico, T. L., Ray, P. H., Dev, I. K., Merrill, B. M. and
            Dallas, W. S.
TITLE       Cloning, sequence analysis, and overexpression of Escherichia
            coli folK, the gene coding for 7,8-dihydro-6-hydroxymethylpterin-
            pyrophosphokinase
JOURNAL     J. Bacteriol. 174 (18), 5971-5977 (1992)
PUBMED      1325970

REFERENCE   20
AUTHORS     Li, S. J. and Cronan, J. E. Jr.
TITLE       The genes encoding the two carboxyltransferase subunits of
            Escherichia coli acetyl-CoA carboxylase
JOURNAL     J. Biol. Chem. 267 (24), 16841-16847 (1992)
PUBMED      1355089
```

```
REFERENCE   21
AUTHORS     Yura, T., Mori, H., Nagai, H., Nagata, T., Ishihama, A., Fujita, N.,
            Isono, K., Mizobuchi, K. and Nakata, A.
TITLE       Systematic sequencing of the Escherichia coli genome: analysis
            of the 0-2.4 min region
JOURNAL     Nucleic Acids Res. 20 (13), 3305-3308 (1992)
PUBMED      1630901

REFERENCE   22
AUTHORS     Ghosh, S. K., Biswas, S. K., Paul, K. and Das, J.
TITLE       Nucleotide and deduced amino acid sequence of the recA gene of
            Vibrio cholerae
JOURNAL     Nucleic Acids Res. 20 (2), 372 (1992)
PUBMED      1741267

REFERENCE   23
AUTHORS     Smallshaw, J. E. and Kelln, R. A.
TITLE       Cloning, nucleotide sequence and expression of the Escherichia
            coli K-12 pyrH gene encoding UMP kinase
JOURNAL     Genetics (Life Sci. Adv.) 11, 59-65 (1992)

REFERENCE   24
AUTHORS     O'Neill, G. P., Grygorczyk, R., Adam, M. and Ford-Hutchinson, A. W.
TITLE       The nucleotide sequence of a voltage-gated chloride channel
            from the electric organ of Torpedo californica
JOURNAL     Biochim. Biophys. Acta 1129 (1), 131-134 (1991)
PUBMED      1721838

REFERENCE   25
AUTHORS     Kajie, S., Ideta, R., Yamato, I. and Anraku, Y.
TITLE       Molecular cloning and DNA sequence of dniR, a gene affecting
            anaerobic expression of the Escherichia coli hexaheme nitrite
            reductase
JOURNAL     FEMS Microbiol. Lett. 67 (2), 205-211 (1991)
PUBMED      1663890

REFERENCE   26
AUTHORS     Hershfield, M. S., Chaffee, S., Koro-Johnson, L., Mary, A.,
            Smith, A. A. and Short, S. A.
TITLE       Use of site-directed mutagenesis to enhance the epitope-
            shielding effect of covalent modification of proteins with polyethylene
            glycol
JOURNAL     Proc. Natl. Acad. Sci. U.S.A. 88 (16), 7185-7189 (1991)
PUBMED      1714590

REFERENCE   27
AUTHORS     Shimizu, I. and Kaji, A.
TITLE       Identification of the promoter region of the ribosome-
            releasing factor cistron (frr)
JOURNAL     J. Bacteriol. 173 (16), 5181-5187 (1991)
PUBMED      1860827

REFERENCE   28
AUTHORS     Poulsen, L. K., Refn, A., Molin, S. and Andersson, P.
TITLE       The gef gene from Escherichia coli is regulated at the level
            of translation
JOURNAL     Mol. Microbiol. 5 (7), 1639-1648 (1991)
PUBMED      1943701

REFERENCE   29
AUTHORS     Poulsen, L. K., Refn, A., Molin, S. and Andersson, P.
TITLE       Topographic analysis of the toxic Gef protein from Escherichia
            coli
JOURNAL     Mol. Microbiol. 5 (7), 1627-1637 (1991)
PUBMED      1943700

REFERENCE   30
AUTHORS     Kawamukai, M., Utsumi, R., Takeda, K., Higashi, A., Matsuda, H.,
            Choi, Y. L. and Komano, T.
TITLE       Nucleotide sequence and characterization of the sfs1 gene:
            sfs1 is involved in CRP*-dependent mal gene expression in Escherichia
            coli
JOURNAL     J. Bacteriol. 173 (8), 2644-2648 (1991)
PUBMED      2013578
```

```
                           -continued
REFERENCE    31
AUTHORS      Hulton, C. S., Higgins, C. F. and Sharp, P. M.
TITLE        ERIC sequences: a novel family of repetitive elements in the
             genomes of Escherichia coli, Salmonella typhimurium and other
             enterobacteria
JOURNAL      Mol. Microbiol. 5 (4), 825-834 (1991)
PUBMED       1713281

REFERENCE    32
AUTHORS      Munro, A. W., Ritchie, G. Y., Lamb, A. J., Douglas, R. M. and
             Booth, I. R.
TITLE        The cloning and DNA sequence of the gene for the
             glutathione-regulated potassium-efflux system KefC of
             Escherichia coli
JOURNAL      Mol. Microbiol. 5 (3), 607-616 (1991)
PUBMED       2046548

REFERENCE    33
AUTHORS      Arigoni, F., Kaminski, P. A., Hennecke, H. and Elmerich, C.
TITLE        Nucleotide sequence of the fixABC region of Azorhizobium
             caulinodans ORS571: similarity of the fixB product with
             eukaryotic flavoproteins, characterization of fixX, and identification of
             nifW
JOURNAL      Mol. Gen. Genet. 225 (3), 514-520 (1991)
PUBMED       1850088

REFERENCE    34
AUTHORS      Mattick, J. S., Anderson, B. J., Cox, P. T., Dalrymple, B. P.,
             Bills, M. M., Hobbs, M. and Egerton, J. R.
TITLE        Gene sequences and comparison of the fimbrial subunits
             representative of Bacteroides nodosus serotypes A to I: class
             I and class II strains
JOURNAL      Mol. Microbiol. 5 (3), 561-573 (1991)
PUBMED       1675419

REFERENCE    35
AUTHORS      Company, M., Arenas, J. and Abelson, J.
TITLE        Requirement of the RNA helicase-like protein PRP22 for release
             of messenger RNA from spliceosomes
JOURNAL      Nature 349 (6309), 487-493 (1991)
PUBMED       1992352

REFERENCE    36
AUTHORS      Umeda, M. and Ohtsubo, E.
TITLE        Four types of IS1 with differences in nucleotide sequence
             reside in the Escherichia coli K-12 chromosome
JOURNAL      Gene 98 (1), 1-5 (1991)
PUBMED       1849492

REFERENCE    37
AUTHORS      Hirvas, L., Koski, P. and Vaara, M.
TITLE        The ompH gene of Yersinia enterocolitica: cloning, sequencing,
             expression, and comparison with known enterobacterial ompH
             sequences
JOURNAL      J. Bacteriol. 173 (3), 1223-1229 (1991)
PUBMED       1991717

REFERENCE    38
AUTHORS      Bouvier, J. and Stragier, P.
TITLE        Nucleotide sequence of the lsp-dapB interval in Escherichia
             coli
JOURNAL      Nucleic Acids Res. 19 (1), 180 (1991)
PUBMED       2011499

REFERENCE    39
AUTHORS      Dicker, I. B. and Seetharam, S.
TITLE        Cloning and nucleotide sequence of the firA gene and the
             firA200(Ts) allele from Escherichia coli
JOURNAL      J. Bacteriol. 173 (1), 334-344 (1991)
PUBMED       1987124

REFERENCE    40
AUTHORS      Grimm, B., Bull, A. and Breu, V.
TITLE        Structural genes of glutamate 1-semialdehyde aminotransferase
             for  porphyrin synthesis in a cyanobacterium and Escherichia coli
JOURNAL      Mol. Gen. Genet. 225 (1), 1-10 (1991)
PUBMED       1900346
```

```
REFERENCE   41
AUTHORS     Allen, B. L., Gerlach, G. F. and Clegg, S.
TITLE       Nucleotide sequence and functions of mrk determinants
            necessary for   expression of type 3 fimbriae in *Klebsiella pneumoniae*
JOURNAL     J. Bacteriol. 173 (2), 916-920 (1991)
PUBMED      1670938

REFERENCE   42
AUTHORS     Chen, H., Lawrence, C. B., Bryan, S. K. and Moses, R. E.
TITLE       Aphidicolin inhibits DNA polymerase II of *Escherichia coli*, an
            alpha-like DNA polymerase
JOURNAL     Nucleic Acids Res. 18 (23), 7185-7186 (1990)
PUBMED      2124684

REFERENCE   43
AUTHORS     Mallonee, D. H., White, W. B. and Hylemon, P. B.
TITLE       Cloning and sequencing of a bile acid-inducible operon from
            *Eubacterium* sp. strain VPI 12708
JOURNAL     J. Bacteriol. 172 (12), 7011-7019 (1990)
PUBMED      2254270

REFERENCE   44
AUTHORS     Young, C., Collins-Emerson, J. M., Terzaghi, E. A. and Scott, D. B.
TITLE       Nucleotide sequence of *Rhizobilm loti* nodI
JOURNAL     Nucleic Acids Res. 18 (22), 6691 (1990)
PUBMED      2251131

REFERENCE   45
AUTHORS     Chen, H., Sun, Y., Stark, T., Beattil, W. and Moses, R. E.
TITLE       Nucleotide sequence and deletion analysis of the polB gene of
            *Escherichia coli*
JOURNAL     DNA Cell Biol. 9 (9), 631-635 (1990)
PUBMED      2261080

REFERENCE   46
AUTHORS     Eilani, G., Delarue, M., Poch, O., Gangloff, J. and Moras, D.
TITLE       Partition of tRNA synthetases into two classes based on
            mutually exclusive sets of sequence motifs
JOURNAL     Nature 347 (6289), 203-206 (1990)
PUBMED      2203971

REFERENCE   47
AUTHORS     Showalter, R. E. and Silverman, M. R.
TITLE       Nucleotide sequence of a gene, hpt, for hypoxanthine
            phosphoribosyltransferase from *Vibrio harveyi*
JOURNAL     Nucleic Acids Res. 18 (15), 4621 (1990)
PUBMED      2388850

REFERENCE   48
AUTHORS     Martin-Verstraete, I., Debarbouille, M., Klier, A. and
            Rapoport, G.
TITLE       Levanase operon of *Bacillus subtilis* includes a fructose-
            specific phosphotransferase system regulating the expression of the
            operon
JOURNAL     J. Mol. Biol. 214 (3), 657-671 (1990)
PUBMED      2117666

REFERENCE   49
AUTHORS     Henrich, B., Monnerjahn, U. and Plapp, R.
TITLE       Peptidase D gene (pepD) of *Escherichia coli* K-12: nucleotide
            sequence, transcript mapping, and comparison with other
            peptidase genes
JOURNAL     J. Bacteriol. 172 (8), 4641-4651 (1990)
PUBMED      1695895

REFERENCE   50
AUTHORS     Nunn, D., Bergman, S. and Lory, S.
TITLE       Products of three accessory genes, pilB, pilC, and pilD, are
            required for biogenesis of *Pseudomonas aeruginosa* pill
JOURNAL     J. Bacteriol. 172 (6), 2911-2919 (1990)
PUBMED      1971619

REFERENCE   51
AUTHORS     Rosenthal, E. R. and Calyo, J. M.
TITLE       The nucleotide sequence of leuC from *Salmonella typhimurium*
JOURNAL     Nucleic Acids Res. 18 (10), 3072 (1990)
PUBMED      2190189
```

```
REFERENCE   52
AUTHORS     Kang, P. J. and Craig, E. A.
TITLE       Identification and characterization of a new Escherichia coli
            gene that is a dosage-dependent suppressor of a dnaK deletion
            mutation
JOURNAL     J. Bacteriol. 172 (4), 2055-2064 (1990)
PUBMED      2180916

REFERENCE   53
AUTHORS     Wurgler, S. M. and Richardson, C. C.
TITLE       Structure and regulation of the gene for dGTP
            triphosphohydrolase from Escherichia coli
JOURNAL     Proc. Natl. Acad. Sci. U.S.A. 87 (7), 2740-2744 (1990)
PUBMED      2157212

REFERENCE   54
AUTHORS     Schaaff, I., Hohmann, S. and Zimmermann, F. K.
TITLE       Molecular analysis of the structural gene for yeast
            transaldolase
JOURNAL     Eur. J. Biochem. 188 (3), 597-603 (1990)
PUBMED      2185015

REFERENCE   55
AUTHORS     Ricca, E. and Calyo, J. M.
TITLE       The nucleotide sequence of leuA from Salmonella typhimurium
JOURNAL     Nucleic Acids Res. 18 (5), 1290 (1990)
PUBMED      2181403

REFERENCE   56
AUTHORS     Honore, N. and Cole, S. T.
TITLE       Nucleotide sequence of the aroP gene encoding the general
            aromatic amino acid transport protein of Escherichia coli K-12:
            homology
            with yeast transport proteins
JOURNAL     Nucleic Acids Res. 18 (3), 653 (1990)
PUBMED      2408019

REFERENCE   57
AUTHORS     Angerer, A., Gaisser, S. and Braun, V.
TITLE       Nucleotide sequences of the sfuA, sfuB, and sfuC genes of
            Serratia marcescens suggest a periplasmic-binding-protein-dependent
            iron
            transport mechanism
JOURNAL     J. Bacteriol. 172 (2), 572-578 (1990)
PUBMED      2404942

REFERENCE   58
AUTHORS     Surin, B. P., Watson, J. M., Hamilton, W. D., Economou, A. and
            Downie, J. A.
TITLE       Molecular characterization of the nodulation gene, nodT, from
            two biovars of Rhizobium leguminosarum
JOURNAL     Mol. Microbiol. 4 (2), 245-252 (1990)
PUBMED      2338917

REFERENCE   59
AUTHORS     Zhou, Z. and Syvanen, M.
TITLE       Identification and sequence of the drpA gene from Escherichia
            coli
JOURNAL     J. Bacteriol. 172 (1), 281-286 (1990)
PUBMED      1688424

REFERENCE   60
AUTHORS     Roncero, M. I., Jepsen, L. P., Stroman, P. and van Heeswijck, R.
TITLE       Characterization of a leuA gene and an ARS element from Mucor
            circinelloides
JOURNAL     Gene 84 (2), 335-343 (1989)
PUBMED      2693214

REFERENCE   61
AUTHORS     Ichikawa, S. and Kaji, A.
TITLE       Molecular cloning and expression of ribosome releasing factor
JOURNAL     J. Biol. Chem. 264 (33), 20054-20059 (1989)
PUBMED      2684966
```

```
REFERENCE   62
AUTHORS     Minami-Ishii, N., Taketani, S., Osumi, T. and Hashimoto, T.
TITLE       Molecular cloning and sequence analysis of the cDNA for rat
            mitochondrial enoyl-CoA hydratase. Structural and evolutionary
            relationships linked to the bifunctional enzyme of the
            peroxisomal beta-oxidation system
JOURNAL     Eur. J. Biochem. 185 (1), 73-78 (1989)
PUBMED      2806264

REFERENCE   63
AUTHORS     Matsubara, Y., Indo, Y., Naito, E., Ozasa, H., Glassberg, R.,
            Vockley, J., Ikeda, Y., Kraus, J. and Tanaka, K.
TITLE       Molecular cloning and nucleotide sequence of cDNAs encoding
            the precursors of rat long chain acyl-coenzyme A, short chain
            acyl-coenzyme A, and isovaleryl-coenzyme A dehydrogenases.
            Sequence
            homology of four enzymes of the acyl-CoA dehydrogenase family
JOURNAL     J. Biol. Chem. 264 (27), 16321-16331 (1989)
PUBMED      2777793

REFERENCE   64
AUTHORS     Roa, B .B., Connolly, D. M. and Winkler, M. E.
TITLE       Overlap between pdxA and ksgA in the complex pdxA-ksgA-apaG-
            apaH operon of *Escherichia coli* K-12
JOURNAL     J. Bacteriol. 171 (9), 4767-4777 (1989)
PUBMED      2670894

REFERENCE   65
AUTHORS     Lindquist, S., Galleni, M., Lindberg, F. and Normark, S.
TITLE       Signalling proteins in enterobacterial AmpC beta-lactamase
            regulation
JOURNAL     Mol. Microbiol. 3 (8), 1091-1102 (1989)
PUBMED      2691840

REFERENCE   66
AUTHORS     Xie, Q. W., Tabor, C. W. and Tabor, H.
TITLE       Spermidine biosynthesis in *Escherichia coli*: promoter and
            termination regions of the speED operon
JOURNAL     J. Bacteriol. 171 (8), 4457-4465 (1989)
PUBMED      2666401

REFERENCE   67
AUTHORS     Sato, S., Nakada, Y. and Shiratsuchi, A.
TITLE       IS421, a new insertion sequence in *Escherichia coli*
JOURNAL     FEBS Lett. 249 (1), 21-26 (1989)
PUBMED      2542093

REFERENCE   68
AUTHORS     Liu, J. D. and Parkinson, J. S.
TITLE       Genetics and sequence analysis of the pcnB locus, an
            *Escherichia coli* gene involved in plasmid copy number control
JOURNAL     J. Bacteriol. 171 (3), 1254-1261 (1989)
PUBMED      2537812

REFERENCE   69
AUTHORS     Henrich, B., Schroeder, U., Frank, R. W. and Plapp, R.
TITLE       Accurate mapping of the *Escherichia coli* pepD gene by sequence
            analysis of its 5' flanking region
JOURNAL     Mol. Gen. Genet. 215 (3), 369-373 (1989)
PUBMED      2651887

REFERENCE   70
AUTHORS     Lipinska, B., Sharma, S. and Georgopoulos, C.
TITLE       Sequence analysis and regulation of the htrA gene of
            *Escherichia coli*: a sigma 32-independent mechanism of heat-inducible
            transcript ion
JOURNAL     Nucleic Acids Res. 16 (21), 10053-10067 (1988)
PUBMED      3057437

REFERENCE   71
AUTHORS     Sung, Y. C. and Fuchs, J. A.
TITLE       Characterization of the cyn operon in *Escherichia coli* K12
JOURNAL     J. Biol. Chem. 263 (29), 14769-14775 (1988)
PUBMED      3049588
```

```
REFERENCE   72
AUTHORS     Lozoya, E., Hoffmann, H., Douglas, C., Schulz, W., Scheel, D. and
            Hahlbrock, K.
TITLE       Primary structures and catalytic properties of isoenzymes
            encoded by the two 4-coumarate: CoA ligase genes in parsley
JOURNAL     Eur. J. Biochem. 176 (3), 661-667 (1988)
PUBMED      3169018

REFERENCE   73
AUTHORS     Andrews, S. C. and Guest, J. R.
TITLE       Nucleotide sequence of the gene encoding the GMP reductase of
            Escherichia coli K12
JOURNAL     Biochem. J. 255 (1), 35-43 (1988)
PUBMED      2904262

REFERENCE   74
AUTHORS     Jaiswal, A. K., McBride, O. W., Adesnik, M. and Nebert, D. W.
TITLE       Human dioxin-inducible cytosolic NAD(P)H: menadione
            oxidoreductase. cDNA sequence and localization of gene to chromosome 16
JOURNAL     J. Biol. Chem. 263 (27), 13572-13578 (1988)
PUBMED      2843525

REFERENCE   75
AUTHORS     Karpel, R., Olami, Y., Taglicht, D., Schuldiner, S. and Padan, E.
TITLE       Sequencing of the gene ant which affects the Na+/H+30 antiporter
            activity in Escherichia coli
JOURNAL     J. Biol. Chem. 263 (21), 10408-10414 (1988)
PUBMED      2839489

REFERENCE   76
AUTHORS     Mellano, M. A. and Cooksey, D. A.
TITLE       Nucleotide sequence and organization of copper resistance
            genes from Pseudomonas syringae pv. tomato
JOURNAL     J. Bacteriol. 170 (6), 2879-2883 (1988)
PUBMED      3372485

REFERENCE   77
AUTHORS     Coleman, J. and Raetz, C.R.
TITLE       First committed step of lipid A biosynthesis in Escherichia
            coli: sequence of the lpxA gene
JOURNAL     J. Bacteriol. 170 (3), 1268-1274 (1988)
PUBMED      3277952

REFERENCE   78
AUTHORS     Gebhard, W., Schreitmuller, T., Hochstrasser, K. and Wachter, E.
TITLE       Complementary DNA and derived amino acid sequence of the
            precursor of one of the three protein components of the inter-alpha-
            trypsin
            inhibitor complex
JOURNAL     FEBS Lett. 229 (1), 63-67 (1988)
PUBMED      2450046

REFERENCE   79
AUTHORS     Tomasiewicz, H. G. and McHenry, C. S.
TITLE       Sequence analysis of the Escherichia coli dnaE gene
JOURNAL     J. Bacteriol. 169 (12), 5735-5744 (1987)
PUBMED      3316192

REFERENCE   80
AUTHORS     Crowell, D. N., Reznikoff, W. S. and Raetz, C. R.
TITLE       Nucleotide sequence of the Escherichia coli gene for lipid A
            disaccharide synthase
JOURNAL     J. Bacteriol. 169 (12), 5727-5734 (1987)
PUBMED      2824445

REFERENCE   81
AUTHORS     Tabor, C. W. and Tabor, H.
TITLE       The speEspeD operon of Escherichia coli. Formation and
            processing of a proenzyme form of S-adenosylmethionine decarboxylase
JOURNAL     J. Biol. Chem. 262 (33), 16037-16040 (1987)
PUBMED      3316212

REFERENCE   82
AUTHORS     Nonet, M. L., Marvel, C. C. and Tolan, D. R.
TITLE       The hisT-purF region of the Escherichia coli K-12 chromosome.
            Identification of additional genes of the hisT and purF
            operons
JOURNAL     J. Biol. Chem. 262 (25), 12209-12217 (1987)
PUBMED      3040734
```

```
REFERENCE   83
AUTHORS     Coulton, J. W., Mason, P. and Allatt, D. D.
TITLE       fhuC and fhuD genes for iron (III)-ferrichrome transport into
            Escherichia coli K-12
JOURNAL     J. Bacteriol. 169 (8), 3844-3849 (1987)
PUBMED      3301821

REFERENCE   84
AUTHORS     Horiuchi, T., Nagasawa, T., Takano, K. and Sekiguchi, M.
TITLE       A newly discovered tRNA(1Asp) gene (aspV) of Escherichia coli
            K12
JOURNAL     Mol. Gen. Genet. 206 (2), 356-357 (1987)
PUBMED      3295485

REFERENCE   85
AUTHORS     Ben-Bassat, A., Bauer, K., Chang, S. Y., Myambo, K., Boosman, A. and
            Chang, S.
TITLE       Processing of the initiation methionine from proteins:
            properties of the Escherichia coli methionine aminopeptidase and its gene
            structure
JOURNAL     J. Bacteriol. 169 (2), 751-757 (1987)
PUBMED      3027045

REFERENCE   86
AUTHORS     Gronger, P., Manian, S. S., Reilander, H., O'Connell, M.,
            Priefer, U. B. and Puhler, A.
TITLE       Organization and partial sequence of a DNA region of the
            Rhizobium leguminosarum symbiotic plasmid pRL6JI containing the genes
            fixABC, nifA, nifB and a novel open reading frame
JOURNAL     Nucleic Acids Res. 15 (1), 31-49 (1987)
PUBMED      3029674

REFERENCE   87
AUTHORS     Richardson, K. K., Richardson, F. C., Crosby, R. M., Swenberg, J. A.
            and Skopek, T. R.
TITLE       DNA base changes and alkylation following in vivo exposure of
            Escherichia coli to N-methyl-N-nitrosourea or N-ethyl-N-
            nitrosourea
JOURNAL     Proc. Natl. Acad. Sci. U.S.A. 84 (2), 344-348 (1987)
PUBMED      3540961

REFERENCE   88
AUTHORS     Chye, M. L. and Pittard, J.
TITLE       Transcription control of the aroP gene in Escherichia coli K-12:
            analysis of operator mutants
JOURNAL     J. Bacteriol. 169 (1), 386-393 (1987)
PUBMED      3025182

REFERENCE   89
AUTHORS     Blanchin-Roland, S., Blanquet, S., Schmitter, J. M. and Fayat, G.
TITLE       The gene for Escherichia coli diadenosine tetraphosphatase is
            located immediately clockwise to folA and forms an operon with
            ksgA
JOURNAL     Mol. Gen. Genet. 205 (3), 515-522 (1986)
PUBMED      3031429

REFERENCE   90
AUTHORS     Takano, K., Nakabeppu, Y., Maki, H., Horiuchi, T. and Sekiguchi, M.
TITLE       Structure and function of dnaQ and mutD mutators of Escherichia
            coli
JOURNAL     Mol. Gen. Genet. 205 (1), 9-13 (1986)
PUBMED      3540531

REFERENCE   91
AUTHORS     Mackie, G. A.
TITLE       Structure of the DNA distal to the gene for ribosomal protein S20
            in Escherichia coli K12: presence of a strong terminator and an IS1
            element
JOURNAL     Nucleic Acids Res. 14 (17), 6965-6981 (1986)
PUBMED      2429258

REFERENCE   92
AUTHORS     Koster, W. and Braun, V.
TITLE       Iron hydroxamate transport of Escherichia coli: nucleotide sequence
            of the fhuB gene and identification of the protein
JOURNAL     Mol. Gen. Genet. 204 (3), 435-442 (1986)
PUBMED      3020380
```

-continued

| | |
|---|---|
| REFERENCE | 93 |
| AUTHORS | Breton, R., Sanfacon, H., Papayannopoulos, I., Biemann, K. and Lapointe, J. |
| TITLE | Glutamyl-tRNA synthetase of *Escherichia coli*. Isolation and primary structure of the gltX gene and homology with other aminoacyl-tRNA synthetases |
| JOURNAL | J. Biol. Chem. 261 (23), 10610-10617 (1986) |
| PUBMED | 3015933 |
| | |
| REFERENCE | 94 |
| AUTHORS | Birnbaum, M. J., Haspel, H. C. and Rosen, O. M. |
| TITLE | Cloning and characterization of a cDNA encoding the rat brain glucose-transporter protein |
| JOURNAL | Proc. Natl. Acad. Sci. U.S.A. 83 (16), 5784-5788 (1986) |
| PUBMED | 3016720 |
| | |
| REFERENCE | 95 |
| AUTHORS | Cox, E. C. and Horner, D. L. |
| TITLE | DNA sequence and coding properties of mutD(dnaQ) a dominant *Escherichia coli* mutator gene |
| JOURNAL | J. Mol. Biol. 190 (1), 113-117 (1986) |
| PUBMED | 3023634 |
| | |
| REFERENCE | 96 |
| AUTHORS | Ohki, M., Tamura, F., Nishimura, S. and Uchida, H. |
| TITLE | Nucleotide sequence of the *Escherichia coli* dnaJ gene and purification of the gene product |
| JOURNAL | J. Biol. Chem. 261 (4), 1778-1781 (1986) |
| PUBMED | 3003084 |
| | |
| REFERENCE | 97 |
| AUTHORS | Coulton, J. W., Mason, P., Cameron, D. R., Carmel, G., Jean, R. and Rode, H. N. |
| TITLE | Protein fusions of beta-galactosidase to the ferrichrome-iron receptor of *Escherichia coli* K-12 |
| JOURNAL | J. Bacteriol. 165 (1), 181-192 (1986) |
| PUBMED | 3079747 |
| | |
| REFERENCE | 98 |
| AUTHORS | Lee, N., Gielow, W., Martin, R., Hamilton, E. and Fowler, A. |
| TITLE | The organization of the araBAD operon of *Escherichia coli* |
| JOURNAL | Gene 47 (2-3), 231-244 (1986) |
| PUBMED | 3549454 |
| | |
| REFERENCE | 99 |
| AUTHORS | Sekiguchi, T., Ortega-Cesena, J., Nosoh, Y., Ohashi, S., Tsuda, K. and Kanaya, S. |
| TITLE | DNA and amino-acid sequences of 3-isopropylmalate dehydrogenase of *Bacillus coagulans*. Comparison with the enzymes of *Saccharomyces cerevisiae* and *Thermus thermophilus* |
| JOURNAL | Biochim. Biophys. Acta 867, 36-44 (1986) |
| | |
| REFERENCE | 100 |
| AUTHORS | Chong, P., Hui, I., Loo, T. and Gillam, S. |
| TITLE | Structural analysis of a new GC-specific insertion element IS186 |
| JOURNAL | FEBS Lett. 192 (1), 47-52 (1985) |
| PUBMED | 2996940 |
| | |
| REFERENCE | 101 |
| AUTHORS | Icho, T., Sparrow, C. P. and Raetz, C. R. |
| TITLE | Molecular cloning and sequencing of the gene for CDP-diglyceride synthetase of *Escherichia coli* |
| JOURNAL | J. Biol. Chem. 260 (22), 12078-12083 (1985) |
| PUBMED | 2995358 |
| | |
| REFERENCE | 102 |
| AUTHORS | Nomura, T., Aiba, H. and Ishihama, A. |
| TITLE | Transcriptional organization of the convergent overlapping dnaQ-rnh genes of *Escherichia coli* |
| JOURNAL | J. Biol. Chem. 260 (11), 7122-7125 (1985) |
| PUBMED | 2987244 |
| | |
| REFERENCE | 103 |
| AUTHORS | Kamio, Y., Lin, C. K., Regue, M. and Wu, H. C. |
| TITLE | Characterization of the ileS-lsp operon in Escherichia coli. Identification of an open reading frame upstream of the ileS gene and potential promoter(s) for the ileS-lsp operon |
| JOURNAL | J. Biol. Chem. 260 (9), 5616-5620 (1985) |
| PUBMED | 2985604 |

```
REFERENCE   104
AUTHORS     Cowing, D. W., Bardwell, J. C., Craig, E. A., Woolford, C.,
            Hendrix, R. W. and Gross, C. A.
TITLE       Consensus sequence for Escherichia coli heat shock gene
            promoters
JOURNAL     Proc. Natl. Acad. Sci. U.S.A. 82 (9), 2679-2683 (1985)
PUBMED      3887408

REFERENCE   105
AUTHORS     Broome-Smith, J. K., Edelman, A., Yousif, S. and Spratt, B. G.
TITLE       The nucleotide sequences of the ponA and ponB genes encoding
            penicillin-binding protein 1A and 1B of Escherichia coli K12
JOURNAL     Eur. J. Biochem. 147 (2), 437-446 (1985)
PUBMED      3882429

REFERENCE   106
AUTHORS     Becerril, B., Valle, F., Merino, E., Riba, L. and Bolivar, F.
TITLE       Repetitive extragenic palindromic (REP) sequences in the
            Escherichia coli gdhA gene
JOURNAL     Gene 37 (1-3), 53-62 (1985)
PUBMED      3902576

REFERENCE   107
AUTHORS     Friedberg, D., Rosenthal, E. R., Jones, J. W. and Calvo, J. M.
TITLE       Characterization of the 3' end of the leucine operon of
            Salmonella typhimurium
JOURNAL     Mol. Gen. Genet. 199 (3), 486-494 (1985)
PUBMED      2993799

REFERENCE   108
AUTHORS     Bouvier, J., Richaud, C., Richaud, F., Patte, J. C. and Stragier, P.
TITLE       Nucleotide sequence and expression of the Escherichia coli
            dapB gene
JOURNAL     J. Biol. Chem. 259 (23), 14829-14834 (1984)
PUBMED      6094578

REFERENCE   109
AUTHORS     Richaud, C., Richaud, F., Martin, C., Haziza, C. and Patte, J. C.
TITLE       Regulation of expression and nucleotide sequence of the
            Escherichia coli dapD gene
JOURNAL     J. Biol. Chem. 259 (23), 14824-14828 (1984)
PUBMED      6094577

REFERENCE   110
AUTHORS     Nuesch, J. and Schumperli, D.
TITLE       Structural and functional organization of the gpt gene region
            of Escherichia coli
JOURNAL     Gene 32 (1-2), 243-249 (1984)
PUBMED      6397401

REFERENCE   111
AUTHORS     Jagadeeswaran, P., Ashman, C. R., Roberts, S. and Langenberg, J.
TITLE       Nucleotide sequence and analysis of deletion mutants of the
            Escherichia coli gpt gene in plasmid pSV2 gpt
JOURNAL     Gene 31 (1-3), 309-313 (1984)
PUBMED      6396164

REFERENCE   112
AUTHORS     Deutch, A. H., Rushlow, K. E. and Smith, C. J.
TITLE       Analysis of the Escherichia coli proBA locus byDNA and
            protein sequencing
JOURNAL     Nucleic Acids Res. 12 (15), 6337-6355 (1984)
PUBMED      6089111

REFERENCE   113
AUTHORS     Bouvier, J., Patte, J. C. and Stragier, P.
TITLE       Multiple regulatory signals in the control region of the
            Escherichia coli carAB operon
JOURNAL     Proc. Natl. Acad. Sci. U.S.A. 81 (13), 4139-4143 (1984)
PUBMED      6377309

REFERENCE   114
AUTHORS     Innis, M. A., Tokunaga, M., Williams, M. E., Loranger, J. M.,
            Chang, S. Y., Chang, S. and Wu, H. C.
TITLE       Nucleotide sequence of the Escherichia coli prolipoprotein
            signal peptidase (lsp) gene
JOURNAL     Proc. Natl. Acad. Sci. U.S.A. 81 (12), 3708-3712 (1984)
PUBMED      6374664
```

```
REFERENCE   115
AUTHORS     Bardwell, J. C. and Craig, E. A.
TITLE       Major heat shock gene of Drosophila and the Escherichia coli
            heat-inducible dnaK gene are homologous
JOURNAL     Proc. Natl. Acad. Sci. U.S.A. 81 (3), 848-852 (1984)
PUBMED      6322174

REFERENCE   116
AUTHORS     Pratt, D. and Subramani, S.
TITLE       Nucleotide sequence of the Escherichia coli xanthine-guanine
            phosphoribosyl transferase gene
JOURNAL     Nucleic Acids Res. 11 (24), 8817-8823 (1983)
PUBMED      6324103

REFERENCE   117
AUTHORS     Richardson, K. K., Fostel, J. and Skopek, T. R.
TITLE       Nucleotide sequence of the xanthine guanine phosphoribosyl
            transferase gene of E. coli
JOURNAL     Nucleic Acids Res. 11 (24), 8809-8816 (1983)
PUBMED      6324102

REFERENCE   118
AUTHORS     Parsot, C., Cossart, P., Saint-Girons, I. and Cohen, G. N.
TITLE       Nucleotide sequence of thrC and of the transcription
            termination region of the threonine operon in Escherichia coli K12
JOURNAL     Nucleic Acids Res. 11 (21), 7331-7345 (1983)
PUBMED      6316258

REFERENCE   119
AUTHORS     Stephens, P. E., Lewis, H. M., Darlison, M. G. and Guest, J. R.
TITLE       Nucleotide sequence of the lipoamide dehydrogenase gene of
            Escherichia coli K12
JOURNAL     Eur. J. Biochem. 135 (3), 519-527 (1983)
PUBMED      6352260

REFERENCE   120
AUTHORS     Stephens, P. E., Darlison, M. G., Lewis, H. M. and Guest, J. R.
TITLE       The pyruvate dehydrogenase complex of Escherichia coli K12.
            Nucleotide sequence encoding the dihydrolipoamide acetyltransferase
            component
JOURNAL     Eur. J. Biochem. 133 (3), 481-489 (1983)
PUBMED      6345153

REFERENCE   121
AUTHORS     Stephens, P. E., Darlison, M. G., Lewis, H. M. and Guest, J. R.
TITLE       The pyruvate dehydrogenase complex of Escherichia coli K12.
            Nucleotide sequence encoding the pyruvate dehydrogenase
            component
JOURNAL     Eur. J. Biochem. 133 (1), 155-162 (1983)
PUBMED      6343085

REFERENCE   122
AUTHORS     Kanaya, S. and Crouch, R. J.
TITLE       Low levels of RNase H activity in Escherichia coli FB2 rnh
            result from a single-base change in the structural gene of RNase H
JOURNAL     J. Bacteriol. 154 (2), 1021-1026 (1983)
PUBMED      6302075

REFERENCE   123
AUTHORS     Overbeeke, N., Bergmans, H., van Mansfeld, F. and Lugtenberg, B.
TITLE       Complete nucleotide sequence of phoE, the structural gene for
            the phosphate limitation inducible outer membrane pore protein of
            Escherichia coli K12
JOURNAL     J. Mol. Biol. 163 (4), 513-532 (1983)
PUBMED      6341601

REFERENCE   124
AUTHORS     Gilson, E., Nikaido, H. and Hofnung, M.
TITLE       Sequence of the malK gene in E. coli K12
JOURNAL     Nucleic Acids Res. 10 (22), 7449-7458 (1982)
PUBMED      6296778

REFERENCE   125
AUTHORS     Stoner, C. M. and Schleif, R.
TITLE       Is the amino acid but not the nucleotide sequence of the
            Escherichia coli araC gene conserved
JOURNAL     J. Mol. Biol. 154 (4), 649-652 (1982)
PUBMED      6283093
```

```
REFERENCE   126
AUTHORS     An, G., Bendiak, D. S., Mamelak, L. A. and Friesen, J. D.
TITLE       Organization and nucleotide sequence of a new ribosomal operon
            in Escherichia coli containing the genes for ribosomal protein S2
            and elongation factor Ts
JOURNAL     Nucleic Acids Res. 9 (16), 4163-4172 (1981)
PUBMED      6272196

REFERENCE   127
AUTHORS     Mackie, G. A.
TITLE       Nucleotide sequence of the gene for ribosomal protein S20 and
            its flanking regions
JOURNAL     J. Biol. Chem. 256 (15), 8177-8182 (1981)
PUBMED      6267039

REFERENCE   128
AUTHORS     Little, J. W., Mount, D. W. and Yanisch-Perron, C. R.
TITLE       Purified lexA protein is a repressor of the recA and lexA
            genes
JOURNAL     Proc. Natl. Acad. Sci. U.S.A. 78 (7), 4199-4203 (1981)
PUBMED      7027255

REFERENCE   129
AUTHORS     Mulligan, R. C. and Berg, P.
TITLE       Factors governing the expression of a bacterial gene in
            mammalian cells
JOURNAL     Mol. Cell. Biol. 1 (5), 449-459 (1981)
PUBMED      6100966

REFERENCE   130
AUTHORS     Lee, N. L., Gielow, W. O. and Wallace, R. G.
TITLE       Mechanism of araC autoregulation and the domains of two
            overlapping promoters, Pc and PBAD, in the L-arabinose regulatory region
            of Escherichia coli
JOURNAL     Proc. Natl. Acad. Sci. U.S.A. 78 (2), 752-756 (1981)
PUBMED      6262769

REFERENCE   131
AUTHORS     Cossart, P., Katinka, M. and Yaniv, M.
TITLE       Nucleotide sequence of the thrB gene of E. coli, and its two
            adjacent regions; the thrAB and thrBC junctions
JOURNAL     Nucleic Acids Res. 9 (2), 339-347 (1981)
PUBMED      6259626

REFERENCE   132
AUTHORS     Miyada, C. G., Horwitz, A. H., Cass, L. G., Timko, J. and Wilcox, G.
TITLE       DNA sequence of the araC regulatory gene from Escherichia coli
            B/r
JOURNAL     Nucleic Acids Res. 8 (22), 5267-5274 (1980)
PUBMED      7008027

REFERENCE   133
AUTHORS     Katinka, M., Cossart, P., Sibilli, L., Saint-Girons, I.,
            Chalvignac, M. A., Le Bras, G., Cohen, G. N. and Yaniv, M.
TITLE       Nucleotide sequence of the thrA gene of Escherichia coli
JOURNAL     Proc. Natl. Acad. Sci. U.S.A. 77 (10), 5730-5733 (1980)
PUBMED      7003595

REFERENCE   134
AUTHORS     Ogden, S., Haggerty, D., Stoner, C. M., Kolodrubetz, D. and
            Schleif, R.
TITLE       The Escherichia coli L-arabinose operon: binding sites of the
            regulatory proteins and a mechanism of positive and negative
            regulation
JOURNAL     Proc. Natl. Acad. Sci. U.S.A. 77 (6), 3346-3350 (1980)
PUBMED      6251457

REFERENCE   135
AUTHORS     Smith, D. R. and Calyo, J. M.
TITLE       Nucleotide sequence of the E coli gene coding for
            dihydrofolate reductase
JOURNAL     Nucleic Acids Res. 8 (10), 2255-2274 (1980)
PUBMED      6159575

REFERENCE   136
AUTHORS     Johnsrud, L.
TITLE       DNA sequence of the transposable element IS1
JOURNAL     Mol. Gen. Genet. 169 (2), 213-218 (1979)
PUBMED      375010
```

```
                      -continued
REFERENCE   137
AUTHORS     Smith, B. R. and Schleif, R.
TITLE       Nucleotide sequence of the L-arabinose regulatory region of
            Escherichia coli K12
JOURNAL     J. Biol. Chem. 253 (19), 6931-6933 (1978)
PUBMED      357433

REFERENCE   138
AUTHORS     Greenfield, L., Boone, T. and WIlcox, G.
TITLE       DNA sequence of the araBAD promoter in Escherichia coli B/r
JOURNAL     Proc. Natl. Acad. Sci. U.S.A. 75 (10), 4724-4728 (1978)
PUBMED      368797

REFERENCE   139
AUTHORS     Young, R. A. and Steitz, J. A.
TITLE       Complementary sequences 1700 nucleotides apart form a
            ribonuclease III cleavage site in Escherichia coli
            ribosomal precursor RNA
JOURNAL     Proc. Natl. Acad. Sci. U.S.A. 75 (8), 3593-3597 (1978)
PUBMED      358189

REFERENCE   140
AUTHORS     Ohtsubo, H. and Ohtsubo, E.
TITLE       Nucleotide sequence of an insertion element, IS1
JOURNAL     Proc. Natl. Acad. Sci. U.S.A. 75 (2), 615-619 (1978)
PUBMED      273224

REFERENCE   141
AUTHORS     Musso, R., Di Lauro, R., Rosenberg, M. and de Crombrugghe, B.
TITLE       Nucleotide sequence of the operator-promoter region of the
            galactose operon of Escherichia coli
JOURNAL     Proc. Natl. Acad. Sci. U.S.A. 74 (1), 106-110 (1977)
PUBMED      319453

REFERENCE   142 (bases 1 to 4646332)
CONSRTM     NCBI Genome Project
TITLE       Direct Submission
JOURNAL     Submitted (10-NOV.-2005) National Center for Biotechnology
            Information, NIH, Bethesda, MD 20894, USA REFERENCE   143 (bases 1 to 4646332)
AUTHORS     Mori, H., Horiuchi, T. and Hirai, A.
TITLE       Direct Submission
JOURNAL     Submitted (22-AUG.-2005) Hirotada Mori, Graduate School of
            Biological Sciences, Nara Institute of Science and Technology;
            8916-5 Takayama, Ikoma, Nara 630-0101, Japan
            (E-mail: hmori@gtc.naist.jp, Tel: 81-743-72-5660, Fax: 81-743-72-
            5669)
COMMENT     PROVISIONAL REFSEQ: This record has not yet been subject to
            final NCBI review. The reference sequence was derived from AP009048.
            COMPLETENESS: full length.

FEATURES    Location/Qualifiers
source      complement(<1 . . . +225861)
            /organism = "Escherichia coli str. K-12 substr. W3110"
            /mol_type = "genomic DNA"
            /strain = "K-12"
            /sub_strain = "W3110"
            /db_xref = "taxon: 316407"

gene        complement(<1 . . . 6)
            /gene = "dcuD"

CDS         complement(<1 . . . 6)
            /gene = "dcuD"
            /note = "ECK3216: JW3196: b3227"
            /codon_start = 1
            /transl_table = 11
            /product = "predicted transporter"
            /protein_id = "AP_003769.1"
            /db_xref = "GI: 89109989"

/translation = "MFGIIISVIVLITMGYLILKNYKPQVVLAAAGIFLMMCGVWLGF
GGVLDPTKSSGYLIVDIYNEILRMLSNRIAGLGLSIMAVGGYARYMERIGASRAMVSL
LSRPLKLIRSPYIILSATYVIGQIMAQFITSASGLGMLLMVTLFPTLVSLGVSRLSAV
AVIATTMSIEWGILETNSIFAAQVAGMKIATYFFHYQLPVASCVIISVAISHFFVQRA
FDKKDKNINHEQAEQKALDNVPPLYYAILPVMPLILMLGSLFLAHVGLMQSELHLVVV
MLLSLTVTMFVEFFRKHNLRETMDDVQAFFDGMGTQFANVVTLVVAGEIFAKGLTTIG
TVDAVIRGAEHSGLGGIGVMIIMALVIAICAIVMGSGNAPFMSFASLIPNIAAGLHVP
AVVMIMPMHFATTLARAVSPITAVVVVTSGIAGVSPFAVVKRTAIPMAVGFVVNMIAT
ITLFY" (SEQ ID NO: 35)
```

-continued

```
primer          330 . . . 348
                /label = "ck nanR3 control primer"

gene            386 . . . 1177
                /gene = "nanR"

CDS             386 . . . 1177
                /gene = "nanR"
                /note = "ECK3215: JW3195: b3226"
                /codon_start = 1
                /transl_table = 11
                /product = "DNA-binding transcriptional dual regulator"
                /protein_id = "AP_003768.1"
                /db_xref = "GI: 89109988"
```

/translation = "MGLMNAFDSQTEDSSPAIGRNLRSRPLARKKLSEMVEEELEQMI
RRREFGEGEQLPSERELMAFFNVGRPSVREALAALKRKGLVQINNGERARVSRPSADT
IIGELSGMAKDFLSHPGGIAHFEQLRLFFESSLVRYAAEHATDEQIDLLAKALEINSQ
SLDNNAAFIRSDVDFHRVLAEIPGNPIFMAIHVALLDWLIAARPTVTDQALHEHNNVS
YQQHIAIVDAIRRHDPDEADRALQSHLNSVSATWHAFGQTTNKKK" (SEQ
ID NO: 36)

```
primer          1005 . . . 1025
                /label = "nanR ck2 control primer"

primer          1126 . . . 1146
                /label = "nanAFck control primer"

promoter        1178 . . . 1278
                /label = "nan operon promoter region"

Site            1187 . . . 1191
                /site_type = "binding site"
                /label = "CAP binding"

Site            1198 . . . 1202
                /site_type = "binding site"
                /label = "CAP binding"

promoter        1241 . . . 1246
                /label = -10 primer_bind     1252 . . . 1301
                /note = "for dnanA:: or dnanATE:: scar deletions"
                /label = "H1-dnanA lambda red primer"

mRNA            1255
                /label = +1 mRNA            1267
                /label = +13 mRNA            1279
                /label = +25 gene            1299 . . . 2192
                /gene = "nanA"

CDS             1299 . . . 2192
                /gene = "nanA"
                /note = "ECK3214: JW3194: b3225"
                /codon_start = 1
                /transl_table = 11
                /product = "N-acetylneuraminate lyase"
                /protein_id = "AP_003767.1"
                /db_xref = "GI: 89109987"
```

/translation = "MATNLRGVMAALLTPFDQQQALDKASLRRLVQFNIQQGIDGLYV
GGSTGEAFVQSLSEREQVLEIVAEEAKGKIKLIAHVGCVSTAESQQLAASAKRYGFDA
VSAVTPFYYPFSFEEHCDHYRAIIDSADGLPMVVYNIPALSGVKLTLDQINTLVTLPG
VGALKQTSGDLYQMEQIRREHPDLVLYNGYDEIFASGLLAGADGGIGSTYNIMGWRYQ
GIVKALKEGDIQTAQKLQTECNKVIDLLIKTGVFRGLKTVLHYMDVVSVPLCRKPFGP
VDEKYLPELKALAQQLMQERG" (SEQ ID NO: 37)

```
Region          1302 . . . 4424
                /label = "DELETION nanATE"
```

```
primer_bind     complement(2175 . . . 2224)
                /label = "H2-dnanA lambda red primer"

gene            2301 . . . 3791
                /gene = "nanT"

CDS             2301 . . . 3791
                /gene = "nanT"
                /note = "ECK3213: JW3193: b3224"
                /codon_start = 1
                /transl_table = 11
                /product = "sialic acid transporter"
                /protein_id = "AP_003766.1"
                /db_xref = "GI: 89109986"

/translation = "MSTTTQNIPWYRHLNRAQWRAFSAAWLGYLLDGFDFVLIALVLT
EVQGEFGLTTVQAASLISRWFGGLMLGAMGDRYGRRLAMVTSIVLFSAGTLAC
GFAPGYITMFIARLVIGMGMAGEYGSSATYVIESWPKHLRNKASGFLISGFSVGAVVA
AQVYSLVVPVWGWRALFFIGILPIIFALWLRKNIPEAEDWKEKHAGKAPVRTMVDILY
RGEHRIANIVMTLAAATALWFCFAGNLQNAAIVAVLGLLCAAIFISFMVQSAGKRWPT
GVMLMVVVLFAFLYSWPIQALLPTYLKTDLAYNPHTVANVLFFSGFGAAVGCCVGGFL
GDWLGTRKAYVCSLLASQLLIIPVFAIGGANVWVLGLLLFFQQMLGQGIAGILPKLIG
GYFDTDQRAAGLGFTYNVGALGGALAPIIGALIAQRLDLGTALASLSFSLTFVVILLI
GLDMPSRVQRWLRPEALRTHDAIDGKPFSGAVPFGSAKNDLVKTKS" (SEQ
ID NO: 38)

primer          complement(2329 . . . 2350)
                /label = "nanARck control primer"

primer_bind     3792 . . . 3841
                /label = "H1-dnanE lambda red primer"

gene            3839 . . . 4528
                /gene = "nanE"

CDS             3839 . . . 4528
                /gene = "nanE"
                /note = "ECK3212: JW3192: b3223"
                /codon_start = 1
                /transl_table = 11
                /product = "predicted N-acetylmannosamine-6-P
                epimerase"
                /protein_id = "AP_003765.1"
                /db_xref = "GI: 89109985"

/translation = "MSLLAQLDQKIAANGGLIVSCQPVPDSPLDKPEIVAAMALAAEQ
AGAVAIRIEGVANLQATRAVVSVPIIGIVKRDLEDSPVRITAYIEDVDALAQAGADII
AIDGTDRPRPVPVETLLARIHHHGLLAMTDCSTPEDGLACQKLGAETIGTTLSGYTTP
ETPEEPDLALVKTLSDAGCRVIAEGRYNTPAQAADAMRHGAWAVTVGSAITRLEHICQ
WYNTAMKKAVL" (SEQ ID NO: 39)

primer_bind     complement(4425 . . . 4474)
                /note = "for dnanATE:: scar deletion"
                /label = "H2-dnanE lambda red primer"

RBS             4425 . . . 4448
                /label = "C-terminal gibberish peptide fused to KD13
                scar peptide"

RBS             4449 . . . 4451
                /label = "NEW STOP gibberish peptide after resolution
                of cassette"

primer_bind     4486 . . . 4530
                /label = "nanK-H1 lambda red primer"

RBS             4515 . . . 4520
                /label = "nanK RBS"

gene            4525 . . . 5400
                /gene = "nanK"

CDS             4525 . . . 5400
                /gene = "nanK"
                /note = "ECK3211: JW5538: b3222"
                /codon_start = 1
                /transl_table = 11
                /product = "predicted N-acetylmannosamine kinase"
                /protein_id = "AP_003764.1"
                /db_xref = "GI: 89109984"
```

-continued

```
/translation = "MTTLAIDIGGTKLAAALIGADGQIRDRRELPTPASQTPEALRDA
LSALVSPLQAHAQRVAIASTGIIRDGSLLALNPHNLGGLLHPPLVKTLEQLTNLPTIA
INDAQAAAWAEFQALDGDITDMVFITVSTGVGGGVVSGCKLLTGPGGLAGHIGHTLAD
PHGPVCGCGRTGCVEATASGRGIAAAAQGELAGADAKTIFTRAGQGDEQAQQLIHRSA
RTLARLIADIKATTDCQCVVVGGSVGLAEGYLALVETYLAQEPAAFHVDLLAAHYRHD
AGLLGAALLAQGEKL" (SEQ ID NO: 40)

RBS             4526...4528
                /label = "Native Stop for NanE"

primer          complement(5065...5083)
                /label = "nanKck1 control primer"

primer_bind     complement(5380...5424)
                /label = "nanK-H2 lambda red primer"

gene            5397...5861
                /gene = "yhcH"

CDS             5397...5861
                /gene = "yhcH"
                /note = "ECK3210: JW3190: b3221"
                /codon_start = 1
                /transl_table = 11
                /product = "hypothetical protein"
                /protein_id = "AP_003763.1"
                /db_xref = "GI: 89109983"

/translation = "MMMGEVQSLPSAGLHPALQDALTLALAARPQEKAPGRYELQGDN
IFMNVMTFNTQSPVEKKAELHEQYIDIQLLLNGEERILFGMAGTARQCEEFHHEDDYQ
LCSTIDNEQAIILKPGMFAVFMPGEPHKPGCVVGEPGEIKKVVVKVKADLMA"
(SEQ ID NO: 41)

ORIGIN
       1 GAACATTGTT GAACTCCGTG TCAAAAGAAA ACGGTCAATC CCATAAACGG CAGATTGAAA
      61 ACAACGATGT TATATTTTTT GCAAGGCTAT TTATGGTGCG GATGTCGTGT TTTTAATTGT
     121 AGGTGAGGTG ATTTTTCATT AAAAAATATG CGCTTATGAT TATTTTGTAA GAACACATTC
     181 ATAATATTCA TAATGCTCGT GAATAGTCTT ATAAATAATT CAAACGGGAT GTTTTTATCT
     241 GCGTTACATT AATTTTTCGC AATAGTTAAT TATTCCGTTA ATTATGGTAA TGATGAGGCA
     301 CAAAGAGAAA ACCCTGCCAT TTTCCCCTAC TTTCAATCCT GTGATAGGAT GTCACTGATG
     361 ATGTTAATCA CACTGACCTT ACAGAATGGG CCTTATGAAC GCATTTGATT CGCAAACCGA
     421 AGATTCTTCA CCTGCAATTG GTCGCAACTT GCGTAGCCGC CCGCTGGCGC GTAAAAAACT
     481 CTCCGAAATG GTGGAAGAAG AGCTGGAACA GATGATCCGC CGTCGTGAAT TTGGCGAAGG
     541 TGAACAATTA CCGTCTGAAC GCGAACTGAT GGCGTTCTTT AACGCTGGGC GTCCTTCGGT
     601 GCGTGAAGCG CTGGCAGCGT TAAAACGCAA AGGTCTGGTG CAAATAAACA ACGGCGAACG
     661 CGCTCGCGTC TCGCGTCCTT CTGCGGACAC TATCATCGGT GAGCTTTCCG GCATGGCGAA
     721 AGATTTCCTT TCTCATCCCG GTGGGATTGC CCATTTCGAA CAATTACGTC TGTTCTTTGA
     781 ATCCAGTCTG GTGCGCTATG CGGCTGAACA TGCCACCGAT GAGCAAATCG ATTTGCTGGC
     841 AAAAGCACTG GAAATCAACA GTCAGTCGCT GGATAACAAC GCGGCATTCA TTCGTTCAGA
     901 CGTTGATTTC CACCGCGTGC TGGCGGAGAT CCCCGGTAAC CCAATCTTCA TTGGCGATCA
     961 CGTTGCCCTG CTCGACTGGC TTATTGCCGC ACGCCCAACG GTTACCGATC AGGCACTGCA
    1021 CGAACATAAC AACGTTAGTT ATCAACAGCA TATTGCGATC GTTGATGCGA TCCGCCGTCA
    1081 TGATCCTGAC GAAGCCGATC GTGCGTTGCA ATCGCATCTC AACAGCGTCT CTGCTACCTG
    1141 GCACGCTTTC GGTCAGACCA CCAACAAAAA GAAATAATGC CACTTTAGTG AAGCAGATCA
    1201 CATTATAAGC TTTCTGTATG GGGTGTTGCT TAATTGATCT GGTATAACAG GTATAAAGGT
    1261 ATATCGTTTA TCAGACAAGC ATCACTTCAG AGGTATTTAT GGCAACGAAT TTACGTGGCG
    1321 TAATGGCTGC ACTCCTGACT CCTTTTGACC AACAACAAGC ACTGGATAAA GCGAGTCTGC
    1381 GTCGCCTGGT TCAGTTCAAT ATTCAGCAGG GCATCGACGG TTTATACGGT GGTGGTTCGA
    1441 CCGGCGAGGC CTTTGTACAA AGCCTTTCCG AGCGTGAACA GGTACTGGAA ATCGTCGCCG
    1501 AAGAGGCGAA AGGTAAGATT AAACTCATCG CCCACGTCGG TTGCGTCAGC ACCGCCGAAA
    1561 GCCAACAACT TGCGGCATCG GCTAAACGTT ATGGCTTCGA TGCCGTCTCC GCCGTCACGC
    1621 CGTTCTACTA TCCTTTCAGC TTTGAAGAAC ACTGCGATCA CTATCGAGTGGG ATTATTGATT
    1681 CGGCGGATGG TTTGCCGATG GTGGTGTACA ACATTCCAGC CCTGAGTGGG GTAAAACTGA
    1741 CCCTGGATCA GATCAACACA CTTGTTACAT TGCCTGGCGT AGGTGCGCTG AAACAGACCT
    1801 CTGGCGATCT CTATCAGATG GAGCAGATCC GTCGTGAACA TCCTGATCTT GTGCTCTATA
    1861 ACGGTTACGA CGAAATCTTC GCCTCTGGTC TGCTGGCGGG CGCTGATGGT GGTATCGGCA
    1921 GTACCTACAA CATCATGGGC TGGCGCTATC AAGGGGATCG TAAGGCGCTG AAGGAAGGCA
    1981 ATATCCGAGC CGCGCAGAAA CTGCAAACTG AATGCAATAA AGTCATTGAT TTACTGATCA
    2041 AAACGGGCGT ATTCCGCGGC CTGAAAACTG TCCTCCATTA TATGGATGTC GTTTCTGTGC
    2101 CGCTGTGCCG CAAACCGTTT GGACCGGTAG ATGAAAAATA TCTGCCAGAA CTGAAGGCGC
    2161 TGGCCCAGCA GTTGATGCAA GAGCGGGT GAGTTGTTTC CCCTGCTCG CCCCTACCGG
    2221 GTGAGGGGAA ATAAACGCAT CTGTACCCTA CAATTTTCAT ACCAAAGCGT GTGGGCATCG
    2281 CCCACCGCGG GAGACTCACA ATGAGTACTA CAACCCAGAA TATCCCGTGG TATCGCCATC
    2341 TCAACCGTGC ACAATGGCGC GCATTTTCCG CTGCCTGGTT GGGATATCTG CTTGACGGTT
    2401 TTGATTTCGT TTTAATCGCC CTGGTACTCA CCGAAGTACA AGGTGAATTC GGGAAGAACA
    2461 CGGTGCAGGC GGCAAGTCTG ATCTCTGCAG CCTTTATCTC TCGCTGGTTC GGCGGCCTGA
    2521 TGCTCGGCGC TATGGGTGAC CGCTACGGGC GTCGTCTGGC AATGGTCACC AGCATCGTTC
    2581 TCTTCTCGGC CGGGACGCTG GCCTGCGGCT TGCGCCAGG CTACATCACC ATGTTTATCG
    2641 CTCGTCTGGT CATCGGCATG GGGATGGCGG TGAATACGG TTCCAGCGCC ACCTATGTCA
    2701 TTGAAAGCTG GCCAAAACAT CTGCGTAACA AAGCCAGTGG TTTTTTGATT TCAGGCTTCT
```

```
-continued
2761  CTGTGGGGGC CGTCGTTGCC GCTCAGGTCT ATAGCCTGGT GGTTCCGGTC TGGGGCTGGC
2821  GTGCGCTGTT CTTTATCGGC ATTTTGCCAA TCATCTTTGC TCTCTGGCTG CGTAAAAACA
2881  TCCCGGAAGC GGAAGACTGG AAAGAGAAAC ACGCAGGTAA AGCACCAGTA CGCACAATGG
2941  TGGATATTCT CTACCGTGGT GAACATCGCA TTGCCAATAT CGTAATGACA CTGGCGGCGG
3001  CTACTGCGCT GTGGTTCTGC TTCGCCGGTA ACCTGCAAAA TGCCGCGATC GTCGCTGTTC
3061  TTGGGCTGTT ATGCGCCGCA ATCTTTATCA GCTTTATGGT GCAGAGTGCA GGCAAACGCT
3121  GGCCAACGGG CGTAATGCTG ATGGTGGTCG TGTTGTTTGC TTTCCTCTAC TCATGGCCGA
3181  TTCAGGCGCT GCTGCCAACG TATCTGAAAA CCGATCTGGC TTATAACCCG CATACTGTAG
3241  CCAATGTGCT GTTCTTTAGT GGCTTTGGCG CGGCGGTGGG ATGCTGCGTA GGTGGCTTCC
3301  TCGGTGACTG GCTGGGAACC CGCAAAGCGT ACGTTTGTAG CCTGCTGGCC TCGCAGCTGC
3361  TGATTATTCC GGTATTTGCG ATTGGCGGCG CAAACGTCTG GGTGCTCGGT CTGTTACTGT
3421  TCTTCCAGCA AATGCTTGGA CAAGGGATCG CCGGGATCTT ACCAAAACTG ATTGGCGGTT
3481  ATTTCGATAC CGACCAGCGT GCAGCGGGCC TGGGCTTTAC CTACAACGTT GGCGCATTGG
3541  GCGGTGCACT GGCCCCAATC ATCGGCGCGT TGATCGCTCA ACGTCTGGAT CTGGGTACTG
3601  CGCTGGCATC GCTCTCGTTC AGTCTGACGT TCGTGGTGAT CCTGCTGATT GGGCTGGATA
3661  TGCCTTCTCG CGTTCAGCGT TGGTTGCGCC CGGAAGCGTT GCGTACTCAT GACGCTATCG
3721  ACGGTAAACC ATTCAGCGGT GCCGTGCCGT TTGGCAGCGC CAAAAACGAT TTAGTCAAAA
3781  CCAAAAGTTA ATCCTGTTGC CCGGTCTATG TACCGGGCCT TTCGCTAAGG GAAGATGTAT
3841  GTCGTTACTT GCACAACTGG ATCAAAAAAT CGCTGCTAAC GGTGGCCTGA TTGTCTCCTG
3901  CCAGCCGGTT CCGGACAGCC CGCTCGATAA ACCCGAAATC GTCGCCGCCA TGGCATTAGC
3961  GGCAGAACAG GCGGGCGCGG TTGCCATTCG CATTGAAGGT GTGGCAAATC TGCAAGCCAC
4021  GCGTGCGGTG GTGAGCGTGC CGATTATTGG AATTGTGAAA CGCGATCTGG AGGATTCTCC
4081  GGTACGCATC ACGGCCTATA TTGAAGATGT TGATGCGCTG GCGCAGGCGG GCGCGGACAT
4141  TATCGCCATT GACGGCACCG ACCGCCCGCG TCCGGTGCCT GTTGAAACGC TGCTGGCACG
4201  TATTCACCAT CACGGTTTAC TGGCGATGAC CGACTGCTCA ACGCCGGAAG ACGGCCTGGC
4261  ATGCCAAAAG CTGGGAGCCG AAATTATTGG CACTACGCTT TCTGGCTATA CCACGCCTGA
4321  AACGCCAGAA GAGCCGGATC TGGCGCTGGT GAAAACGTTG AGCGACGCCG GATGTCGGGT
4381  GATTGCCGAA GGGCGTTACA ACACGCCTGC TCAGGCGGCG GATGCGATGC GCCACGGCGC
4441  GTGGGCGGTG ACGGTCGGTT CTGCAATCAC GCGTCTTGAG CACATTTGTC AGTGGTACAA
4501  CACAGCGATG AAAAAGGCGG TGCTATGACC ACACTGGCGA TTGATATCGG CGGTACTAAA
4561  CTTGCCGCCG CGCTGATTGG CGCTGACGGG CAGATCCGCG ATCGTCGTGA ACTTCCTACG
4621  CCAGCCAGCC AGACACCAGA AGCCTTGCGT GATGCCTTAT CCGCATTAGT CTCTCCGTTG
4681  CAAGCTCATG CGCAGCGGGT TGCCATCGCT TCGACCGGGA TAATCCGTGA CGGCAGCTTG
4741  CTGGCGCTTA ATCCGCATAA TCTTGGTGGA TTGCTACACT TTCCGTTAGT CAAAACGCTG
4801  GAACAACTTA CCAATTTGCC GACCATTGCC ATTAACGACG CGCAGGCCGC AGCATGGGCG
4861  GAGTTTCAGG CGCTGGATGG CGATATAACC GATATGGTCT TTATCACCGT TTCCACCGGC
4921  GTTGGCGGCG GTGTAGTGAG CGGCTGCAAA CTGCTTACCG GCCCTGGCGG TCTGGCGGGG
4981  CATATCGGGC ATACGCTTGC CGATCCACAC GGCCCAGTCT GCGGCTGTGG ACGCACAGGT
5041  TGCGTGGAAG CGATTGCTTC TGGTCGCGGC ATTGCAGCGG CAGCGCAGGG GGAGTTGGCT
5101  GGCGCGGATG CGAAAACTAT TTTCACGCGC GCCGGGCAGG GTGACGAGCA GGCGCAGCAG
5161  CTGATTCACC GCTCCGCACG TACGCTTGCA AGGCTGATCG CTGATATTAA AGCCACAACT
5221  GATTGCCAGT GCGTGGTGGT CGGTGGCAGC GTTGGTCTGG CAGAAGGGTA TCTGGCGCTG
5281  GTGGAAACGT ATCTGGCGCA GGAGCCAGCG GCATTTCATG TTGATTTACT GGCGGCGCAT
5341  TACCGCCATG ATGCAGGTTT ACTTGGGGCT GCGCTGTTGG CCCAGGGAGA AAAATTATGA
5401  TGATGGGTGA AGTACAGTCA TTACCGTCTG CTGGGTTACA TCCTGCGTTA CAGGACGCGT
5461  TAACGCTGGC ATTAGCTGCC AGACCGCAAG AAAAAGCGCC GGGTCGTTAC GAATTACAGG
5521  GCGACAATAT CTTTATGAAT GTCATGACGT TTAACACTCA ATCGCCCGTC GAGAAAAAAG
5581  CGGAATTGCA CGAGCAATAC ATTGATATCC AGCTGTTATT AAACGGTGAG GAACGGATTC
5641  TGTTTGGCAT GGCAGGCACT GCGCGTCAGT GTGAAGAGTT CCACCATGAG GATGATTATC
5701  AGCTTTGCAG CACCATTGAT AACGAGCAAG CCATCATCTT AAAACCGGGA ATGTTCGCCG
5761  TGTTTATGCC AGGTGAACCG CATAAACCAG GATGCGTTGT CGGCGAGCCT GGAGAGATTA
5821  AAAAGGTTGT GGTGAAGGTT AAGGCTGATT TAATGGCTTA A (SEQ ID NO: 42)
//
```

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for producing an N-acetylglucosamine-containing oligosaccharide in a bacterium, wherein said N-acetylglucosamine-containing oligosaccharide comprises Lacto-N-triose 2 (LNT2), Lacto-N-tetraose (LNT), Lacto-N-neotetraose (LNnT), Lacto-N-fucopentaose I (LNF I), Lacto-N-fucopentaose II (LNF II), Lacto-N-fucopentaose III (LNF III), Lacto-N-fucopentaose V (LNF V), Lacto-N-difucohexaose I (LDFH I), Lacto-N-difucohexaose II (LDFH II), or Lacto-N-neodifucohexaose II (LFNnDFH II), the method comprising:

(i) providing a bacterium, said bacterium comprising β-galactosidase activity,
an exogenous UDP-GlcNAc:Galα/β-R β 3-N-acetylglucosaminyltransferase gene and
a functional lactose permease gene; and (ii) culturing said bacterium in the presence of lactose.

2. The method of claim 1, wherein said bacterium comprises an increased UDP-GlcNAc production capability by overexpressing a positive endogenous regulator of UDP-GlcNac synthesis.

3. The method of claim 2, wherein said increased UDP-GlcNAc production capability comprises overexpression of an E. coli gene selected from a nagC gene, a glmS gene, a glmY gene, a glmZ gene or any combination thereof.

4. The method of claim 2, wherein said increased UDP-GlcNAc production capability comprises overexpression of E. coli nagC gene.

5. The method of claim 2, wherein said increased UDP-GlcNAc production capability comprises overexpression of E. coli nagC and E. coli glmS.

6. The method of claim 2, wherein said increased UDP-GlcNAc production capability comprises overexpression of E. coli nagC and E. coli glmY.

7. The method of claim 2, wherein said increased UDP-GlcNAc production capability comprises overexpression of E. coli nagC and E. coli glmZ.

8. The method of claim 1, wherein said bacterium is *E. coli*.

9. A method of purifying an N-acetylglucosamine-containing oligosaccharide produced the method of claim 1, comprising binding said oligosaccharide from a bacterial cell lysate or bacterial cell culture supernatant of said bacterium to a carbon column, and eluting said oligosaccharide from said column.

10. The method of claim 1, further comprising retrieving said N-acetylglucosamine-containing oligosaccharide from said bacterium or from a culture supernatant of said bacterium.

11. The method of claim 2, wherein said increased UDP-GlcNAc production capability comprises overexpression of *E. coli* glmS.

12. The method of claim 2, wherein said increased UDP-GlcNAc production capability comprises overexpression of *E. coli* glmY.

13. The method of claim 2, wherein said increased UDP-GlcNAc production capability comprises overexpression of *E. coli* glmZ.

14. The method of claim 1, wherein said bacterium depletes residual lactose after producing the N-acetylglucosamine-containing oligosaccharide.

* * * * *

SEQUENCE LISTING

<160> NUMBER OF SEQ ID NOS: 43

<210> SEQ ID NO 1
<211> LENGTH: 5877
<212> TYPE: DNA

<213> ORGANISM: Escherichia coli

<400> SEQUENCE: 1

| | | | | | |
|---|---|---|---|---|---|
| gcagcggaac | tcacaaggca | ccataacgtc | ccctccctga | taacgctgat | actgtggtcg | 60 |
| cggttatgcc | agttggcatc | ttcacgtaaa | tagagcaaat | agtcccgcgc | ctggctggcg | 120 |
| gtttgccata | gccgttgcga | ctgctgccag | tattgccagc | catagagtcc | acttgcgctt | 180 |
| agcatgacca | aaatcagcat | cgcgaccagc | gtttcaatca | gcgtataacc | acgttgtgtt | 240 |
| ttcatgccgg | cagtatggag | cgaggagaaa | aaaagacgag | ggccagtttc | tatttcttcg | 300 |
| gcgcatcttc | cggactattt | acgccgttgc | aggacgttgc | aaaatttcgg | aaggcgtct | 360 |
| cgaagaattt | aacggagggt | aaaaaaaccg | acgcacactg | gcgtcggctc | tggcaggatg | 420 |
| tttcgtaatt | agatagccac | cggcgcttta | ttaaacctac | tatgaccatg | attacggatt | 480 |
| cactggccgt | cgttttacaa | cgtcgtgact | gggaaaaccc | tggcgttacc | caacttaatc | 540 |
| gccttgcagc | acatcccct | ttcgccagct | ggcgtaatag | cgaagaggcc | cgcaccgatc | 600 |
| gcccttccca | acagttgcgc | agcctgaatg | gcgaatggcg | ctttgcctgg | tttccggcac | 660 |
| cagaagcggt | gccggaaagc | tggctggagt | gcgatcttcc | tgaggccgat | actgtcgtcg | 720 |
| tccccctcaaa | ctggcagatg | cacgttacg | atgcgcccat | ctacaccaac | gtgacctatc | 780 |
| ccattacggt | caatccgccg | tttgttccca | cggagaatcc | gacgggttgt | tactcgctca | 840 |
| catttaatgt | tgatgaaagc | tggctacagg | aaggccagac | gcgaattatt | tttgatggcg | 900 |
| ttaactcggc | gtttcatctg | tggtgcaacg | ggcgctgggt | cggttacggc | caggacagtc | 960 |
| gtttgccgtc | tgaatttgac | ctgagcgcat | ttttacgcgc | cggagaaaac | cgcctcgcgg | 1020 |
| tgatggtgct | gcgctggagt | gacggcagtt | atctggaaga | tcaggatatg | tggcggatga | 1080 |
| gcggcatttt | ccgtgacgtc | tcgttgctgc | ataaaccgac | tacacaaatc | agcgatttcc | 1140 |
| atgttgccac | tcgctttaat | gatgatttca | gccgcgctgt | actggaggct | gaagttcaga | 1200 |
| tgtgcggcga | gttgcgtgac | tacctacggg | taacagtttc | tttatggcag | ggtgaaacgc | 1260 |
| aggtcgccag | cggcaccgcg | cctttcggcg | gtgaaattat | cgatgagcgt | ggtggttatg | 1320 |
| ccgatcgcgt | cacactacgt | ctgaacgtcg | aaaacccgaa | actgtggagc | gccgaaatcc | 1380 |
| cgaatctcta | tcgtgcggtg | gttgaactgc | acaccgccga | cggcacgctg | attgaagcag | 1440 |
| aagcctgcga | tgtcggtttc | gcgcaggtgc | ggattgaaaa | tggtctgctg | ctgctgaacg | 1500 |
| gcaagccgtt | gctgattcga | ggcgttaacc | gtcacgagca | tcatcctctg | catggtcagg | 1560 |
| tcatggatga | gcagacgatg | gtgcaggata | tcctgctgat | gaagcagaac | aactttaacg | 1620 |
| ccgtgcgctg | ttcgcattat | ccgaaccatc | cgctgtggta | cacgctgtgc | gaccgctacg | 1680 |
| gcctgtatgt | ggtggatgaa | gccaatattg | aaacccacgg | catggtgcca | atgaatcgtc | 1740 |
| tgaccgatga | tccgcgctgg | ctaccggcga | tgagcgaacg | cgtaacgcga | atggtgcagc | 1800 |
| gcgatcgtaa | tcacccgagt | gtgatcatct | ggtcgctggg | gaatgaatca | ggccacggcg | 1860 |
| ctaatcacga | cgcgctgtat | cgctggatca | aatctgtcga | tccttcccgc | ccggtgcagt | 1920 |
| atgaaggcgg | cggagccgac | accacggcca | ccgatattat | tgcccgatg | tacgcgcgcg | 1980 |
| tggatgaaga | ccagccctc | ccggctgtgc | cgaaatggtc | catcaaaaaa | tggctttcgc | 2040 |
| tacctggaga | gacgcgcccg | ctgatccttt | gcgaatacgc | ccacgcgatg | ggtaacagtc | 2100 |
| ttggcggttt | cgctaaatac | tggcaggcgt | ttcgtcagta | tccccgttta | cagggcggct | 2160 |
| tcgtctggga | ctgggtggat | cagtcgctga | ttaaatatga | tgaaaacggc | aacccgtggt | 2220 |
| cggcttacgg | cggtgatttt | ggcgatacgc | cgaacgatcg | ccagttctgt | atgaacggtc | 2280 |

-continued

| | | |
|---|---|---|
| tggtctttgc cgaccgcacg ccgcatccag cgctgacgga agcaaaacac cagcagcagt | 2340 |
| ttttccagtt ccgtttatcc gggcaaacca tcgaagtgac cagcgaatac ctgttccgtc | 2400 |
| atagcgataa cgagctcctg cactggatgg tggcgctgga tggtaagccg ctggcaagcg | 2460 |
| gtgaagtgcc tctggatgtc gctccacaag gtaaacagtt gattgaactg cctgaactac | 2520 |
| cgcagccgga gagcgccggg caactctggc tcacagtacg cgtagtgcaa ccgaacgcga | 2580 |
| ccgcatggta agaagccggg cacatcagcg cctggcagca gtggcgtctg gcggaaaacc | 2640 |
| tcagtgtgac gctccccgcc gcgtcccacg ccatcccgca tctgaccacc agcgaaatgg | 2700 |
| atttttgcat cgagctgggt aataagcgtt ggcaatttaa ccgccagtca ggctttcttt | 2760 |
| cacagatgtg gattggcgat aaaaaacaac tgttgacgcc gctgcgcgat cagttcaccc | 2820 |
| gtgcaccgct ggataacgac attggcgtaa gtgaagcgac ccgcattgac cctaacgcct | 2880 |
| gggtcgaacg ctggaaggcg gcgggccatt accaggccga agcagcgttg ttgcagtgca | 2940 |
| cggcagatac acttgctgat gcggtgctga ttacgaccgc tcacgcgtgg cagcatcagg | 3000 |
| ggaaaacctt atttatcagc cggaaaacct accggattga tggtagtggt caaatggcga | 3060 |
| ttaccgttga tgttgaagtg gcgagcgata caccgcatcc ggcgcggatt ggcctgaact | 3120 |
| gccagctggc gcaggtagca gagcgggtaa actggctcgg attagggccg caagaaaact | 3180 |
| atcccgaccg ccttactgcc gcctgttttg accgctggga tctgccattg tcagacatgt | 3240 |
| atacccgta cgtcttcccg agcgaaaacg gtctgcgctg cgggacgcgc gaattgaatt | 3300 |
| atggcccaca ccagtggcgc ggcgacttcc agttcaacat cagccgctac agtcaacagc | 3360 |
| aactgatgga aaccagccat cgccatctgc tgcacgcgga agaaggcaca tggctgaata | 3420 |
| tcgacggttt ccatatgggg attggtggcg acgactcctg gagcccgtca gtatcggcgg | 3480 |
| aattccagct gagcgccggt cgctaccatt accagttggt ctggtgtcaa aaataagcgg | 3540 |
| ccgctttatg taggctggag ctgcttcgaa gttcctatac tttctagaga ataggaactt | 3600 |
| cggaatagga acttcaagat cccccttatta gaagaactcg tcaagaaggc gatagaaggc | 3660 |
| gatgcgctgc gaatcgggag cggcgatacc gtaaagcacg aggaagcggt cagcccattc | 3720 |
| gccgccaagc tcttcagcaa tatcacgggt agccaacgct atgtcctgat agcggtccgc | 3780 |
| cacacccagc cggccacagt cgatgaatcc tgaaaagcgg ccattttcca ccatgatatt | 3840 |
| cggcaagcag gcatcgccat gggtcacgac gagatcctcg ccgtcgggca tgcgcgcctt | 3900 |
| gagcctggcg aacagttcgg ctggcgcgag cccctgatgc tcttcgtcca gatcatcctg | 3960 |
| atcgacaaga ccgcttcca tccgagtacg tgctcgctcg atgcgatgtt tcgcttggtg | 4020 |
| gtcgaatggg caggtagccg gatcaagcgt atgcagccgc cgcattgcat cagccatgat | 4080 |
| ggatactttc tcggcaggag caaggtgaga tgacaggaga tcctgccccg gcacttcgcc | 4140 |
| caatagcagc cagtcccttc ccgcttcagt gacaacgtcg agcacagctg cgcaaggaac | 4200 |
| gcccgtcgtg gccagccacg atagccgcgc tgcctcgtcc tgcagttcat tcagggcacc | 4260 |
| ggacaggtcg gtcttgacaa aaagaaccgg gcgcccctgc gctgacagcc ggaacacggc | 4320 |
| ggcatcagag cagccgattg tctgttgtgc ccagtcatag ccgaatagcc tctccaccca | 4380 |
| agcggccgga gaacctgcgt gcaatccatc ttgttcaatc atgcgaaacg atcctcatcc | 4440 |
| tgtctcttga tcagatcttg atccctgcg ccatcagatc cttggcggca agaaagccat | 4500 |
| ccagtttact ttgcagggct tcccaacctt accagggggc gccccagctg gcaattccgg | 4560 |
| ttcgcttgct gtccataaaa ccgcccagtc tagctatcgc catgtaagcc cactgcaagc | 4620 |

```
tacctgctttt ctctttgcgc ttgcgttttc ccttgtccag atagcccagt agctgacatt    4680
catccggggt cagcaccgtt tctgcggact ggctttctac gtgttccgct tcctttagca    4740
gcccttgcgc cctgagtgct tgcggcagcg tgagcttcaa aagcgctctg aagttcctat    4800
actttctaga gaataggaac ttcgaactgc aggtcgacgg atccccggaa tcatggttcc    4860
tcaggaaacg tgttgctgtg ggctgcgacg atatgcccag accatcatga tcacacccgc    4920
gacaatcatc gggatggaaa gaatttgccc catgctgatg tactgcaccc aggcaccggt    4980
aaactgcgcg tcgggctggc ggaaaaactc aacaatgatg cgaaacgcgc cgtaaccaat    5040
caggaacaaa cctgagacag ctcccattgg gcgtggttta cgaatataca ggttgaggat    5100
aataaacagc accacacctt ccagcagcag ctcgtaaagc tgtgatgggt ggcgcggcag    5160
cacaccgtaa gtgtcgaaaa tggattgcca ctgcgggttg gtttgcagca gcaaaatatc    5220
ttctgtacgg gagccaggga acagcatggc aaacgggaag ttcgggtcaa cgcggcccca    5280
caattcaccg ttaataaagt tgcccagacg cccggcacca agaccaaacg gaatgagtgg    5340
tgcgataaaa tcagagacct ggaagaagga acgtttagta cggcgggcga agataatcat    5400
caccacgata acgccaatca ggccgccgtg gaaagacatg ccgccgtccc agacacggaa    5460
cagatacagc ggatcggcca taaactgcgg gaaattgtag aacagaacat aaccaatacg    5520
tcccccgagg aagacgccga ggaagcccgc atagagtaag ttttcaactt cattttttggt    5580 ccagccgctg cccggacgat cgcccgtcg tgttgccagc cacattgcaa aaatgaaacc    5640
caccagatac atcaggccgt accagtgaag cgccacgggt cctattgaga aaatgaccgg    5700
atcaaactcc ggaaaatgca gatagctact ggtcatctgt caccacaagt tcttgttatt    5760
tcgctgaaag agaacagcga ttgaaatgcg cgccgcaggt ttcaggcgct ccaaaggtgc    5820
gaataatagc acaaggggac ctggctggtt gccggatacc gttaaaagat atgtata       5877

<210> SEQ ID NO 2
<211> LENGTH: 5409
<212> TYPE: DNA
<213> ORGANISM: Artificial Sequence
<220> FEATURE:
<223> OTHER INFORMATION: engineered plasmid

<400> SEQUENCE: 2
tcgcgcgttt cggtgatgac ggtgaaaacc tctgacacat gcagctcccg gagacggtca      60
cagcttgtct gtaagcggat gccggagcag acaagcccg tcagggcgcg tcagcgggtg     120
ttggcgggtg tcggggctgg cttaactatg cggcatcaga gcagattgta ctgagagtgc     180
accatatatg cggtgtgaaa taccgcacag atgcgtaagg agaaaatacc gcatcaggcg     240
cctcctcaac ctgtatattc gtaaaccacg cccaatggga gctgtctcag gtttgttcct     300
gattggttac ggcgcgtttc gcatcattgt tgagtttttc cgccagcccg acgcgcagtt     360
taccggtgcc tgggtgcagt acatcagcat ggggcaaatt cttttccatcc cgatgattgt     420 cgcgggtgtg atcatgatgg tctgggcata tcgtcgcagc ccacagcaac acgtttcctg     480
aggaaccatg aaacagtatt tagaactgat gcaaaaagtg ctcgacgaag gcacacagaa     540
aaacgaccgt accggaaccg gaacgctttc catttttggt catcgatgc gttttaacct     600 gcaagatgga ttcccgctgg tgacaactaa acgttgccac ctgcgttcca tcatccatga     660
actgctgtgg tttctgcagg gcgacactaa cattgcttat ctacacgaaa acaatgtcac     720
catctgggac gaatgggccg atgaaaacg cgacctcggg ccagtgtatg gtaaacagtg     780
gcgcgcctgg ccaacgccag atggtcgtca tattgaccag atcactacgg tactgaacca     840
```

```
gctgaaaaac gacccggatt cgcgccgcat tattgtttca gcgtggaacg taggcgaact    900
ggataaaatg gcgctggcac cgtgccatgc attcttccag ttctatgtgg cagacggcaa    960
actctcttgc cagctttatc agcgctcctg tgacgtcttc ctcggcctgc cgttcaacat   1020
tgccagctac gcgttattgg tgcatatgat ggcgcagcag tgcgatctgg aagtgggtga   1080
ttttgtctgg accggtggcg acacgcatct gtacagcaac catatggatc aaactcatct   1140
gcaattaagc cgcgaaccgc gtccgctgcc gaagttgatt atcaaacgta aacccgaatc   1200
catcttcgac taccgtttcg aagactttga gattgaaggc tacgatccgc atccgggcat   1260
taaagcgccg gtggctatct aattacgaaa catcctgcca gagccgacgc cagtgtgcgt   1320
cggttttttt accctccgtt aaattcttcg agacgccttc ccgaaggcgc cattcgccat   1380
tcaggctgcg caactgttgg gaagggcgat cggtgcgggc ctcttcgcta ttacgccagc   1440
tggcgaaagg gggatgtgct gcaaggcgat taagttgggt aacgccaggg ttttcccagt   1500
cacgacgttg taaaacgacg gccagtgcca agcttactgc tcacaagaaa aaaggcacgt   1560
catctgacgt gcctttttta tttgtactac cctgtacgat tactgcaggt cgactctaga   1620
tgcatgctcg agtcaacggt ttttcagcaa tcggtgcaaa atgccgaagt attgcctcaa   1680
ggtaaacagc cgccgcatcc tgccgtctgc cgcaaaatcc agccacgcgc cggcgggcag   1740
cgtgtccgtc cgtttgaagc attggtacaa aaaccggcgg gcgcgttcaa aatcttcttc   1800
cggcaaatgt ttctccagca attcatacgc tactgctttt atttggcggt attcaaggct   1860
gtcgaaccgg gttttaaaac ccatagactg caaaaaatcg tttctggcgg ttttttggat   1920
gccttgcgcg atttcgtgtt ggcggatgct gtatttggat gaaacctgat tggcgtgaag   1980
gcggtatttg accaaggctt cgggataata agccagcctg cccaatttgc tgacatcgta   2040
ccaaaattgg taatcttccg cccaatcccg ctcggtgttg taacgcaaac cgccgtcaat   2100
gacgctgcgc ctcataatca tcgtgttgtt gtgtatgggg ttgccgaaag ggaaaaagtc   2160
ggcaatgtct tcgtgtcggg tcggtttttt ccaaattttg ccgtgttcgt ggtgccgcgc   2220
cagccggttg ccgtcctttt cttccgacaa aacttccagc cacgcaccca tcgcgatgat   2280
gctgcggtct ttttccatct cacccacgat tttctcaatc cagtcggggg cggcaatatc   2340
gtctgcatcg gtgcgcgcaa tatattcccc ccccccccc gactttgcca attcatccag   2400
cccgatgttt aaagagggaa tcagaccgga attgcgcggc tgcgcgagga tgcggatgcg   2460
gccgtcctgt tcttggaaac gctgggcaat ggcaagcgta ccgtccgtcg agccgtcatc   2520
gacaatcaaa atatccaagt tgcgccaagt ttgattcacg acggcggcta atgattgggc   2580
gaaatatttt tctacgttgt aggcgcaaat caatacgctg actaaaggct gcaatttatt   2640
ctcccgatag gcacgatgcc gtctgaaggc ttcagacggc atatgtatat ctccttcttg   2700
aattctaaca attgattgaa tgtatgcaaa taaatgcata caccataggt gtggtttaat   2760
ttgatgccct tttcagggc tggaatgtgt aagagcgggg ttatttatgc tgttgttttt   2820
ttgttactcg ggaagggctt tacctcttcc gcataaacgc ttccatcagc gtttatagtt   2880
aaaaaaatct ttcggaactg gttttgcgct tacccccaacc aacaggggat tgctgctttt   2940
ccattgagcc tgtttctctg cgcgacgttc gcggcggcgt gtttgtgcat ccatctggat   3000
tctcctgtca gttagctttg gtggtgtgtg gcagttgtag tcctgaacga aaaccccccg   3060
cgattggcac attggcagct aatccggaat cgcacttacg gccaatgctt cgtttcgtat   3120
cacacacccc aaagccttct gctttgaatg ctgcccttct tcagggctta atttttaaga   3180
```

```
gcgtcaccctt catggtggtc agtgcgtcct gctgatgtgc tcagtatcac cgccagtggt    3240
atttatgtca acaccgccag agataattta tcaccgcaga tggttatctg tatgtttttt    3300
atatgaattt attttttgca gggggcatt gtttggtagg tgagagatca attctgcatt    3360
aatgaatcgg ccaacgcgcg gggagaggcg gtttgcgtat tgggcgctct tccgcttcct    3420
cgctcactga ctcgctgcgc tcggtcgttc ggctgcggcg agcggtatca gctcactcaa    3480
aggcggtaat acggttatcc acagaatcag gggataacgc aggaaagaac atgtgagcaa    3540
aaggccagca aaaggccagg aaccgtaaaa aggccgcgtt gctggcgttt ttccataggc    3600
tccgcccccc tgacgagcat cacaaaaatc gacgctcaag tcagaggtgg cgaaacccga    3660
caggactata aagataccag gcgtttcccc ctggaagctc cctcgtgcgc tctcctgttc    3720
cgaccctgcc gcttaccgga tacctgtccg cctttctccc ttcgggaagc gtggcgcttt    3780
ctcatagctc acgctgtagg tatctcagtt cggtgtaggt cgttcgctcc aagctgggct    3840
gtgtgcacga accccccgtt cagcccgacc gctgcgcctt atccggtaac tatcgtcttg    3900
agtccaaccc ggtaagacac gacttatcgc cactggcagc agccactggt aacaggatta    3960
gcagagcgag gtatgtaggc ggtgctacag agttcttgaa gtggtggcct aactacggct    4020
acactagaag gacagtattt ggtatctgcg ctctgctgaa gccagttacc ttcggaaaaa    4080
gagttggtag ctcttgatcc ggcaaacaaa ccaccgctgg tagcggtggt ttttttgttt    4140
gcaagcagca gattacgcgc agaaaaaaag gatctcaaga agatcctttg atcttttcta    4200
cggggtctga cgctcagtgg aacgaaaact cacgttaagg gattttggtc atgagattat    4260
caaaaaggat cttcacctag atccttttaa attaaaaatg aagttttaaa tcaatctaaa    4320
gtatatatga gtaaacttgg tctgacagtt accaatgctt aatcagtgag gcacctatct    4380
cagcgatctg tctatttcgt tcatccatag ttgcctgact ccccgtcgtg tagataacta    4440
cgatacggga gggcttacca tctggcccca gtgctgcaat gataccgcga acccacgct    4500 caccggctcc agatttatca gcaataaacc agccagccgg aagggccgag cgcagaagtg    4560
gtcctgcaac tttatccgcc tccatccagt ctattaattg ttgccgggaa gctagagtaa    4620
gtagttcgcc agttaatagt ttgcgcaacg ttgttgccat tgctacaggc atcgtggtgt    4680
cacgctcgtc gtttggtatg gcttcattca gctccggttc ccaacgatca aggcgagtta    4740
catgatcccc catgttgtgc aaaaaagcgg ttagctcctt cggtcctccg atcgttgtca    4800
gaagtaagtt ggccgcagtg ttatcactca tggttatggc agcactgcat aattctctta    4860
ctgtcatgcc atccgtaaga tgcttttctg tgactggtga gtactcaacc aagtcattct    4920
gagaatagtg tatgcggcga ccgagttgct cttgcccggc gtcaatacgg gataataccg    4980
cgccacatag cagaacttta aaagtgctca tcattggaaa acgttcttcg ggcgaaaac    5040 tctcaaggat cttaccgctg ttgagatcca gttcgatgta acccactcgt gcacccaact    5100
gatcttcagc atcttttact ttcaccagcg tttctgggtg agcaaaaaca ggaaggcaaa    5160
atgccgcaaa aaagggaata agggcgacac ggaaatgttg aatactcata ctcttccttt    5220
ttcaatatta ttgaagcatt tatcagggtt attgtctcat gagcggatac atatttgaat    5280
gtatttagaa aaataaacaa ataggggttc cgcgcacatt tccccgaaaa gtgccacctg    5340
acgtctaaga aaccattatt atcatgacat taacctataa aaataggcgt atcacgaggc    5400
cctttcgtc                                                            5409
```

<210> SEQ ID NO 3
<211> LENGTH: 6233

<212> TYPE: DNA
<213> ORGANISM: Artificial Sequence
<220> FEATURE:
<223> OTHER INFORMATION: engineered plasmid

<400> SEQUENCE: 3

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatatg cggtgtgaaa taccgcacag atgcgtaagg agaaaatacc gcatcaggcg     240
cctcctcaac ctgtatattc gtaaaccacg cccaatggga gctgtctcag gtttgttcct     300
gattggttac ggcgcgtttc gcatcattgt tgagtttttc cgccagcccg acgcgcagtt     360
taccggtgcc tgggtgcagt acatcagcat ggggcaaatt ctttccatcc cgatgattgt     420
cgcgggtgtg atcatgatgg tctgggcata tcgtcgcagc ccacagcaac acgtttcctg     480
aggaaccatg aaacagtatt tagaactgat gcaaaaagtg ctcgacgaag gcacacagaa     540
aaacgaccgt accggaaccg gaacgctttc catttttggt catcagatgc gttttaacct     600
gcaagatgga ttcccgctgg tgacaactaa acgttgccac ctgcgttcca tcatccatga     660
actgctgtgg tttctgcagg gcgacactaa cattgcttat ctacacgaaa acaatgtcac     720
catctgggac gaatgggccg atgaaaacgg cgacctcggg ccagtgtatg gtaaacagtg     780
gcgcgcctgg ccaacgccag atggtcgtca tattgaccag atcactacgg tactgaacca     840
gctgaaaaac gacccggatt cgcgccgcat tattgtttca gcgtggaacg taggcgaact     900
ggataaaatg gcgctggcac cgtgccatgc attcttccag ttctatgtgg cagacggcaa     960
actctcttgc cagctttatc agcgctcctg tgacgtcttc ctcggcctgc cgttcaacat    1020
tgccagctac gcgttattgg tgcatatgat ggcgcagcag tgcgatctgg aagtgggtga    1080
ttttgtctgg accggtggcg acacgcatct gtacagcaac catatggatc aaactcatct    1140
gcaattaagc cgcgaaccgc gtccgctgcc gaagttgatt atcaaacgta acccgaatc    1200
catcttcgac taccgtttcg aagactttga gattgaaggc tacgatccgc atccgggcat    1260
taaagcgccg gtggctatct aattacgaaa catcctgcca gagccgacgc cagtgtgcgt    1320
cggttttttt accctccgtt aaattcttcg agacgccttc ccgaaggcgc cattcgccat    1380
tcaggctgcg caactgttgg gaagggcgat cggtgcgggc ctcttcgcta ttacgccagc    1440
tggcgaaagg gggatgtgct gcaaggcgat taagttgggt aacgccaggg ttttcccagt    1500
cacgacgttg taaaacgacg gccagtgcca agcttactgc tcacaagaaa aaaggcacgt    1560
catctgacgt gccttttta tttgtactac cctgtacgat tactgcaggt cgactctaga    1620
tgcatgctcg agttattatt taatatattt acaatagatg aaggacgcaa tcgtacggat    1680
accgccgaac aggtagttaa tgttaccggt caggaagaag cacttcattt tgataaccag    1740
gtcgttaacc atcaccatgt acaggttttt ttttgcggta gactgacctt cgtgcaggcg    1800
gtagtagaac aggtattccg gcaggttttg gaacttgatt tttgccaggc tcagacggtt    1860
ccacagctcg taatcttcgg agtagttaga aaacatataa ccaccgatgc tcgcgatgac    1920
tttttacga acattacgc tcgggtgaac aatacaacac ttatacggca ggttttaac    1980
gatgtccagg ttctcttccg gcagtttggt cttgttgatt tcacgacctt tgtcgtcaat    2040
aaagattgcg ttggtaccca caacatctac gtacggattg ttcttcagga agtcaacctg    2100
tttagtaaaa cggtccgggt gagagatgtc gtcagagtcc atacgggcaa taaattcgcc    2160
```

```
gttgctcagg tcgatcgctt tgttcaggga gtacggcagg taagcgatgt tagtgcggat    2220
cagtttgatt ttgtcgttaa ctttgtgttt cagttcgtta tagaagtcgt cagtgcagca    2280
gttcgcaacg atgatgattt cgaagctgct gaaggtctga acaggatgc tgttgatcgc     2340
ttcgtccaga aaagggtttt tcttgttaac aggcaggata acgctcacaa ccgggtgggt    2400
agattccgcg gattccgctt catcgatgat catatgtata tctccttctt ctcgagtcaa    2460
cggttttca gcaatcggtg caaaatgccg aagtattgcc tcaaggtaaa cagccgccgc     2520
atcctgccgt ctgccgcaaa atccagccac gcgccggcgg gcagcgtgtc cgtccgtttg    2580
aagcattggt acaaaaaccg gcgggcgcgt tcaaaatctt cttccggcaa atgtttctcc    2640
agcaattcat acgctactgc ttttatttgg cggtattcaa ggctgtcgaa ccgggttttta   2700
aaacccatag actgcaaaaa atcgtttctg gcggttttt ggatgccttg cgcgatttcg     2760
tgttggcgga tgctgtattt ggatgaaacc tgattggcgt gaaggcggta tttgaccaag    2820
gcttcgggat aataagccag cctgcccaat ttgctgacat cgtaccaaaa ttggtaatct    2880
tccgcccaat cccgctcggt gttgtaacgc aaaccgccgt caatgacgct gcgcctcata    2940
atcatcgtgt tgttgtgtat ggggttgccg aaagggaaaa agtcggcaat gtcttcgtgt    3000
cgggtcggtt ttttccaaat tttgccgtgt tcgtggtgcc gcgccagccg gttgccgtcc    3060
ttttcttccg acaaaacttc cagccacgca cccatcgcga tgatgctgcg gtcttttcc    3120
atctcaccca cgattttctc aatccagtcg ggggcggcaa tatcgtctgc atcggtgcgc    3180
gcaatatatt cccccccccc cccgacttt gccaattcat ccagcccgat gtttaaagag    3240
ggaatcagac cggaattgcg cggctgcgcg aggatgcgga tgcggccgtc ctgttcttgg    3300
aaacgctggg caatggcaag cgtaccgtcc gtcgagccgt catcgacaat caaaatatcc    3360
aagttgcgcc aagtttgatt cacgacgcg gctaatgatt gggcgaaata tttttctacg     3420
ttgtaggcgc aaatcaatac gctgactaaa ggctgcaatt tattctcccg ataggcacga    3480
tgccgtctga aggcttcaga cggcatatgt atatctcctt cttgaattct aacaattgat    3540
tgaatgtatg caaataaatg catacaccat aggtgtggtt taatttgatg cccttttca    3600
gggctggaat gtgtaagagc ggggttattt atgctgttgt tttttgtta ctcgggaagg     3660
gctttacctc ttccgcataa acgcttccat cagcgtttat agttaaaaaa atctttcgga    3720
actggttttg cgcttacccc aaccaacagg ggatttgctg cttccattg agcctgtttc     3780
tctgcgcgac gttcgcggcg gcgtgtttgt gcatccatct ggattctcct gtcagttagc    3840
tttggtggtt tgtggcagtt gtagtcctga acgaaaaccc ccgcgattg gcacattggc     3900
agctaatccg gaatcgcact acggccaat gcttcgtttc gtatcacaca ccccaaagcc     3960
ttctgctttg aatgctgccc ttcttcaggg cttaattttt aagagcgtca ccttcatggt    4020
ggtcagtgcg tcctgctgat gtgctcagta tcaccgccag tggtatttat gtcaacaccg    4080
ccagagataa tttatcaccg cagatggtta tctgtatgtt ttttatatga atttattttt    4140
tgcaggggg cattgtttgg taggtgagag atcaattctg cattaatgaa tcggccaacg     4200
cgcggggaga ggcggtttgc gtattggcg ctcttccgct tcctcgctca ctgactcgct     4260
gcgctcggtc gttcggctgc ggcgagcggt atcagctcac tcaaaggcgg taatacggtt    4320
atccacagaa tcaggggata acgcaggaaa gaacatgtga gcaaaaggcc agcaaaaggc    4380
caggaaccgt aaaaaggccg cgttgctggc gtttttccat aggctccgcc ccctgacga    4440
gcatcacaaa aatcgacgct caagtcagag gtggcgaaac ccgacaggac tataagata    4500
ccaggcgttt ccccctggaa gctccctcgt gcgctctcct gttccgaccc tgccgcttac    4560
```

```
cggatacctg tccgcctttc tcccttcggg aagcgtggcg ctttctcata gctcacgctg    4620
taggtatctc agttcggtgt aggtcgttcg ctccaagctg gctgtgtgc acgaaccccc    4680 cgttcagccc gaccgctgcg ccttatccgg taactatcgt cttgagtcca acccggtaag    4740
acacgactta tcgccactgg cagcagccac tggtaacagg attagcagag cgaggtatgt    4800
aggcggtgct acagagttct tgaagtggtg gcctaactac ggctacacta aaggacagt    4860 atttggtatc tgcgctctgc tgaagccagt taccttcgga aaaagagttg gtagctcttg    4920
atccggcaaa caaaccaccg ctggtagcgg tggtttttt gtttgcaagc agcagattac    4980
gcgcagaaaa aaaggatctc aagaagatcc tttgatcttt tctacggggt ctgacgctca    5040
gtggaacgaa aactcacgtt aagggatttt ggtcatgaga ttatcaaaaa ggatcttcac    5100
ctagatcctt ttaaattaaa aatgaagttt taaatcaatc taaagtatat atgagtaaac    5160
ttggtctgac agttaccaat gcttaatcag tgaggcacct atctcagcga tctgtctatt    5220
tcgttcatcc atagttgcct gactccccgt cgtgtagata actacgatac gggagggctt    5280
accatctggc cccagtgctg caatgatacc gcgagaccca cgctcaccgg ctccagattt    5340
atcagcaata aaccagccag ccggaagggc cgagcgcaga agtggtcctg caactttatc    5400
cgcctccatc cagtctatta attgttgccg ggaagctaga gtaagtagtt cgccagttaa    5460 tagtttcgc aacgttgttg ccattgctac aggcatcgtg gtgtcacgct cgtcgtttgg    5520
tatggcttca ttcagctccg gttcccaacg atcaaggcga gttacatgat cccccatgtt    5580
gtgcaaaaaa gcggttagct ccttcggtcc tccgatcgtt gtcagaagta agttggccgc    5640
agtgttatca ctcatggtta tggcagcact gcataattct cttactgtca tgccatccgt    5700
aagatgcttt tctgtgactg gtgagtactc aaccaagtca ttctgagaat agtgtatgcg    5760
gcgaccgagt tgctcttgcc cggcgtcaat acgggataat accgcgccac atagcagaac    5820
tttaaaagtg ctcatcattg gaaaacgttc ttcggggcga aaactctcaa ggatcttacc    5880
gctgttgaga tccagttcga tgtaacccac tcgtgcaccc aactgatctt cagcatcttt    5940
tactttcacc agcgtttctg ggtgagcaaa aacaggaagg caaaatgccg caaaaaaggg    6000
aataagggcg acacggaaat gttgaatact catactcttc cttttcaat attattgaag    6060 catttatcag ggttattgtc tcatgagcgg atacatattt gaatgtattt agaaaaataa    6120
acaaataggg gttccgcgca catttccccg aaaagtgcca cctgacgtct aagaaaccat    6180
tattatcatg acattaacct ataaaaatag gcgtatcacg aggcccttc gtc           6233
```

<210> SEQ ID NO 4
<211> LENGTH: 6254
<212> TYPE: DNA
<213> ORGANISM: Artificial Sequence
<220> FEATURE:
<223> OTHER INFORMATION: engineered plasmid

<400> SEQUENCE: 4

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatatg cggtgtgaaa taccgcacag atgcgtaagg agaaaatacc gcatcaggcg    240
cctcctcaac ctgtatattc gtaaaccacg cccaatggga gctgtctcag gtttgttcct    300
gattggttac ggcgcgtttc gcatcattgt tgagttttc cgccagcccg acgcgcagtt    360
```

```
taccggtgcc tgggtgcagt acatcagcat ggggcaaatt ctttccatcc cgatgattgt    420
cgcgggtgtg atcatgatgg tctgggcata tcgtcgcagc ccacagcaac acgtttcctg    480
aggaaccatg aaacagtatt tagaactgat gcaaaaagtg ctcgacgaag gcacacagaa    540
aaacgaccgt accggaaccg gaacgctttc cattttggt catcagatgc gttttaacct     600
gcaagatgga ttcccgctgg tgacaactaa acgttgccac ctgcgttcca tcatccatga    660
actgctgtgg tttctgcagg cgacactaa cattgcttat ctacacgaaa acaatgtcac     720
catctgggac gaatgggccg atgaaaacgg cgacctcggg ccagtgtatg gtaaacagtg    780
gcgcgcctgg ccaacgccag atggtcgtca tattgaccag atcactacgg tactgaacca    840
gctgaaaaac gacccggatt cgcgccgcat tattgtttca gcgtggaacg taggcgaact    900
ggataaaatg gcgctggcac cgtgccatgc attcttccag ttctatgtgg cagacggcaa    960
actctcttgc cagctttatc agcgctcctg tgacgtcttc ctcggcctgc cgttcaacat   1020
tgccagctac gcgttattgg tgcatatgat ggcgcagcag tgcgatctgg aagtgggtga   1080
ttttgtctgg accggtggcg acacgcatct gtacagcaac catatggatc aaactcatct   1140
gcaattaagc cgcgaaccgc gtccgctgcc gaagttgatt atcaaacgta aacccgaatc   1200
catcttcgac taccgtttcg aagactttga gattgaaggc tacgatccgc atccgggcat   1260
taaagcgccg gtggctatct aattacgaaa catcctgcca gagccgacgc cagtgtgcgt   1320
cggttttttt accctccgtt aaattcttcg agacgccttc ccgaaggcgc cattcgccat   1380
tcaggctgcg caactgttgg aagggcgat cggtgcgggc ctcttcgcta ttacgccagc    1440
tggcgaaagg gggatgtgct gcaaggcgat taagttgggt aacgccaggg ttttcccagt   1500
cacgacgttg taaaacgacg gccagtgcca agcttactgc tcacaagaaa aaaggcacgt   1560
catctgacgt gccttttta tttgtactac cctgtacgat tactgcaggt cgactctaga   1620
tgcatgctcg agttatacaa actgccaata tttcaaatat ttaaaatgga gttctctcat   1680
taaggcgatt ttagggctat aaggttcttc ttttcgtgct atcgtagaga tttgctcatc   1740
atcagcgatc acaaaaggtt gtaacaccag atttttcacg ccatggataa agtagcgtc    1800
cattatcgta tccacaggaa caacccattt tcggctgcat ttcaaaaaaa ctttggcaat   1860
cttaggcgtg atcacatagc cttgagtccc caccccttcg ctataagctt taatgatccc   1920
cacacgctct tgtatctcgt ggttttatg gctcaatggc tcactttta cactggcatc     1980
atacaataaa tgcatcaagc ggatatagcc taactcttgg atgtgttttt ctaaaaaatc   2040
caagccctct ttaaaatcct cttcaaggt tatatcgtct tctaaaatac agatcgcttc    2100
attgagttct atgcattttt cccacaagga ataatgactc gcatagcacc caagctcccc   2160
caagctcata aacttcgcat ggtattttaa agcgtaataa aacttagaaa cctcactgat   2220
gagattggtt gtaatcccca tgtctttgat gttttgcgtg atgaaataag ggtgtaaatg   2280
ctttttcact aaggggtgca acccgccttc aaaagtttta gaataaatcg catcaaaaat   2340
ttgcgcttgg tggtgggtgg cattgatgct attgagtaaa gttgtggtgt ctctaaaaac   2400
taaaccaaat gtatcgcaca ctttttgatt taaagaaatg gcaaaacac gcatatgtat    2460
atctccttct tctcgagtca acggttttc agcaatcggt gcaaaatgcc gaagtattgc    2520
ctcaaggtaa acagccgccg catcctgccg tctgccgcaa atccagcca cgcgccggcg    2580
ggcagcgtgt ccgtccgttt gaagcattgg tacaaaaacc ggcgggcgcg ttcaaaatct   2640
tcttccggca aatgtttctc cagcaattca tacgctactg cttttatttg gcggtattca   2700
aggctgtcga accgggtttt aaaacccata gactgcaaaa aatcgtttct ggcggttttt   2760
```

```
tggatgcctt gcgcgatttc gtgttggcgg atgctgtatt tggatgaaac ctgattggcg   2820
tgaaggcggt atttgaccaa ggcttcggga taataagcca gcctgcccaa tttgctgaca   2880
tcgtaccaaa attggtaatc ttccgcccaa tcccgctcgg tgttgtaacg caaaccgccg   2940
tcaatgacgc tgcgcctcat aatcatcgtg ttgttgtgta tggggttgcc gaaagggaaa   3000
aagtcggcaa tgtcttcgtg tcgggtcggt ttttccaaa ttttgccgtg ttcgtggtgc    3060
cgcgccagcc ggttgccgtc cttttcttcc gacaaaactt ccagccacgc acccatcgcg   3120
atgatgctgc ggtcttttc catctcaccc acgatttct caatccagtc ggggcggca     3180 atatcgtctg catcggtgcg cgcaatatat tcccccccc ccccgactt tgccaattca    3240 tccagcccga tgtttaaaga gggaatcaga ccggaattgc gcggctgcgc gaggatgcgg   3300
atgcggccgt cctgttcttg gaaacgctgg gcaatggcaa cgtaccgtc cgtcgagccg    3360 tcatcgacaa tcaaaatatc caagttgcgc caagtttgat tcacgacggc ggctaatgat   3420
tgggcgaaat atttttctac gttgtaggcg caaatcaata cgctgactaa aggctgcaat   3480
ttattctccc gataggcacg atgccgtctg aaggcttcag acggcatatg tatatctcct   3540
tcttgaattc taacaattga ttgaatgtat gcaaataaat gcatacacca taggtgtggt   3600
ttaatttgat gccctttttc agggctggaa tgtgtaagag cggggttatt tatgctgttg   3660 ttttttgtt actcgggaag ggctttacct cttccgcata aacgcttcca tcagcgttta    3720
tagttaaaaa aatctttcgg aactggtttt gcgcttaccc caaccaacag gggatttgct   3780
gctttccatt gagcctgttt ctctgcgcga cgttcgcggc ggcgtgtttg tgcatccatc   3840
tggattctcc tgtcagttag ctttggtggt gtgtggcagt tgtagtcctg aacgaaaacc   3900
ccccgcgatt ggcacattgg cagctaatcc ggaatcgcac ttacggccaa tgcttcgttt   3960
cgtatcacac accccaaagc cttctgcttt gaatgctgcc cttcttcagg gcttaatttt   4020
taagagcgtc accttcatgg tggtcagtgc gtcctgctga tgtgctcagt atcaccgcca   4080
gtggtattta tgtcaacacc gccagagata atttatcacc gcagatggtt atctgtatgt   4140
tttttatatg aatttatttt ttgcagggg gcattgtttg gtaggtgaga gatcaattct    4200
gcattaatga atcggccaac gcgcggggag aggcggtttg cgtattgggc gctcttccgc   4260
ttcctcgctc actgactcgc tgcgctcggt cgttcggctg cggcgagcgg tatcagctca   4320
ctcaaaggcg gtaatacggt tatccacaga atcaggggat aacgcaggaa agaacatgtg   4380
agcaaaaggc cagcaaaagg ccaggaaccg taaaaaggcc gcgttgctgg cgttttccca   4440
taggctccgc cccctgacg agcatcacaa aaatcgacgc tcaagtcaga ggtggcgaaa    4500
cccgacagga ctataaagat accaggcgtt tcccctgga agctccctcg tgcgctctcc    4560
tgttccgacc ctgccgctta ccggatacct gtccgccttt ctcccttcgg gaagcgtggc   4620
gctttctcat agctcacgct gtaggtatct cagttcggtg taggtcgttc gctccaagct   4680
gggctgtgtg cacgaacccc ccgttcagcc cgaccgctgc gccttatccg gtaactatcg   4740
tcttgagtcc aacccggtaa gacacgactt atcgccactg gcagcagcca ctggtaacag   4800
gattagcaga gcgaggtatg taggcggtgc tacagagttc ttgaagtggt ggcctaacta   4860
cggctacact agaaggacag tatttggtat ctgcgctctg ctgaagccag ttaccttcgg   4920
aaaaagagtt ggtagctctt gatccggcaa acaaaccacc gctggtagcg gtggtttttt   4980
tgtttgcaag cagcagatta cgcgcagaaa aaaaggatct caagaagatc ctttgatctt   5040
ttctacgggg tctgacgctc agtggaacga aaactcacgt taagggattt tggtcatgag   5100
```

| | | |
|---|---|---|
| attatcaaaa aggatcttca cctagatcct tttaaattaa aaatgaagtt ttaaatcaat | 5160 | |
| ctaaagtata tatgagtaaa cttggtctga cagttaccaa tgcttaatca gtgaggcacc | 5220 | |
| tatctcagcg atctgtctat ttcgttcatc catagttgcc tgactccccg tcgtgtagat | 5280 | |
| aactacgata cgggagggct taccatctgg ccccagtgct gcaatgatac cgcgagaccc | 5340 | |
| acgctcaccg gctccagatt tatcagcaat aaaccagcca gccggaaggg ccgagcgcag | 5400 | |
| aagtggtcct gcaactttat ccgcctccat ccagtctatt aattgttgcc gggaagctag | 5460 | |
| agtaagtagt tcgccagtta atagtttgcg caacgttgtt gccattgcta caggcatcgt | 5520 | |
| ggtgtcacgc tcgtcgtttg gtatggcttc attcagctcc ggttcccaac gatcaaggcg | 5580 | |
| agttacatga tcccccatgt tgtgcaaaaa agcggttagc tccttcggtc ctccgatcgt | 5640 | |
| tgtcagaagt aagttggccg cagtgttatc actcatggtt atggcagcac tgcataattc | 5700 | |
| tcttactgtc atgccatccg taagatgctt ttctgtgact ggtgagtact caaccaagtc | 5760 | |
| attctgagaa tagtgtatgc ggcgaccgag ttgctcttgc ccggcgtcaa tacgggataa | 5820 | |
| taccgcgcca catagcagaa ctttaaaagt gctcatcatt ggaaaacgtt cttcggggcg | 5880 | |
| aaaactctca aggatcttac cgctgttgag atccagttcg atgtaaccca ctcgtgcacc | 5940 | |
| caactgatct tcagcatctt ttactttcac cagcgtttct gggtgagcaa aaacaggaag | 6000 | |
| gcaaaatgcc gcaaaaaagg gaataagggc gacacggaaa tgttgaatac tcatactctt | 6060 | |
| cctttttcaa tattattgaa gcatttatca gggttattgt ctcatgagcg gatacatatt | 6120 | |
| tgaatgtatt tagaaaaata aacaaatagg ggttccgcgc acatttcccc gaaaagtgcc | 6180 | |
| acctgacgtc taagaaacca ttattatcat gacattaacc tataaaaata ggcgtatcac | 6240 | |
| gaggcccttt cgtc | 6254 | |

<210> SEQ ID NO 5
<211> LENGTH: 7680
<212> TYPE: DNA
<213> ORGANISM: Artificial Sequence
<220> FEATURE:
<223> OTHER INFORMATION: engineered plasmid

<400> SEQUENCE: 5

| | | |
|---|---|---|
| gtacccagct tttgttccct ttagtgaggg ttaattgcgc gcttggcgta atcatggtca | 60 | |
| tagctgtttc ctgtgtgaaa ttgttatccg ctcacaattc cacacaacat acgagccgga | 120 | |
| agcataaagt gtaaagcctg gggtgcctaa tgagtgagct aactcacatt aattgcgttg | 180 | |
| cgctcactgc ccgctttcca gtcgggaaac ctgtcgtgcc agctgcatta atgaatcggc | 240 | |
| caacgcgcgg ggagaggcgg tttgcgtatt gggcgcatgc ataaaaactg ttgtaattca | 300 | |
| ttaagcattc tgccgacatg gaagccatca caaacggcat gatgaacctg aatcgccagc | 360 | |
| ggcatcagca ccttgtcgcc ttgcgtataa tatttgccca tggtgaaaac ggggcgaag | 420 | |
| aagttgtcca tattggccac gtttaaatca aaactggtga actcacccca gggattggct | 480 | |
| gagacgaaaa acatattctc aataaaccct ttagggaaat aggccaggtt ttcaccgtaa | 540 | |
| cacgccacat cttgcgaata tatgtgtaga aactgccgga atcgtcgtg gtattcactc | 600 | |
| cagagcgatg aaaacgtttc agtttgctca tggaaaacgg tgtaacaagg gtgaacacta | 660 | |
| tcccatatca ccagctcacc gtctttcatt gccatacgga attccggatg agcattcatc | 720 | |
| aggcgggcaa gaatgtgaat aaaggccgga taaaacttgt gcttattttt ctttacggtc | 780 | |
| tttaaaaagg ccgtaatatc cagctgaacg gtctggttat aggtacattg agcaactgac | 840 | |
| tgaaatgcct caaaatgttc tttacgatgc cattgggata tatcaacggt ggtatatcca | 900 | |

```
gtgatttttt tctccatttt agcttcctta gctcctgaaa atctcgataa ctcaaaaaat    960
acgcccggta gtgatcttat ttcattatgg tgaaagttgg aacctcttac gtgccgatca   1020
acgtctcatt ttcgccaaaa gttggcccag ggcttcccgg tatcaacagg gacaccagga   1080
tttatttatt ctgcgaagtg atcttccgtc acaggtattt attcgaagac gaaagggcct   1140
cgtgatacgc ctatttttat aggttaatgt catgataata atggtttctt agacgtcagg   1200
tggcactttt cggggaaatg tgcgcgcccg cgttcctgct ggcgctgggc ctgtttctgg   1260
cgctggactt cccgctgttc cgtcagcagc ttttcgccca cggccttgat gatcgcggcg   1320
gccttggcct gcatatcccg attaacggc cccaggggcgt ccagaacggg cttcaggcgc   1380
tcccgaaggt ctcgggccgt ctcttgggct tgatcggcct tcttgcgcat ctcacgcgct   1440
cctgcggcgg cctgtagggc aggctcatac ccctgccgaa ccgcttttgt cagccggtcg   1500
gccacggctt ccggcgtctc aacgcgcttt gagattccca gcttttcggc caatccctgc   1560
ggtgcatagg cgcgtggctc gaccgcttgc gggctgatgg tgacgtggcc cactggtggc   1620
cgctccaggg cctcgtagaa cgcctgaatg cgcgtgtgac gtgccttgct gccctcgatg   1680
ccccgttgca gccctagatc ggccacagcg gccgcaaacg tggtctggtc gcgggtcatc   1740
tgcgctttgt tgccgatgaa ctccttggcc gacagcctgc cgtcctgcgt cagcggcacc   1800
acgaacgcgg tcatgtgcgg gctggtttcg tcacggtgga tgctggccgt cacgatgcga   1860
tccgccccgt acttgtccgc cagccacttg tgcgccttct cgaagaacgc cgcctgctgt   1920
tcttggctgg ccgacttcca ccattccggg ctggccgtca tgacgtactc gaccgccaac   1980
acagcgtcct tgcgccgctt ctctggcagc aactcgcgca gtcggcccat cgcttcatcg   2040
gtgctgctgg ccgcccagtg ctcgttctct ggcgtcctgc tggcgtcagc gttgggcgtc   2100
tcgcgctcgc ggtaggcgtg cttgagactg gccgccacgt tgcccatttt cgccagcttc   2160
ttgcatcgca tgatcgcgta tgccgccatg cctgcccctc cctttggtg tccaaccggc   2220
tcgacggggg cagcgcaagg cggtgcctcc ggcgggccac tcaatgcttg agtatactca   2280
ctagactttg cttcgcaaag tcgtgaccgc ctacggcggc tgcggcgccc tacgggcttg   2340
ctctccgggc ttcgccctgc gcggtcgctg cgctcccttg ccagcccgtg gatatgtgga   2400
cgatggccgc gagcggccac cggctggctc gcttcgctcg gccgtggac aaccctgctg   2460
gacaagctga tggacaggct gcgcctgccc acgagcttga ccacagggat tgcccaccgg   2520
ctacccagcc ttcgaccaca tacccaccgg ctccaactgc gcggcctgcg gccttgcccc   2580
atcaattttt ttaattttct ctggggaaaa gcctccggcc tgcggcctgc gcgcttcgct   2640
tgccggttgg acaccaagtg gaaggcgggt caaggctcgc gcagcgaccg cgcagcggct   2700
tggccttgac gcgcctggaa cgacccaagc ctatgcgagt gggggcagtc gaaggcgaag   2760
cccgcccgcc tgccccccga gcctcacggc ggcgagtgcg ggggttccaa gggggcagcg   2820
ccaccttggg caaggccgaa ggccgcgcag tcgatcaaca agccccggag gggccacttt   2880
ttgccggagg gggagccgcg ccgaaggcgt ggggggaaccc cgcaggggtg ccccttctttg   2940
ggcaccaaag aactagatat agggcgaaat gcgaaagact taaaaatcaa caacttaaaa   3000
aagggggta cgcaacagct cattgcggca ccccccgcaa tagctcattg cgtaggttaa   3060
agaaaatctg taattgactg ccacttttac gcaacgcata attgttgtcg cgctgccgaa   3120
aagttgcagc tgattgcgca tggtgccgca accgtgcggc accctaccgc atggagataa   3180
gcatggccac gcagtccaga gaaatcggca ttcaagccaa gaacaagccc ggtcactggg   3240
```

-continued

```
tgcaaacgga acgcaaagcg catgaggcgt gggccgggct tattgcgagg aaacccacgg    3300
cggcaatgct gctgcatcac ctcgtggcgc agatgggcca ccagaacgcc gtggtggtca    3360
gccagaagac actttccaag ctcatcggac gttctttgcg gacggtccaa tacgcagtca    3420
aggacttggt ggccgagcgc tggatctccg tcgtgaagct caacgcccc ggcaccgtgt     3480 cggcctacgt ggtcaatgac cgcgtggcgt ggggccagcc ccgcgaccag ttgcgcctgt    3540
cggtgttcag tgccgccgtg gtggttgatc acgacgacca ggacgaatcg ctgttggggc    3600
atggcgacct gcgccgcatc ccgaccctgt atccgggcga gcagcaacta ccgaccggcc    3660
ccggcgagga gccgcccagc cagcccggca ttccgggcat ggaaccagac ctgccagcct    3720
tgaccgaaac ggaggaatgg gaacggcgcg ggcagcagcg cctgccgatg cccgatgagc    3780
cgtgttttct ggacgatggc gagccgttgg agccgccgac acgggtcacg ctgccgcgcc    3840
ggtagcactt gggttgcgca gcaacccgta agtgcgctgt tccagactat cggctgtagc    3900
cgcctcgccg ccctatacct tgtctgcctc cccgcgttgc gtcgcggtgc atggagccgg    3960
gccacctcga cctgaatgga agccggcggc acctcgctaa cggattcacc gttttatca    4020 ggctctggga ggcagaataa atgatcatat cgtcaattat tacctccacg gggagagcct    4080
gagcaaactg gcctcaggca tttgagaagc acacggtcac actgcttccg gtagtcaata    4140
aaccggtaaa ccagcaatag acataagcgg ctatttaacg accctgccct gaaccgacga    4200
ccgggtcgaa tttgctttcg aatttctgcc attcatccgc ttattatcac ttattcaggc    4260
gtagcaccag gcgtttaagg gcaccaataa ctgccttaaa aaaattacgc cccgccctgc    4320
cactcatcgc agtcggccta ttggttaaaa aatgagctga tttaacaaaa atttaacgcg    4380
aattttaaca aaatattaac gcttacaatt ccattcgcc attcaggctg cgcaactgtt     4440
gggaagggcg atcggtgcgg gcctcttcgc tattacgcca gctggcgaaa gggggatgtg    4500
ctgcaaggcg attaagttgg gtaacgccag ggttttccca gtcacgacgt tgtaaaacga    4560
cggccagtga gcgcgcgtaa tacgactcac tatagggcga attggagctc caccgcggtg    4620
gcggccgctc tagaactagt ggatccccg gctgcagga attcgatatc aagcttatcg      4680
ataccgtcga cctcgagtta agtctctaat cgattgtttt ccaatggaat ggttataaaa    4740
tctttggttt ttagtcttga aaatcttcta ggattttcta tgtaagtttt tgtataaata    4800
ttatattgct ttaataaatt taatatattt ttattgcatt ttaaggttat tttttccata    4860
tctgttcaac cttttttaaa tcctccaaac agtcaatatc taaacttgag ctttcgtcca    4920
ttaaaaaatg cttggttttg ctttgtaaaa agctaggatt gttaaaaat cttttatct      4980 ttaaaatata aattgcacca ttgctcatat aagttttagg caattttgc cttggcataa     5040 aaggatattc atcattacaa atccctgcta aatcgccaca atcattacaa acaaaggctt    5100
ttagaatttt attatcacat tcgcttacgc taattagggc atttgcattg ctatttttat    5160
aaagattaaa agcttcatta atatgaatat ttgttcttag cggtgaagtg ggttgtaaaa    5220
aaactacatc ttcataatct ttataaaatt ttagagcatg taacagcact ttatcgcttg    5280
tggtatcatc ttgtgcaagg ctaattgggc gttttaaaat atcaacattt tgactttttg    5340
cataatttaa aatttcatca ctatcactgc ttacaacaac tttactaatg cttttagcat    5400
ttagtgcagc tttgatcgtg tagtaaatta aggtttatt gtttaataaa accaaatttt    5460
tatttttaat acccttgag ccaccacgag cagggattat tgctaagctc atttatatc     5520 cttaaaaact ttttgtgtgc tgagttaaa aaaatctccg ctttgtaaat attcaaaaaa    5580
taattttgag ctatctaaaa tctctaactt agcgctaaat aaatcttgtt ttttatgaat    5640
```

```
agtgttaata gcttttagta tttcatcact atttgcatta actttttagtg tattttcatt    5700 gccaagtctt ccatttttgtc ttgagccaac taaaatccct gctgttttta agtataaggc    5760
ctcttttaaa atacaacttg aattacctat tataaaatca gcattttta acaaagttat      5820 aaaatactca atctaagcg atggaaaaag cttaaatcta gggttatttt taaactcttc      5880
atagctttgc aagattaatt caaaacctaa atcattattt ggataaataa caatataatt     5940
tttattactt tgtatcagtg cttttactaa attgtctgct tgattttaa tgctagtaat      6000 ttcagttgta acaggatgaa acataagcaa agcgtagttt tcataattta tatcataata    6060 ttttttttgct tcgctaagtg aaattttatt atcgttaaa agttctaaat caggcgaacc    6120
tatgataaaa atagattttt catcttctcc aagctgcatt aaacgccttt ttgcaaactc   6180
atcatttact aaatgaatat gagctagttt tgatatagcg tggcgtaagc tatcgtcaat   6240
agttcctgaa atctctccgc cttcaatatg cgctactaag atattattta atgctccaac   6300
aatagctgct gctaaaggct caattctatc tccatgtact acgattaaat caggttttag   6360
ctcatttgca taccttgaaa atccatcaat tgtagtagct aaagccttat cagtttgata   6420
atatttatca taatttataa attcataaat attttttaaag ccattttat aaagttcttt   6480 aactgtatag ccaaaatttt tacttaagtg cattcctgtt gcaaagatgt aaagttcaaa   6540
ttcgcttgag ttttgcaccc tgtacattaa agatttaatc ttagaataat cagccctaga   6600
gcctgttata aaaaggattt tttttcacgca aaatcctcat agcttaactg agcatcattt   6660
tctatatctc ttaatgcttt tttgcctaaa atattttcaa attcagccgc actaattcca   6720
ccaagtccag gtcttttaac ccaaatatta tccatagata aaacttcgcc ttttttaata   6780
tctttaatgc taactacact tgcaaaggca aaatcaattg taacttgttc ttgtttagcc   6840
gcttttttac tttcattatt tcctcttatt atagccattt gctcactttg tataattagc   6900
tcttttaaag cctttgtatc catagaacaa actatatcag gccacttct atgcatacta    6960 tcagtaaaat gtctttcaag cacacaagct ccaagtacaa ctgcacctaa acacgcaaga    7020
ttatctgttg tgtggtcgct taagcctacc atacaagaaa attctttttt taactcaagc    7080
atagcgttta atcttacaag attatgcggg gttgggtaaa gattggtcgt gtgcattaaa    7140
acaaaaggaa tttcattgtc taataagatt tttacagttg gttttatact ttcaatacta    7200
ttcattcctg tgctaactat cataggcttt ttaaaggctg ctatgtgttt aataagcgga   7260
taattattac actcacctga accaatctta aaagcactaa ctcccatatc ttctaagcgg    7320
ttcgcacctg cacgagaaaa aggtgtgcta agataaacaa gacctaattt ttctgtgtat   7380
tctttaagtg ctagctcatc tttataatcc aaagcacatt tttgcataat ctcataaatg    7440
cttatttttg cattaccagg aattactttt ttagcggcct tactcatctc atcttcaaca    7500
atatgagttt gatgctttat aatcttagca cctgcgctaa aggctgcatc taccataatt    7560
ttagctagtt ctaaactgcc attatgatta atgcctattt caggtacgac taagggtgct    7620
ttttcttcac ttatgattat attttgtatt tttatttctt tcatttattt tcctccttag    7680
```

<210> SEQ ID NO 6
<211> LENGTH: 4426
<212> TYPE: DNA
<213> ORGANISM: Artificial Sequence
<220> FEATURE:
<223> OTHER INFORMATION: engineered plasmid

<400> SEQUENCE: 6

```
ctaaattgta agcgttaata ttttgttaaa attcgcgtta aattttgtt aaatcagctc     60
atttttaac caataggccg aaatcggcaa atcccttat aaatcaaaag aatagaccga    120
gataggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tggagctcca    660
ccgcggtggc ggccgctcta gaactagtgg atccctagac tgcaatacaa acacctgttt    720
cacaatttgg cagatcagcc caaaaaagta cattctcttc ttttacaata cctagtttta    780
tcattacttg aactaaagga cttctcaaag cagtttcacg atcagttata gtttctgtcg    840
atgtaaaaac tataaattta attttttcag ctggtatcgt gaaatataaa gagctcgcta    900
taccagcaac tgcatcagga agcatatctg tcatcatcaa aacttcaaat gatattttg     960
atggaatatc aaccattgaa ggatagtttt gcattattaa tgtattaatg ataccgccac   1020
cagggtgacc tttgaagaac aaatcataac tattgcctaa ataatgtggg ctcgattcat   1080
taattgcatt attaatgaca ttaatttgtt gtttcgcata atactctctt tcatggttac   1140
cagcccatac agtcgtacct gtaaacacaa agtttggtaa attagatgaa ttatattcat   1200
tttgtaattt ttgtttgtca aaattaacaa tcgataagaa taattcttgt tgtttgctat   1260
tgaattttt gaaaccatcc cattgcattt gctttaaact atcaccaata tagtctcgta   1320
actcatgtaa tgatggttct aaagttaaat aatcttttct taaaaaatgg tagttagctg   1380
gatatagttt ttgccagtta taaacagatg atgttcctgt atttgaagtg tcttcattga   1440
taccattaat gacatcctca agataatctt taccaatttt taaattatct gttttattta   1500
atgtatctct ccagttatat aaatttacat attctgctga accatcatca tataaatcta   1560
tatttgttac cgtaacgtta ttaaacgaat ttaattcttt tagtattggc actaaattat   1620
caaatgaatg agcagtgtta gagctaagtt taacattcaa tctatgcttt gtttgtgctt   1680
gcttaacaat ttcttgtact aagtcagctg gtgtatggtt atttatcaat gcaaacgatg   1740
taatatttaa ctctttcatt tgctcatcag tcggaactat tctcccccaa gctatatatc   1800
tttgtgctgt aggattttct tcttccgatt taataatatc cattagctgc tgaagagttg   1860
gaagagatgc atgatcaaca taaacctcta agatggagc cactacgttt aatgttactt   1920
ttgttatata tttttcacct ttattactaa caccattaaa atcaaagcag tacttttcat   1980
cgtcatctaa tcgtggcgcc actacagata atgatattga ctctttattt tgttctgtta   2040
atagttgttg cgtaccacaa gtttgtaccc aagagtgttt tgtaaaagag atgtttgatt   2100
gattaattgg ctctaaatta acatactcct catcaataat agttttatta atatcatttt   2160
taataataga ttgtgtattt tcttctgaca tggtctgttt cctcctcgag gggggcccg    2220
gtacccagct tttgttccct ttagtgaggg ttaattgcgc gcttggcgta atcatggtca   2280
tagctgtttc ctgtgtgaaa ttgttatccg ctcacaattc cacacaacat acgagccgga   2340
agcataaagt gtaaagcctg ggtgcctaa tgagtgagct aactcacatt aattgcgttg   2400
```

-continued

```
cgctcactgc ccgctttcca gtcgggaaac ctgtcgtgcc agctgcatta atgaatcggc    2460
caacgcgcgg ggagaggcgg tttgcgtatt gggcgctctt ccgcttcctc gctcactgac    2520
tcgctgcgct cggtcgttcg gctgcggcga gcggtatcag ctcactcaaa ggcggtaata    2580
cggttatcca cagaatcagg ggataacgca ggaaagaaca tgtgagcaaa aggccagcaa    2640
aaggccagga accgtaaaaa ggccgcgttg ctggcgtttt tccataggct ccgcccccct    2700
gacgagcatc acaaaaatcg acgctcaagt cagaggtggc gaaacccgac aggactataa    2760
agataccagg cgtttccccc tggaagctcc ctcgtgcgct ctcctgttcc gaccctgccg    2820
cttaccggat acctgtccgc ctttctccct tcgggaagcg tggcgctttc tcatagctca    2880
cgctgtaggt atctcagttc ggtgtaggtc gttcgctcca agctgggctg tgtgcacgaa    2940
ccccccgttc agcccgaccg ctgcgcctta tccggtaact atcgtcttga gtccaacccg    3000
gtaagacacg acttatcgcc actggcagca gccactggta acaggattag cagagcgagg    3060
tatgtaggcg gtgctacaga gttcttgaag tggtggccta actacggcta cactagaagg    3120
acagtatttg gtatctgcgc tctgctgaag ccagttacct tcggaaaaag agttggtagc    3180
tcttgatccg gcaaacaaac caccgctggt agcggtggtt tttttgtttg caagcagcag    3240
attacgcgca gaaaaaagg atcctttga tcttttctac ggggtctgac    3300
gctcagtgga cgaaaactc acgttaaggg attttggtca tgagattatc aaaaaggatc    3360
ttcacctaga tccttttaaa ttaaaaatga agttttaaat caatctaaag tatatatgag    3420
taaacttggt ctgacagtta ccaatgctta atcagtgagg cacctatctc agcgatctgt    3480
ctatttcgtt catccatagt tgcctgactc cccgtcgtgt agataactac gatacgggag    3540
ggcttaccat ctggccccag tgctgcaatg ataccgcgag acccacgctc accggctcca    3600
gatttatcag caataaacca gccagccgga agggccgagc gcagaagtgg tcctgcaact    3660
ttatccgcct ccatccagtc tattaattgt tgccgggaag ctagagtaag tagttcgcca    3720
gttaatagtt tgcgcaacgt tgttgccatt gctacaggca tcgtggtgtc acgctcgtcg    3780
tttggtatgg cttcattcag ctccggttcc caacgatcaa ggcgagttac atgatccccc    3840
atgttgtgca aaaaagcggt tagctccttc ggtcctccga tcgttgtcag aagtaagttg    3900
gccgcagtgt tatcactcat ggttatggca gcactgcata attctcttac tgtcatgcca    3960
tccgtaagat gcttttctgt gactggtgag tactcaacca agtcattctg agaatagtgt    4020
atgcggcgac cgagttgctc ttgcccggcg tcaatacggg ataataccgc gccacatagc    4080
agaactttaa aagtgctcat cattggaaaa cgttcttcgg ggcgaaaact ctcaaggatc    4140
ttaccgctgt tgagatccag ttcgatgtaa cccactcgtg cacccaactg atcttcagca    4200
tcttttactt tcaccagcgt ttctgggtga gcaaaaacag gaaggcaaaa tgccgcaaaa    4260
aagggaataa gggcgacacg gaaatgttga atactcatac tcttcctttt tcaatattat    4320
tgaagcattt atcagggtta ttgtctcatg agcggataca tatttgaatg tatttagaaa    4380
aataaacaaa taggggttcc gcgcacattt ccccgaaaag tgccac                   4426
```

<210> SEQ ID NO 7
<211> LENGTH: 22
<212> TYPE: DNA
<213> ORGANISM: Artificial Sequence
<220> FEATURE:
<223> OTHER INFORMATION: chemically synthesized oligonucleotide

<400> SEQUENCE: 7

```
ctcgaggagg aaacagacca tg                                              22
```

<210> SEQ ID NO 8
<211> LENGTH: 28
<212> TYPE: DNA
<213> ORGANISM: Artificial Sequence
<220> FEATURE:
<223> OTHER INFORMATION: chemically synthesized oligonucleotide

<400> SEQUENCE: 8

```
ctcgaggaaa gagggacaa actagatg                                         28
```

<210> SEQ ID NO 9
<211> LENGTH: 4432
<212> TYPE: DNA
<213> ORGANISM: Artificial Sequence
<220> FEATURE:
<223> OTHER INFORMATION: engineered plasmid

<400> SEQUENCE: 9

```
ctaaattgta agcgttaata ttttgttaaa attcgcgtta aattttttgtt aaatcagctc      60
atttttaac caataggccg aaatcggcaa atcccttat aaatcaaaag aatagaccga       120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta atcggaacc ctaaagggag      300
cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg aagggcgat cggtgcgggc ctcttcgcta ttacgccagc tggcgaaagg     540
gggatgtgct gcaaggcgat taagttgggt aacgccaggg ttttcccagt cacgacgttg     600
taaaacgacg gccagtgagc gcgcgtaata cgactcacta tagggcgaat tggagctcca     660
ccgcggtggc ggccgctcta gaactagtgg atccctagac tgcaatacaa acacctgttt     720
cacaatttgg cagatcagcc caaaaagta cattctcttc ttttacaata cctagttta     780
tcattacttg aactaaagga cttctcaaag cagtttcacg atcagttata gtttctgtcg     840
atgtaaaaac tataaattta attttttcag ctggtatcgt gaaatataaa gagctcgcta     900
taccagcaac tgcatcagga agcatatctg tcatcatcaa aacttcaaat gatatttttg     960
atggaatatc aaccattgaa ggatagtttt gcattattaa tgtattaatg ataccgccac    1020
cagggtgacc tttgaagaac aaatcataac tattgcctaa ataatgtggg ctcgattcat    1080
taattgcatt attaatgaca ttaatttgtt gtttcgcata atactctctt tcatggttac    1140
cagcccatac agtcgtacct gtaaacacaa agtttggtaa attagatgaa ttatattcat    1200
tttgtaattt tgtttgtca aaattaacaa tcgataagaa taattcttgt tgtttgctat    1260
tgaattttt gaaaccatcc cattgcattt gctttaaact atcaccaata tagtctcgta    1320
actcatgtaa tgatggttct aaagttaaat aatctttcct taaaaatgg tagttagctg    1380
gatatagttt ttgccagtta taaacagatg atgttcctgt atttgaagtg tcttcattga    1440
taccattaat gacatcctca agataatctt taccaatttt taaattatct gttttattta    1500
atgtatctct ccagttatat aaatttacat attctgctga accatcatca tataaatcta    1560
tatttgttac cgtaacgtta ttaaacgaat ttaattcttt tagtattggc actaaattat    1620
caaatgaatg agcagtgtta gagctaagtt taacattcaa tctatgcttt gtttgtgctt    1680
```

```
gcttaacaat tcttgtact aagtcagctg gtgtatggtt atttatcaat gcaaacgatg   1740
taatatttaa ctctttcatt tgctcatcag tcggaactat tctcccccaa gctatatatc   1800
tttgtgctgt aggattttct tcttccgatt taataatatc cattagctgc tgaagagttg   1860
gaagagatgc atgatcaaca taaacctcta aagatggagc cactacgttt aatgttactt   1920
ttgttatata tttttcacct ttattactaa caccattaaa atcaaagcag tacttttcat   1980
cgtcatctaa tcgtggcgcc actacagata atgatattga ctctttattt tgttctgtta   2040
atagttgttg cgtaccacaa gtttgtaccc aagagtgttt tgtaaaagag atgtttgatt   2100
gattaattgg ctctaaatta acatactcct catcaataat agttttatta atatcatttt   2160
taataataga ttgtgtattt tcttctgaca tctagtttgt ccctctttc ctcgagggg    2220 ggcccggtac ccagcttttg ttcccttag tgagggttaa ttgcgcgctt ggcgtaatca    2280
tggtcatagc tgtttcctgt gtgaaattgt tatccgctca caattccaca caacatacga   2340 gccgaagca taaagtgtaa agcctggggt gcctaatgag tgagctaact cacattaatt    2400
gcgttgcgct cactgcccgc tttccagtcg ggaaacctgt cgtgccagct gcattaatga   2460
atcggccaac gcgcggggag aggcggtttg cgtattgggc gctcttccgc ttcctcgctc   2520
actgactcgc tgcgctcggt cgttcggctg cggcgagcgg tatcagctca ctcaaaggcg   2580
gtaatacggt tatccacaga atcaggggat aacgcaggaa agaacatgtg agcaaaaggc   2640
cagcaaaagg ccaggaaccg taaaaaggcc gcgttgctgg cgtttttcca taggctccgc   2700 cccctgacg agcatcacaa aaatcgacgc tcaagtcaga ggtggcgaaa cccgacagga   2760
ctataaagat accaggcgtt tccccctgga agctccctcg tgcgctctcc tgttccgacc   2820
ctgccgctta ccggatacct gtccgccttt ctcccttcgg gaagcgtggc gctttctcat   2880
agctcacgct gtaggtatct cagttcggtg taggtcgttc gctccaagct gggctgtgtg   2940 cacgaaccc ccgttcagcc cgaccgctgc gccttatccg gtaactatcg tcttgagtcc   3000
aacccggtaa gacacgactt atcgccactg gcagcagcca ctggtaacag gattagcaga   3060
gcgaggtatg taggcggtgc tacagagttc ttgaagtggt ggcctaacta cggctacact   3120
agaaggacag tatttggtat ctgcgctctg ctgaagccag ttaccttcgg aaaaagagtt   3180
ggtagctctt gatccggcaa acaaaccacc gctggtagcg gtggtttttt tgtttgcaag   3240
cagcagatta cgcgcagaaa aaaaggatct caagaagatc ctttgatctt ttctacgggg   3300
tctgacgctc agtggaacga aaactcacgt taagggattt tggtcatgag attatcaaaa   3360
aggatcttca cctagatcct tttaaattaa aaatgaagtt ttaaatcaat ctaaagtata   3420
tatgagtaaa cttggtctga cagttaccaa tgcttaatca gtgaggcacc tatctcagcg   3480
atctgtctat ttcgttcatc catagttgcc tgactcccg tcgtgtagat aactacgata   3540
cgggagggct taccatctgg ccccagtgct gcaatgatac cgcgagaccc acgctcaccg   3600
gctccagatt tatcagcaat aaaccagcca gccggaaggg ccgagcgcag aagtggtcct   3660
gcaactttat ccgcctccat ccagtctatt aattgttgcc gggaagctag agtaagtagt   3720
tcgccagtta atagtttgcg caacgttgtt gccattgcta caggcatcgt ggtgtcacgc   3780
tcgtcgtttg gtatggcttc attcagctcc ggttcccaac gatcaaggcg agttacatga   3840
tcccccatgt tgtgcaaaaa agcggttagc tccttcggtc ctccgatcgt tgtcagaagt   3900
aagttggccg cagtgttatc actcatggtt atggcagcac tgcataattc tcttactgtc   3960
atgccatccg taagatgctt ttctgtgact ggtgagtact caaccaagtc attctgagaa   4020
```

```
tagtgtatgc ggcgaccgag ttgctcttgc ccggcgtcaa tacgggataa taccgcgcca   4080
catagcagaa ctttaaaagt gctcatcatt ggaaaacgtt cttcggggcg aaaactctca   4140
aggatcttac cgctgttgag atccagttcg atgtaaccca ctcgtgcacc caactgatct   4200
tcagcatctt ttactttcac cagcgtttct gggtgagcaa aaacaggaag gcaaaatgcc   4260
gcaaaaaagg gaataagggc gacacggaaa tgttgaatac tcatactctt cctttttcaa   4320
tattattgaa gcatttatca gggttattgt ctcatgagcg gatacatatt tgaatgtatt   4380
tagaaaaata aacaaatagg ggttccgcgc acatttcccc gaaaagtgcc ac          4432

<210> SEQ ID NO 10
<211> LENGTH: 19
<212> TYPE: DNA
<213> ORGANISM: Artificial Sequence
<220> FEATURE:
<223> OTHER INFORMATION: chemically synthesized oligonucleotide

<400> SEQUENCE: 10
ctttattaaa cctactatg                                                  19

<210> SEQ ID NO 11
<211> LENGTH: 19
<212> TYPE: DNA
<213> ORGANISM: Artificial Sequence
<220> FEATURE:
<223> OTHER INFORMATION: chemically synthesized oligonucleotide

<400> SEQUENCE: 11
ctttcttcaa cctactatg                                                  19

<210> SEQ ID NO 12
<211> LENGTH: 7916
<212> TYPE: DNA
<213> ORGANISM: Artificial Sequence
<220> FEATURE:
<223> OTHER INFORMATION: engineered plasmid

<400> SEQUENCE: 12
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatatg cggtgtgaaa taccgcacag atgcgtaagg agaaaatacc gcatcaggcg    240
ccactagtgt tgaggaaaac gattggctga acaaaaaaca gactgatcga ggtcattttt    300
gagtgcaaaa agtgctgtaa ctctgaaaaa gcgatggtag aatccatttt taagcaaacg    360
gtgattttga aaaatgggta acaacgtcgt cgtactgggc acccaatggg gtgacgaagg    420
taaaggtaag atcgtcgatc ttctgactga acgggctaaa tatgttgtac gctaccaggg    480
cggtcacaac gcaggccata ctctcgtaat caacggtgaa aaaccgttc tccatcttat    540 tccatcaggt attctccgcg agaatgtaac cagcatcatc ggtaacggtg ttgtgctgtc    600
tccggccgcg ctgatgaaag agatgaaaga actggaagac cgtggcatcc ccgttcgtga    660
gcgtctgctg ctgtctgaag catgtccgct gatccttgat tatcacgttg cgctggataa    720
cgcgcgtgag aaagcgcgtg gcgcgaaagc gatcggcacc accggtcgtg gtatcgggcc    780
tgcttatgaa gataaagtag cacgtcgcgg tctgcgtgtt ggcgaccttt tcgacaaaga    840
aaccttcgct gaaaaactga agaagtgat ggaatatcac aacttccagt tggttaacta    900
ctacaaagct gaagcggttg attaccagaa agttctggat gatacgatgg ctgttgccga    960
```

```
catcctgact tctatggtgg ttgacgtttc tgacctgctc gaccaggcgc gtcagcgtgg    1020
cgatttcgtc atgtttgaag gtgcgcaggg tacgctgctg gatatcgacc acggtactta    1080
tccgtacgta acttcttcca acaccactgc tggtggcgtg gcgaccggtt ccggcctggg    1140
cccgcgttat gttgattacg ttctgggtat cctcaaagct tactccactc gtgtaggtgc    1200
aggtccgttc ccgaccgaac tgtttgatga aactggcgag ttcctctgca agcagggtaa    1260
cgaattcggc gcaactacgg ggcgtcgtcg tcgtaccggc tggctggaca ccgttgccgt    1320
tcgtcgtgcg gtacagctga actccctgtc tggcttctgc ctgactaaac tggacgttct    1380
ggatggcctg aaagaggtta aactctgcgt ggcttaccgt atgccggatg gtcgcgaagt    1440
gactaccact ccgctggcag ctgacgactg gaaaggtgta gagccgattt acgaaaccat    1500
gccgggctgg tctgaatcca ccttcggcgt gaaagatcgt agcggcctgc cgcaggcggc    1560
gctgaactat atcaagcgta ttgaagagct gactggtgtg ccgatcgata tcatctctac    1620
cggtccggat cgtactgaaa ccatgattct gcgcgacccg ttcgacgcgt aattctggta    1680
cgcctggcag atattttgcc tgccgggcga acagtgtgat acattgctgt gtcgggtaag    1740
ccattacgct atccgacaca gtgttaaatc ctcgcttttt tccttcccca gatctggcgc    1800
cattcgccat tcaggctgcg caactgttgg gaagggcgat cggtgcgggc ctcttcgcta    1860
ttacgccagc tggcgaaagg gggatgtgct gcaaggcgat taagttgggt aacgccaggg    1920
ttttcccagt cacgacgttg taaaacgacg gccagtgcca agcttactgc tcacaagaaa    1980
aaaggcacgt catctgacgt gccttttta tttgtactac cctgtacgat tactgcaggt    2040
cgacttaatt ttccagcaaa tgctggagca aaataccgtt gagcatggcg cgttttacca    2100
gcgcaaaagc gccgattgcc gagcggtgat ccagctcaga acgtaccacc ggcagattag    2160
tgcgaaacgc cttcagcgcc tgggtattaa tgcagctttc aatagcaggg agcagcactt    2220
tatcggcttc ggtgatttca ccggcaataa caatttttg cggattaaat aagttgatag    2280
caatggcgat ggttttaccc agatgacgac cgacatactc aattacttcc gacgccagac    2340
tatcgccttt gttcgcggct ttgcagatag ttttgatggt gcagtcgtcc agcggcacgc    2400
ggctctggta gccctgcttt aacagattca acacccgttg ttcaatggca gcgttggcag    2460
cgatagtttc caggcagcca agttgccgc agtggcagcg ttcacccagc ggttcgacct    2520
gaatatggcc aatttcaccg acgttgccgt tgcggccaat aaaaatgcgc ccgttagaga    2580
taatcccggc cccggttccg cgatggacac gcaccagaat ggagtcttcg caatcctgac    2640
ttgcaccgaa gtagtgctcc gccagcgcca gactacggat atcgtgacca acgaaacagg    2700
tcactttaaa acgttcttcc agagcttcta ccagccccca gttttctacc tgaatatgcg    2760
gcatgtaatg aattttgccg ctgtccgggt caacaagccc tggcaggatc accgaaatcg    2820
cgatcagctc gcgcagtttg cgctggtagc tatcaataaa ctgagcaatg cattcaaca    2880 gggcatgttc cagcgtttgc tgggtacgtt ccggcagcgg gtaatgttct ctgccagca    2940 ctttgctgct gagatcaaac agagtgatgg tggcgtcatg acgaccaagc cgtacgccga    3000
ttgcgtggaa attgcgggtt tcggtgacga tggagatagc gcggcggccc ccggtggagg    3060
cctgctgatc aacttctttg atcagcccgc gttcgataag ctgacgcgta attttggtta    3120
cgctggcggg ggcaagctgg ctttgctcgg caatctgaat ccgcgagatt ggcccgtact    3180
ggtcaatcag gcgataaacc gccgcgctgt taagctgttt tacgagatca acattaccta    3240
tctgagcttg tccgcctggt gtcatatgta tatctccttc ttgtcgactc tagatgcatg    3300
```

```
ctcgagatta ctcaaccgta accgattttg ccaggttacg cggctggtca acgtcggtgc    3360
ctttgatcag cgcgacatgg taagccagca gctgcagcgg aacggtgtag aagatcggtg    3420
caatcacctc ttccacatgc ggcatctcga tgatgtgcat gttatcgcta cttacaaaac    3480
ccgcatcctg atcggcgaag acatacaact gaccgccacg cgcgcgaact tcttcaatgt    3540
tggatttcag ttttccagc aattcgttgt tcggtgcaac aacataacc ggcatatcgg       3600 catcaattag cgccagcgga ccgtgtttca gttcgccagc agcgtaggct tcagcgtgaa    3660
tgtaagagat ctctttcaac ttcaatgcgc cttccagcgc gattgggtac tgatcgccac    3720
ggcccaggaa cagcgcgtga tgtttgtcag agaaatcttc tgccagcgct tcaatgcgtt    3780
tgtcctgaga cagcatctgc tcaatacggc tcggcagcgc ctgcagacca tgcacgatgt    3840
catgttcaat ggaggcatcc agacctttca ggcgagacag cttcgccacc agcatcaaca    3900
gcacagttaa ctgagtggtg aatgctttag tggatgccac gccgatttct gtacccgcgt    3960
tggtcattag cgccagatcg gattcgcgca ccagagaaga acccggaacg ttacagattg    4020
ccagtgaacc aaggtaaccc agctctttcg acagacgcag gccagccagg gtatccgcgg    4080
tttcgccaga ctgtgacaag gtgatcatca ggctgttacg acgcacggca gatttgcgat    4140
agcggaattc agaggcgatt tcgacgtcgc acggaatacc tgctagcgat tcaaaccagt    4200
agcgggaaac cataccggag ttataagaag taccacaggc gaggatctga atatgctcaa    4260
ccttcgacag cagttcgtcg cgcgttcggtc ccagctcgct taaatcaacc tgaccgtggc    4320
tgatgcgtcc ggtaagggtg ttttgatcg cgttcggctg ttcgtagatc tctttctgca    4380
tgtagtgacg gtaaatgcct ttatcgcccg cgtcatattg cagattggat tcgatatcct    4440
gacgttttac ttccgcgcca gttttatcga agatgtttac cgaacggcga gtgatttccg    4500
caatatcgcc ctcttcaagg aagataaagc gacgggtcac cggcaacagc gccagctggt    4560
cagaagcgat aaagttttcg cccatcccca ggccaatcac cagcggacta ccagaacgtg    4620
ccgccagcag ggtatccggg tgacgggagt ccatgatcac tgtaccgtac gcaccacgca    4680
gctgcgggat agcacgcaga acggcctcac gcagagtccc gccttgtttc agctcccagt    4740
tcaccagatg ggcaatcact tcggtgtcgg tttcagaaac gaaggtatag ccacgcgctt    4800
ttagctcttc acgcagcggt tcatggtttt cgatgatgcc gttatgcacc accacaatgt    4860
gttcagaaac atgcggatgc gcattcactt ctgaaggttc accgtgggtc gcccagcgag    4920
tgtgagcaat accagtgccg ccatgcagag gatgttcttc cgctgcctgt gccagcatct    4980
ggactttacc gaggcgacgc aggcgggtca tatgaccttc tgcatcaaca acggccagac    5040
cggcagagtc atatccgcgg tattccagac gacgtaaacc ttcaagaagg atttctgcta    5100
catcacgttg cgcgatcgcg ccaacaattc cacacatatg tatatctcct tcttgaattc    5160
taacaattga ttgaatgtat gcaaataaat gcatacacca taggtgtggt ttaatttgat    5220 gcccttttc agggctggaa tgtgtaagag cggggttatt tatgctgttg ttttttgtt      5280 actcgggaag ggctttacct cttccgcata acgcttcca tcagcgttta tagttaaaaa     5340
aatctttcgg aactggtttt gcgcttaccc caaccaacag gggatttgct gcttccatt    5400 gagcctgttt ctctgcgcga cgttcgcggc ggcgtgtttg tgcatccatc tggattctcc    5460
tgtcagttag ctttggtggt gtgtggcagt tgtagtcctg aacgaaaacc ccccgcgatt    5520
ggcacattgg cagctaatcc ggaatcgcac ttacggccaa tgcttcgttt cgtatcacac    5580
accccaaagc cttctgcttt gaatgctgcc cttcttcagg gcttaatttt taagagcgtc    5640
accttcatgg tggtcagtgc gtcctgctga tgtgctcagt atcaccgcca gtggtattta    5700
```

```
tgtcaacacc gccagagata atttatcacc gcagatggtt atctgtatgt ttttatatg    5760
aatttatttt ttgcagggggg gcattgtttg gtaggtgaga gatcaattct gcattaatga  5820
atcggccaac gcgcggggag aggcggtttg cgtattgggc gctcttccgc tgctagcgga   5880
gtgtatactg gcttactatg ttggcactga tgagggtgtc agtgaagtgc ttcatgtggc   5940
aggagaaaaa aggctgcacc ggtgcgtcag cagaatatgt gatacaggat atattccgct   6000
tcctcgctca ctgactcgct acgctcggtc gttcgactgc ggcgagcgga atggcttac    6060
gaacggggcg gagatttcct ggaagatgcc aggaagatac ttaacaggga agtgagaggg   6120
ccgcggcaaa gccgttttc cataggctcc gcccccctga caagcatcac gaaatctgac    6180
gctcaaatca gtggtggcga acccgacag gactataaag ataccaggcg tttccccctg    6240
gcggctccct cgtgcgctct cctgttcctg cctttcggtt taccggtgtc attccgctgt   6300
tatggccgcg tttgtctcat tccacgcctg acactcagtt ccgggtaggc agttcgctcc   6360
aagctggact gtatgcacga acccccccgtt cagtccgacc gctgcgcctt atccggtaac  6420
tatcgtcttg agtccaaccc ggaaagacat gcaaaagcac cactggcagc agccactggt  6480
aattgattta gaggagttag tcttgaagtc atgcgccggt taaggctaaa ctgaaaggac   6540
aagttttggt gactgcgctc ctccaagcca gttacctcgg ttcaaagagt tggtagctca   6600
gagaaccttc gaaaaaccgc cctgcaaggc ggttttttcg ttttcagagc aagagattac   6660
gcgcagacca aaacgatctc aagaagatca tcttattaat cagataaaat atttctaggc   6720
ggccgcgaac gaaaactcac gttaagggat tttggtcatg agattatcaa aaggatctt    6780
cacctagatc cttttaaatt aaaaatgaag ttttaaatca atctaaagta tatatgagta   6840
aacttggtct gacagttacc aatgcttaat cagtgaggca cctatctcag cgatctgtct   6900
atttcgttca tccatagttg cctgactccc cgtcgtgtag ataactacga tacgggaggg   6960
cttaccatct ggccccagtg ctgcaatgat accgcgagac ccacgctcac cggctccaga   7020
tttatcagca ataaaccagc cagccggaag ggccgagcgc agaagtggtc ctgcaacttt   7080
atccgcctcc atccagtcta ttaattgttg ccgggaagct agagtaagta gttcgccagt   7140
taatagtttg cgcaacgttg ttgccattgc tacaggcatc gtggtgtcac gctcgtcgtt   7200
tggtatggct tcattcagct ccggttccca acgatcaagg cgagttacat gatccccat    7260
gttgtgcaaa aaagcggtta gctccttcgg tcctccgatc gttgtcagaa gtaagttggc   7320
cgcagtgtta tcactcatgg ttatggcagc actgcataat tctcttactg tcatgccatc   7380
cgtaagatgc ttttctgtga ctggtgagta ctcaaccaag tcattctgag aatagtgtat   7440
gcggcgaccg agttgctctt gcccggcgtc aatacgggat aataccgcgc cacatagcag   7500
aactttaaaa gtgctcatca ttggaaaacg ttcttcgggg cgaaaactct caaggatctt   7560
accgctgttg agatccagtt cgatgtaacc cactcgtgca cccaactgat cttcagcatc   7620
ttttactttc accagcgttt ctgggtgagc aaaaacagga aggcaaaatg ccgcaaaaaa   7680
gggaataagg gcgacacgga aatgttgaat actcatactc ttcctttttc aatattattg   7740
aagcatttat cagggttatt gtctcatgag cggatacata tttgaatgta tttagaaaaa   7800
taaacaaata ggggttccgc gcacatttcc ccgaaaagtg ccacctgacg tctaagaaac   7860
cattattatc atgacattaa cctataaaaa taggcgtatc acgaggccct ttcgtc       7916
```

<210> SEQ ID NO 13
<211> LENGTH: 372
<212> TYPE: PRT

<213> ORGANISM: Campylobacter jejuni

<400> SEQUENCE: 13

Met Lys Lys Ile Leu Phe Ile Thr Gly Ser Arg Ala Asp Tyr Ser Lys
1               5                   10                  15

Ile Lys Ser Leu Met Tyr Arg Val Gln Asn Ser Ser Glu Phe Glu Leu
            20                  25                  30

Tyr Ile Phe Ala Thr Gly Met His Leu Ser Lys Asn Phe Gly Tyr Thr
        35                  40                  45

Val Lys Glu Leu Tyr Lys Asn Gly Phe Lys Asn Ile Tyr Glu Phe Ile
    50                  55                  60

Asn Tyr Asp Lys Tyr Tyr Gln Thr Asp Lys Ala Leu Ala Thr Thr Ile
65                  70                  75                  80

Asp Gly Phe Ser Arg Tyr Ala Asn Glu Leu Lys Pro Asp Leu Ile Val
                85                  90                  95

Val His Gly Asp Arg Ile Glu Pro Leu Ala Ala Ala Ile Val Gly Ala
            100                 105                 110

Leu Asn Asn Ile Leu Val Ala His Ile Glu Gly Gly Glu Ile Ser Gly
        115                 120                 125

Thr Ile Asp Asp Ser Leu Arg His Ala Ile Ser Lys Leu Ala His Ile
130                 135                 140

His Leu Val Asn Asp Glu Phe Ala Lys Arg Arg Leu Met Gln Leu Gly
145                 150                 155                 160

Glu Asp Glu Lys Ser Ile Phe Ile Ile Gly Ser Pro Asp Leu Glu Leu
                165                 170                 175

Leu Asn Asp Asn Lys Ile Ser Leu Ser Glu Ala Lys Lys Tyr Tyr Asp
            180                 185                 190

Ile Asn Tyr Glu Asn Tyr Ala Leu Leu Met Phe His Pro Val Thr Thr
        195                 200                 205

Glu Ile Thr Ser Ile Lys Asn Gln Ala Asp Asn Leu Val Lys Ala Leu
210                 215                 220

Ile Gln Ser Asn Lys Asn Tyr Ile Val Ile Tyr Pro Asn Asn Asp Leu
225                 230                 235                 240

Gly Phe Glu Leu Ile Leu Gln Ser Tyr Glu Glu Phe Lys Asn Asn Pro
                245                 250                 255

Arg Phe Lys Leu Phe Pro Ser Leu Arg Phe Glu Tyr Phe Ile Thr Leu
            260                 265                 270

Leu Lys Asn Ala Asp Phe Ile Ile Gly Asn Ser Ser Cys Ile Leu Lys
        275                 280                 285

Glu Ala Leu Tyr Leu Lys Thr Ala Gly Ile Leu Val Gly Ser Arg Gln
290                 295                 300

Asn Gly Arg Leu Gly Asn Glu Asn Thr Leu Lys Val Asn Ala Asn Ser
305                 310                 315                 320

Asp Glu Ile Leu Lys Ala Ile Asn Thr Ile His Lys Lys Gln Asp Leu
                325                 330                 335

Phe Ser Ala Lys Leu Glu Ile Leu Asp Ser Ser Lys Leu Phe Phe Glu
            340                 345                 350

Tyr Leu Gln Ser Gly Asp Phe Phe Lys Leu Ser Thr Gln Lys Val Phe
        355                 360                 365

Lys Asp Ile Lys
370

<210> SEQ ID NO 14
<211> LENGTH: 346

```
<212> TYPE: PRT
<213> ORGANISM: Campylobacter jejuni

<400> SEQUENCE: 14

Met Lys Glu Ile Lys Ile Gln Asn Ile Ile Ser Glu Glu Lys Ala
1               5                   10                  15

Pro Leu Val Val Pro Glu Ile Gly Ile Asn His Asn Gly Ser Leu Glu
                20                  25                  30

Leu Ala Lys Ile Met Val Asp Ala Ala Phe Ser Ala Gly Ala Lys Ile
            35                  40                  45

Ile Lys His Gln Thr His Ile Val Glu Asp Glu Met Ser Lys Ala Ala
        50                  55                  60

Lys Val Ile Pro Gly Asn Ala Lys Ile Ser Ile Tyr Glu Ile Met
65                  70                  75                  80

Gln Lys Cys Ala Leu Asp Tyr Lys Asp Glu Leu Ala Leu Lys Glu Tyr
                85                  90                  95

Thr Glu Lys Leu Gly Leu Val Tyr Leu Ser Thr Pro Phe Ser Arg Ala
                100                 105                 110

Gly Ala Asn Arg Leu Glu Asp Met Gly Val Ser Ala Phe Lys Ile Gly
            115                 120                 125

Ser Gly Glu Cys Asn Asn Tyr Pro Leu Ile Lys His Ile Ala Ala Phe
        130                 135                 140

Lys Lys Pro Met Ile Val Ser Thr Gly Met Asn Ser Ile Glu Ser Ile
145                 150                 155                 160

Lys Pro Thr Val Lys Ile Leu Leu Asp Asn Glu Ile Pro Phe Val Leu
                165                 170                 175

Met His Thr Thr Asn Leu Tyr Pro Thr Pro His Asn Leu Val Arg Leu
            180                 185                 190

Asn Ala Met Leu Glu Leu Lys Lys Glu Phe Ser Cys Met Val Gly Leu
        195                 200                 205

Ser Asp His Thr Thr Asp Asn Leu Ala Cys Leu Gly Ala Val Val Leu
210                 215                 220

Gly Ala Cys Val Leu Glu Arg His Phe Thr Asp Ser Met His Arg Ser
225                 230                 235                 240

Gly Pro Asp Ile Val Cys Ser Met Asp Thr Lys Ala Leu Lys Glu Leu
                245                 250                 255

Ile Ile Gln Ser Glu Gln Met Ala Ile Ile Arg Gly Asn Asn Glu Ser
            260                 265                 270

Lys Lys Ala Ala Lys Gln Glu Gln Val Thr Ile Asp Phe Ala Phe Ala
        275                 280                 285

Ser Val Val Ser Ile Lys Asp Ile Lys Lys Gly Val Leu Ser Met
290                 295                 300

Asp Asn Ile Trp Val Lys Arg Pro Gly Leu Gly Ile Ser Ala Ala
305                 310                 315                 320

Glu Phe Glu Asn Ile Leu Gly Lys Lys Ala Leu Arg Asp Ile Glu Asn
                325                 330                 335

Asp Ala Gln Leu Ser Tyr Glu Asp Phe Ala
            340                 345

<210> SEQ ID NO 15
<211> LENGTH: 221
<212> TYPE: PRT
<213> ORGANISM: Campylobacter jejuni

<400> SEQUENCE: 15
```

Met Ser Leu Ala Ile Ile Pro Ala Arg Gly Gly Ser Lys Gly Ile Lys
1               5                   10                  15

Asn Lys Asn Leu Val Leu Leu Asn Asn Lys Pro Leu Ile Tyr Tyr Thr
            20                  25                  30

Ile Lys Ala Ala Leu Asn Ala Lys Ser Ile Ser Lys Val Val Val Ser
            35                  40                  45

Ser Asp Ser Asp Glu Ile Leu Asn Tyr Ala Lys Ser Gln Asn Val Asp
50                  55                  60

Ile Leu Lys Arg Pro Ile Ser Leu Ala Gln Asp Thr Thr Ser Asp
65                  70                  75                  80

Lys Val Leu Leu His Ala Leu Lys Phe Tyr Lys Asp Tyr Glu Asp Val
            85                  90                  95

Val Phe Leu Gln Pro Thr Ser Pro Leu Arg Thr Asn Ile His Ile Asn
            100                 105                 110

Glu Ala Phe Asn Leu Tyr Lys Asn Ser Asn Ala Asn Ala Leu Ile Ser
            115                 120                 125

Val Ser Glu Cys Asp Asn Lys Ile Leu Lys Ala Phe Val Cys Asn Asp
130                 135                 140

Cys Gly Asp Leu Ala Gly Ile Cys Asn Asp Glu Tyr Pro Phe Met Pro
145                 150                 155                 160

Arg Gln Lys Leu Pro Lys Thr Tyr Met Ser Asn Gly Ala Ile Tyr Ile
            165                 170                 175

Leu Lys Ile Lys Glu Phe Leu Asn Asn Pro Ser Phe Leu Gln Ser Lys
            180                 185                 190

Thr Lys His Phe Leu Met Asp Glu Ser Ser Ser Leu Asp Ile Asp Cys
            195                 200                 205

Leu Glu Asp Leu Lys Lys Val Glu Gln Ile Trp Lys Lys
210                 215                 220

<210> SEQ ID NO 16
<211> LENGTH: 349
<212> TYPE: PRT
<213> ORGANISM: Neisseria meningitidis

<400> SEQUENCE: 16

Met Pro Ser Glu Ala Phe Arg Arg His Arg Ala Tyr Arg Glu Asn Lys
1               5                   10                  15

Leu Gln Pro Leu Val Ser Val Leu Ile Cys Ala Tyr Asn Val Glu Lys
            20                  25                  30

Tyr Phe Ala Gln Ser Leu Ala Ala Val Val Asn Gln Thr Trp Arg Asn
            35                  40                  45

Leu Asp Ile Leu Ile Val Asp Asp Gly Ser Thr Asp Gly Thr Leu Ala
50                  55                  60

Ile Ala Gln Arg Phe Gln Glu Gln Asp Gly Ile Arg Ile Leu Ala
65                  70                  75                  80

Gln Pro Arg Asn Ser Gly Leu Ile Pro Ser Leu Asn Ile Gly Leu Asp
            85                  90                  95

Glu Leu Ala Lys Ser Gly Gly Gly Glu Tyr Ile Ala Arg Thr Asp
            100                 105                 110

Ala Asp Asp Ile Ala Ala Pro Asp Trp Ile Glu Lys Ile Val Gly Glu
            115                 120                 125

Met Glu Lys Asp Arg Ser Ile Ile Ala Met Gly Ala Trp Leu Glu Val
            130                 135                 140

Leu Ser Glu Glu Lys Asp Gly Asn Arg Leu Ala Arg His His Glu His
145                 150                 155                 160

```
Gly Lys Ile Trp Lys Lys Pro Thr Arg His Glu Asp Ile Ala Asp Phe
                165                 170                 175

Phe Pro Phe Gly Asn Pro Ile His Asn Asn Thr Met Ile Met Arg Arg
            180                 185                 190

Ser Val Ile Asp Gly Gly Leu Arg Tyr Asn Thr Glu Arg Asp Trp Ala
        195                 200                 205

Glu Asp Tyr Gln Phe Trp Tyr Asp Val Ser Lys Leu Gly Arg Leu Ala
    210                 215                 220

Tyr Tyr Pro Glu Ala Leu Val Lys Tyr Arg Leu His Ala Asn Gln Val
225                 230                 235                 240

Ser Ser Lys Tyr Ser Ile Arg Gln His Glu Ile Ala Gln Gly Ile Gln
                245                 250                 255

Lys Thr Ala Arg Asn Asp Phe Leu Gln Ser Met Gly Phe Lys Thr Arg
            260                 265                 270

Phe Asp Ser Leu Glu Tyr Arg Gln Ile Lys Ala Val Ala Tyr Glu Leu
        275                 280                 285

Leu Glu Lys His Leu Pro Glu Glu Asp Phe Glu Arg Ala Arg Arg Phe
    290                 295                 300

Leu Tyr Gln Cys Phe Lys Arg Thr Asp Thr Leu Pro Ala Gly Ala Trp
305                 310                 315                 320

Leu Asp Phe Ala Ala Asp Gly Arg Met Arg Arg Leu Phe Thr Leu Arg
                325                 330                 335

Gln Tyr Phe Gly Ile Leu His Arg Leu Leu Lys Asn Arg
            340                 345

<210> SEQ ID NO 17
<211> LENGTH: 273
<212> TYPE: PRT
<213> ORGANISM: Helicobacter pylori

<400> SEQUENCE: 17

Met Arg Val Phe Ala Ile Ser Leu Asn Gln Lys Val Cys Asp Thr Phe
1               5                   10                  15

Gly Leu Val Phe Arg Asp Thr Thr Leu Leu Asn Ser Ile Asn Ala
            20                  25                  30

Thr His His Gln Ala Gln Ile Phe Asp Ala Ile Tyr Ser Lys Thr Phe
        35                  40                  45

Glu Gly Gly Leu His Pro Leu Val Lys Lys His Leu His Pro Tyr Phe
    50                  55                  60

Ile Thr Gln Asn Ile Lys Asp Met Gly Ile Thr Thr Asn Leu Ile Ser
65                  70                  75                  80

Glu Val Ser Lys Phe Tyr Tyr Ala Leu Lys Tyr His Ala Lys Phe Met
                85                  90                  95

Ser Leu Gly Glu Leu Gly Cys Tyr Ala Ser His Tyr Ser Leu Trp Glu
            100                 105                 110

Lys Cys Ile Glu Leu Asn Glu Ala Ile Cys Ile Leu Glu Asp Asp Ile
        115                 120                 125

Thr Leu Lys Glu Asp Phe Lys Glu Gly Leu Asp Phe Leu Glu Lys His
    130                 135                 140

Ile Gln Glu Leu Gly Tyr Ile Arg Leu Met His Leu Leu Tyr Asp Ala
145                 150                 155                 160

Ser Val Lys Ser Glu Pro Leu Ser His Lys Asn His Glu Ile Gln Glu
                165                 170                 175

Arg Val Gly Ile Ile Lys Ala Tyr Ser Glu Gly Val Gly Thr Gln Gly
```

```
            180                 185                 190
Tyr Val Ile Thr Pro Lys Ile Ala Lys Val Phe Leu Lys Cys Ser Arg
            195                 200                 205

Lys Trp Val Val Pro Val Asp Thr Ile Met Asp Ala Thr Phe Ile His
        210                 215                 220

Gly Val Lys Asn Leu Val Leu Gln Pro Phe Val Ile Ala Asp Asp Glu
225                 230                 235                 240

Gln Ile Ser Thr Ile Ala Arg Lys Glu Glu Pro Tyr Ser Pro Lys Ile
                245                 250                 255

Ala Leu Met Arg Glu Leu His Phe Lys Tyr Leu Lys Tyr Trp Gln Phe
            260                 265                 270

Val

<210> SEQ ID NO 18
<211> LENGTH: 265
<212> TYPE: PRT
<213> ORGANISM: Escherichia coli

<400> SEQUENCE: 18

Met Ile Ile Asp Glu Ala Glu Ser Ala Glu Ser Thr His Pro Val Val
1               5                   10                  15

Ser Val Ile Leu Pro Val Asn Lys Lys Asn Pro Phe Leu Asp Glu Ala
            20                  25                  30

Ile Asn Ser Ile Leu Ser Gln Thr Phe Ser Ser Phe Glu Ile Ile Ile
        35                  40                  45

Val Ala Asn Cys Cys Thr Asp Asp Phe Tyr Asn Glu Leu Lys His Lys
50                  55                  60

Val Asn Asp Lys Ile Lys Leu Ile Arg Thr Asn Ile Ala Tyr Leu Pro
65                  70                  75                  80

Tyr Ser Leu Asn Lys Ala Ile Asp Leu Ser Asn Gly Glu Phe Ile Ala
                85                  90                  95

Arg Met Asp Ser Asp Asp Ile Ser His Pro Asp Arg Phe Thr Lys Gln
            100                 105                 110

Val Asp Phe Leu Lys Asn Asn Pro Tyr Val Asp Val Val Gly Thr Asn
        115                 120                 125

Ala Ile Phe Ile Asp Asp Lys Gly Arg Glu Ile Asn Lys Thr Lys Leu
130                 135                 140

Pro Glu Glu Asn Leu Asp Ile Val Lys Asn Leu Pro Tyr Lys Cys Cys
145                 150                 155                 160

Ile Val His Pro Ser Val Met Phe Arg Lys Lys Val Ile Ala Ser Ile
                165                 170                 175

Gly Gly Tyr Met Phe Ser Asn Tyr Ser Glu Asp Tyr Glu Leu Trp Asn
            180                 185                 190

Arg Leu Ser Leu Ala Lys Ile Lys Phe Gln Asn Leu Pro Glu Tyr Leu
        195                 200                 205

Phe Tyr Tyr Arg Leu His Glu Gly Gln Ser Thr Ala Lys Lys Asn Leu
    210                 215                 220

Tyr Met Val Met Val Asn Asp Leu Val Ile Lys Met Lys Cys Phe Phe
225                 230                 235                 240

Leu Thr Gly Asn Ile Asn Tyr Leu Phe Gly Gly Ile Arg Thr Ile Ala
                245                 250                 255

Ser Phe Ile Tyr Cys Lys Tyr Ile Lys
            260                 265
```

<210> SEQ ID NO 19
<211> LENGTH: 406
<212> TYPE: PRT
<213> ORGANISM: Escherichia coli

<400> SEQUENCE: 19

Met Thr Pro Gly Gly Gln Ala Gln Ile Gly Asn Val Asp Leu Val Lys
1               5                   10                  15

Gln Leu Asn Ser Ala Ala Val Tyr Arg Leu Ile Asp Gln Tyr Gly Pro
            20                  25                  30

Ile Ser Arg Ile Gln Ile Ala Glu Gln Ser Gln Leu Ala Pro Ala Ser
        35                  40                  45

Val Thr Lys Ile Thr Arg Gln Leu Ile Glu Arg Gly Leu Ile Lys Glu
    50                  55                  60

Val Asp Gln Gln Ala Ser Thr Gly Gly Arg Arg Ala Ile Ser Ile Val
65                  70                  75                  80

Thr Glu Thr Arg Asn Phe His Ala Ile Gly Val Arg Leu Gly Arg His
                85                  90                  95

Asp Ala Thr Ile Thr Leu Phe Asp Leu Ser Ser Lys Val Leu Ala Glu
            100                 105                 110

Glu His Tyr Pro Leu Pro Glu Arg Thr Gln Gln Thr Leu Glu His Ala
        115                 120                 125

Leu Leu Asn Ala Ile Ala Gln Phe Ile Asp Ser Tyr Gln Arg Lys Leu
    130                 135                 140

Arg Glu Leu Ile Ala Ile Ser Val Ile Leu Pro Gly Leu Val Asp Pro
145                 150                 155                 160

Asp Ser Gly Lys Ile His Tyr Met Pro His Ile Gln Val Glu Asn Trp
                165                 170                 175

Gly Leu Val Glu Ala Leu Glu Glu Arg Phe Lys Val Thr Cys Phe Val
            180                 185                 190

Gly His Asp Ile Arg Ser Leu Ala Leu Ala Glu His Tyr Phe Gly Ala
        195                 200                 205

Ser Gln Asp Cys Glu Asp Ser Ile Leu Val Arg Val His Arg Gly Thr
    210                 215                 220

Gly Ala Gly Ile Ile Ser Asn Gly Arg Ile Phe Ile Gly Arg Asn Gly
225                 230                 235                 240

Asn Val Gly Glu Ile Gly His Ile Gln Val Glu Pro Leu Gly Glu Arg
                245                 250                 255

Cys His Cys Gly Asn Phe Gly Cys Leu Glu Thr Ile Ala Ala Asn Ala
            260                 265                 270

Ala Ile Glu Gln Arg Val Leu Asn Leu Leu Lys Gln Gly Tyr Gln Ser
        275                 280                 285

Arg Val Pro Leu Asp Asp Cys Thr Ile Lys Thr Ile Cys Lys Ala Ala
    290                 295                 300

Asn Lys Gly Asp Ser Leu Ala Ser Glu Val Ile Glu Tyr Val Gly Arg
305                 310                 315                 320

His Leu Gly Lys Thr Ile Ala Ile Ala Ile Asn Leu Phe Asn Pro Gln
                325                 330                 335

Lys Ile Val Ile Ala Gly Glu Ile Thr Glu Ala Asp Lys Val Leu Leu
            340                 345                 350

Pro Ala Ile Glu Ser Cys Ile Asn Thr Gln Ala Leu Lys Ala Phe Arg
        355                 360                 365

Thr Asn Leu Pro Val Val Arg Ser Glu Leu Asp His Arg Ser Ala Ile
    370                 375                 380

```
Gly Ala Phe Ala Leu Val Lys Arg Ala Met Leu Asn Gly Ile Leu Leu
385                 390                 395                 400

Gln His Leu Leu Glu Asn
                405

<210> SEQ ID NO 20
<211> LENGTH: 609
<212> TYPE: PRT
<213> ORGANISM: Escherichia coli

<400> SEQUENCE: 20

Met Cys Gly Ile Val Gly Ala Ile Ala Gln Arg Asp Val Ala Glu Ile
1               5                   10                  15

Leu Leu Glu Gly Leu Arg Arg Leu Glu Tyr Arg Gly Tyr Asp Ser Ala
                20                  25                  30

Gly Leu Ala Val Val Asp Ala Glu Gly His Met Thr Arg Leu Arg Arg
            35                  40                  45

Leu Gly Lys Val Gln Met Leu Ala Gln Ala Ala Glu Glu His Pro Leu
50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
        115                 120                 125

Ala His Leu Val Asn Trp Glu Leu Lys Gln Gly Gly Thr Leu Arg Glu
130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
            180                 185                 190

Asp Gln Leu Ala Leu Leu Pro Val Thr Arg Arg Phe Ile Phe Leu Glu
        195                 200                 205

Glu Gly Asp Ile Ala Glu Ile Thr Arg Arg Ser Val Asn Ile Phe Asp
210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Arg His Tyr Met Gln Lys Glu
                245                 250                 255

Ile Tyr Glu Gln Pro Asn Ala Ile Lys Asn Thr Leu Thr Gly Arg Ile
            260                 265                 270

Ser His Gly Gln Val Asp Leu Ser Glu Leu Gly Pro Asn Ala Asp Glu
        275                 280                 285

Leu Leu Ser Lys Val Glu His Ile Gln Ile Leu Ala Cys Gly Thr Ser
290                 295                 300

Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
                325                 330                 335

Ala Val Arg Arg Asn Ser Leu Met Ile Thr Leu Ser Gln Ser Gly Glu
            340                 345                 350
```

```
Thr Ala Asp Thr Leu Ala Gly Leu Arg Leu Ser Lys Glu Leu Gly Tyr
            355                 360                 365

Leu Gly Ser Leu Ala Ile Cys Asn Val Pro Gly Ser Ser Leu Val Arg
        370                 375                 380

Glu Ser Asp Leu Ala Leu Met Thr Asn Ala Gly Thr Glu Ile Gly Val
385                 390                 395                 400

Ala Ser Thr Lys Ala Phe Thr Thr Gln Leu Thr Val Leu Leu Met Leu
                405                 410                 415

Val Ala Lys Leu Ser Arg Leu Lys Gly Leu Asp Ala Ser Ile Glu His
            420                 425                 430

Asp Ile Val His Gly Leu Gln Ala Leu Pro Ser Arg Ile Glu Gln Met
        435                 440                 445

Leu Ser Gln Asp Lys Arg Ile Glu Ala Leu Ala Glu Asp Phe Ser Asp
    450                 455                 460

Lys His His Ala Leu Phe Leu Arg Gly Asp Gln Tyr Pro Ile Ala
465                 470                 475                 480

Leu Glu Gly Ala Leu Lys Leu Lys Glu Ile Ser Tyr Ile His Ala Glu
                485                 490                 495

Ala Tyr Ala Ala Gly Glu Leu Lys His Gly Pro Leu Ala Leu Ile Asp
            500                 505                 510

Ala Asp Met Pro Val Ile Val Ala Pro Asn Asn Glu Leu Leu Glu
        515                 520                 525

Lys Leu Lys Ser Asn Ile Glu Glu Val Arg Ala Arg Gly Gly Gln Leu
    530                 535                 540

Tyr Val Phe Ala Asp Gln Asp Ala Gly Phe Val Ser Ser Asp Asn Met
545                 550                 555                 560

His Ile Ile Glu Met Pro His Val Glu Val Ile Ala Pro Ile Phe
                565                 570                 575

Tyr Thr Val Pro Leu Gln Leu Leu Ala Tyr His Val Ala Leu Ile Lys
            580                 585                 590

Gly Thr Asp Val Asp Gln Pro Arg Asn Leu Ala Lys Ser Val Thr Val
        595                 600                 605

Glu

<210> SEQ ID NO 21
<211> LENGTH: 514
<212> TYPE: PRT
<213> ORGANISM: Photobacterium sp. JT-ISH-224

<400> SEQUENCE: 21

Met Lys Asn Phe Leu Leu Thr Leu Ile Leu Leu Thr Ala Cys Asn
1               5                   10                  15

Asn Ser Glu Glu Asn Thr Gln Ser Ile Ile Lys Asn Asp Ile Asn Lys
                20                  25                  30

Thr Ile Ile Asp Glu Glu Tyr Val Asn Leu Glu Pro Ile Asn Gln Ser
            35                  40                  45

Asn Ile Ser Phe Thr Lys His Ser Trp Val Gln Thr Cys Gly Thr Gln
    50                  55                  60

Gln Leu Leu Thr Glu Gln Asn Lys Glu Ser Ile Ser Leu Ser Val Val
65                  70                  75                  80

Ala Pro Arg Leu Asp Asp Asp Glu Lys Tyr Cys Phe Asp Phe Asn Gly
                85                  90                  95

Val Ser Asn Lys Gly Glu Lys Tyr Ile Thr Lys Val Thr Leu Asn Val
                100                 105                 110
```

```
Val Ala Pro Ser Leu Glu Val Tyr Val Asp His Ala Ser Leu Pro Thr
            115                 120                 125

Leu Gln Gln Leu Met Asp Ile Ile Lys Ser Glu Glu Asn Pro Thr
    130                 135                 140

Ala Gln Arg Tyr Ile Ala Trp Gly Arg Ile Val Pro Thr Asp Glu Gln
145                 150                 155                 160

Met Lys Glu Leu Asn Ile Thr Ser Phe Ala Leu Ile Asn Asn His Thr
                165                 170                 175

Pro Ala Asp Leu Val Gln Glu Ile Val Lys Gln Ala Gln Thr Lys His
                180                 185                 190

Arg Leu Asn Val Lys Leu Ser Ser Asn Thr Ala His Ser Phe Asp Asn
                195                 200                 205

Leu Val Pro Ile Leu Lys Glu Leu Asn Ser Phe Asn Asn Val Thr Val
            210                 215                 220

Thr Asn Ile Asp Leu Tyr Asp Asp Gly Ser Ala Glu Tyr Val Asn Leu
225                 230                 235                 240

Tyr Asn Trp Arg Asp Thr Leu Asn Lys Thr Asp Asn Leu Lys Ile Gly
                245                 250                 255

Lys Asp Tyr Leu Glu Asp Val Ile Asn Gly Ile Asn Glu Asp Thr Ser
                260                 265                 270

Asn Thr Gly Thr Ser Ser Val Tyr Asn Trp Gln Lys Leu Tyr Pro Ala
                275                 280                 285

Asn Tyr His Phe Leu Arg Lys Asp Tyr Leu Thr Leu Glu Pro Ser Leu
                290                 295                 300

His Glu Leu Arg Asp Tyr Ile Gly Asp Ser Leu Lys Gln Met Gln Trp
305                 310                 315                 320

Asp Gly Phe Lys Lys Phe Asn Ser Lys Gln Gln Glu Leu Phe Leu Ser
                325                 330                 335

Ile Val Asn Phe Asp Lys Gln Lys Leu Gln Asn Glu Tyr Asn Ser Ser
                340                 345                 350

Asn Leu Pro Asn Phe Val Phe Thr Gly Thr Thr Val Trp Ala Gly Asn
                355                 360                 365

His Glu Arg Glu Tyr Tyr Ala Lys Gln Gln Ile Asn Val Ile Asn Asn
                370                 375                 380

Ala Ile Asn Glu Ser Ser Pro His Tyr Leu Gly Asn Ser Tyr Asp Leu
385                 390                 395                 400

Phe Phe Lys Gly His Pro Gly Gly Ile Ile Asn Thr Leu Ile Met
                405                 410                 415

Gln Asn Tyr Pro Ser Met Val Asp Ile Pro Ser Lys Ile Ser Phe Glu
                420                 425                 430

Val Leu Met Met Thr Asp Met Leu Pro Asp Ala Val Ala Gly Ile Ala
                435                 440                 445

Ser Ser Leu Tyr Phe Thr Ile Pro Ala Glu Lys Ile Lys Phe Ile Val
                450                 455                 460

Phe Thr Ser Thr Glu Thr Ile Thr Asp Arg Glu Thr Ala Leu Arg Ser
465                 470                 475                 480

Pro Leu Val Gln Val Met Ile Lys Leu Gly Ile Val Lys Glu Glu Asn
                485                 490                 495

Val Leu Phe Trp Ala Asp Leu Pro Asn Cys Glu Thr Gly Val Cys Ile
                500                 505                 510

Ala Val
```

<210> SEQ ID NO 22
<211> LENGTH: 156
<212> TYPE: PRT
<213> ORGANISM: Escherichia coli

<400> SEQUENCE: 22

```
Met Lys Thr Gln Arg Gly Tyr Thr Leu Ile Glu Thr Leu Val Ala Met
1               5                   10                  15

Leu Ile Leu Val Met Leu Ser Ala Ser Gly Leu Tyr Gly Trp Gln Tyr
            20                  25                  30

Trp Gln Gln Ser Gln Arg Leu Trp Gln Thr Ala Ser Gln Ala Arg Asp
        35                  40                  45

Tyr Leu Leu Tyr Leu Arg Glu Asp Ala Asn Trp His Asn Arg Asp His
    50                  55                  60

Ser Ile Ser Val Ile Arg Glu Gly Thr Leu Trp Cys Leu Val Ser Ser
65                  70                  75                  80

Ala Ala Gly Ala Asn Thr Cys His Gly Ser Ser Pro Leu Val Phe Val
                85                  90                  95

Pro Arg Trp Pro Glu Val Glu Met Ser Asp Leu Thr Pro Ser Leu Ala
            100                 105                 110

Phe Phe Gly Leu Arg Asn Thr Ala Trp Ala Gly His Ile Arg Phe Lys
        115                 120                 125

Asn Ser Thr Gly Glu Trp Trp Leu Val Val Ser Pro Trp Gly Arg Leu
    130                 135                 140

Arg Leu Cys Gln Gln Gly Glu Thr Glu Gly Cys Leu
145                 150                 155
```

<210> SEQ ID NO 23
<211> LENGTH: 37
<212> TYPE: DNA
<213> ORGANISM: Escherichia coli

<400> SEQUENCE: 23
cagtcagtca ggcgccttcg ggaaggcgtc tcgaaga                    37

<210> SEQ ID NO 24
<211> LENGTH: 84
<212> TYPE: DNA
<213> ORGANISM: Escherichia coli

<400> SEQUENCE: 24
ggcgtcggct ctggcaggat gtttcgtaat tagatagcca ccggcgcttt aggaaaccta    60
ctatgaccat gattacggat tcac                                          84

<210> SEQ ID NO 25
<211> LENGTH: 84
<212> TYPE: DNA
<213> ORGANISM: Escherichia coli

<400> SEQUENCE: 25
ggcgtcggct ctggcaggat gtttcgtaat tagatagcca ccggcgcttt attaaaccta    60
ctatgaccat gattacggat tcac                                          84

<210> SEQ ID NO 26
<211> LENGTH: 84
<212> TYPE: DNA
<213> ORGANISM: Escherichia coli

<400> SEQUENCE: 26

<210> SEQ ID NO 27
<211> LENGTH: 84
<212> TYPE: DNA
<213> ORGANISM: Escherichia coli

<400> SEQUENCE: 27
ggcgtcggct ctggcaggat gtttcgtaat tagatagcca ccggcgcttt aggaaaccta    60
ctatgaccat gattacggat tcac                                          84

<210> SEQ ID NO 28
<211> LENGTH: 68
<212> TYPE: DNA
<213> ORGANISM: Escherichia coli

<400> SEQUENCE: 28
cggctctggc aggatgtttc gtaattagat agccaccggc gctttattaa acctactatg    60
accatgat                                                            68

<210> SEQ ID NO 29
<211> LENGTH: 1024
<212> TYPE: PRT
<213> ORGANISM: Escherichia coli

<400> SEQUENCE: 29

Met Thr Met Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asp Arg Pro
        35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Trp Leu Glu Cys Asp Leu Pro
65                  70                  75                  80

Glu Ala Asp Thr Val Val Val Pro Ser Asn Trp Gln Met His Gly Tyr
                85                  90                  95

Asp Ala Pro Ile Tyr Thr Asn Val Thr Tyr Pro Ile Thr Val Asn Pro
            100                 105                 110

Pro Phe Val Pro Thr Glu Asn Pro Thr Gly Cys Tyr Ser Leu Thr Phe
        115                 120                 125

Asn Val Asp Glu Ser Trp Leu Gln Glu Gly Gln Thr Arg Ile Ile Phe
    130                 135                 140

Asp Gly Val Asn Ser Ala Phe His Leu Trp Cys Asn Gly Arg Trp Val
145                 150                 155                 160

Gly Tyr Gly Gln Asp Ser Arg Leu Pro Ser Glu Phe Asp Leu Ser Ala
                165                 170                 175

Phe Leu Arg Ala Gly Glu Asn Arg Leu Ala Val Met Val Leu Arg Trp
            180                 185                 190

Ser Asp Gly Ser Tyr Leu Glu Asp Gln Asp Met Trp Arg Met Ser Gly
        195                 200                 205

Ile Phe Arg Asp Val Ser Leu Leu His Lys Pro Thr Thr Gln Ile Ser
    210                 215                 220

Asp Phe His Val Ala Thr Arg Phe Asn Asp Asp Phe Ser Arg Ala Val

-continued

```
            225                 230                 235                 240

Leu Glu Ala Glu Val Gln Met Cys Gly Glu Leu Arg Asp Tyr Leu Arg
                245                 250                 255

Val Thr Val Ser Leu Trp Gln Gly Glu Thr Gln Val Ala Ser Gly Thr
                260                 265                 270

Ala Pro Phe Gly Gly Glu Ile Ile Asp Glu Arg Gly Tyr Ala Asp
            275                 280                 285

Arg Val Thr Leu Arg Leu Asn Val Glu Asn Pro Lys Leu Trp Ser Ala
            290                 295                 300

Glu Ile Pro Asn Leu Tyr Arg Ala Val Val Glu Leu His Thr Ala Asp
305                 310                 315                 320

Gly Thr Leu Ile Glu Ala Glu Ala Cys Asp Val Gly Phe Arg Glu Val
                325                 330                 335

Arg Ile Glu Asn Gly Leu Leu Leu Asn Gly Lys Pro Leu Leu Ile
            340                 345                 350

Arg Gly Val Asn Arg His Glu His His Pro Leu His Gly Gln Val Met
            355                 360                 365

Asp Glu Gln Thr Met Val Gln Asp Ile Leu Leu Met Lys Gln Asn Asn
370                 375                 380

Phe Asn Ala Val Arg Cys Ser His Tyr Pro Asn His Pro Leu Trp Tyr
385                 390                 395                 400

Thr Leu Cys Asp Arg Tyr Gly Leu Tyr Val Val Asp Glu Ala Asn Ile
                405                 410                 415

Glu Thr His Gly Met Val Pro Met Asn Arg Leu Thr Asp Asp Pro Arg
                420                 425                 430

Trp Leu Pro Ala Met Ser Glu Arg Val Thr Arg Met Val Gln Arg Asp
            435                 440                 445

Arg Asn His Pro Ser Val Ile Ile Trp Ser Leu Gly Asn Glu Ser Gly
450                 455                 460

His Gly Ala Asn His Asp Ala Leu Tyr Arg Trp Ile Lys Ser Val Asp
465                 470                 475                 480

Pro Ser Arg Pro Val Gln Tyr Glu Gly Gly Gly Ala Asp Thr Thr Ala
                485                 490                 495

Thr Asp Ile Ile Cys Pro Met Tyr Ala Arg Val Asp Glu Asp Gln Pro
            500                 505                 510

Phe Pro Ala Val Pro Lys Trp Ser Ile Lys Lys Trp Leu Ser Leu Pro
            515                 520                 525

Gly Glu Thr Arg Pro Leu Ile Leu Cys Glu Tyr Ala His Ala Met Gly
            530                 535                 540

Asn Ser Leu Gly Gly Phe Ala Lys Tyr Trp Gln Ala Phe Arg Gln Tyr
545                 550                 555                 560

Pro Arg Leu Gln Gly Gly Phe Val Trp Asp Trp Val Asp Gln Ser Leu
                565                 570                 575

Ile Lys Tyr Asp Glu Asn Gly Asn Pro Trp Ser Ala Tyr Gly Gly Asp
            580                 585                 590

Phe Gly Asp Thr Pro Asn Asp Arg Gln Phe Cys Met Asn Gly Leu Val
            595                 600                 605

Phe Ala Asp Arg Thr Pro His Pro Ala Leu Thr Glu Ala Lys His Gln
            610                 615                 620

Gln Gln Phe Phe Gln Phe Arg Leu Ser Gly Gln Thr Ile Glu Val Thr
625                 630                 635                 640

Ser Glu Tyr Leu Phe Arg His Ser Asp Asn Glu Leu Leu His Trp Met
                645                 650                 655
```

Val Ala Leu Asp Gly Lys Pro Leu Ala Ser Gly Glu Val Pro Leu Asp
            660                 665                 670

Val Ala Pro Gln Gly Lys Gln Leu Ile Glu Leu Pro Glu Leu Pro Gln
            675                 680                 685

Pro Glu Ser Ala Gly Gln Leu Trp Leu Thr Val Arg Val Val Gln Pro
        690                 695                 700

Asn Ala Thr Ala Trp Ser Glu Ala Gly His Ile Ser Ala Trp Gln Gln
705                 710                 715                 720

Trp Arg Leu Ala Glu Asn Leu Ser Val Thr Leu Pro Ala Ala Ser His
                725                 730                 735

Ala Ile Pro His Leu Thr Thr Ser Glu Met Asp Phe Cys Ile Glu Leu
            740                 745                 750

Gly Asn Lys Arg Trp Gln Phe Asn Arg Gln Ser Gly Phe Leu Ser Gln
            755                 760                 765

Met Trp Ile Gly Asp Lys Lys Gln Leu Leu Thr Pro Leu Arg Asp Gln
    770                 775                 780

Phe Thr Arg Ala Pro Leu Asp Asn Asp Ile Gly Val Ser Glu Ala Thr
785                 790                 795                 800

Arg Ile Asp Pro Asn Ala Trp Val Glu Arg Trp Lys Ala Ala Gly His
                805                 810                 815

Tyr Gln Ala Glu Ala Ala Leu Leu Gln Cys Thr Ala Asp Thr Leu Ala
            820                 825                 830

Asp Ala Val Leu Ile Thr Thr Ala His Ala Trp Gln His Gln Gly Lys
        835                 840                 845

Thr Leu Phe Ile Ser Arg Lys Thr Tyr Arg Ile Asp Gly Ser Gly Gln
    850                 855                 860

Met Ala Ile Thr Val Asp Val Glu Val Ala Ser Asp Thr Pro His Pro
865                 870                 875                 880

Ala Arg Ile Gly Leu Asn Cys Gln Leu Ala Gln Val Ala Glu Arg Val
                885                 890                 895

Asn Trp Leu Gly Leu Gly Pro Gln Glu Asn Tyr Pro Asp Arg Leu Thr
            900                 905                 910

Ala Ala Cys Phe Asp Arg Trp Asp Leu Pro Leu Ser Asp Met Tyr Thr
        915                 920                 925

Pro Tyr Val Phe Pro Ser Glu Asn Gly Leu Arg Cys Gly Thr Arg Glu
    930                 935                 940

Leu Asn Tyr Gly Pro His Gln Trp Arg Gly Asp Phe Gln Phe Asn Ile
945                 950                 955                 960

Ser Arg Tyr Ser Gln Gln Leu Met Glu Thr Ser His Arg His Leu
                965                 970                 975

Leu His Ala Glu Glu Gly Thr Trp Leu Asn Ile Asp Gly Phe His Met
            980                 985                 990

Gly Ile Gly Gly Asp Asp Ser Trp  Ser Pro Ser Val Ser  Ala Glu Phe
        995                 1000                1005

Gln Leu Ser Ala Gly Arg Tyr  His Tyr Gln Leu Val  Trp Cys Gln
    1010                1015                1020

Lys

<210> SEQ ID NO 30
<211> LENGTH: 264
<212> TYPE: PRT
<213> ORGANISM: Escherichia coli

<400> SEQUENCE: 30

```
Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

<210> SEQ ID NO 31
<211> LENGTH: 70
<212> TYPE: DNA
<213> ORGANISM: Escherichia coli

<400> SEQUENCE: 31
tctgggcata tcgtcgcagc ccacagcaac acgtttcctg aggaaccatg attccgggga   60
tccgtcgacc                                                         70

<210> SEQ ID NO 32
<211> LENGTH: 291
<212> TYPE: PRT
<213> ORGANISM: Escherichia coli

<400> SEQUENCE: 32

Met Thr Ser Ser Tyr Leu His Phe Pro Glu Phe Asp Pro Val Ile Phe
1               5                   10                  15

Ser Ile Gly Pro Val Ala Leu His Trp Tyr Gly Leu Met Tyr Leu Val
            20                  25                  30

Gly Phe Ile Phe Ala Met Trp Leu Ala Thr Arg Arg Ala Asn Arg Pro
```

```
                35                  40                  45
Gly Ser Gly Trp Thr Lys Asn Glu Val Glu Asn Leu Leu Tyr Ala Gly
 50                  55                  60

Phe Leu Gly Val Phe Leu Gly Arg Ile Gly Tyr Val Leu Phe Tyr
 65                  70                  75                  80

Asn Phe Pro Gln Phe Met Ala Asp Pro Leu Tyr Leu Phe Arg Val Trp
                 85                  90                  95

Asp Gly Gly Met Ser Phe His Gly Gly Leu Ile Gly Val Ile Val Val
                100                 105                 110

Met Ile Ile Phe Ala Arg Arg Thr Lys Arg Ser Phe Phe Gln Val Ser
                115                 120                 125

Asp Phe Ile Ala Pro Leu Ile Pro Phe Gly Leu Gly Ala Gly Arg Leu
130                 135                 140

Gly Asn Phe Ile Asn Gly Glu Leu Trp Gly Arg Val Asp Pro Asn Phe
145                 150                 155                 160

Pro Phe Ala Met Leu Phe Pro Gly Ser Arg Thr Glu Asp Ile Leu Leu
                165                 170                 175

Leu Gln Thr Asn Pro Gln Trp Gln Ser Ile Phe Asp Thr Tyr Gly Val
                180                 185                 190

Leu Pro Arg His Pro Ser Gln Leu Tyr Glu Leu Leu Glu Gly Val
            195                 200                 205

Val Leu Phe Ile Ile Leu Asn Leu Tyr Ile Arg Lys Pro Arg Pro Met
210                 215                 220

Gly Ala Val Ser Gly Leu Phe Leu Ile Gly Tyr Gly Ala Phe Arg Ile
225                 230                 235                 240

Ile Val Glu Phe Phe Arg Gln Pro Asp Ala Gln Phe Thr Gly Ala Trp
                245                 250                 255

Val Gln Tyr Ile Ser Met Gly Gln Ile Leu Ser Ile Pro Met Ile Val
            260                 265                 270

Ala Gly Val Ile Met Met Val Trp Ala Tyr Arg Arg Ser Pro Gln Gln
            275                 280                 285

His Val Ser
   290

<210> SEQ ID NO 33
<211> LENGTH: 40
<212> TYPE: DNA
<213> ORGANISM: Escherichia coli

<400> SEQUENCE: 33
cagtcagtca ggcgcctcct caacctgtat attcgtaaac                              40

<210> SEQ ID NO 34
<211> LENGTH: 5877
<212> TYPE: DNA
<213> ORGANISM: Escherichia coli

<400> SEQUENCE: 34
gcagcggaac tcacaaggca ccataacgtc ccctccctga taacgctgat actgtggtcg       60
cggttatgcc agttggcatc ttcacgtaaa tagagcaaat agtcccgcgc ctggctggcg      120
gtttgccata gccgttgcga ctgctgccag tattgccagc catagagtcc acttgcgctt      180
agcatgacca aaatcagcat cgcgaccagc gtttcaatca gcgtataacc acgttgtgtt      240
ttcatgccgg cagtatggag cgaggagaaa aaagacgag ggccagtttc tatttcttcg      300
gcgcatcttc cggactattt acgccgttgc aggacgttgc aaaatttcgg gaaggcgtct      360
```

```
cgaagaattt aacggagggt aaaaaaaccg acgcacactg gcgtcggctc tggcaggatg    420
tttcgtaatt agatagccac cggcgcttta ttaaacctac tatgaccatg attacggatt    480
cactggccgt cgttttacaa cgtcgtgact gggaaaaccc tggcgttacc caacttaatc    540
gccttgcagc acatcccct ttcgccagct ggcgtaatag cgaagaggcc cgcaccgatc     600
gcccttccca acagttgcgc agcctgaatg gcgaatggcg ctttgcctgg tttccggcac    660
cagaagcggt gccggaaagc tggctggagt gcgatcttcc tgaggccgat actgtcgtcg    720 tccccctcaaa ctggcagatg cacggttacg atgcgcccat ctacaccaac gtgacctatc    780
ccattacggt caatccgccg tttgttccca cggagaatcc gacgggttgt tactcgctca    840
catttaatgt tgatgaaagc tggctacagg aaggccagac gcgaattatt tttgatggcg    900
ttaactcggc gtttcatctg tggtgcaacg ggcgctgggt cggttacggc caggacagtc    960
gtttgccgtc tgaatttgac ctgagcgcat ttttacgcgc cggagaaaac cgcctcgcgg    1020
tgatggtgct gcgctggagt gacggcagtt atctggaaga tcaggatatg tggcggatga    1080
gcggcatttt ccgtgacgtc tcgttgctgc ataaaccgac tacacaaatc agcgatttcc    1140
atgttgccac tcgctttaat gatgatttca gccgcgctgt actggaggct gaagttcaga    1200
tgtgcggcga gttgcgtgac tacctacggg taacagtttc tttatggcag ggtgaaacgc    1260
aggtcgccag cggcaccgcg cctttcggcg gtgaaattat cgatgagcgt ggtggttatg    1320
ccgatcgcgt cacactacgt ctgaacgtcg aaaacccgaa actgtggagc gccgaaatcc    1380
cgaatctcta tcgtgcggtg gttgaactgc acaccgccga cggcacgctg attgaagcag    1440
aagcctgcga tgtcggtttc gcgcgaggtgc ggattgaaaa tggtctgctg ctgctgaacg    1500
gcaagccgtt gctgattcga ggcgttaacc gtcacgagca tcatcctctg catggtcagg    1560
tcatggatga gcagacgatg gtgcaggata tcctgctgat gaagcagaac aactttaacg    1620
ccgtgcgctg ttcgcattat ccgaaccatc cgctgtggta cacgctgtgc gaccgctacg    1680
gcctgtatgt ggtggatgaa gccaatattg aaacccacgg catggtgcca atgaatcgtc    1740
tgaccgatga tccgcgctgg ctaccggcga tgagcgaacg cgtaacgcga atggtgcagc    1800
gcgatcgtaa tcacccgagt gtgatcatct ggtcgctggg gaatgaatca ggccacggcg    1860
ctaatcacga cgcgctgtat cgctggatca aatctgtcga tccttcccgc ccggtgcagt    1920
atgaaggcgg cggagccgac accacggcca ccgatattat ttgcccgatg tacgcgcgcg    1980
tggatgaaga ccagccttc ccggctgtgc cgaaatggtc catcaaaaaa tggctttcgc     2040
tacctggaga gacgcgcccg ctgatccttt gcgaatacgc ccacgcgatg ggtaacagtc    2100
ttggcggttt cgctaaatac tggcaggcgt ttcgtcagta tccccgttta cagggcggct    2160
tcgtctggga ctgggtggat cagtcgctga ttaaatatga tgaaaacggc aacccgtggt    2220
cggcttacgg cggtgatttt ggcgatacgc cgaacgatcg ccagttctgt atgaacggtc    2280
tggtctttgc cgaccgcacg ccgcatccag cgctgacgga agcaaaacac cagcagcagt    2340
ttttccagtt ccgtttatcc gggcaaaacca tcgaagtgac cagcgaatac ctgttccgtc    2400
atagcgataa cgagctcctg cactggatgg tggcgctgga tggtaagccg ctggcaagcg    2460
gtgaagtgcc tctggatgtc gctccacaag gtaaacagtt gattgaactg cctgaactac    2520
cgcagccgga gagcgccggg caactctggc tcacagtacg cgtagtgcaa ccgaacgcga    2580
ccgcatggtc agaagccggg cacatcagcg cctggcagca gtggcgtctg gcggaaaacc    2640
tcagtgtgac gctccccgcc gcgtcccacg ccatcccgca tctgaccacc agcgaaatgg    2700
```

```
attttttgcat cgagctgggt aataagcgtt ggcaatttaa ccgccagtca ggctttcttt    2760
cacagatgtg gattggcgat aaaaaacaac tgttgacgcc gctgcgcgat cagttcaccc    2820
gtgcaccgct ggataacgac attggcgtaa gtgaagcgac ccgcattgac cctaacgcct    2880
gggtcgaacg ctggaaggcg gcgggccatt accaggccga agcagcgttg ttgcagtgca    2940
cggcagatac acttgctgat gcggtgctga ttacgaccgc tcacgcgtgg cagcatcagg    3000
ggaaaacctt atttatcagc cggaaaacct accggattga tggtagtggt caaatgcgga    3060
ttaccgttga tgttgaagtg gcgagcgata caccgcatcc ggcgcggatt ggcctgaact    3120
gccagctggc gcaggtagca gagcgggtaa actggctcgg attagggccg caagaaaact    3180
atcccgaccg ccttactgcc gcctgttttg accgctggga tctgccattg tcagacatgt    3240
ataccccgta cgtcttcccg agcgaaaacg gtctgcgctg cgggacgcgc gaattgaatt    3300
atggcccaca ccagtggcgc ggcgacttcc agttcaacat cagccgctac agtcaacagc    3360
aactgatgga aaccagccat cgccatctgc tgcacgcgga agaaggcaca tggctgaata    3420
tcgacggttt ccatatgggg attggtggcg acgactcctg gagcccgtca gtatcggcgg    3480
aattccagct gagcgccggt cgctaccatt accagttggt ctggtgtcaa aaataagcgg    3540
ccgctttatg taggctggag ctgcttcgaa gttcctatac tttctagaga ataggaactt    3600
cggaatagga acttcaagat ccccttatta gaagaactcg tcaagaaggc gatagaaggc    3660
gatgcgctgc gaatcgggag cggcgatacc gtaaagcacg aggaagcggt cagcccattc    3720
gccgccaagc tcttcagcaa tatcacgggt agccaacgct atgtcctgat agcggtccgc    3780
cacacccagc cggccacagt cgatgaatcc tgaaaagcgg ccattttcca ccatgatatt    3840
cggcaagcag gcatcgccat gggtcacgac gagatcctcg ccgtcgggca tgcgcgcctt    3900
gagcctggcg aacagttcgg ctggcgcgag cccctgatgc tcttcgtcca gatcatcctg    3960
atcgacaaga ccggcttcca tccgagtacg tgctcgctcg atgcgatgtt tcgcttggtg    4020
gtcgaatggg caggtagccg gatcaagcgt atgcagccgc cgcattgcat cagccatgat    4080
ggatactttc tcggcaggag caaggtgaga tgacaggaga tcctgccccg gcacttcgcc    4140
caatagcagc cagtcccttc ccgcttcagt gacaacgtcg agcacagctg cgcaaggaac    4200
gcccgtcgtg gccagccacg atagccgcgc tgcctcgtcc tgcagttcat tcagggcacc    4260
ggacaggtcg gtcttgacaa aaagaaccgg gcgcccctgc gctgacagcc ggaacacggc    4320
ggcatcagag cagccgattg tctgttgtgc ccagtcatag ccgaatagcc tctccaccca    4380
agcggccgga gaacctgcgt gcaatccatc ttgttcaatc atgcgaaacg atcctcatcc    4440
tgtctcttga tcagatcttg atcccctgcg ccatcagatc cttggcggca agaaagccat    4500
ccagtttact ttgcagggct tcccaacctt accagagggc gccccagctg gcaattccgg    4560
ttcgcttgct gtccataaaa ccgcccagtc tagctatcgc catgtaagcc cactgcaagc    4620
tacctgcttt ctctttgcgc ttgcgttttc ccttgtccag atagcccagt agctgacatt    4680
catccggggt cagcaccgtt tctgcggact ggctttctac gtgttccgct tcctttagca    4740
gcccttgcgc cctgagtgct tgcggcagcg tgagcttcaa aagcgctctg aagttcctat    4800
actttctaga gaataggaac ttcgaactgc aggtcgacgg atccccggaa tcatggttcc    4860
tcaggaaacg tgttgctgtg ggctgcgacg atatgcccag accatcatga tcacacccgc    4920
gacaatcatc gggatggaaa gaatttgccc catgctgatg tactgcaccc aggcaccggt    4980
aaactgcgcg tcgggctggc ggaaaaactc aacaatgatg cgaaacgcgc cgtaaccaat    5040
caggaacaaa cctgagacag ctcccattgg gcgtggttta cgaatataca ggttgaggat    5100
```

-continued

```
aataaacagc accacacctt ccagcagcag ctcgtaaagc tgtgatgggt ggcgcggcag    5160
cacaccgtaa gtgtcgaaaa tggattgcca ctgcgggttg gtttgcagca gcaaaatatc    5220
ttctgtacgg gagccaggga acagcatggc aaacgggaag ttcgggtcaa cgcggcccca    5280
caattcaccg ttaataaagt tgcccagacg cccggcacca agaccaaacg gaatgagtgg    5340
tgcgataaaa tcagagacct ggaagaagga acgtttagta cggcgggcga agataatcat    5400
caccacgata acgccaatca ggccgccgtg aaagacatg ccgccgtccc agacacggaa     5460
cagatacagc ggatcggcca taaactgcgg gaaattgtag aacagaacat aaccaatacg    5520
tcccccgagg aagacgccga ggaagcccgc atagagtaag ttttcaactt cattttggt     5580 ccagccgctg cccggacgat tcgcccgtcg tgttgccagc acattgcaa aaatgaaacc     5640 caccagatac atcaggccgt accagtgaag cgccacgggt cctattgaga aaatgaccgg    5700
atcaaactcc ggaaaatgca gatagctact ggtcatctgt caccacaagt tcttgttatt    5760
tcgctgaaag agaacagcga ttgaaatgcg cgccgcaggt ttcaggcgct ccaaaggtgc    5820
gaataatagc acaaggggac ctggctggtt gccggatacc gttaaaagat atgtata       5877
```

<210> SEQ ID NO 35
<211> LENGTH: 455
<212> TYPE: PRT
<213> ORGANISM: Escherichia coli

<400> SEQUENCE: 35

```
Met Phe Gly Ile Ile Ile Ser Val Ile Val Leu Ile Thr Met Gly Tyr
1               5                   10                  15

Leu Ile Leu Lys Asn Tyr Lys Pro Gln Val Val Leu Ala Ala Ala Gly
                20                  25                  30

Ile Phe Leu Met Met Cys Gly Val Trp Leu Gly Phe Gly Gly Val Leu
            35                  40                  45

Asp Pro Thr Lys Ser Ser Gly Tyr Leu Ile Val Asp Ile Tyr Asn Glu
        50                  55                  60

Ile Leu Arg Met Leu Ser Asn Arg Ile Ala Gly Leu Gly Leu Ser Ile
65                  70                  75                  80

Met Ala Val Gly Gly Tyr Ala Arg Tyr Met Glu Arg Ile Gly Ala Ser
                85                  90                  95

Arg Ala Met Val Ser Leu Leu Ser Arg Pro Leu Lys Leu Ile Arg Ser
            100                 105                 110

Pro Tyr Ile Ile Leu Ser Ala Thr Tyr Val Ile Gly Gln Ile Met Ala
        115                 120                 125

Gln Phe Ile Thr Ser Ala Ser Gly Leu Gly Met Leu Leu Met Val Thr
    130                 135                 140

Leu Phe Pro Thr Leu Val Ser Leu Gly Val Ser Arg Leu Ser Ala Val
145                 150                 155                 160

Ala Val Ile Ala Thr Thr Met Ser Ile Glu Trp Gly Ile Leu Glu Thr
                165                 170                 175

Asn Ser Ile Phe Ala Ala Gln Val Ala Gly Met Lys Ile Ala Thr Tyr
            180                 185                 190

Phe Phe His Tyr Gln Leu Pro Val Ala Ser Cys Val Ile Ile Ser Val
        195                 200                 205

Ala Ile Ser His Phe Val Gln Arg Ala Phe Asp Lys Lys Asp Lys
    210                 215                 220

Asn Ile Asn His Glu Gln Ala Glu Gln Lys Ala Leu Asp Asn Val Pro
225                 230                 235                 240
```

-continued

```
Pro Leu Tyr Tyr Ala Ile Leu Pro Val Met Pro Ile Leu Met Leu
                245                 250                 255

Gly Ser Leu Phe Leu Ala His Val Gly Leu Met Gln Ser Glu Leu His
            260                 265                 270

Leu Val Val Val Met Leu Leu Ser Leu Thr Val Thr Met Phe Val Glu
        275                 280                 285

Phe Phe Arg Lys His Asn Leu Arg Glu Thr Met Asp Asp Val Gln Ala
290                 295                 300

Phe Phe Asp Gly Met Gly Thr Gln Phe Ala Asn Val Val Thr Leu Val
305                 310                 315                 320

Val Ala Gly Glu Ile Phe Ala Lys Gly Leu Thr Thr Ile Gly Thr Val
                325                 330                 335

Asp Ala Val Ile Arg Gly Ala Glu His Ser Gly Leu Gly Gly Ile Gly
                340                 345                 350

Val Met Ile Ile Met Ala Leu Val Ile Ala Ile Cys Ala Ile Val Met
            355                 360                 365

Gly Ser Gly Asn Ala Pro Phe Met Ser Phe Ala Ser Leu Ile Pro Asn
        370                 375                 380

Ile Ala Ala Gly Leu His Val Pro Ala Val Val Met Ile Met Pro Met
385                 390                 395                 400

His Phe Ala Thr Thr Leu Ala Arg Ala Val Ser Pro Ile Thr Ala Val
                405                 410                 415

Val Val Val Thr Ser Gly Ile Ala Gly Val Ser Pro Phe Ala Val Val
                420                 425                 430

Lys Arg Thr Ala Ile Pro Met Ala Val Gly Phe Val Val Asn Met Ile
                435                 440                 445

Ala Thr Ile Thr Leu Phe Tyr
                450                 455

<210> SEQ ID NO 36
<211> LENGTH: 263
<212> TYPE: PRT
<213> ORGANISM: Escherichia coli

<400> SEQUENCE: 36

Met Gly Leu Met Asn Ala Phe Asp Ser Gln Thr Glu Asp Ser Ser Pro
1               5                   10                  15

Ala Ile Gly Arg Asn Leu Arg Ser Arg Pro Leu Ala Arg Lys Lys Leu
            20                  25                  30

Ser Glu Met Val Glu Glu Glu Leu Gln Met Ile Arg Arg Arg Glu
        35                  40                  45

Phe Gly Glu Gly Glu Gln Leu Pro Ser Glu Arg Glu Leu Met Ala Phe
    50                  55                  60

Phe Asn Val Gly Arg Pro Ser Val Arg Glu Ala Leu Ala Ala Leu Lys
65                  70                  75                  80

Arg Lys Gly Leu Val Gln Ile Asn Asn Gly Glu Arg Ala Arg Val Ser
                85                  90                  95

Arg Pro Ser Ala Asp Thr Ile Ile Gly Glu Leu Ser Gly Met Ala Lys
            100                 105                 110

Asp Phe Leu Ser His Pro Gly Gly Ile Ala His Phe Glu Gln Leu Arg
        115                 120                 125

Leu Phe Phe Glu Ser Ser Leu Val Arg Tyr Ala Ala Glu His Ala Thr
    130                 135                 140

Asp Glu Gln Ile Asp Leu Leu Ala Lys Ala Leu Glu Ile Asn Ser Gln
```

```
               145                 150                 155                 160
       Ser Leu Asp Asn Asn Ala Ala Phe Ile Arg Ser Asp Val Asp Phe His
                       165                 170                 175

Arg Val Leu Ala Glu Ile Pro Gly Asn Pro Ile Phe Met Ala Ile His
                       180                 185                 190

Val Ala Leu Leu Asp Trp Leu Ile Ala Ala Arg Pro Thr Val Thr Asp
                       195                 200                 205

Gln Ala Leu His Glu His Asn Asn Val Ser Tyr Gln Gln His Ile Ala
                       210                 215                 220

Ile Val Asp Ala Ile Arg Arg His Asp Pro Asp Glu Ala Asp Arg Ala
       225                 230                 235                 240

Leu Gln Ser His Leu Asn Ser Val Ser Ala Thr Trp His Ala Phe Gly
                       245                 250                 255

Gln Thr Thr Asn Lys Lys Lys
                       260

<210> SEQ ID NO 37
<211> LENGTH: 297
<212> TYPE: PRT
<213> ORGANISM: Escherichia coli

<400> SEQUENCE: 37

Met Ala Thr Asn Leu Arg Gly Val Met Ala Ala Leu Leu Thr Pro Phe
       1               5                   10                  15

Asp Gln Gln Gln Ala Leu Asp Lys Ala Ser Leu Arg Arg Leu Val Gln
                       20                  25                  30

Phe Asn Ile Gln Gln Gly Ile Asp Gly Leu Tyr Val Gly Gly Ser Thr
                       35                  40                  45

Gly Glu Ala Phe Val Gln Ser Leu Ser Glu Arg Glu Gln Val Leu Glu
               50                  55                  60

Ile Val Ala Glu Glu Ala Lys Gly Lys Ile Lys Leu Ile Ala His Val
       65                  70                  75                  80

Gly Cys Val Ser Thr Ala Glu Ser Gln Gln Leu Ala Ala Ser Ala Lys
                       85                  90                  95

Arg Tyr Gly Phe Asp Ala Val Ser Ala Val Thr Pro Tyr Tyr Tyr Pro
                       100                 105                 110

Phe Ser Phe Glu Glu His Cys Asp His Tyr Arg Ala Ile Ile Asp Ser
                       115                 120                 125

Ala Asp Gly Leu Pro Met Val Val Tyr Asn Ile Pro Ala Leu Ser Gly
               130                 135                 140

Val Lys Leu Thr Leu Asp Gln Ile Asn Thr Leu Val Thr Leu Pro Gly
       145                 150                 155                 160

Val Gly Ala Leu Lys Gln Thr Ser Gly Asp Leu Tyr Gln Met Glu Gln
                       165                 170                 175

Ile Arg Arg Glu His Pro Asp Leu Val Leu Tyr Asn Gly Tyr Asp Glu
                       180                 185                 190

Ile Phe Ala Ser Gly Leu Leu Ala Gly Ala Asp Gly Gly Ile Gly Ser
                       195                 200                 205

Thr Tyr Asn Ile Met Gly Trp Arg Tyr Gln Gly Ile Val Lys Ala Leu
               210                 215                 220

Lys Glu Gly Asp Ile Gln Thr Ala Gln Lys Leu Gln Thr Glu Cys Asn
       225                 230                 235                 240

Lys Val Ile Asp Leu Leu Ile Lys Thr Gly Val Phe Arg Gly Leu Lys
                       245                 250                 255
```

Thr Val Leu His Tyr Met Asp Val Val Ser Val Pro Leu Cys Arg Lys
            260                 265                 270

Pro Phe Gly Pro Val Asp Glu Lys Tyr Leu Pro Glu Leu Lys Ala Leu
        275                 280                 285

Ala Gln Gln Leu Met Gln Glu Arg Gly
    290                 295

<210> SEQ ID NO 38
<211> LENGTH: 496
<212> TYPE: PRT
<213> ORGANISM: Escherichia coli

<400> SEQUENCE: 38

Met Ser Thr Thr Thr Gln Asn Ile Pro Trp Tyr Arg His Leu Asn Arg
1               5                   10                  15

Ala Gln Trp Arg Ala Phe Ser Ala Ala Trp Leu Gly Tyr Leu Leu Asp
            20                  25                  30

Gly Phe Asp Phe Val Leu Ile Ala Leu Val Leu Thr Glu Val Gln Gly
        35                  40                  45

Glu Phe Gly Leu Thr Thr Val Gln Ala Ala Ser Leu Ile Ser Ala Ala
    50                  55                  60

Phe Ile Ser Arg Trp Phe Gly Gly Leu Met Leu Gly Ala Met Gly Asp
65                  70                  75                  80

Arg Tyr Gly Arg Arg Leu Ala Met Val Thr Ser Ile Val Leu Phe Ser
                85                  90                  95

Ala Gly Thr Leu Ala Cys Gly Phe Ala Pro Gly Tyr Ile Thr Met Phe
            100                 105                 110

Ile Ala Arg Leu Val Ile Gly Met Gly Met Ala Gly Glu Tyr Gly Ser
        115                 120                 125

Ser Ala Thr Tyr Val Ile Glu Ser Trp Pro Lys His Leu Arg Asn Lys
    130                 135                 140

Ala Ser Gly Phe Leu Ile Ser Gly Phe Ser Val Gly Ala Val Val Ala
145                 150                 155                 160

Ala Gln Val Tyr Ser Leu Val Val Pro Val Trp Gly Trp Arg Ala Leu
                165                 170                 175

Phe Phe Ile Gly Ile Leu Pro Ile Ile Phe Ala Leu Trp Leu Arg Lys
            180                 185                 190

Asn Ile Pro Glu Ala Glu Asp Trp Lys Glu Lys His Ala Gly Lys Ala
        195                 200                 205

Pro Val Arg Thr Met Val Asp Ile Leu Tyr Arg Gly Glu His Arg Ile
    210                 215                 220

Ala Asn Ile Val Met Thr Leu Ala Ala Ala Thr Ala Leu Trp Phe Cys
225                 230                 235                 240

Phe Ala Gly Asn Leu Gln Asn Ala Ala Ile Val Ala Val Leu Gly Leu
                245                 250                 255

Leu Cys Ala Ala Ile Phe Ile Ser Phe Met Val Gln Ser Ala Gly Lys
            260                 265                 270

Arg Trp Pro Thr Gly Val Met Leu Met Val Val Leu Phe Ala Phe
        275                 280                 285                Phe

Leu Tyr Ser Trp Pro Ile Gln Ala Leu Leu Pro Thr Tyr Leu Lys Thr
    290                 295                 300

Asp Leu Ala Tyr Asn Pro His Thr Val Ala Asn Val Leu Phe Phe Ser
305                 310                 315                 320

Gly Phe Gly Ala Ala Val Gly Cys Cys Val Gly Gly Phe Leu Gly Asp
                325                 330                 335

```
Trp Leu Gly Thr Arg Lys Ala Tyr Val Cys Ser Leu Ala Ser Gln
                340                 345                 350

Leu Leu Ile Ile Pro Val Phe Ala Ile Gly Gly Ala Asn Val Trp Val
            355                 360                 365

Leu Gly Leu Leu Leu Phe Phe Gln Gln Met Leu Gly Gln Gly Ile Ala
370                 375                 380

Gly Ile Leu Pro Lys Leu Ile Gly Gly Tyr Phe Asp Thr Asp Gln Arg
385                 390                 395                 400

Ala Ala Gly Leu Gly Phe Thr Tyr Asn Val Gly Ala Leu Gly Gly Ala
                405                 410                 415

Leu Ala Pro Ile Ile Gly Ala Leu Ile Ala Gln Arg Leu Asp Leu Gly
            420                 425                 430

Thr Ala Leu Ala Ser Leu Ser Phe Ser Leu Thr Phe Val Val Ile Leu
        435                 440                 445

Leu Ile Gly Leu Asp Met Pro Ser Arg Val Gln Arg Trp Leu Arg Pro
450                 455                 460

Glu Ala Leu Arg Thr His Asp Ala Ile Asp Gly Lys Pro Phe Ser Gly
465                 470                 475                 480

Ala Val Pro Phe Gly Ser Ala Lys Asn Asp Leu Val Lys Thr Lys Ser
                485                 490                 495

<210> SEQ ID NO 39
<211> LENGTH: 229
<212> TYPE: PRT
<213> ORGANISM: Escherichia coli

<400> SEQUENCE: 39

Met Ser Leu Leu Ala Gln Leu Asp Gln Lys Ile Ala Ala Asn Gly Gly
1               5                   10                  15

Leu Ile Val Ser Cys Gln Pro Val Pro Asp Ser Pro Leu Asp Lys Pro
            20                  25                  30

Glu Ile Val Ala Ala Met Ala Leu Ala Ala Glu Gln Ala Gly Ala Val
        35                  40                  45

Ala Ile Arg Ile Glu Gly Val Ala Asn Leu Gln Ala Thr Arg Ala Val
    50                  55                  60

Val Ser Val Pro Ile Ile Gly Ile Val Lys Arg Asp Leu Glu Asp Ser
65                  70                  75                  80

Pro Val Arg Ile Thr Ala Tyr Ile Glu Asp Val Asp Ala Leu Ala Gln
                85                  90                  95

Ala Gly Ala Asp Ile Ile Ala Ile Asp Gly Thr Asp Arg Pro Arg Pro
            100                 105                 110

Val Pro Val Glu Thr Leu Leu Ala Arg Ile His His Gly Leu Leu
        115                 120                 125

Ala Met Thr Asp Cys Ser Thr Pro Glu Asp Gly Leu Ala Cys Gln Lys
    130                 135                 140

Leu Gly Ala Glu Ile Ile Gly Thr Thr Leu Ser Gly Tyr Thr Thr Pro
145                 150                 155                 160

Glu Thr Pro Glu Glu Pro Asp Leu Ala Leu Val Lys Thr Leu Ser Asp
                165                 170                 175

Ala Gly Cys Arg Val Ile Ala Glu Gly Arg Tyr Asn Thr Pro Ala Gln
            180                 185                 190

Ala Ala Asp Ala Met Arg His Gly Ala Trp Ala Val Thr Val Gly Ser
        195                 200                 205

Ala Ile Thr Arg Leu Glu His Ile Cys Gln Trp Tyr Asn Thr Ala Met
```

Lys Lys Ala Val Leu
225

<210> SEQ ID NO 40
<211> LENGTH: 291
<212> TYPE: PRT
<213> ORGANISM: Escherichia coli

<400> SEQUENCE: 40

Met Thr Thr Leu Ala Ile Asp Ile Gly Gly Thr Lys Leu Ala Ala
1               5                   10                  15

Leu Ile Gly Ala Asp Gly Gln Ile Arg Asp Arg Arg Glu Leu Pro Thr
            20                  25                  30

Pro Ala Ser Gln Thr Pro Glu Ala Leu Arg Asp Ala Leu Ser Ala Leu
        35                  40                  45

Val Ser Pro Leu Gln Ala His Ala Gln Arg Val Ala Ile Ala Ser Thr
    50                  55                  60

Gly Ile Ile Arg Asp Gly Ser Leu Leu Ala Leu Asn Pro His Asn Leu
65                  70                  75                  80

Gly Gly Leu Leu His Phe Pro Leu Val Lys Thr Leu Glu Gln Leu Thr
                85                  90                  95

Asn Leu Pro Thr Ile Ala Ile Asn Asp Ala Gln Ala Ala Ala Trp Ala
            100                 105                 110

Glu Phe Gln Ala Leu Asp Gly Asp Ile Thr Asp Met Val Phe Ile Thr
        115                 120                 125

Val Ser Thr Gly Val Gly Gly Val Val Ser Gly Cys Lys Leu Leu
    130                 135                 140

Thr Gly Pro Gly Gly Leu Ala Gly His Ile Gly His Thr Leu Ala Asp
145                 150                 155                 160

Pro His Gly Pro Val Cys Gly Cys Gly Arg Thr Gly Cys Val Glu Ala
                165                 170                 175

Ile Ala Ser Gly Arg Gly Ile Ala Ala Ala Gln Gly Glu Leu Ala
            180                 185                 190

Gly Ala Asp Ala Lys Thr Ile Phe Thr Arg Ala Gly Gln Gly Asp Glu
        195                 200                 205

Gln Ala Gln Gln Leu Ile His Arg Ser Ala Arg Thr Leu Ala Arg Leu
    210                 215                 220

Ile Ala Asp Ile Lys Ala Thr Thr Asp Cys Gln Cys Val Val Val Gly
225                 230                 235                 240

Gly Ser Val Gly Leu Ala Glu Gly Tyr Leu Ala Leu Val Glu Thr Tyr
                245                 250                 255

Leu Ala Gln Glu Pro Ala Ala Phe His Val Asp Leu Leu Ala Ala His
            260                 265                 270

Tyr Arg His Asp Ala Gly Leu Leu Gly Ala Ala Leu Leu Ala Gln Gly
        275                 280                 285

Glu Lys Leu
    290

<210> SEQ ID NO 41
<211> LENGTH: 154
<212> TYPE: PRT
<213> ORGANISM: Escherichia coli

<400> SEQUENCE: 41

Met Met Met Gly Glu Val Gln Ser Leu Pro Ser Ala Gly Leu His Pro

```
  1               5                  10                 15
Ala Leu Gln Asp Ala Leu Thr Leu Ala Leu Ala Ala Arg Pro Gln Glu
                 20                 25                 30
Lys Ala Pro Gly Arg Tyr Glu Leu Gln Gly Asp Asn Ile Phe Met Asn
                 35                 40                 45
Val Met Thr Phe Asn Thr Gln Ser Pro Val Glu Lys Lys Ala Glu Leu
 50                 55                 60
His Glu Gln Tyr Ile Asp Ile Gln Leu Leu Leu Asn Gly Glu Glu Arg
 65                 70                 75                 80
Ile Leu Phe Gly Met Ala Gly Thr Ala Arg Gln Cys Glu Glu Phe His
                 85                 90                 95
His Glu Asp Asp Tyr Gln Leu Cys Ser Thr Ile Asp Asn Glu Gln Ala
                 100                105                110
Ile Ile Leu Lys Pro Gly Met Phe Ala Val Phe Met Pro Gly Glu Pro
                 115                120                125
His Lys Pro Gly Cys Val Val Gly Glu Pro Gly Glu Ile Lys Lys Val
                 130                135                140
Val Val Lys Val Lys Ala Asp Leu Met Ala
145                 150
```

<210> SEQ ID NO 42
<211> LENGTH: 5861
<212> TYPE: DNA
<213> ORGANISM: Escherichia coli

<400> SEQUENCE: 42

```
gaacattgtt gaactccgtg tcaaaagaaa acggtcaatc ccataaacgg cagattgaaa    60
acaacgatgt tatatttttt gcaaggctat ttatggtgcg gatgtcgtgt ttttaattgt   120
aggtgaggtg attttcatt aaaaaatatg cgcttatgat tattttgtaa gaacacattc   180
ataatattca taatgctcgt gaatagtctt ataaataatt caaacgggat gtttttatct   240
gcgttacatt aattttcgc aatagttaat tattccgtta attatggtaa tgatgaggca   300
caaagagaaa accctgccat tttcccctac tttcaatcct gtgataggat gtcactgatg   360
atgttaatca cactgacctt acagaatggg ccttatgaac gcatttgatt cgcaaaccga   420
agattcttca cctgcaattg gtcgcaactt gcgtagccgc cgctggcgc gtaaaaaact   480
ctccgaaatg gtggaagaag agctggaaca gatgatccgc cgtcgtgaat tggcgaagg   540
tgaacaatta ccgtctgaac gcgaactgat ggcgttcttt aacgtcgggc gtccttcggt   600
gcgtgaagcg ctggcagcgt taaaacgcaa aggtctggtg caaataaaca acggcgaacg   660
cgctcgcgtc tcgcgtcctt ctgcggacac tatcatcggt gagctttccg gcatggcgaa   720
agatttcctt tctcatcccg gtgggattgc ccatttcgaa caattacgtc tgttctttga   780
atccagtctg gtgcgctatg cggctgaaca tgccaccgat gagcaaatcg atttgctggc   840
aaaagcactg gaaatcaaca gtcagtcgct ggataacaac gcggcattca ttcgttcaga   900
cgttgatttc caccgcgtgc tggcggagat ccccggtaac ccaatcttca tggcgatcca   960
cgttgccctg ctcgactggc ttattgccgc acgcccaacg gttaccgatc aggcactgca  1020
cgaacataac aacgttagtt atcaacagca tattgcgatc gttgatgcga tccgccgtca  1080
tgatcctgac gaagccgatc gtgcgttgca atcgcatctc aacagcgtct ctgctacctg  1140
gcacgctttc ggtcagacca ccaacaaaaa gaaataatgc cactttagtg aagcagatcg  1200
cattataagc tttctgtatg gggtgttgct taattgatct ggtataacag gtataaaggt  1260
```

-continued

```
atatcgttta tcagacaagc atcacttcag aggtatttat ggcaacgaat ttacgtggcg    1320
taatggctgc actcctgact cctttt gacc aacaacaagc actggataaa gcgagtctgc    1380
gtcgcctggt tcagttcaat attcagcagg gcatcgacgg tttatacgtg ggtggttcga    1440
ccggcgaggc ctttgtacaa agcctttccg agcgtgaaca ggtactggaa atcgtcgccg    1500
aagaggcgaa aggtaagatt aaactcatcg cccacgtcgg ttgcgtcagc accgccgaaa    1560
gccaacaact tgcggcatcg gctaaacgtt atggcttcga tgccgtctcc gccgtcacgc    1620
cgttctacta tcctttcagc tttgaagaac actgcgatca ctatcgggca attattgatt    1680
cggcggatgg tttgccgatg gtggtgtaca acattccagc cctgagtggg gtaaaactga    1740
ccctggatca gatcaacaca cttgttacat tgcctggcgt aggtgcgctg aaacagacct    1800
ctggcgatct ctatcagatg gagcagatcc gtcgtgaaca tcctgatctt gtgctctata    1860
acggttacga cgaaatcttc gcctctggtc tgctggcggg cgctgatggt ggtatcggca    1920
gtacctacaa catcatgggc tggcgctatc aggggatcgt taaggcgctg aaagaaggcg    1980
atatccagac cgcgcagaaa ctgcaaactg aatgcaataa agtcattgat ttactgatca    2040
aaacgggcgt attccgcggc ctgaaaactg tcctccatta tatggatgtc gtttctgtgc    2100
cgctgtgccg caaaccgttt ggaccggtag atgaaaaata tctgccagaa ctgaaggcgc    2160
tggcccagca gttgatgcaa gagcgcgggt gagttgtttc ccctcgctcg ccctaccgg    2220 gtgagggaaa ataaacgcat ctgtacccta caattttcat accaaagcgt gtgggcatcg    2280
cccaccgcgg gagactcaca atgagtacta caacccagaa tatcccgtgg tatcgccatc    2340
tcaaccgtgc acaatggcgc gcattttccg ctgcctggtt gggatatctg cttgacggtt    2400
ttgatttcgt tttaatcgcc ctggtactca ccgaagtaca aggtgaattc gggctgacga    2460
cggtgcaggc ggcaagtctg atctctgcag cctttatctc tcgctggttc ggcggcctga    2520
tgctcggcgc tatgggtgac cgctacgggc gtcgtctggc aatggtcacc agcatcgttc    2580
tcttctcggc cgggacgctg gcctgcgct ttgcgccagg ctacatcacc atgtttatcg    2640
ctcgtctggt catcggcatg gggatggcgg gtgaatacgg ttccagcgcc acctatgtca    2700
ttgaaagctg gccaaaacat ctgcgtaaca aagccagtgg tttttgatt tcaggcttct    2760 ctgtggggc cgtcgttgcc gctcaggtct atagcctggt ggttccggtc tggggctggc    2820
gtgcgctgtt ctttatcggc attttgccaa tcatctttgc tctctggctg cgtaaaaaca    2880
tcccggaagc ggaagactgg aaagagaaac acgcaggtaa agcaccagta cgcacaatgg    2940
tggatattct ctaccgtggt gaacatcgca ttgccaatat cgtaatgaca ctggcggcgg    3000
ctactgcgct gtggttctgc ttcgccggta acctgcaaaa tgccgcgatc gtcgctgttc    3060
ttgggctgtt atgcgccgca atctttatca gctttatggt gcagagtgca ggcaaacgct    3120
ggccaacggg cgtaatgctg atggtggtcg tgttgtttgc tttcctctac tcatggccga    3180
ttcaggcgct gctgccaacg tatctgaaaa ccgatctggc ttataaccg catactgtag    3240 ccaatgtgct gttctttagt ggctttggcg cggcggtggg atgctgcgta ggtggcttcc    3300
tcggtgactg gctgggaacc cgcaaagcgt acgtttgtag cctgctggcc tcgcagctgc    3360
tgattattcc ggtatttgcg attggcgcg caaacgtctg ggtgctcggt ctgttactgt    3420
tcttccagca aatgcttgga caagggatcg ccgggatctt accaaaactg attggcggtt    3480
atttcgatac cgaccagcgt gcagcggcc tgggctttac ctacaacgtt ggcgcattgg    3540
gcggtgcact ggccccaatc atcggcgcgt tgatcgctca acgtctggat ctgggtactg    3600
cgctggcatc gctctcgttc agtctgacgt tcgtggtgat cctgctgatt gggctggata    3660
```

```
tgccttctcg cgttcagcgt tggttgcgcc cggaagcgtt gcgtactcat gacgctatcg   3720
acggtaaacc attcagcggt gccgtgccgt ttggcagcgc caaaaacgat ttagtcaaaa   3780
ccaaaagtta atcctgttgc ccggtctatg taccgggcct ttcgctaagg gaagatgtat   3840
gtcgttactt gcacaactgg atcaaaaaat cgctgctaac ggtggcctga ttgtctcctg   3900
ccagccggtt ccggacagcc cgctcgataa acccgaaatc gtcgccgcca tggcattagc   3960
ggcagaacag gcgggcgcgg ttgccattcg cattgaaggt gtggcaaatc tgcaagccac   4020
gcgtgcggtg gtgagcgtgc cgattattgg aattgtgaaa cgcgatctgg aggattctcc   4080
ggtacgcatc acggcctata ttgaagatgt tgatgcgctg gcgcaggcgg cgcggacat    4140 tatcgccatt gacggcaccg accgcccgcg tccggtgcct gttgaaacgc tgctggcacg   4200
tattcaccat cacggtttac tggcgatgac cgactgctca acgccggaag acggcctggc   4260
atgccaaaag ctgggagccg aaattattgg cactacgctt tctggctata ccacgcctga   4320
aacgccagaa gagccggatc tggcgctggt gaaaacgttg agcgacgccg gatgtcgggt   4380
gattgccgaa gggcgttaca acacgcctgc tcaggcggcg gatgcgatgc ccacggcgc    4440 gtgggcggtg acgtcggtt ctgcaatcac gcgtcttgag cacatttgtc agtggtacaa    4500
cacagcgatg aaaaaggcgg tgctatgacc acactggcga ttgatatcgg cggtactaaa   4560
cttgccgccg cgctgattgg cgctgacggg cagatccgcg atcgtcgtga acttcctacg   4620
ccagccagcc agacaccaga agccttgcgt gatgccttat ccgcattagt ctctccgttg   4680
caagctcatg cgcagcgggt tgccatcgct tcgaccggga taatccgtga cggcagcttg   4740
ctggcgctta atccgcataa tcttggtgga ttgctacact ttccgttagt caaaacgctg   4800
gaacaactta ccaatttgcc gaccattgcc attaacgacg cgcaggccgc agcatgggcg   4860
gagtttcagg cgctggatgg cgatataacc gatatggtct ttatcaccgt ttccaccggc   4920
gttggcggcg gtgtagtgag cggctgcaaa ctgcttaccg gccctggcgg tctggcgggg   4980
catatcgggc atacgcttgc cgatccacac ggcccagtct gcggctgtgg acgcacaggt   5040
tgcgtggaag cgattgcttc tggtcgcggc attgcagcgg cagcgcaggg ggagttggct   5100
ggcgcggatg cgaaaactat tttcacgcgc gccgggcagg gtgacgagca ggcgcagcag   5160
ctgattcacc gctccgcacg tacgcttgca aggctgatcg ctgatattaa agccacaact   5220
gattgccagt gcgtggtggt cggtggcagc gttggtctgg cagaagggta tctggcgctg   5280
gtggaaacgt atctggcgca ggagccagcg gcatttcatg ttgatttact ggcggcgcat   5340
taccgccatg atgcaggttt acttggggct gcgctgttgg cccagggaga aaaattatga   5400
tgatgggtga agtacagtca ttaccgtctg ctgggttaca tcctgcgtta caggacgcgt   5460
taacgctggc attagctgcc agaccgcaag aaaaagcgcc gggtcgttac gaattacagg   5520
gcgacaatat ctttatgaat gtcatgacgt ttaacactca atcgcccgtc gagaaaaaag   5580
cggaattgca cgagcaatac attgatatcc agctgttatt aaacggtgag gaacggattc   5640
tgtttggcat ggcaggcact gcgcgtcagt gtgaagagtt ccaccatgag gatgattatc   5700
agctttgcag caccattgat aacgagcaag ccatcatctt aaaaccggga atgttcgccg   5760
tgtttatgcc aggtgaaccg cataaaccag gatgcgttgc cggcgagcct ggagagatta   5820
aaaaggttgt ggtgaaggtt aaggctgatt taatggctta a                       5861
```

<210> SEQ ID NO 43
<211> LENGTH: 264
<212> TYPE: PRT

```
<213> ORGANISM: Escherichia coli

<400> SEQUENCE: 43

Met Lys Gln Tyr Leu Glu Leu Met Gln Lys Val Leu Asp Glu Gly Thr
1               5                   10                  15
Gln Lys Asn Asp Arg Thr Gly Thr Gly Thr Leu Ser Ile Phe Gly His
            20                  25                  30
Gln Met Arg Phe Asn Leu Gln Asp Gly Phe Pro Leu Val Thr Thr Lys
        35                  40                  45
Arg Cys His Leu Arg Ser Ile Ile His Glu Leu Leu Trp Phe Leu Gln
    50                  55                  60
Gly Asp Thr Asn Ile Ala Tyr Leu His Glu Asn Asn Val Thr Ile Trp
65                  70                  75                  80
Asp Glu Trp Ala Asp Glu Asn Gly Asp Leu Gly Pro Val Tyr Gly Lys
                85                  90                  95
Gln Trp Arg Ala Trp Pro Thr Pro Asp Gly Arg His Ile Asp Gln Ile
            100                 105                 110
Thr Thr Val Leu Asn Gln Leu Lys Asn Asp Pro Asp Ser Arg Arg Ile
        115                 120                 125
Ile Val Ser Ala Trp Asn Val Gly Glu Leu Asp Lys Met Ala Leu Ala
    130                 135                 140
Pro Cys His Ala Phe Phe Gln Phe Tyr Val Ala Asp Gly Lys Leu Ser
145                 150                 155                 160
Cys Gln Leu Tyr Gln Arg Ser Cys Asp Val Phe Leu Gly Leu Pro Phe
                165                 170                 175
Asn Ile Ala Ser Tyr Ala Leu Leu Val His Met Met Ala Gln Gln Cys
            180                 185                 190
Asp Leu Glu Val Gly Asp Phe Val Trp Thr Gly Gly Asp Thr His Leu
        195                 200                 205
Tyr Ser Asn His Met Asp Gln Thr His Leu Gln Leu Ser Arg Glu Pro
    210                 215                 220
Arg Pro Leu Pro Lys Leu Ile Ile Lys Arg Lys Pro Glu Ser Ile Phe
225                 230                 235                 240
Asp Tyr Arg Phe Glu Asp Phe Glu Ile Glu Gly Tyr Asp Pro His Pro
                245                 250                 255
Gly Ile Lys Ala Pro Val Ala Ile
            260
```